United States Patent
Barawkar et al.

(10) Patent No.: US 9,006,177 B2
(45) Date of Patent: Apr. 14, 2015

(54) FUSED TRICYCLIC COMPOUNDS AS ADENOSINE RECEPTOR ANTAGONIST

(75) Inventors: Dinesh Barawkar, Hinjewadi (IN); Sujay Basu, Hinjewadi (IN); Vidya Ramdas, Hinjewadi (IN); Minakshi Naykodi, Hinjewadi (IN); Meena Patel, Hinjewadi (IN); Yogesh Shejul, Hinjewadi (IN); Sachin Thorat, Hinjewadi (IN); Anil Panmand, Hinjewadi (IN)

(73) Assignee: Advinus Therapeutics Limited, Bangalore (IN)

(*) Notice: Subject to any disclaimer, the term of this patent is extended or adjusted under 35 U.S.C. 154(b) by 0 days.

(21) Appl. No.: 13/825,665

(22) PCT Filed: Sep. 22, 2011

(86) PCT No.: PCT/IN2011/000657
§ 371 (c)(1),
(2), (4) Date: May 30, 2013

(87) PCT Pub. No.: WO2012/038980
PCT Pub. Date: Mar. 29, 2012

(65) Prior Publication Data
US 2013/0252885 A1    Sep. 26, 2013

(30) Foreign Application Priority Data
Sep. 24, 2010  (IN) .......................... 2808/CHE/2010

(51) Int. Cl.
| A61K 38/28 | (2006.01) |
| A61P 5/50 | (2006.01) |
| C07D 487/14 | (2006.01) |
| A61K 31/519 | (2006.01) |
| A61K 31/5377 | (2006.01) |
| A61K 45/06 | (2006.01) |
| C07D 519/00 | (2006.01) |

(52) U.S. Cl.
CPC ............ *C07D 487/14* (2013.01); *A61K 31/519* (2013.01); *A61K 31/5377* (2013.01); *A61K 45/06* (2013.01); *C07D 519/00* (2013.01)

(58) Field of Classification Search
None
See application file for complete search history.

(56) References Cited

FOREIGN PATENT DOCUMENTS

| WO | WO 2008121748 A2 * 10/2008 |
| WO |    2008121748 A2   3/2013 |

OTHER PUBLICATIONS

International Search Report for International Application No. PCT/IN2011/000657; Date of Mailing: Feb. 14, 2012; 4 pages.

* cited by examiner

*Primary Examiner* — Marcela M Cordero Garcia
*Assistant Examiner* — Kaipeen Yang
(74) *Attorney, Agent, or Firm* — Perkins Coie LLP

(57) ABSTRACT

The present disclosure relates to fused tricyclic compounds of formula (I) or its tautomers, polymorphs, stereoisomers, prodrugs, solvate or a pharmaceutically acceptable salts, or pharmaceutical compositions containing them and methods of treating conditions and diseases that are mediated by thereof as A2A adenosine receptor antagonists. The compounds of the present disclosure are useful in the treatment, prevention or suppression of diseases and disorders that may be susceptible to improvement by the mediation of adenosine A2A receptor. Such conditions include, but are not limited to, Parkinsons disease, restless leg syndrome, Alzheimers disease, neurodegenerative disorder, inflammation, wound healing, dermal fibrosis, nocturnal myoclonus, cerebral ischaemia, myocardial ischemia, Huntington's disease, multiple system atrophy, corticobasal degeneration, Wilson's disease or other disorders of basal ganglia which results in dyskinesias, post traumatic stress disorder, hepatic cirrhosis, sepsis, spinal cord injury, retinopathy, hypertension, social memory impairment, depression, neuroprotection, narcolepsy or other sleep related disorders, attention deficit hyperactivity disorder, drug addiction, post traumatic stress disorder and vascular injury and the like. The present disclosure also relates to methods for the preparation of such compounds, and to pharmaceutical compositions containing them.

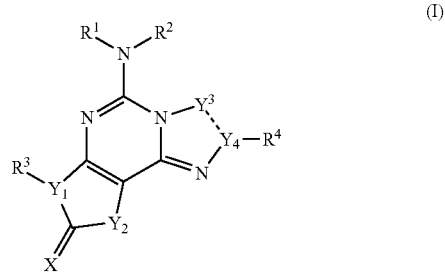

(I)

14 Claims, No Drawings

FUSED TRICYCLIC COMPOUNDS AS ADENOSINE RECEPTOR ANTAGONIST

TECHNICAL FIELD

The present disclosure relates to a series of substituted fused tricyclic compounds, their tautomers, polymorphs, stereoisomers, prodrugs, solvates, pharmaceutically acceptable salts, pharmaceutical compositions containing them and methods of treating conditions and diseases that are mediated by adenosine receptor (AR) activity. These compounds are useful in the treatment, prevention or suppression of diseases and disorders that may be susceptible to improvement by antagonism of the adenosine receptor. The disclosure also relates to methods for the preparation of such compounds, and to pharmaceutical compositions containing them.

BACKGROUND

The effects of adenosine are mediated through at least four specific cell membrane receptors so far identified and classified as $A_1$, $A_{2A}$, $A_{2B}$ and $A_3$ belonging to G protein-coupled receptor family. The $A_1$ and $A_3$ receptors down-regulate cellular cAMP levels through their coupling to G protein, which inhibit adenylate cyclase. In contrast, $A_{2A}$ and $A_{2B}$ receptors couple to G protein that activate adenylate cyclase and increase intracellular levels of cAMP. Through these receptors, adenosine regulates the wide range of physiological functions.

Advances in understanding the role of adenosine and its receptors in physiology and pathophysiology, as well as new developments in medicinal chemistry of these receptors have identified potential therapeutic areas for drug development. With the combination of pharmacological data, using selective ligands and genetically modified mice, important progress has been made toward an understanding of the role of ARs in a variety of diseases, such as inflammatory conditions, sepsis, heart attack, ischemia-reperfusion injury, vascular injury, spinal cord injury, chronic obstructive pulmonary disease (COPD), asthma, diabetes, obesity, inflammatory bowel disease, retinopathy, and Parkinson's Disease (PD).

Movement disorder constitutes a serious health problem, especially among the elderly. These movement disorders can often be the result of brain lesions. Disorders involving the basal ganglia which result in movement disorders include Parkinson's disease, Huntington's chorea and Wilson's disease. Tremor, rigidity, akinesia and postural changes are four classic symptoms of Parkinson's disease, it is also associated with depression, dementia and overall cognitive decline. Parkinson's disease has a prevalence of 1 per 1000 of the total population and increases to 1 per 100 for those aged over 60 years. Degeneration of dopaminergic neurons in the substantia nigra and the subsequent reductions in the interstitial concentrations of dopamine in the striatum are critical to the development of Parkinson's disease. About 80% of cells from the substantia nigra can be destroyed before the clinical symptoms of Parkinson's disease become apparent PD is a progressive, incurable disorder with no definite preventive treatment, although drugs are available to alleviate the symptoms and/or slow down the progress of the disease. Current therapy is based on dopamine replacement therapy, the most common drug treatments being dopaminomimetic agents, including L-DOPA, a dopamine precursor, as well as direct or indirect dopamine receptor agonists. L-DOPA is the mainstay in the treatment of PD, but because of tolerance problems and a wide range of adverse reactions, including involuntary movements and vomiting, a strong demand for new therapies exists. Among the various strategies, A2A AR blockers are considered a potential approach to treatment of the disease. Within the brain A2A ARs are richly expressed in the striatum, nucleus accumbens, and olfactory tubercle. A coexpression of A2A with D2 dopamine receptors has been reported in the GABAergic striatopallidal neurons where adenosine and dopamine agonists exert antagonistic effects in the regulation of locomotor activity. Activation of A2A ARs in striatopallidal neurons decreases the affinity of D2 receptors for dopamine, antagonizing the effects of D2 receptors. The negative interaction between A2A and D2 receptors is at the basis of the use of A2A antagonists as a novel therapeutic approach in the treatment of PD. (Pharmacol. Ther. 2005, 105, 267). The recent discovery that the A2A can form functional heteromeric receptor complexes with other Gprotein-coupled receptors such as D2 and the mGlu5 receptors has also suggested new opportunities for the potential of A2A antagonists in PD. (J. Mol. Neurosci. 2005, 26, 209).

A2A knockout (KO) mice transient focal ischemia caused less neuronal damage in comparison to their wild-type (WT) littermates (J. Neurosci. 1999, 19, 9192.). Therefore, it seems that tonic activation of A2A ARs may be responsible for dangerous signal during injury, in contrast to the neuroprotective effects induced by endogenous A1 activation. Recently, selective inactivation or reconstitution of A2A ARs in bone-marrow cells revealed their contribution to the development of ischemic brain injury (J. F. Nat. Med. 2004, 10, 1081) Blockade of A2A ARs has recently been implicated in the treatment of movement disorders such as Parkinson's disease (Trends Pharmacol. Sci. 1997, 18, 338-344) and in the treatment of cerebral ischaemia (Life Sci. 1994, 55, 61-65). The potential utility of A2A AR antagonists in the treatment of Parkinson's disease has been reviewed (CNS drugs, 1998, 10, 311-320). One advantage of A2A AR antagonist therapy is that the underlying neurodegenerative disorder may also be treated ((Ann. N.Y. Acad. Sci. 1997, 825 (Neuroprotective Agents), 3048). In particular, blockade of A2A AR function confers neuroprotection against MPTP-induced neurotoxicity in mice (Neurosci. 2001, 21, RC143).

Alzheimer's disease (AD) is a neurodegenerative disorder of the central nervous system manifested by cognitive and memory deterioration, a variety of neuropsychiatric symptoms, behavioral disturbances, and progressive impairment of daily life activities. Recent research suggests that adenosine receptors play important roles in the modulation of cognitive function. Epidemiological studies have found an association between coffee (a nonselective adenosine receptor antagonist) consumption and improved cognitive function in AD patients and in the elderly. Long-term administration of caffeine in transgenic animal models showed a reduced amyloid burden in brain with better cognitive performance. Antagonists of adenosine A2A receptors mimic these beneficial effects of caffeine on cognitive function. Neuronal cell cultures with amyloid beta in the presence of an A2A receptor antagonist completely prevented amyloid beta-induced neurotoxicity. These findings suggest that the adenosinergic system constitutes a new therapeutic target for AD, and caffeine and A2A receptor antagonists may have promise to manage cognitive dysfunction in AD (Curr Neuropharmacol. 2009 September; 7(3): 207-216).

High expression of A2A ARs has been found in platelets, leukocytes, vascular smooth muscle, and endothelial cells with important implications in the regulation of inflammatory responses. It is now well established that stimulation of the A2A AR in immune cells induces anti-inflammatory effects, mostly due to its ability to increase cAMP levels, which has strong immunosuppressive effects (Trends Immunol. 2005, 26, 299). Stimulation of A2A ARs inhibits neutrophil adherence to the endothelium, degranulation of activated neutrophils and monocytes, plus superoxide anion generation. A2A ARs have been recently defined as sensors and terminators of proinflammatory activities. The strongest evidence for the key role of A2A in inflammation is derived by the elegant study using mice deficient in A2A ARs (Nature 2001, 414, 916). In this model the lack of A2A subtype leads to increased tissue inflammation and damage, thus suggesting a negative and nonredundant regulatory role for the A2A AR. This model permits one to appreciate that adenosinergic regulation of immune cells is fundamental in normal physiological control of inflammation in vivo in spite of the fact that other Gs-protein-coupled receptors and cAMP elevating ligands are present, such as cathecolamines, prostaglandins, dopamine, and histamine (Trends Immunol. 2005, 26, 299). Interestingly, the A2A AR has been demonstrated to be involved in promotion of wound healing and angiogenesis in healing wounds (Am. J. Physiol. Regul. Integr. Comp. Physiol. 2005, 289, R283). Moreover, it plays an active role in the pathogenesis of dermal fibrosis, suggesting a role for antagonists as novel therapeutic approach in the treatment and prevention of dermal fibrosis in diseases such as scleroderma (Arthritis Rheum. 2006, 54, 2632) as well as hepatic fibrosis (Br. J. Pharmacol. 2006 August; 148(8):1144-55). Studies also suggest that A2A receptor antagonists may be beneficial for social memory impairment and hypertension (Behav Brain Res. 2005 Apr. 30; 159(2):197-205), sepsis (J. Immunol. 2006 May 1; 176(9):5616-26), spinal cord injury and neuroprotection (J. Neuroinflammation. 2011 Apr. 12; 8:31), retinopathy (IVOS, January 2000, vol. 41 (1), 230-243, depression (Neurology. 2003 Dec. 9; 61(11 Suppl 6):S82-7), narcolepsy and other sleep related disorders (Prog Neurobiol. 2007 December; 83(5):332-47), attention-deficit hyperactivity disorder (ADHD) (Behav Pharmacol. 2009 March; 20(2):134-45; Clinical Genetics (2000), 58(1), 31-40 and references therein), Antagonists of the A$_2$A receptor are potentially useful therapies for the treatment of addiction. Major drugs of abuse (opiates, cocaine, ethanol, and the like) either directly or indirectly modulate dopamine signaling in neurons particularly those found in the nucleus accumbens, which contain high levels Of A$_{2A}$ adenosine receptors. Dependence has been shown to be augmented by the adenosine signaling pathway, and it has been shown that administration of an A$_2$A receptor antagonist redues the craving for addictive substances ("The Critical Role of Adenosine A$_2$A Receptors and Gi βγ Subunits in Alcoholism and Addiction: From Cell Biology to Behavior", by Ivan Diamond and Lina Yao, (The Cell Biology of Addiction, 2006, pp 291-316) and "Adaptations in Adenosine Signaling in Drug Dependence: Therapeutic Implications", by Stephen P. Hack and Macdonald J. Christie, Critical Review in Neurobiology, Vol. 15, 235-274 (2003)). See also Alcoholism: Clinical and Experimental Research (2007), 31(8), 1302-1307.

A2A receptors may be beneficial for the treatment or prevention of disorders such as a movement disorder, for example, Parkinson's disease or progressive supernuclear palsy, Restless leg syndrome, nocturnal myoclonus, cerebral ischaemia, Huntington's disease, multiple system atrophy, corticobasal degeneration, Wilson's disease or other disorders of basal ganglia which results in dyskinesias, post traumatic stress disorder. See for example WO200013682, WO200012409, WO2009156737, WO200911442, WO2008121748, WO2001092264, WO2007038284, WO2008002596, WO2009111449, WO2009111442, WO2008121748, WO2009156737, WO2003022283, WO2005044245, WO2008077557, WO2009111449, WO2009705138, WO2009111442, WO2007035542, WO20080870661, WO2008070529, WO2005116026, WO2009055548, WO2007133983, WO2010045006, WO2010045015, WO2010045008 WO2009015236.

We have now found out that compounds of the present invention are potent antagonists of the A2A adenosine receptor and can therefore be used in the treatment of the diseases mentioned above.

SUMMARY

The present disclosure provides compounds of formula (I), their tautomers, polymorphs, stereoisomers, prodrugs, solvates, pharmaceutically acceptable salts, pharmaceutical compositions containing them and methods of treating conditions and diseases that are mediated by adenosine receptor activity,

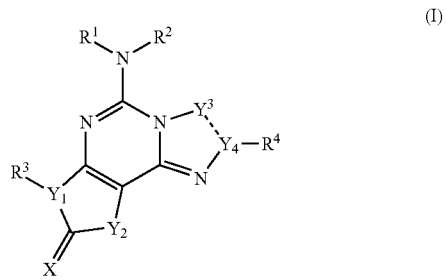

(I)

wherein
— represents a single bond or a double bond;
X is selected from O, S or NR$^a$;
Y$_1$ is selected from N or CH;
Y$_2$ is selected from NR$^5$, O or CR$^5$R$^6$;
Y$_3$ is selected from N, CH, CH$_2$, C(=O) or C(=S);
Y$_4$ is selected from N, C or CH;
R$^1$ and R$^2$ are independently selected from hydrogen or alkyl;
R$^3$ is A-Z—B-Q;
  wherein, A is absent or is a group selected from alkylene, alkenylene or alkynylene;
    wherein one or more methylene groups is optionally replaced by hetero atoms or groups such as —O—, —S(O)p-, —N(R$^a$)—, or —C(O); alkylene, alkenylene and alkynylene is optionally substituted with —(CR$^d$R$^e$)$_n$OR$^7$, (CR$^d$R$^e$)$_n$COOR$^7$, —(CR$^d$R$^e$)$_n$NR$^8$R$^9$, cyano, halogen, haloalkyl, perhaloalkyl, alkoxyalkoxy, alkyl or cycloalkyl;
  Z is absent or is selected from a cycloalkyl or a heterocyclyl;
    wherein cycloalkyl and heterocyclyl are unsubstituted or substituted independently with 1, 2, or 3 substituents independently selected from alkyl, alkenyl, alkynyl, acyl, —(CR$^d$R$^e$)$_n$OR$^7$, (CR$^d$R$^e$)$_n$COOR$^7$, —(CR$^d$R$^e$)$_n$NR$^8$R$^9$, aminocarbonyl, alkoxycarbonylamino, halogen, haloalkyl, perhaloalkyl, azido, cyano, keto, thiocarbonyl, —SO$_3$H, aminocarbonylamino, nitro, —S(O)$_2$NR$^a$R$^a$, —NR$^b$S(O)$_2$R$^b$ or —S(O)$_p$R$^c$;
  B is absent or is a group selected from alkylene, alkenylene or alkynylene; wherein one or more methylene groups is optionally replaced by hetero atoms or groups such as —O—, —S(O)p-, —N(R$^a$)—, or —C(O); alkylene, alkenylene and alkynylene is optionally substituted with hydroxy, amino, aminoalkyl, cyano, halogen, haloalkyl, perhaloalkyl, carboxy, carboxyalkyl, alkoxy, hydroxyalkyl, alkoxyalkyl, alkoxyalkoxy or alkyl;

Q is selected from hydrogen, alkyl, cycloalkyl, cycloalkylalkyl, aryl, arylalkyl, heterocyclyl, heterocyclylalkyl, heteroaryl or heteroarylalkyl;

wherein alkyl, cycloalkyl, cycloalkylalkyl, aryl, arylalkyl, heterocyclyl, heterocyclylalkyl, heteroaryl and heteroarylalkyl are unsubstituted or substituted independently with 1, 2, or 3 substituents independently selected from alkyl, alkenyl, alkynyl, halogen, haloalkyl, perhaloalkyl, azido, cyano, nitro, keto, thiocarbonyl, cyanoalkyl, cyanoalkylcarbonyl, —(CR$^d$R$^e$)OR$^7$, —(CR$^d$R$^e$)$_n$C(O)R$^7$, —(CR$^d$R$^e$)$_n$SR$^7$, —(CR$^d$R$^e$)$_n$COOR$^7$, —(CR$^d$R$^e$)$_n$NR$^8$R$^9$, —(CR$^d$R$^e$)$_n$C(O)NR$^8$R$^9$, —(CR$^d$R$^e$)$_n$NR$^8$C(O)OR$^7$, —(CR$^d$R$^e$)$_n$NR$^8$C(O)NR$^8$R$^9$, —NR$^b$S(O)$_2$R$^b$, —S(O)$_p$R$^c$, —SO$_3$H, —S(O)$_2$NR$^a$R$^a$, cycloalkyl, cycloalkenyl, cycloalkylalkyl aryl, arylalkyl, heterocyclyl, heterocyclylalkyl, heteroaryl or heteroarylalkyl;

wherein each substituent is unsubstituted or substituted with 1, 2, or 3 substituents independently selected from alkyl, carboxy, carboxyalkyl, aminocarbonyl, hydroxy, alkoxy, halogen, haloalkyl, perhaloalkyl, haloalkoxy, perhaloalkoxy, amino, substituted amino, cyano or —S(O)$_p$R$^c$;

R$^4$ is selected from the group consisting of hydrogen, alkyl, alkenyl, alkynyl, haloalkyl, hydroxyalkyl, carboxyalkyl, cycloalkyl, cycloalkylalkyl, aryl, arylalkyl, heterocyclyl, heterocyclylalkyl, heteroaryl and heteroarylalkyl;

wherein alkyl, alkenyl, alkynyl, cycloalkyl, cycloalkylalkyl, arylalkyl, aryl, heteroaryl, heteroarylalkyl, heterocyclyl, and heterocyclylalkyl are unsubstituted or substituted independently with up to four substituents independently selected from alkyl, alkenyl, alkynyl, acyl, —(CR$^d$R$^e$)$_n$OR$^7$, (CR$^d$R$^e$)$_n$COOR$^7$, —(CR$^d$R$^e$)$_n$NR$^8$R$^9$, aminocarbonyl, alkoxycarbonylamino, aminocarbonylamino, azido, cyano, halogen, haloalkyl, perhaloalkyl, keto, nitro, —S(O)$_2$NR$^b$R$^b$, —NR$^b$S(O)$_2$R$^b$ or —S(O)$_p$R$^c$, thiocarbonyl, —SO$_3$H, cycloalkyl, cycloalkenyl, aryl, heteroaryl or heterocyclyl;

R$^5$ and R$^6$ are independently selected from the group consisting of hydrogen, hydroxy, —(CR$^d$R$^e$)$_n$OR$^7$, (CR$^d$R$^e$)$_n$COOR$^7$, —(CR$^d$R$^e$)$_n$NR$^8$R$^9$, cyanoalkyl, haloalkyl, alkoxyalkoxyalkyl, alkyl, alkenyl, alkynyl, cycloalkyl, cycloalkylalkyl, aryl, arylalkyl, heterocyclyl, heterocyclylalkyl, heteroaryl and heteroarylalkyl;

R$^7$ is selected from hydrogen, alkyl, halogen, haloalkyl, —(CR$^d$R$^e$)$_n$OR$^7$, —(CR$^d$R$^e$)$_n$COOR$^7$, —(CR$^e$R$^e$)$_n$C(O)R$^7$, carbonylamino, cycloalkyl, cycloalkylalkyl, aryl, arylalkyl, heteroaryl, heteroarylalkyl, heterocyclyl or heterocyclylalkyl;

R$^8$ and R$^9$ are independently selected from the group consisting of hydrogen, alkyl, haloalkyl, —(CR$^d$R$^e$)$_n$OR$^7$, —(CR$^d$R$^e$)C(O)R$^7$, aryl, arylalkyl, heteroaryl, heteroarylalkyl, cycloalkyl, cycloalkylalkyl, heterocyclyl and heterocyclylalkyl, or R$^8$ and R$^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, alkenyl, alkynyl, nitro, cyano, —(CR$^d$R$^e$)$_n$OR$^7$, —(CR$^d$R$^e$)$_n$SR$^7$, —(CR$^d$R$^e$)$_n$NR$^8$R$^9$, oxo, alkylsulfonyl, —(CR$^d$R$^e$)COOR$^7$, —(CR$^d$R$^e$)$_n$C(O)NR$^8$R$^9$, cycloalkyl, cycloalkylalkyl, aryl, arylalkyl, heterocyclyl, heterocyclylalkyl, heteroaryl, or heteroarylalkyl;

R$^a$ is selected from hydrogen or alkyl;

R$^b$ each is independently selected from the group consisting of hydrogen, alkyl, acyl, carboxyalkyl, carbonylamino, cycloalkyl, cycloalkylalkyl, aryl, arylalkyl, heteroaryl, heteroarylalkyl, heterocyclyl and heterocyclylalkyl;

R$^c$ is selected from alkyl, cycloalkyl, aryl, heterocyclyl or heteroaryl;

R$^d$ and R$^e$ are independently selected from the group consisting of hydrogen, —OR$^7$, halogen, haloalkyl, perhaloalkyl and alkyl;

n is 0, 1, 2, 3 or 4, and p is 0, 1 or 2.

DETAILED DESCRIPTION OF THE INVENTION

Definitions

In the structural formulae given herein and throughout the present disclosure, the following terms have the indicated meaning, unless specifically stated otherwise.

The term "optionally substituted" as used herein means that the group in question is either unsubstituted or substituted with one or more of the substituents specified. When the group in question is substituted with more than one substituent, the substituent may be same or different.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methyl, ethyl, n-propyl, iso-propyl, n-butyl, iso-butyl, t-butyl, n-hexyl, n-decyl, tetradecyl, and the like.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkyl" or "substituted alkylene" refers to: 1) an alkyl group or alkylene group as defined above, having 1, 2, 3, 4 or 5 substituents, preferably 1, 2 or 3 substituents, selected from the group consisting of alkenyl, alkynyl, alkoxy, cycloalkyl, cycloalkenyl, acyl, acylamino, acyloxy, amino, monoalkylamino, dialkylamino, arylamino, heteroarylamino, aminocarbonyl, alkoxycarbonylamino, azido, cyano, halogen, hydroxy, hydroxyalkyl, keto, thiocarbonyl, carboxy, carboxyalkyl, —SO$_3$H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$, where each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where R$^b$ is hydrogen, alkyl, aryl, heteroaryl or heterocyclyl. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF$_3$, amino, substituted amino, cyano, and —S(O)$_p$R$^c$, where R$^c$ is alkyl, aryl, or heteroaryl and p is 0, 1 or 2;

or 2) an alkyl group or alkylene group as defined above that is interrupted by 1, 2, 3, 4, 5, 6, 7, 8, 9 or 10 atoms independently selected from oxygen, sulphur and NR$^d$, where R$^d$ is selected from hydrogen, alkyl, cycloalkyl, cycloalkenyl, aryl, heteroaryl and heterocyclyl, carbonylalkyl, carboxyester, carboxyamide and sulfonyl. All substituents may be optionally further substituted by alkyl, alkoxy, halogen, $CF_3$, amino, substituted amino, cyano, or $-S(O)_pR^c$, in which $R^c$ is alkyl, aryl, or heteroaryl and p is 0, 1, or 2;

or 3) an alkyl or alkylene as defined above that has 1, 2, 3, 4 or 5 substituents as defined above, as well as interrupted by 1, 2, 3, 4, 5, 6, 7, 8, 9 or 10 atoms as defined above.

The term "alkenyl" refers to a monoradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 double bond (vinyl), preferably 1 double bond. Preferred alkenyl groups include ethenyl or vinyl($-CH=CH_2$), 1-propylene or allyl ($-CH_2CH=CH_2$), isopropylene ($-C(CH_3)=CH_2$), bicyclo[2.2.1]heptene, and the like.

The term "alkenylene" refers to a diradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 double bond (vinyl), preferably 1 double bond.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, thiocarbonyl, carboxy, carboxyalkyl. $SO_3H$, aryl, aryloxy, heteroaryl, aminocarbonylamino, heteroaryloxy, heterocyclyl, heterocyclyloxy, hydroxyamino, alkoxyamino, nitro, $-S(O)_2NR^aR^a$, $-NR^aS(O)_2R^a$ and $-S(O)_pR^b$ where each $R^a$ is independently selected from the group consisting of hydrogen, alkyl, cycloalkyl, cycloalkylalkyl, aryl, arylalkyl, heteroaryl heteroarylalkyl, heterocyclyl, heterocyclylalkyl and heterocyclyloxy, where $R^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, $CF_3$, amino, substituted amino, cyano, and $-S(O)_pR^c$, where $R^c$ is alkyl, aryl, or heteroaryl and p is 0, 1 or 2.

The term "alkynyl" refers to a monoradical of an unsaturated hydrocarbon, preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 sites of acetylene (triple bond) unsaturation, preferably 1 triple bond. Preferred alkynyl groups include ethynyl, ($-C\equiv CH$), propargyl (or prop-1-yn-3-yl, $-CH_2C\equiv CH$), homopropargyl (or but-1-yn-4-yl, $-CH_2CH_2C\equiv CH$) and the like. The term "alkynylene" refers to a diradical of a branched or an unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 sites of acetylene (triple bond) unsaturation, preferably 1 triple bond.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, $-SO_3H$, aryl, aryloxy, heteroaryl, aminocarbonylamino, heteroaryloxy, heterocyclyl, heterocyclyloxy, hydroxyamino, alkoxyamino, nitro, $-S(O)_2NR^aR^a$, $-NR^aS(O)_2R^a$ and $-S(O)_pR^b$, where each $R^a$ is independently selected from the group consisting of hydrogen, alkyl, cycloalkyl, cycloalkylalkyl, aryl, arylalkyl, heteroaryl heteroarylalkyl, heterocyclyl, heterocyclylalkyl and heterocyclyloxy, where $R^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, $CF_3$, amino, substituted amino, cyano, and $-S(O)_pR^e$ where $R^e$ is alkyl, aryl, or heteroaryl and p is 0, 1 or 2.

The term "cycloalkyl" refers to unless otherwise mentioned, carbocyclic groups of from 3 to 20 carbon atoms having a single cyclic ring or multiple condensed rings which may be saturated or partially unsaturated. Such cycloalkyl groups include, by way of example, single ring structures such as cyclopropyl, cyclobutyl, cyclopentyl, cyclopentenyl, cyclohexyl, cyclohexenyl, cyclooctyl, and the like, or multiple ring structures such as adamantanyl, bicyclo[2.2.1]heptane, bicyclo[2.2.2]octane, 1,3,3-trimethylbicyclo[2.2.1] hept-2-yl, (2,3,3-trimethylbicyclo[2.2.1]hept-2-yl), or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, oxo, thiocarbonyl, aryl, aryloxy, heteroaryl, aminosulfonyl, aminocarbonylamino, heteroaryloxy, heterocyclyl, heterocyclyloxy, hydroxyamino, alkoxyamino, nitro, $-C(O)R$ and $-S(O)_pR^b$, where R is hydrogen, hydroxyl, alkoxy, alkyl and cyclocalkyl, heterocyclyloxy where $R^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, $CF_3$, amino, substituted amino, cyano, and $-S(O)_pR^c$, where $R^c$ is alkyl, aryl, or heteroaryl and p is 0, 1 or 2.

"Halo" or "Halogen", alone or in combination with any other term means halogens such as chloro (Cl), fluoro (F), bromo (Br) and iodo (I).

"Haloalkyl" refers to a straight chain or branched chain haloalkyl group with 1 to 6 carbon atoms. The alkyl group may be partly or totally halogenated. Representative examples of haloalkyl groups include but are not limited to fluoromethyl, chloromethyl, bromomethyl, difluoromethyl, dichloromethyl, dibromomethyl, trifluoromethyl, trichloromethyl, 2-fluoroethyl, 2-chloroethyl, 2-bromoethyl, 2,2,2-trifluoroethyl, 3-fluoropropyl, 3-chloropropyl, 3-bromopropyl and the like.

The term "alkoxy" refers to the group $R'''-O-$, where $R'''$ is optionally substituted alkyl or optionally substituted cycloalkyl, or optionally substituted alkenyl or optionally substituted alkynyl; or optionally substituted cycloalkenyl, where alkyl, alkenyl, alkynyl, cycloalkyl and cycloalkenyl are as defined herein. Representative examples of alkoxy groups include but are not limited to methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "aminocarbonyl" refers to the group —C(O)NR'R' where each R' is independently hydrogen, alkyl, aryl, heteroaryl, heterocyclyl or both R' groups are joined to form a heterocyclic group (e.g. morpholino). Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and —$S(O)_pR^c$, where $R^c$ is alkyl, aryl, or heteroaryl and p is 0, 1 or 2.

The term "acylamino" refers to the group NR"C(O)R" where each R" is independently hydrogen, alkyl, aryl, heteroaryl, or heterocyclyl. Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and —$S(O)_pR^c$, where $R^c$ is alkyl, aryl, or heteroaryl and p is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may be optionally further substituted by alkyl, carboxy, carboxyalkyl, aminocarbonyl, hydroxy, alkoxy, halogen, $CF_3$, amino, substituted amino, cyano, or —$S(O)_pR^c$, where $R^c$ is alkyl, aryl, or heteroaryl and p is 0, 1 or 2.

"Alkoxyalkyl" refers to alkyl groups as defined above wherein at least one of the hydrogen atoms of the alkyl group is replaced by an alkoxy group as defined above. Representative examples of alkoxyalkyl groups include but are not limited to methoxymethyl, methoxyethyl, ethoxymethyl and the like.

"Aryloxyalkyl" refers to the group alkyl-O-aryl. Representative examples of aryloxyalkyl include but are not limited to phenoxymethyl, naphthyloxymethyl, phenoxyethyl, naphthyloxyethyl and the like.

"Di alkylamino" refers to an amino group, to which two same or different straight chain or branched chain alkyl groups with 1 to 6 carbon atoms are bound. Representative examples of di alkylamino include but are not limited to dimethylamino, diethylamino, methylethylamino, dipropylamino, dibutylamino and the like.

"Cycloalkylalkyl" refers to an alkyl radical as defined above which is substituted by a cycloalkyl radical as defined above. Representative examples of cycloalkylalkyl include but are not limited to cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

"Aminoalkyl" refers to an amino group that is attached to $(C_{1-6})$alkylene as defined herein. Representative examples of aminoalkyl include but are not limited to aminomethyl, aminoethyl, 1-aminopropyl, 2-aminopropyl, and the like. The amino moiety of aminoalkyl may be substituted once or twice with alkyl to provide alkylaminoalkyl and dialkylaminoalkyl respectively. Representative examples of alkylaminoalkyl include but are not limited to methylaminomethyl, methylaminoethyl, methylaminopropyl, ethylaminoethyl and the like. Representative examples of dialkylaminoalkyl include but are not limited to dimethylaminomethyl, dimethylaminoethyl, dimethylaminopropyl, N-methyl-N-ethylaminoethyl and the like.

The term "aryl" refers to an aromatic carbocyclic group of 6 to 20 carbon atoms having a single ring (e.g. phenyl) or multiple rings (e.g. biphenyl), or multiple condensed (fused) rings (e.g. naphthyl or anthranyl). Preferred aryls include phenyl, naphthyl and the like. The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained the aryl or arylene groups may optionally be substituted with 1, 2, 3 4 or 5 substituents, preferably 1, 2 or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, carboxy, carboxyalkyl, —$SO_3H$, aryl, aryloxy, heteroaryl, aminosulfonyl, aminocarbonylamino, heteroaryloxy, heterocyclyl, heterocyclyloxy, hydroxyamino, alkoxyamino, nitro, —$S(O)_2NR^aR^a$, —$NR^aS(O)_2R^a$ and —$S(O)_pR^b$ where each $R^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; where $R^b$ is hydrogen, alkyl, aryl, heterocyclyl or heteroaryl and p is 0, 1 or 2. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, $CF_3$, amino, substituted amino, cyano, and —$S(O)_pR^c$ where le is hydrogen, alkyl, aryl, or heteroaryl and p is 0, 1 or 2.

The term "arylalkyl" refers to an aryl group covalently linked to an alkylene group, where aryl and alkylene are defined herein.

"Optionally substituted arylalkyl" refers to an optionally substituted aryl group covalently linked to an optionally substituted alkylene group. Such arylalkyl groups are exemplified by benzyl, phenethyl, naphthylmethyl, and the like.

The term "aryloxy" refers to the group aryl-O— wherein the aryl group is as defined above, and includes optionally substituted aryl groups as also defined above.

The term "arylthio" refers to the group —S-aryl, where aryl is as defined herein including optionally substituted aryl groups as also defined above.

The term "substituted amino" refers to the group —NR'R' where each R' is independently selected from the group consisting of hydrogen, alkyl, cycloalkyl, carboxyalkyl, alkoxycarbonyl, aryl, heteroaryl and heterocyclyl. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, $CF_3$, amino, substituted amino, cyano, and —$S(O)_pR^c$, where $R^c$ is alkyl, aryl, or heteroaryl and p is 0, 1 or 2.

The term "carboxyalkyl" refers to the groups alkylene-C(O)OH.

The term "alkylcarboxyalkyl" refers to the groups -alkylene-C(O)$OR^d$ where $R^d$ is alkyl, cycloalkyl, where alkyl, cycloalkyl are as defined herein, and may be optionally further substituted by alkyl, halogen, $CF_3$, amino, substituted amino, cyano, or —$S(O)_pR^c$, in which $R^c$ is alkyl, aryl, or heteroaryl and p is 0, 1 or 2.

The term "heteroaryl" refers to an aromatic cyclic group having 1, 2, 3, 4, 5, 6, 7, 8, 9, 10, 11, 12, 13, 14, or 15 carbon atoms and 1, 2, 3 or 4 heteroatoms selected from oxygen, nitrogen and sulphur within at least one ring. Such heteroaryl groups can have a single ring (e.g. pyridinyl or furanyl) or multiple condensed rings (e.g. indolizinyl, benzooxazolyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, quinoxaline, quinazoline, cinnoline, pteridine, carbazole, carboline, phenanthridine, acridine, phenanthroline, isothiazole, phenazine, isoxazole, phenoxazine, phenothiazine, furan, thiophene, oxazole, thiazole, triazole, triazine and the like.

The term "heteroarylene" refers to a diradical of a heteroaryl group as defined above. Unless otherwise constrained the heteroaryl or hetarylene groups can be optionally substituted with 1, 2, 3, 4 or 5 substituents, preferably 1, 2 or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, thiocarbonyl, carboxy, carboxyalkyl, —SO$_3$H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$, where each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; where R$^b$ is hydrogen, alkyl, aryl, heterocyclyl or heteroaryl, and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, CF$_3$, amino, substituted amino, cyano, and —S(O)$_n$R$^c$, where R$^c$ is alkyl, aryl, or heteroaryl and n is 0, 1 or 2.

The term "heteroarylalkyl" refers to a heteroaryl group covalently linked to an alkylene group, where heteroaryl and alkylene are defined herein.

"Optionally substituted heteroarylalkyl" refers to an optionally substituted heteroaryl group covalently linked to an optionally substituted alkylene group. Such heteroarylalkyl groups are exemplified by 3-pyridylmethyl, quinolin-8-ylethyl, 4-methoxythiazol-2-ylpropyl, and the like.

The term "heterocyclyl" refers to a saturated or partially unsaturated group having a single ring or multiple condensed rings, unless otherwise mentioned, having from 1 to 40 carbon atoms and from 1 to 10 hetero atoms, preferably 1, 2, 3 or 4 heteroatoms, selected from nitrogen, sulphur, phosphorus, and/or oxygen within the ring. Heterocyclic groups can have a single ring or multiple condensed rings, and include dihydrofuranyl, tetrahydrofuranyl, morpholinyl, pyrrolidinyl, dihydropyrrole, dihydropyranyl, tetrahydropyranyl, pyrazolidinyl, imidazolidinyl, dihydropyridinyl, tetrahydropyridinyl, piperidinyl, dihydropyrazinyl, tetrahydropyrazinyl, piperazinyl, dihydropyridinyl, benzodioxolyl, tetrahydroquinolinyl, tetrahydroisoquinolinyl, tetrahydronaphthyridinyl, tetrahydrothienopyridinyl and the like. Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, oxo, —C(O)R where R is hydrogen, hydroxyl, alkoxy, alkyl and cyclocalkyl, thiocarbonyl, carboxy, carboxyalkyl, aryl, aryloxy, heteroaryl, aminosulfonyl, aminocarbonylamino, heteroaryloxy, heterocyclyl, heterocyclyloxy, hydroxyamino, alkoxyamino, nitro, and —S(O)$_p$R$^b$, where R$^b$ is hydrogen, alkyl, aryl, heterocyclyl or heteroaryl and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, CF$_3$, amino, substituted amino, cyano, and —S(O)$_n$R$^c$, where R$^c$ is alkyl, aryl, or heteroaryl and n is 0, 1 or 2.

The term "heterocyclylalkyl" refers to a heterocyclyl group covalently linked to an alkylene group, where heterocyclyl and alkylene are defined herein.

"Optionally substituted heterocyclylalkyl" refers to an optionally substituted heterocyclyl group covalently linked to an optionally substituted alkylene group.

The term "heteroaryloxy" refers to the group heteroaryl-O—.

The term "thiol" refers to the group —SH.

The term "substituted alkylthio" refers to the group —S-substituted alkyl.

The term "heteroarylthio" refers to the group —S-heteroaryl wherein the heteroaryl group is as defined above including optionally substituted heteroaryl groups as also defined above.

The term "sulfoxide" refers to a group —S(O).

"Substituted sulfoxide" refers to a group —S(O)R, in which R is substituted alkyl, substituted aryl, or substituted heteroaryl, as defined herein.

The term "sulfone" refers to a group —S(O)$_2$R.

The term "substituted sulfone" refers to a group —S(O)$_2$R, in which R is alkyl, aryl, or heteroaryl.

The compounds of the present disclosure may have the ability to crystallize in more than one form, a characteristic known as polymorphism, and all such polymorphic forms ("polymorphs") are encompassed within the scope of the present disclosure. Polymorphism generally can occur as a response to changes in temperature or pressure or both, and can also result from variations in the crystallization process. Polymorphs can be distinguished by various physical characteristics, and typically the x-ray diffraction patterns, solubility behavior, and melting point of the compound are used to distinguish polymorphs.

The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds.

Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the present disclosure are congeners, analogs, hydrolysis products, metabolites and precursor or prodrugs of the compound. In general, unless otherwise indicated, all physical forms are equivalent for the uses contemplated herein and are intended to be within the scope of the present invention.

"Prodrug" refers to a derivative of a drug molecule as, for example, esters, carbonates, carbamates, ureas, amides or phosphates that requires a transformation within the body to release the active drug. Prodrugs are frequently, although not necessarily, pharmacologically inactive until converted to the parent drug. Prodrugs may be obtained by bonding a promoiety (defined herein) typically via a functional group, to a drug.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach or the agent may be supplied exogenously.

"Pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the present disclosure are quaternary ammonium compounds wherein an equivalent of an anion (M-) is associated with the positive charge of the N atom. M- may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. M- is preferably an anion selected from chloride, bromide, iodide, sulphate, nitrate, acetate, maleate, oxalate, succinate or trifluoroacetate. More preferably M- is chloride, bromide, trifluoroacetate or methanesulphonate.

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present disclosure are inert organic solvents. The term "q.s." means adding a quantity sufficient to achieve a stated function, e.g., to bring a solution to the desired volume (i.e., 100%).

The present disclosure provides compounds of formula I, or its tautomers, polymorphs, stereoisomers, prodrugs, solvate or a pharmaceutically acceptable salts thereof, pharmaceutical compositions containing them and methods of treating conditions and diseases that are mediated by adenosine receptor activity,

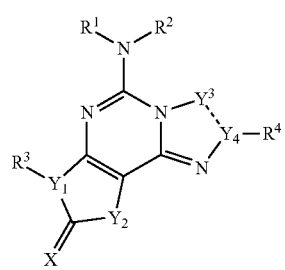

wherein
— represents a single bond or a double bond;
X is selected from O, S or $NR^a$;
$Y_1$ is selected from N or CH;
$Y_2$ is selected from $NR^5$, O or $CR^5R^6$;
$Y_3$ is selected from N, CH, $CH_2$, C(=O) or C(=S);
$Y_4$ is selected from N, C or CH;
$R^1$ and $R^2$ are independently selected from hydrogen or alkyl;
$R^3$ is A-Z—B-Q;
  wherein, A is absent or is a group selected from alkylene, alkenylene or alkynylene;
    wherein one or more methylene groups is optionally replaced by hetero atoms or groups such as —O—, —S(O)$_p$—, —N($R^a$)—, or —C(O); alkylene, alkenylene and alkynylene is optionally substituted with —$(CR^dR^e)_n OR^7$, $(CR^dR^e)_n COOR^7$, —$(CR^dR^e)_n NR^8 R^9$, cyano, halogen, haloalkyl, perhaloalkyl, alkoxyalkoxy, alkyl or cycloalkyl;
  Z is absent or is selected from a cycloalkyl or a heterocyclyl;
    wherein cycloalkyl and heterocyclyl are unsubstituted or substituted independently with 1, 2, or 3 substituents independently selected from alkyl, alkenyl, alkynyl, acyl, —$(CR^dR^e)_n OR^7$, $(CR^dR^e)_n COOR^7$, —$(CR^dR^e)_n NR^8 R^9$, aminocarbonyl, alkoxycarbonylamino, halogen, haloalkyl, perhaloalkyl, azido, cyano, keto, thiocarbonyl, —$SO_3H$, aminocarbonylamino, nitro, —$S(O)_2 NR^a R^a$, —$NR^b S(O)_2 R^b$ or —$S(O)_p R^c$;
  B is absent or is a group selected from alkylene, alkenylene or alkynylene; wherein one or more methylene groups is optionally replaced by hetero atoms or groups such as —O—, —S(O)$_p$—, —N($R^a$)—, or —C(O); alkylene, alkenylene and alkynylene is optionally substituted with hydroxy, amino, aminoalkyl, cyano, halogen, haloalkyl, perhaloalkyl, carboxy, carboxyalkyl, alkoxy, hydroxyalkyl, alkoxyalkyl, alkoxyalkoxy or alkyl;
  Q is selected from hydrogen, alkyl, cycloalkyl, cycloalkylalkyl, aryl, arylalkyl, heterocyclyl, heterocyclylalkyl, heteroaryl or heteroarylalkyl;
    wherein alkyl, cycloalkyl, cycloalkylalkyl, aryl, arylalkyl, heterocyclyl, heterocyclylalkyl, heteroaryl and heteroarylalkyl are unsubstituted or substituted independently with 1, 2, or 3 substituents independently selected from alkyl, alkenyl, alkynyl, halogen, haloalkyl, perhaloalkyl, azido, cyano, nitro, keto, thiocarbonyl, cyanoalkyl, cyanoalkylcarbonyl, —$(CR^dR^e)_n OR^7$, —$(CR^dR^e)_n C(O)R^7$, —$(CR^dR^e)_n SR^7$, —$(CR^dR^e)_n COOR^7$, —$(CR^dR^e)_n NR^8 R^9$, —$(CR^dR^e)_n C(O)NR^8 R^9$, —$(CR^dR^e)_n NR^8 C(O)OR^7$, —$(CR^dR^e)_n NR^8 C(O)NR^8 R^9$, —$NR^b S(O)_2 R^b$, —$S(O)_p R^c$, —$SO_3 H$, —$S(O)_2 NR^a R^a$, cycloalkyl, cycloalkenyl, cycloalkylalkyl aryl, arylalkyl, heterocyclyl, heterocyclylalkyl, heteroaryl or heteroarylalkyl;

wherein each substituent is unsubstituted or substituted with 1, 2, or 3 substituents independently selected from alkyl, carboxy, carboxyalkyl, aminocarbonyl, hydroxy, alkoxy, halogen, haloalkyl, perhaloalkyl, haloalkoxy, perhaloalkoxy, amino, substituted amino, cyano or —S(O)$_p$R$^c$;

$R^4$ is selected from the group consisting of hydrogen, alkyl, alkenyl, alkynyl, haloalkyl, hydroxyalkyl, carboxyalkyl, cycloalkyl, cycloalkylalkyl, aryl, arylalkyl, heterocyclyl, heterocyclylalkyl, heteroaryl and heteroarylalkyl;

wherein alkyl, alkenyl, alkynyl, cycloalkyl, cycloalkylalkyl, arylalkyl, aryl, heteroaryl, heteroarylalkyl, heterocyclyl, and heterocyclylalkyl are unsubstituted or substituted independently with up to four substituents independently selected from alkyl, alkenyl, alkynyl, acyl, —(CR$^d$R$^e$)$_n$OR$^7$, (CR$^d$R$^e$)$_n$COOR$^7$, —(CR$^d$R$^e$)$_n$NR$^8$R$^9$, aminocarbonyl, alkoxycarbonylamino, aminocarbonylamino, azido, cyano, halogen, haloalkyl, perhaloalkyl, keto, nitro, —S(O)$_2$NR$^b$R$^b$, —NR$^b$S(O)$_2$R$^b$ or —S(O)$_p$R$^c$, thiocarbonyl, —SO$_3$H, cycloalkyl, cycloalkenyl, aryl, heteroaryl or heterocyclyl;

$R^5$ and $R^6$ are independently selected from the group consisting of hydrogen, hydroxy, —(CR$^d$R$^e$)$_n$OR$^7$, (CR$^d$R$^e$)$_n$COOR$^7$, —(CR$^d$R$^e$)$_n$NR$^8$R$^9$, cyanoalkyl, haloalkyl, alkoxyalkoxyalkyl, alkyl, alkenyl, alkynyl, cycloalkyl, cycloalkylalkyl, aryl, arylalkyl, heterocyclyl, heterocyclylalkyl, heteroaryl and heteroarylalkyl;

$R^7$ is selected from hydrogen, alkyl, halogen, haloalkyl, —(CR$^d$R$^e$)$_n$OR$^7$, —(CR$^d$R$^e$)$_n$COOR$^7$, —(CR$^e$R$^e$)C(O)R$^7$, carbonylamino, cycloalkyl, cycloalkylalkyl, aryl, arylalkyl, heteroaryl, heteroarylalkyl, heterocyclyl or heterocyclylalkyl;

$R^8$ and $R^9$ are independently selected from the group consisting of hydrogen, alkyl, haloalkyl, —(CR$^d$R$^e$)$_n$OR$^7$, —(CR$^d$R$^e$)$_n$C(O)R$^7$, aryl, arylalkyl, heteroaryl, heteroarylalkyl, cycloalkyl, cycloalkylalkyl, heterocyclyl and heterocyclylalkyl, or $R^8$ and $R^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, alkenyl, alkynyl, nitro, cyano, —(CR$^d$R$^e$)$_n$OR$^7$, —(CR$^d$R$^e$)$_n$SR$^7$, —(CR$^d$R$^e$)$_n$NR$^8$R$^9$, oxo, alkylsulfonyl, —(CR$^d$R$^e$)$_n$COOR$^7$, —(CR$^d$R$^e$)C(O)NR$^8$R$^9$, cycloalkyl, cycloalkylalkyl, aryl, arylalkyl, heterocyclyl, heterocyclylalkyl, heteroaryl, or heteroarylalkyl;

$R^a$ is selected from hydrogen or alkyl;

$R^b$ each is independently selected from the group consisting of hydrogen, alkyl, acyl, carboxyalkyl, carbonylamino, cycloalkyl, cycloalkylalkyl, aryl, arylalkyl, heteroaryl, heteroarylalkyl, heterocyclyl and heterocyclylalkyl;

$R^c$ is selected from alkyl, cycloalkyl, aryl, heterocyclyl or heteroaryl;

$R^d$ and $R^e$ are independently selected from the group consisting of hydrogen, —OR$^7$, halogen, haloalkyl, perhaloalkyl and alkyl;

n is 0, 1, 2, 3 or 4 and p is 0, 1 or 2.

According to another embodiment, the present disclosure relates to compounds of formula (I) or its tautomers, polymorphs, stereoisomers, prodrugs, solvate or a pharmaceutically acceptable salts thereof, wherein, — represents a double bond;

X is selected from O, S or NR$^a$;

$Y_1$ is selected from N or CH;

$Y_2$ is selected from NR$^5$ or CR$^5$R$^6$;

$Y_3$ is selected from N, CH or CH$_2$;

$Y_4$ is selected from N or C;

$R^1$ and $R^2$ are independently selected from hydrogen or alkyl;

$R^3$ is -A-Z—B-Q;

wherein, A is absent or is alkylene wherein one or more methylene groups is optionally replaced by hetero atoms or groups such as —O—, —S(O)p-, —N(R$^a$)—, or —C(O); alkylene is optionally substituted with —(CR$^d$R$^e$)$_n$OR$^7$, cyano, halogen, haloalkyl, perhaloalkyl, alkyl or cycloalkyl;

Z is absent or is selected from a cycloalkyl or a heterocyclyl;

wherein cycloalkyl and heterocyclyl are unsubstituted or substituted independently with 1, 2, or 3 substituents independently selected from alkyl, acyl, —(CR$^d$R$^e$)$_n$OR$^7$, (CR$^d$R$^e$)COOR$^7$, —(CR$^d$R$^e$)$_n$NR$^8$R$^9$, aminocarbonyl, alkoxycarbonylamino, halogen, haloalkyl, perhaloalkyl, azido, cyano, halogen, keto, thiocarbonyl, —SO$_3$H, aminocarbonylamino, nitro, —S(O)$_2$NR$^a$R$^a$, —NR$^b$S(O)$_2$R$^b$ or —S(O)$_p$R$^c$;

B is absent or is alkylene wherein one or more methylene groups is optionally replaced by hetero atoms or groups such as —O—, —S(O)p-, —N(R$^a$)—, or —C(O); alkylene is optionally substituted with hydroxy, amino, aminoalkyl, cyano, halogen, haloalkyl, perhaloalkyl, carboxy, carboxyalkyl, alkoxy, hydroxyalkyl, alkoxyalkyl, alkoxyalkoxy or alkyl;

Q is selected from hydrogen, alkyl, cycloalkyl, cycloalkylalkyl, aryl, arylalkyl, heterocyclyl, heterocyclylalkyl, heteroaryl or heteroarylalkyl;

wherein alkyl, cycloalkyl, cycloalkylalkyl, aryl, arylalkyl, heterocyclyl, heterocyclylalkyl, heteroaryl and heteroarylalkyl are unsubstituted or substituted independently with 1, 2, or 3 substituents independently selected from alkyl, alkenyl, alkynyl, alkoxy, alkoxyalkyl, haloalkyl, perhaloalkyl, azido, cyano, nitro, halogen, keto, thiocarbonyl, cyanoalkyl, cyanoalkylcarbonyl, —(CR$^d$R$^e$)$_n$OR$^7$, —(CR$^d$R$^e$)$_n$C(O)R$^7$, —(CR$^d$R$^e$)$_n$SR$^7$, —(CR$^d$R$^e$)$_n$COOR$^7$, —(CR$^d$R$^e$)$_n$NR$^8$R$^9$, —(CR$^d$R$^e$)$_n$C(O)NR$^8$R$^9$, —(CR$^d$R$^e$)$_n$NR$^8$C(O)OR$^7$, —(CR$^d$R$^e$)$_n$NR$^8$C(O)NR$^8$R$^9$, —NR$^b$S(O)$_2$R$^b$, —S(O)$_p$R$^c$, —SO$_3$H, —S(O)$_2$NR$^a$R$^a$, cycloalkyl, cycloalkenyl, cycloalkylalkyl aryl, arylalkyl, heterocyclyl, heterocyclylalkyl, heteroaryl or heteroarylalkyl;

wherein each substituent is unsubstituted or substituted with 1, 2, or 3 substituents independently selected from alkyl, carboxy, carboxyalkyl, aminocarbonyl, hydroxy, alkoxy, halogen, haloalkyl, perhaloalkyl, haloalkoxy, perhaloalkoxy, amino, substituted amino, cyano or —S(O)$_p$R$^c$;

$R^4$ is selected from the group consisting of hydrogen, alkyl, haloalkyl, hydroxyalkyl, carboxyalkyl, cycloalkyl, cycloalkylalkyl, aryl, arylalkyl, heterocyclyl, heterocyclylalkyl, heteroaryl and heteroarylalkyl;

wherein alkyl, cycloalkyl, cycloalkylalkyl, arylalkyl, aryl, heteroaryl, heteroarylalkyl, heterocyclyl, and heterocyclylalkyl are unsubstituted or independently substituted with up to four substituents independently selected from alkyl, acyl, —(CR$^d$R$^e$)$_n$OR$^7$, (CR$^d$R$^e$)$_n$COOR$^7$, —(CR$^d$R$^e$)$_n$NR$^8$R$^9$, aminocarbonyl, alkoxycarbonylamino, aminocarbonylamino, azido, cyano, halogen, haloalkyl, perhaloalkyl, keto, nitro, —S(O)$_2$NR$^b$R$^b$, —NR$^b$S(O)$_2$R$^b$ or —S(O)$_p$R$^e$, thiocarbonyl, —SO$_3$H, cycloalkyl, cycloalkenyl, aryl, heteroaryl or heterocyclyl;

R$^5$ and R$^6$ are independently selected from the group consisting of hydrogen, hydroxy, —(CR$^d$R$^e$)$_n$OR$^7$, (CR$^d$R$^e$)$_n$COOR$^7$, —(CR$^d$R$^e$)$_n$NR$^8$R$^9$, cyanoalkyl, haloalkyl, alkoxyalkoxyalkyl, alkyl, alkenyl, alkynyl, cycloalkyl, cycloalkylalkyl, aryl, arylalkyl, heterocyclyl, heterocyclylalkyl, heteroaryl and heteroarylalkyl;

R$^7$ is selected from hydrogen, alkyl, halogen, haloalkyl, —(CR$^d$R$^e$)$_n$OR$^7$, —(CR$^d$R$^e$)$_n$COOR$^7$, —(CR$^e$R$^e$)$_n$C(O)R$^7$, carbonylamino, cycloalkyl, cycloalkylalkyl, aryl, arylalkyl, heteroaryl, heteroarylalkyl, heterocyclyl or heterocyclylalkyl;

R$^8$ and R$^9$ are independently selected from the group consisting of hydrogen, alkyl, haloalkyl, —(CR$^d$R$^e$)$_n$OR$^7$, —(CR$^d$R$^e$)$_n$C(O)R$^7$, aryl, arylalkyl, heteroaryl, heteroarylalkyl, cycloalkyl, cycloalkylalkyl, heterocyclyl and heterocyclylalkyl, or R$^8$ and R$^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, alkenyl, alkynyl, nitro, cyano, —(CR$^d$R$^e$)$_n$OR$^7$, —(CR$^d$R$^e$)$_n$SR$^7$, —(CR$^d$R$^e$)$_n$NR$^8$R$^9$, oxo, alkylsulfonyl, —(CR$^d$R$^e$)$_n$COOR$^7$, —(CR$^d$R$^e$)$_n$C(O)NR$^8$R$^9$, cycloalkyl, cycloalkylalkyl, aryl, arylalkyl, heterocyclyl, heterocyclylalkyl, heteroaryl, or heteroarylalkyl;

R$^a$ is selected from hydrogen or alkyl;

R$^b$ at each occurrence is independently selected from the group consisting of hydrogen, alkyl, acyl, carboxyalkyl, carbonylamino, cycloalkyl, cycloalkylalkyl, aryl, arylalkyl, heteroaryl, heteroarylalkyl, heterocyclyl or heterocyclylalkyl;

R$^c$ is selected from alkyl, cycloalkyl, aryl, heterocyclyl or heteroaryl;

R$^d$ and R$^e$ are independently selected from the group consisting of hydrogen, —OR', halogen, haloalkyl, perhaloalkyl and alkyl;

n is 0, 1, 2, 3 or 4 and p is 0, 1 or 2.

According to another embodiment, the present disclosure relates to compounds of formula (I) or its tautomers, polymorphs, stereoisomers, prodrugs, solvate or a pharmaceutically acceptable salts thereof, wherein, — represents a double bond;

X is selected from O or S;

Y$_1$ represents N;

Y$_2$ represents NR$^5$;

Y$_3$ represents N;

Y$_4$ represents C;

R$^1$ and R$^2$ are independently selected from hydrogen or alkyl;

R$^3$ is A-Z—B-Q;

wherein, A is absent or is alkylene wherein one or more methylene groups is optionally replaced by hetero atoms or groups such as —O—, —S(O)p-, —N(R$^a$)—, or —C(O);

Z is absent or is a heterocyclyl;

wherein the heterocyclyl is unsubstituted or substituted independently with 1, 2, or 3 substituents independently selected from alkyl, acyl, —(CR$^d$R$^e$)$_n$OR$^7$, (CR$^d$R$^e$)$_n$COOR$^7$, —(CR$^d$R$^e$)$_n$NR$^8$R$^9$, haloalkyl, perhaloalkyl, cyano, halogen, keto, thiocarbonyl, —SO$_3$H, nitro, —S(O)$_2$NR$^a$R$^a$, —NR$^b$S(O)$_2$R$^b$ or —S(O)$_p$R$^c$;

B is absent or is alkylene wherein one or more methylene groups is optionally replaced by hetero atoms or groups such as —O—, —S(O)p-, —N(R$^a$)—, or —C(O);

Q is selected from hydrogen, alkyl, cycloalkyl, aryl, heterocyclyl, or heteroaryl;

wherein alkyl, cycloalkyl, aryl, heterocyclyl and heteroaryl are unsubstituted or independently substituted with 1, 2, or 3 substituents independently selected from alkyl, alkoxy, alkoxyalkyl, haloalkyl, perhaloalkyl, azido, cyano, nitro, halogen, keto, thiocarbonyl, cyanoalkyl, cyanoalkylcarbonyl, —(CR$^d$R$^e$)$_n$OR$^7$, —(CR$^d$R$^e$)$_n$C(O)R$^7$, —(CR$^d$R$^e$)$_n$SR$^7$, —(CR$^d$R$^e$)$_n$COOR$^7$, —(CR$^d$R$^e$)$_n$NR$^8$R$^9$, (CR$^d$R$^e$)$_n$C(O)NR$^8$R$^9$, —(CR$^d$R$^e$)$_n$NR$^8$C(O)OR$^7$, —(CR$^d$R$^e$)$_n$NR$^8$C(O)NR$^8$R$^9$, —NR$^b$S(O)$_2$R$^b$, —S(O)$_p$R$^c$, —SO$_3$H, —S(O)$_2$NR$^a$R$^a$, cycloalkyl, cycloalkenyl, cycloalkylalkyl aryl, arylalkyl, heterocyclyl, heterocyclylalkyl, heteroaryl or heteroarylalkyl;

wherein each substituent is unsubstituted or substituted with 1, 2, or 3 substituents independently selected from alkyl, carboxy, carboxyalkyl, aminocarbonyl, hydroxy, alkoxy, halogen, haloalkyl, perhaloalkyl, haloalkoxy, perhaloalkoxy, amino, substituted amino, cyano or —S(O)$_p$R$^c$;

R$^4$ is selected from the group consisting of hydrogen, alkyl, haloalkyl, hydroxyalkyl, carboxyalkyl, cycloalkyl, cycloalkylalkyl, aryl, arylalkyl, heterocyclyl, heterocyclylalkyl, heteroaryl and heteroarylalkyl;

wherein alkyl, cycloalkyl, cycloalkylalkyl, arylalkyl, aryl, heteroaryl, heteroarylalkyl, heterocyclyl, and heterocyclylalkyl are unsubstituted or independently substituted with up to four substituents independently selected from alkyl, acyl, —(CR$^d$R$^e$)$_n$OR$^7$, (CR$^d$R$^e$)$_n$COOR$^7$, —(CR$^d$R$^e$)NR$^8$R$^9$, aminocarbonyl, alkoxycarbonylamino, aminocarbonylamino, azido, cyano, halogen, haloalkyl, perhaloalkyl, keto, nitro, —S(O)$_2$NR$^b$R$^b$, —NR$^b$S(O)$_2$R$^b$ or —S(O)$_p$R$^c$, thiocarbonyl, —SO$_3$H, cycloalkyl, cycloalkenyl, aryl, heteroaryl or heterocyclyl;

R$^5$ and R$^6$ are independently selected from the group consisting of hydrogen, hydroxy, —(CR$^d$R$^e$)$_n$OR$^7$, (CR$^d$R$^e$)$_n$COOR$^7$, —(CR$^d$R$^e$)$_n$NR$^8$R$^9$, cyanoalkyl, haloalkyl, alkoxyalkoxyalkyl, alkyl, alkenyl, alkynyl, cycloalkyl, cycloalkylalkyl, aryl, arylalkyl, heterocyclyl, heterocyclylalkyl, heteroaryl and heteroarylalkyl;

R$^7$ is selected from hydrogen, alkyl, halogen, haloalkyl, —(CR$^d$R$^e$)$_n$, OR$^7$, (CR$^d$R$^e$)$_n$COOR$^7$, —(CR$^e$R$^e$)C(O)R$^7$, carbonylamino, cycloalkyl, cycloalkylalkyl, aryl, arylalkyl, heteroaryl, heteroarylalkyl, heterocyclyl or heterocyclylalkyl;

R$^8$ and R$^9$ are independently selected from the group consisting of hydrogen, alkyl, haloalkyl, —(CR$^d$R$^e$)$_n$OR$^7$, —(CR$^d$R$^e$)$_n$C(O)R$^7$, aryl, arylalkyl, heteroaryl, heteroarylalkyl, cycloalkyl, cycloalkylalkyl, heterocyclyl and heterocyclylalkyl, or R$^8$ and R$^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, alkenyl, alkynyl, nitro, cyano, —(CR$^d$R$^e$)$_n$OR$^7$, —(CR$^d$R$^e$)$_n$SR$^7$, —(CR$^d$R$^e$)$_n$NR$^8$R$^9$, oxo, alkylsulfonyl, —(CR$^d$R$^e$)$_n$COOR$^7$, —(CR$^d$R$^e$)$_n$C(O)NR$^8$R$^9$, cycloalkyl, cycloalkylalkyl, aryl, arylalkyl, heterocyclyl, heterocyclylalkyl, heteroaryl, or heteroarylalkyl;

R$^a$ is selected from hydrogen or alkyl;

R$^b$ at each occurrence is independently selected from the group consisting of hydrogen, alkyl, acyl, carboxyalkyl, carbonylamino, cycloalkyl, cycloalkylalkyl, aryl, arylalkyl, heteroaryl, heteroarylalkyl, heterocyclyl or heterocyclylalkyl;

$R^c$ is selected from alkyl, cycloalkyl, aryl, heterocyclyl or heteroaryl;

$R^d$ and $R^e$ are independently selected from the group consisting of hydrogen, —$OR^7$, halogen, haloalkyl, perhaloalkyl and alkyl;

n is 0, 1, 2, 3 or 4 and p is 0, 1 or 2.

According to another embodiment, the present disclosure relates to compounds of formula (I) or its tautomers, polymorphs, stereoisomers, prodrugs, solvate or a pharmaceutically acceptable salts thereof, wherein, — represents a double bond;

X selected from O or S;

$Y_1$ represents N;

$Y_2$ represents $NR^5$;

$Y_3$ represents N;

$Y_4$ represents C;

$R^1$ and $R^2$ are independently selected from hydrogen or alkyl;

$R^3$ is -A-Z—B-Q;

wherein, A is absent or is alkylene wherein one or more methylene groups is optionally replaced by hetero atoms or groups such as —O— or —N($R^a$)—;

Z is absent or is a heterocyclyl;

wherein the heterocyclyl is unsubstituted or substituted independently with 1, 2, or 3 substituents independently selected from alkyl, —$(CR^dR^e)_nOR^7$, $(CR^dR^e)_nCOOR^7$, haloalkyl, perhaloalkyl, cyano, halogen, keto or thiocarbonyl;

B is absent or is alkylene wherein one or more methylene groups is optionally replaced by hetero atoms or groups such as —O—, —N($R^a$)—, or —C(O);

Q is selected from hydrogen, alkyl, cycloalkyl, aryl, heterocyclyl, or heteroaryl;

wherein alkyl, cycloalkyl, aryl, heterocyclyl and heteroaryl are unsubstituted or independently substituted with 1, 2, or 3 substituents independently selected from alkyl, alkoxy, alkoxyalkyl, haloalkyl, perhaloalkyl, cyano, halogen, keto, thiocarbonyl, cyanoalkyl, —$(CR^dR^e)_nOR^7$, —$(CR^dR^e)_nC(O)R^7$, —$(CR^dR^e)COOR^7$, —$(CR^dR^e)_nNR^8R^9$, —$(CR^dR^e)_nC(O)NR^8R^9$, —$(CR^dR^e)_nNR^8C(O)OR^7$, —$S(O)_pR^c$, —$S(O)_2NR^aR^a$, cycloalkyl, cycloalkenyl, aryl, heterocyclyl or heteroaryl;

wherein each substituent is unsubstituted or substituted with 1, 2, or 3 substituents independently selected from alkyl, carboxy, carboxyalkyl, aminocarbonyl, hydroxy, alkoxy, halogen, haloalkyl, perhaloalkyl, haloalkoxy, perhaloalkoxy, amino, substituted amino, cyano or —$S(O)_pR^c$;

$R^4$ is selected from the group consisting of hydrogen, alkyl, haloalkyl, hydroxyalkyl, cycloalkyl, aryl, heterocyclyl and heteroaryl;

wherein alkyl, cycloalkyl, aryl, heteroaryl and heterocyclyl are unsubstituted or independently substituted with up to four substituents independently selected from alkyl, —$(CR^dR^e)_nOR^7$, $(CR^dR^e)_nCOOR^7$, —$(CR^dR^e)NR^8R^9$, cyano, halogen, haloalkyl, perhaloalkyl, nitro, —$S(O)_2NR^bR^b$, —$NR^bS(O)_2R^b$, —$S(O)_pR^c$, thiocarbonyl, —$SO_3H$, cycloalkyl, aryl, heteroaryl or heterocyclyl;

$R^5$ is selected from the group consisting of hydrogen, hydroxy, haloalkyl, —$(CR^dR^e)_nOR^7$, —$(CR^dR^e)_nCOOR^7$, alkoxyalkoxyalkyl, alkyl, alkenyl, alkynyl, cycloalkyl, cycloalkylalkyl, aryl, arylalkyl, heterocyclyl, heterocyclylalkyl, heteroaryl and heteroarylalkyl;

$R^7$ is selected from hydrogen, alkyl, halogen, haloalkyl, —$(CR^dR^e)_nOR^7$, —$(CR^dR^e)_nCOOR^7$, —$(CR^eR^e)_nC(O)R^7$, cycloalkyl, aryl, heteroaryl or heterocyclyl;

$R^8$ and $R^9$ are independently selected from the group consisting of hydrogen, alkyl, haloalkyl, —$(CR^dR^e)_nOR^7$, —$(CR^dR^e)_nC(O)R^7$, aryl, arylalkyl, heteroaryl, heteroarylalkyl, cycloalkyl, cycloalkylalkyl, heterocyclyl and heterocyclylalkyl, or $R^8$ and $R^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, nitro, cyano, —$(CR^dR^e)_nOR^7$, —$(CR^dR^e)_nNR^8R^9$, oxo, alkylsulfonyl, —$(CR^dR^e)_nCOOR^7$ or —$(CR^dR^e)_nC(O)NR^8R^9$;

$R^a$ is selected from hydrogen or alkyl;

$R^b$ at each occurrence is independently selected from the group consisting of hydrogen, alkyl, acyl, carboxyalkyl, carbonylamino, cycloalkyl, cycloalkylalkyl, aryl, arylalkyl, heteroaryl, heteroarylalkyl, heterocyclyl and heterocyclylalkyl;

$R^c$ is selected from alkyl, cycloalkyl, aryl, heterocyclyl or heteroaryl;

$R^d$ and $R^e$ are independently selected from the group consisting of hydrogen, —$OR^7$, halogen, haloalkyl, perhaloalkyl or alkyl;

n is 0, 1, 2, 3 or 4 and p is 0, 1 or 2.

According to another embodiment, the present disclosure relates to compounds of formula (I) or its tautomers, polymorphs, stereoisomers, prodrugs, solvate or a pharmaceutically acceptable salts thereof, wherein, — represents a double bond;

X is selected from O or S;

$Y_1$ represents N;

$Y_2$ represents $NR^5$;

$Y_3$ represents N;

$Y_4$ represents C;

$R^1$ and $R^2$ are independently selected from hydrogen or alkyl;

$R^3$ is -A-Z—B-Q;

wherein, A is absent or is alkylene wherein one or more methylene groups is optionally replaced by hetero atoms or groups such as —O— or —N($R^a$)—;

Z is absent or is a heterocyclyl selected from dihydrofuranyl, tetrahydrofuranyl, morpholinyl, pyrrolidinyl, dihydropyrrole, dihydropyranyl, tetrahydropyranyl, pyrazolidinyl, imidazolidinyl, dihydropyridinyl, tetrahydropyridinyl, piperidinyl, dihydropyrazinyl, tetrahydropyrazinyl, piperazinyl or dihydropyridinyl;

wherein the heterocyclyl is unsubstituted or substituted independently with 1, 2, or 3 substituents independently selected from alkyl, —$(CR^dR^e)_nOR^7$, $(CR^dR^e)_nCOOR^7$, haloalkyl, perhaloalkyl, cyano or halogen;

B is absent or is alkylene wherein one or more methylene groups is optionally replaced by hetero atoms or groups such as —O—, —N($R^a$)—, or —C(O);

Q is selected from hydrogen, alkyl, cyclopropyl, cyclopentyl, cyclohexyl phenyl, tetrahydrofuranyl, pyrrolidinyl, tetrahydropyridinyl, tetrahydropyranyl, piperazinyl, benzodiaxolyl, tetrahydroquinolinyl, morpholinyl, tetrahydronaphthyridinyl, tetrahydrothienopyridinyl, furanyl, pyridinyl, pyrimidinyl, oxazolyl, thiazolyl, oxadiazolyl, thiadiazolyl, indolyl, quinolinyl, isoquinolinyl or benzooxazolyl;

wherein Q is unsubstituted or substituted with 1, 2, or 3 substituents independently selected from alkyl, alkoxy, alkoxyalkyl, haloalkyl, perhaloalkyl, cyano, halogen, keto, thiocarbonyl, cyanoalkyl, —(CR$^d$R$^e$)$_n$OR$^7$, —(CR$^d$R$^e$)$_n$C(O)R$^7$, —(CR$^d$R$^e$)$_n$COOR$^7$, —(CR$^d$R$^e$)$_n$NR$^8$R$^9$, —(CR$^d$R$^e$)$_n$C(O)NR$^8$R$^9$, —(CR$^d$R$^e$)$_n$NR$^8$C(O)OR$^7$, —S(O)$_p$R$^c$, —SO$_3$H, —S(O)$_2$NR$^a$R$^a$, cycloalkyl, cycloalkenyl, aryl, heterocyclyl or heteroaryl;
  wherein each substituent is unsubstituted or substituted with 1, 2, or 3 substituents independently selected from alkyl, carboxy, carboxyalkyl, aminocarbonyl, hydroxy, alkoxy, halogen, haloalkyl, perhaloalkyl, haloalkoxy, perhaloalkoxy, amino, substituted amino, cyano or —S(O)$_p$R$^e$;
R$^4$ is selected from the group consisting of hydrogen, alkyl, phenyl, naphthyl, furanyl, thiazolyl, oxazolyl, thiadiazolyl, oxadiazolyl, pyrazinyl, pyridinyl and pyrimidinyl;
  wherein R$^4$ is unsubstituted or substituted with up to four substituents independently selected from alkyl, —(CR$^d$R$^e$)$_n$OR$^7$, (CR$^d$R$^e$)$_n$COOR$^7$, —(CR$^d$R$^e$)$_n$NR$^8$R$^9$, cyano, halogen, haloalkyl, perhaloalkyl or cycloalkyl;
R$^5$ is selected from the group consisting of hydrogen, hydroxy, haloalkyl, —(CR$^d$R$^e$)$_n$OR$^7$, —(CR$^d$R$^e$)$_n$COOR$^7$, alkoxyalkoxyalkyl, alkyl, alkenyl, alkynyl, cycloalkyl, cycloalkylalkyl, aryl, arylalkyl, heterocyclyl, heterocyclylalkyl, heteroaryl and heteroarylalkyl;
R$^7$ is selected from hydrogen, alkyl, halogen, haloalkyl, —(CR$^d$R$^e$)$_n$OR$^7$, —(CR$^d$R$^e$)$_n$COOR$^7$, —(CR$^e$R$^e$)$_n$C(O)R$^7$, cycloalkyl, aryl, heteroaryl or heterocyclyl;
R$^8$ and R$^9$ are independently selected from the group consisting of hydrogen, alkyl, haloalkyl, —(CR$^d$R$^e$)$_n$OR$^7$, —(CR$^d$R$^e$)$_n$C(O)R$^7$, aryl, arylalkyl, heteroaryl, heteroarylalkyl, cycloalkyl, cycloalkylalkyl, heterocyclyl and heterocyclylalkyl, or
R$^8$ and R$^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, nitro, cyano, —(CR$^d$R$^e$)$_n$OR$^7$, —(CR$^d$R$^e$)$_n$NR$^8$R$^9$, oxo, alkylsulfonyl, —(CR$^d$R$^e$)$_n$COOR$^7$ or —(CR$^d$R$^e$)$_n$C(O)NR$^8$R$^9$;
R$^a$ is selected from hydrogen or alkyl;
R$^b$ each is independently selected from the group consisting of hydrogen, alkyl, acyl, carboxyalkyl, carbonylamino, cycloalkyl, cycloalkylalkyl, aryl, arylalkyl, heteroaryl, heteroarylalkyl, heterocyclyl and heterocyclylalkyl;
R$^c$ is selected from alkyl, cycloalkyl, aryl, heterocyclyl or heteroaryl;
R$^d$ and R$^e$ are independently selected from the group consisting of hydrogen, —OR$^7$, halogen, haloalkyl, perhaloalkyl and alkyl;
n is 0, 1, 2, 3 or 4 and
p is 0, 1 or 2.

Particular embodiments of the present disclosure are compounds of formula I or its tautomers, polymorphs, stereoisomers, prodrugs, solvate or a pharmaceutically acceptable salts thereof, selected from the group consisting of, 5-Amino-8-(2-furyl)-3-[2-[4-[4-(2-methoxyethoxy)phenyl]piperazin-1-yl]ethyl]-1-methyl-[1,2,4]triazolo[5,1-f]purin-2-one, 5-Amino-8-(2-furyl)-3-(2-hydroxyethyl)-1-methyl-[1,2,4]triazolo[5,1-f]purin-2-one, 5-Amino-3-[2-[4-(2,4-difluorophenyl)piperazin-1-yl]ethyl]-8-(2-furyl)-1-methyl-[1,2,4]triazolo[5,1-f]purin-2-one, 5-Amino-8-(2-furyl)-3-[2-[4-(4-methoxyphenyl)piperazin-1-yl]ethyl]-1-methyl-[1,2,4]triazolo[5,1-f]purin-2-one, 5-Amino-8-(2-furyl)-1-methyl-3-(2-morpholinoethyl)-[1,2,4]triazolo[5,1-f]purin-2-one, 5-Amino-3-[2-[4-(2,4-difluorophenyl)-1-piperidyl]ethyl]-8-(2-furyl)-1-methyl-[1,2,4]triazolo[5,1-f]purin-2-one, 5-Amino-8-(2-furyl)-1-methyl-3-[2-[4-(5-methyl-2-pyridyl)piperazin-1-yl]ethyl]-[1,2,4]triazolo[5,1-f]purin-2-one, 5-Amino-8-(2-furyl)-1-methyl-3-[2-[4-(p-tolyl)piperazin-1-yl]ethyl]-[1,2,4]triazolo[5,1-f]purin-2-one, 5-Amino-8-(2-furyl)-1-methyl-3-[2-[4-(3-methyl-2-oxo-butyl)piperazin-1-yl]ethyl]-[1,2,4]triazolo[5,1-f]purin-2-one, 5-Amino-3-[2-[4-(2-fluoro-4-methoxy-phenyl)piperazin-1-yl]ethyl]-8-(2-furyl)-1-methyl-[1,2,4]triazolo[5,1-f]purin-2-one, 5-Amino-8-(2-furyl)-3-[2-[4-(2-methoxy-1,1-dimethyl-ethoxy)phenyl]piperazin-1-yl]ethyl]-1-methyl-[1,2,4]triazolo[5,1-f]purin-2-one, 5-Amino-8-(2-furyl)-3-[2-[4-(6-methoxy-3-pyridyl)piperazin-1-yl]ethyl]-1-methyl-[1,2,4]triazolo[5,1-f]purin-2-one, 5-Amino-3-[2-[4-[3-fluoro-4-(2-methoxyethoxy)phenyl]piperazin-1-yl]ethyl]-8-(2-furyl)-1-methyl-[1,2,4]triazolo[5,1-f]purin-2-one, 5-Amino-8-(2-furyl)-3-[2-[4-[4-(1-hydroxy-1-methyl-ethyl)phenyl]piperazin-1-yl]ethyl]-1-methyl-[1,2,4]triazolo[5,1-f]purin-2-one, 5-Amino-3-[2-[4-(4-fluorophenyl)-4-hydroxy-1-piperidyl]ethyl]-8-(2-furyl)-1-methyl-[1,2,4]triazolo[5,1-f]purin-2-one, 5-Amino-8-(2-furyl)-3-[2-[4-[4-(2-methoxy-2-methyl-propoxy)phenyl]piperazin-1-yl]ethyl]-1-methyl-[1,2,4]triazolo[5,1-f]purin-2-one, 5-Amino-3-[2-[4-[4-(cyclopropoxy)phenyl]piperazin-1-yl]ethyl]-8-(2-furyl)-1-methyl-[1,2,4]triazolo[5,1-f]purin-2-one, 5-Amino-3-[2-[4-(4-fluorophenyl)-3,6-dihydro-2H-pyridin-1-yl]ethyl]-8-(2-furyl)-1-methyl-[1,2,4]triazolo[5,1-f]purin-2-one, 5-Amino-8-(2-furyl)-3-[2-[4-hydroxy-4-(4-methoxyphenyl)-1-piperidyl]ethyl]-1-methyl-[1,2,4]triazolo[5,1-f]purin-2-one, 5-Amino-3-[2-[4-[3,5-difluoro-4-(2-methoxyethoxy)phenyl]piperazin-1-yl]ethyl]-8-(2-furyl)-1-methyl-[1,2,4]triazolo[5,1-f]purin-2-one, 5-Amino-3-[2-[4-[2,5-difluoro-4-(2-methoxyethoxy)phenyl]piperazin-1-yl]ethyl]-8-(2-furyl)-1-methyl-[1,2,4]triazolo[5,1-f]purin-2-one, 5-Amino-3-[2-[4-(2,2-difluoro-1,3-benzodioxol-5-yl)piperazin-1-yl]ethyl]-8-(2-furyl)-1-methyl-[1,2,4]triazolo[5,1-f]purin-2-one, 5-Amino-8-(2-furyl)-3-[2-[4-[4-(2-methoxyethoxy)phenyl]-3,3-dimethyl-piperazin-1-yl]ethyl]-1-methyl-[1,2,4]triazolo[5,1-f]purin-2-one, 5-Amino-3-[2-(4-butylpiperazin-1-yl)ethyl]-8-(2-furyl)-1-methyl-[1,2,4]triazolo[5,1-f]purin-2-one, 5-Amino-8-(2-furyl)-3-[2-(4-hydroxy-4-methyl-1-piperidyl)ethyl]-1-methyl-[1,2,4]triazolo[5,1-f]purin-2-one, 5-Amino-3-[2-[4-[4-[2-(cyclopropoxy)ethoxy]phenyl]piperazin-1-yl]ethyl]-8-(2-furyl)-1-methyl-[1,2,4]triazolo[5,1-f]purin-2-one, 5-Amino-8-(2-furyl)-3-[2-[4-[(4-methoxyphenyl)methyl]piperazin-1-yl]ethyl]-1-methyl-[1,2,4]triazolo[5,1-f]purin-2-one, 5-Amino-8-(2-furyl)-3-[2-[4-[[4-(2-methoxyethoxy)phenyl]methyl]piperazin-1-yl]ethyl]-1-methyl-[1,2,4]triazolo[5,1-f]purin-2-one, 5-Amino-8-(2-furyl)-3-[(4-methoxyphenyl)methyl]-1-methyl-[1,2,4]triazolo[5,1-f]purin-2-one,
5-Amino-8-(2-furyl)-3-[2-[4-(4-methoxyphenyl)piperazin-1-yl]ethyl]-1-methyl-[1,2,4]triazolo[5,1-f]purin-2-one,
5-Amino-8-(2-furyl)-3-[2-[4-[3-(2-methoxyethoxy)phenyl]piperazin-1-yl]ethyl]-1-methyl-[1,2,4]triazolo[5,1-f]purin-2-one,
5-Amino-3-[2-[4-[2-fluoro-4-(2-methoxyethoxy)phenyl]piperazin-1-yl]ethyl]-8-(2-furyl)-1-methyl-[1,2,4]triazolo[5,1-f]purin-2-one,
4-[4-[2-[5-Amino-8-(2-furyl)-1-methyl-2-oxo-[1,2,4]triazolo[5,1-f]purin-3yl]ethyl]piperazin-1-yl]benzonitrile,
4-[4-[2-[5-Amino-8-(2-furyl)-1-methyl-2-oxo-[1,2,4]triazolo[5,1-f]purin-3-yl]ethyl]piperazin-1-yl]-2-fluoro-benzonitrile,
5-Amino-8-(2-furyl)-1-methyl-3-[2-[4-[4-(trifluoromethyl)phenyl]piperazin-1-yl]ethyl]-[1,2,4]triazolo[5,1-f]purin-2-one,
5-Amino-8-(2-furyl)-1-methyl-3-[2-[4-[4-(trifluoromethyl)thiazol-2-yl]piperazin-1-yl]ethyl]-[1,2,4]triazolo[5,1-f]purin-2-one,
5-Amino-3-[2-[4-(cyclopropylmethyl)piperazin-1-yl]ethyl]-8-(2-furyl)-1-methyl-[1,2,4]triazolo[5,1-f]purin-2-one,
5-Amino-3-[2-(4-ethylpiperazin-1-yl)ethyl]-8-(2-furyl)-1-methyl-[1,2,4]triazolo[5,1-f]purin-2-one,
4-[2-[5-Amino-8-(2-furyl)-1-methyl-2-oxo-[1,2,4]triazolo[5,1-f]purin-3-yl]ethyl]-N,N-dimethyl-piperazine-1-sulfonamide,
5-Amino-8-(2-furyl)-1-methyl-3-[2-[4-(4-tetrahydrofuran-3-yloxyphenyl)piperazin-1-yl]ethyl]-[1,2,4]triazolo[5,1-f]purin-2-one,
5-Amino-8-(2-furyl)-1-methyl-3-[2-[4-(4-tetrahydropyran-4-yloxyphenyl)piperazin-1-yl]ethyl]-[1,2,4]triazolo[5,1-f]purin-2-one,
5-Amino-8-(2-furyl)-1-methyl-3-[2-[4-[4-(tetrahydrofuran-2-ylmethoxy)phenyl]piperazin-1-yl]ethyl]-[1,2,4]triazolo[5,1-f]purin-2-one,
5-Amino-8-(2-furyl)-1-methyl-3-[2-(3-methyl-7,8-dihydro-5H-1,6-naphthyridin-6-yl)ethyl]-[1,2,4]triazolo[5,1-f]purin-2-one,
5-Amino-3-[2-(6,7-dihydro-4H-thieno[3,2-c]pyridin-5-yl)ethyl]-8-(2-furyl)-1-methyl-[1,2,4]triazolo[5,1-f]purin-2-one,
5-Amino-8-(2-furyl)-3-[2-[4-[4-(2-methoxyethoxy)phenyl]piperazin-1-yl]propyl]-1-methyl-[1,2,4]triazolo[5,1-f]purin-2-one,
5-Amino-3-[2-[3-(4-fluorophenyl)-2,5-dihydropyrrol-1-yl]ethyl]-8-(2-furyl)-1-methyl-[1,2,4]triazolo[5,1-f]purin-2-one,
5-Amino-3-[2-[4-[4-(2-methoxyethoxy)phenyl]piperazin-1-yl]ethyl]-1-methyl-8-(5-methyl-2-furyl)-[1,2,4]triazolo[5,1-f]purin-2-one,
5-Amino-8-(5-cyclopropyl-2-furyl)-3-[2-[4-[4-(2-methoxyethoxy)phenyl]piperazin-1-yl]ethyl]-1-methyl-[1,2,4]triazolo[5,1-f]purin-2-one,
5-Amino-3-[2-(2,4-difluoroanilino)ethyl]-8-(2-furyl)-1-methyl-[1,2,4]triazolo[5,1-f]purin-2-one,
5-Amino-3-[3-[4-(4-fluorophenyl)piperazin-1-yl]propyl]-8-(2-furyl)-1-methyl-[1,2,4]triazolo[5,1-f]purin-2-one,
5-Amino-8-(2-furyl)-3-[3-[4-[4-(2-methoxyethoxy)phenyl]piperazin-1-yl]propyl]-1-methyl-[1,2,4]triazolo[5,1-f]purin-2-one,
5-Amino-8-(2-furyl)-3-[2-[4-(4-methoxyphenyl)-3,6-dihydro-2H-pyridin-1-yl]ethyl]-1-methyl-[1,2,4]triazolo[5,1-f]purin-2-one,
5-Amino-8-(2-furyl)-3-[2-[4-[4-(2-methoxy-1,1-dimethylethyl)phenyl]piperazin-1-yl]ethyl]-1-methyl-[1,2,4]triazolo[5,1-f]purin-2-one,
5-Amino-8-(2-furyl)-1-methyl-3-(2-piperazin-1-ylethyl)-[1,2,4]triazolo[5,1-f]purin-2-one,
5-Amino-8-(2-furyl)-3-[2-[4-(1H-indole-2-carbonyl)piperazin-1-yl]ethyl]-1-methyl-[1,2,4]triazolo[5,1-f]purin-2-one,
5-Amino-8-(2-furyl)-3-[2-(4-isopropoxyphenyl)ethyl]-1-methyl-[1,2,4]triazolo[5,1-f]purin-2-one,
5-Amino-8-(2-furyl)-1-methyl-3-[2-[4-[(2S)-pyrrolidine-2-carbonyl]piperazin-1-yl]ethyl]-[1,2,4]triazolo[5,1-f]purin-2-one,
5-Amino-8-(2-furyl)-3-[2-(4-methoxyphenyl)ethyl]-1-methyl-[1,2,4]triazolo[5,1-f]purin-2-one,
5-amino-3-[2-[4-[4-(difluoromethoxy)phenyl]piperazin-1-yl]ethyl]-8-(2-furyl)-1-methyl-[1,2,4]triazolo[5,1-f]purin-2-one,
5-Amino-8-(2-furyl)-1-methyl-3-[2-[4-[3-(5-methyl-1,3,4-oxadiazol-2-yl)phenyl]piperazin-1-yl]ethyl]-[1,2,4]triazolo[5,1-f]purin-2-one,
5-Amino-3-[2-[4-[2-fluoro-4-(5-methyl-1,2,4-oxadiazol-3-yl)phenyl]piperazin-1-yl]ethyl]-8-(2-furyl)-1-methyl-[1,2,4]triazolo[5,1-f]purin-2-one,
5-Amino-3-[2-[4-(6-fluoro-2-methyl-1,3-benzoxazol-5-yl)piperazin-1-yl]ethyl]-8-(2-furyl)-1-methyl-[1,2,4]triazolo[5,1-f]purin-2-one,
5-Amino-3-[2-[4-(cyclopropanecarbonyl)piperazin-1-yl]ethyl]-8-(2-furyl)-1-methyl-[1,2,4]triazolo[5,1-f]purin-2-one,
5-Amino-3-[2-[4-(2-cyclopropylacetyl)piperazin-1-yl]ethyl]-8-(2-furyl)-1-methyl-[1,2,4]triazolo[5,1-f]purin-2-one,
5-Amino-8-(2-furyl)-3-[2-[4-[4-(2-hydroxyethoxy)phenyl]piperazin-1-yl]ethyl]-1-methyl-[1,2,4]triazolo[5,1-f]purin-2-one,
5-Amino-8-(2-furyl)-3-[2-[4-(4-hydroxyphenyl)piperazin-1-yl]ethyl]-1-methyl-[1,2,4]triazolo[5,1-f]purin-2-one,
5-Amino-1-(cyclopropylmethyl)-3-[2-[4-(4-ethoxyphenyl)piperazin-1-yl]ethyl]-8-(2-furyl)-[1,2,4]triazolo[5,1-f]purin-2-one,
5-Amino-1-(cyclopropylmethyl)-3-[2-[4-(4-fluorophenyl)piperazin-1-yl]ethyl]-8-(2-furyl)-[1,2,4]triazolo[5,1-f]purin-2-one,
5-Amino-1-(cyclopropylmethyl)-3-[2-[4-(2,4-difluorophenyl)piperazin-1-yl]ethyl]-8-(2-furyl)-[1,2,4]triazolo[5,1-f]purin-2-one,
5-Amino-1-(cyclopropylmethyl)-8-(2-furyl)-3-[2-[4-[4-(2-methoxyethoxy)phenyl]piperazin-1-yl]ethyl]-[1,2,4]triazolo[5,1-f]purin-2-one,
5-Amino-1-(cyclopropylmethyl)-3-[2-(4-fluorophenoxy)ethyl]-8-(2-furyl)-[1,2,4]triazolo[5,1-f]purin-2-one,
5-Amino-8-(2-furyl)-1-methyl-3-[2-[2-oxo-5-(trifluoromethyl)-1-pyridyl]ethyl]-[1,2,4]triazolo[5,1-f]purin-2-one,
5-Amino-3-[2-[4-(2,4-difluorophenyl)pyrazol-1-yl]ethyl]-1-ethyl-8-(2-furyl)-[1,2,4]triazolo[5,1-f]purin-2-one,
1-[2-[5-Amino-1-(cyclopropylmethyl)-8-(2-furyl)-2-oxo-[1,2,4]triazolo[5,1-f]purin-3-yl]ethyl]pyrazole-4-carboxylic acid,
1-[2-[5-Amino-8-(2-furyl)-1-methyl-2-oxo-[1,2,4]triazolo[5,1-f]purin-3-yl]ethyl]pyrazole-4-carboxylic acid,
1-[2-[5-amino-1-(cyclopropylmethyl)-8-(2-furyl)-2-oxo-[1,2,4]triazolo[5,1-f]purin-3-yl]ethyl]-N-cyclopropyl-pyrazole-4-carboxamide,
1-[2-[5-amino-1-(cyclopropylmethyl)-8-(2-furyl)-2-oxo-[1,2,4]triazolo[5,1-f]purin-3-yl]ethyl]-N,N-diethyl-pyrazole-4-carboxamide, 1-[2-[5-Amino-1-(cyclopropylmethyl)-8-(2-furyl)-2-oxo-[1,2,4]triazolo[5,1-f]purin-3-yl]ethyl]-N-cyclopropyl-5-methyl-pyrazole-3-carboxamide, 2-[2-[5-Amino-1-(cyclopropylmethyl)-8-(2-furyl)-2-oxo-[1,2,4]triazolo[5,1-f]purin-3-yl]ethyl]-N-cyclopropyl-5-methyl-pyrazole-3-carboxamide, 1-[2-[5-Amino-8-(2-furyl)-1-methyl-2-oxo-[1,2,4]triazolo[5,1-f]purin-3-yl]ethyl]-N-methyl-pyrazole-3-carboxamide, 1-[2-[5-Amino-8-(2-furyl)-1-methyl-2-oxo-[1,2,4]triazolo[5,1-f]purin-3-yl]ethyl]-N,N-diethyl-pyrazole-4-carboxamide, 1-[2-[5-amino-8-(2-furyl)-1-methyl-2-oxo-[1,2,4]triazolo[5,1-f]purin-3-yl]ethyl]pyrazole-4-carboxamide, 5-Amino-8-(2-furyl)-3-[2-[4-[(3R)-3-hydroxypyrrolidine-1-carbonyl]pyrazol-1-yl]ethyl]-1-methyl-[1,2,4]triazolo[5,1-f]purin-2-one, 1-[2-[5-Amino-8-(2-furyl)-1-methyl-2-oxo-[1,2,4]triazolo[5,1-f]purin-3-yl]ethyl]-N-methyl-pyrazole-4-carboxamide, 1-[2-[5-Amino-8-(2-furyl)-1-methyl-2-oxo-[1,2,4]triazolo[5,1-f]purin-3-yl]ethyl]-N-cyclopropyl-pyrazole-3-carboxamide, 1-[2-[5-Amino-8-(2-furyl)-1-methyl-2-oxo-[1,2,4]triazolo[5,1-f]purin-3-yl]ethyl]-N-cyclopropyl-pyrazole-4-carboxamide, 5-Amino-8-(2-furyl)-3-[2-[4-(3-hydroxyazetidine-1-carbonyl)pyrazol-1-yl]ethyl]-1-methyl-[1,2,4]triazolo[5,1-f]purin-2-one, 5-Amino-1-ethyl-8-(2-furyl)-3-[2-[4-[4-(2-methoxyethoxy)phenyl]piperazin-1-yl]ethyl]-[1,2,4]triazolo[5,1-f]purin-2-one, 5-Amino-3-[2-[4-(2,4-difluorophenyl)piperazin-1-yl]ethyl]-1-ethyl-8-(2-furyl)-[1,2,4]triazolo[5,1-f]purin-2-one, 5-Amino-1-ethyl-3-{2-[4-(4-fluoro-phenyl)-piperidin-1-yl]-ethyl}-8-furan-2-yl-1,3-dihydro-[1,2,4]triazolo[5,1-f]purin-2-one, 5-Amino-1-ethyl-8-(2-furyl)-3-[2-(3-methyl-7,8-dihydro-5H-1,6-naphthyridin-6-yl)ethyl]-[1,2,4]triazolo[5,1-f]purin-2-one, 5-Amino-8-(2-furyl)-3-[2-[4-[4-(2-methoxyethoxy)phenyl]piperazin-1-yl]ethyl]-1-(2,2,2-trifluoroethyl)-[1,2,4]triazolo[5,1-f]purin-2-one, 5-Amino-3-{2-[4-(2,4-difluoro-phenyl)-piperazin-1-yl]-ethyl}-8-furan-2-yl-1-(2,2,2-trifluoro-ethyl)-1,3-dihydro-[1,2,4]triazolo[5,1-f]purin-2-one, 5-Amino-8-(2-furyl)-3-[2-[4-[4-(2-methoxyethoxy)phenyl]piperazin-1-yl]ethyl]-1-(2-methoxyethyl)-[1,2,4]triazolo[5,1-f]purin-2-one, 5-amino-3-[2-[4-(4-fluorophenyl)piperazin-1-yl]ethyl]-8-(2-furyl)-1-(2-methoxyethyl)-[1,2,4]triazolo[5,1-f]purin-2-one, 5-Amino-3-[2-[4-(4-fluorophenyl)piperazin-1-yl]ethyl]-8-(2-furyl)-1-(2-hydroxyethyl)-[1,2,4]triazolo[5,1-f]purin-2-one one, 5-Amino-1-cyclopropyl-8-(2-furyl)-3-[2-[4-[4-(2-methoxyethoxy)phenyl]piperazin-1-yl]ethyl]-[1,2,4]triazolo[5,1-f]purin-2-one, 5-Amino-8-(2-furyl)-3-[2-[4-[4-(2-methoxyethoxy)phenyl]piperazin-1-yl]ethyl]-1-(2,2,2-trifluoroethyl)-[1,2,4]triazolo[5,1-f]purin-2-one, 5-Amino-3-[2-[4-[4-(2-methoxyethoxy)phenyl]piperazin-1-yl]ethyl]-1-methyl-8-thiazol-2-yl-[1,2,4]triazolo[5,1-f]purin-2-one, 5-Amino-3-[2-[4-[3-fluoro-4-(2-methoxyethoxy)phenyl]piperazin-1-yl]ethyl]-1-methyl-8-thiazol-2-yl-[1,2,4]triazolo[5,1-f]purin-2-one, 5-Amino-3-[2-[4-(2-cyclopropylacetyl)piperazin-1-yl]ethyl]-1-methyl-8-thiazol-2-yl-[1,2,4]triazolo[5,1-f]purin-2-one, 5-Amino-3-[2-[4-(4-methoxyphenyl)piperazin-1-yl]ethyl]-1-methyl-8-thiazol-2-yl-[1,2,4]triazolo[5,1-f]purin-2-one, 5-Amino-1-methyl-3-[2-[4-(p-tolyl)piperazin-1-yl]ethyl]-8-thiazol-2-yl-[1,2,4]triazolo[5,1-f]purin-2-one, 5-Amino-1-methyl-3-[2-(3-methyl-7,8-dihydro-5H-1,6-naphthyridin-6-yl)ethyl]-8-thiazol-2-yl-[1,2,4]triazolo[5,1-f]purin-2-one, 4-[4-[2-(5-Amino-1-methyl-2-oxo-8-thiazol-2-yl-[1,2,4]triazolo[5,1-f]purin-3-yl)ethyl]piperazin-1-yl]benzonitrile, 5-Amino-1-methyl-3-[2-[4-[3-(5-methyl-1,3,4-oxadiazol-2-yl)phenyl]piperazin-1-yl]ethyl]-8-thiazol-2-yl-[1,2,4]triazolo[5,1-f]purin-2-one, 5-amino-3-[2-[4-[4-(1-hydroxy-1-methyl-ethyl)phenyl]piperazin-1-yl]ethyl]-1-methyl-8-thiazol-2-yl-[1,2,4]triazolo[5,1-f]purin-2-one, 5-Amino-3-[2-[4-[4-(2-methoxyethoxy)phenyl]piperazin-1-yl]ethyl]-1-methyl-8-(2-pyridyl)-[1,2,4]triazolo[5,1-f]purin-2-one, 5-Amino-3-[2-[4-(2,4-difluorophenyl)piperazin-1-yl]ethyl]-1-methyl-8-(2-pyridyl)-[1,2,4]triazolo[5,1-f]purin-2-one, 4-[4-[2-[5-Amino-1-methyl-2-oxo-8-(2-pyridyl)-[1,2,4]triazolo[5,1-f]purin-3-yl]ethyl]piperazin-1-yl]benzonitrile, 5-Amino-3-[2-[4-[4-(1-hydroxy-1-methyl-ethyl)phenyl]piperazin-1-yl]ethyl]-1-methyl-8-(2-pyridyl)-[1,2,4]triazolo[5,1-f]purin-2-one, 5-Amino-3-[2-[4-[4-(2-methoxyethoxy)phenyl]piperazin-1-yl]ethyl]-1-methyl-8-pyrazin-2-yl-[1,2,4]triazolo[5,1-f]purin-2-one, 5-Amino-3-[2-[4-(2,4-difluorophenyl)piperazin-1-yl]ethyl]-1-methyl-8-pyrazin-2-yl-[1,2,4]triazolo[5,1-f]purin-2-one, 5-Amino-3-[2-[4-[2-fluoro-4-(2-methoxyethoxy)phenyl]piperazin-1-yl]ethyl]-1-methyl-8-pyrazin-2-yl-[1,2,4]triazolo[5,1-f]purin-2-one, 5-Amino-8-(2-furyl)-3-[[1-(4-methoxyphenyl)pyrrolidin-3-yl]methyl]-1-methyl-[1,2,4]triazolo[5,1-f]purin-2-one, 5-Amino-8-(2-furyl)-3-[[1-[4-(2-methoxyethoxy)phenyl]pyrrolidin-3-yl]methyl]-1-methyl-[1,2,4]triazolo[5,1-f]purin-2-onehyl}-1-methyl-1,3-dihydro-[1,2,4]triazolo[5,1-i]purin-2-one, 5-amino-8-(2-furyl)-3-[2-[4-[4-(2-methoxyethoxy)phenyl]piperazin-1-yl]ethyl]-1-methyl-[1,2,4]triazolo[5,1-f]purine-2-thione, and 8-(2-furyl)-3-[2-[4-[4-(2-methoxyethoxy)phenyl]piperazin-1-yl]ethyl]-1-methyl-5-(methylamino)-[1,2,4]triazolo[5,1-f]purin-2-one.

Another embodiment of the present disclosure relates to a compound of formula (I) or its tautomers, polymorphs, stereoisomers, prodrugs, solvate or a pharmaceutically acceptable salts thereof, for treating disease or disorder susceptible to improvement by antagonism of $A_{2A}$ receptor.

Yet another embodiment of the present disclosure relates to a compound of formula (I) or its tautomers, polymorphs, stereoisomers, prodrugs, solvate or a pharmaceutically acceptable salts thereof, for treating. Parkinsons disease, restless leg syndrome, Alzheimers disease, neurodegenerative disorder, inflammation, wound healing, dermal fibrosis, nocturnal myoclonus, cerebral ischaemia, myocardial ischemia, Huntington's disease, multiple system atrophy, corticobasal degeneration, Wilson's disease or other disorders of basal ganglia which results in dyskinesias, post traumatic stress disorder, hepatic cirrhosis, sepsis, spinal cord injury, retinopathy, hypertension, social memory impairment, depression, neuroprotection, narcolepsy or other sleep related disorders, attention deficit hyperactivity disorder, drug addiction, post traumatic stress disorder and vascular injury.

The present disclosure also relates to a method of treating a disease in a mammal that is alleviable by treatment with an $A_{2A}$ adenosine receptor antagonist comprising administering a therapeutically effective amount of the compounds of Formula I or its tautomers, polymorphs, stereoisomers, prodrugs, solvate or pharmaceutically acceptable salts thereof.

The present disclosure also relates to a method of treating a disease state in a mammal that is alleviable by treatment with an $A_{2A}$ adenosine receptor antagonist comprising administering a therapeutically effective amount of the compounds of Formula I or its tautomers, polymorphs, stereoisomers, prodrugs, solvate or a pharmaceutically acceptable salts thereof, in particular treatment, prevention or suppression of diseases and disorders that may be susceptible to improvement by antagonism of the adenosine receptor, such as Parkinsons disease, restless leg syndrome, Alzheimers disease, neurodegenerative disorder, inflammation, wound healing, dermal fibrosis, nocturnal myoclonus, cerebral ischaemia, myocardial ischemia, Huntington's disease, multiple system atrophy, corticobasal degeneration, Wilson's disease or other disorders of basal ganglia which results in dyskinesias, post traumatic stress disorder, hepatic cirrhosis, sepsis, spinal cord injury, retinopathy, hypertension, social memory impairment, depression, neuroprotection, narcolepsy or other sleep related disorders, attention deficit hyperactivity disorder, drug addiction, post traumatic stress disorder and vascular injury.

The present disclosure further relates to the process of preparation of compounds of formula I or its tautomers, polymorphs, stereoisomers, prodrugs, solvate or pharmaceutically acceptable salts thereof.

The compounds of formula (I) is prepared as outlined in the Scheme 1 to 5 below:

Scheme 1:

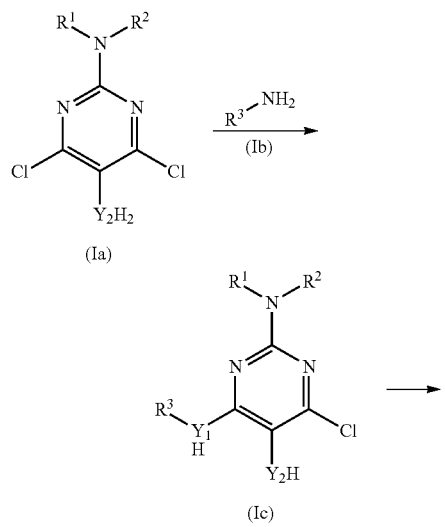

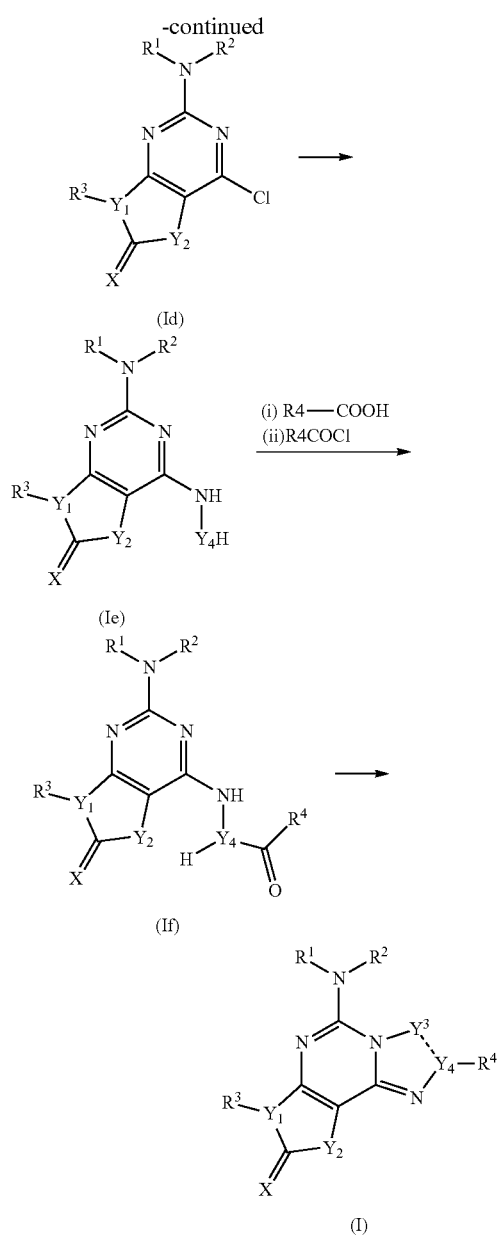

The compound of formula (Ia) wherein all symbols are defined herein above, is either available commercially or may be prepared by methods well known in the art (WO91/01310A1). The compound of formula (Ia) may be reacted with amine of formula (Ib) to obtain compound of formula (Ic) wherein all symbols are defined herein above. The reaction temperature may range from 50-100° C. and the reaction time may range from 4 to 24 hours. After completion of reaction the desired product (Ic) may be isolated by conventional methods.

The compound of formula (Ic) may be cyclised to obtain compound of formula (Id) by a known method in the literature. The reaction temperature may range from 10-50° C. and the reaction time may range from 4 to 48 hours. After completion of reaction the desired product (Id) may be isolated by conventional methods.

The compound of formula (Id) may be reacted with $NH_2Y_4H$ to obtain compound of formula (Ie). The reaction temperature may range from 50-100° C. and the reaction time may range from 4 to 24 hours. After completion of reaction the desired product (Ie) may be isolated by conventional method.

The compound of formula (Ie) may be reacted with a carboxylic acid $R^4COOH$ wherein $R^4$ is defined earlier, to yield a formula (If). The temperature may range from 20-30° C. and the reaction time may range from 4 to 24 hours. After completion of reaction the product of formula (If) may be isolated by conventional method.

The compound (If) may also be prepared from reaction of (Ie) and with an acid halide $R^4COCl$ to yield (If). The reaction temperature may range from 0-30° C. and the reaction time may range from 1 to 24 hours. After completion of reaction the product (If) was isolated by conventional method.

Compounds of formula (If) may be dehydrated using dehydrating reagent. The reaction temperature may range from 50-100° C. and the reaction time may range from 8 to 24 hours. After completion of reaction, the desired compound of formula (I) wherein all symbols are defined herein above may be isolated by conventional methods.

The compound of formula (2c) may be cyclised to obtain compound of formula (2d) by a known method in the literature. In general the formation of compound (2c) is achieved by using CDI, phosgene, triphosgene, 4-nitriphenyl chloroformate, thiophosgene and the like in the presence of a solvent such as DCM, THF, DMF, ACN, and the like and a base such as $K_2CO_3$, $NaHCO_3$, Et3N, pyridine and the like. The reaction temperature may range from 10-50° C. and the reaction time may range from 4 to 48 hours. After completion of reaction the desired product (2d) may be isolated by conventional methods. The compound of formula (2d) may be reacted with formula $R^5$-L1 where in $R^5$ is as defined above and L1 is a leaving group such as mesylate, tosylate or halo such as bromine, chlorine or iodine and base such as $K_2CO_3$, $Cs_2CO_3$ or NaH in an inert solvent such as DMF, DMA to obtain compound of formula (2e). The reaction temperature may range from 25-60° C. and the reaction time may range from 4 to 24 hours. After completion of reaction the desired product (2e) may be isolated by conventional method.

The compound of formula (2e) may be reacted with hydrazine hydrate without solvent or in a solvent such as methanol,

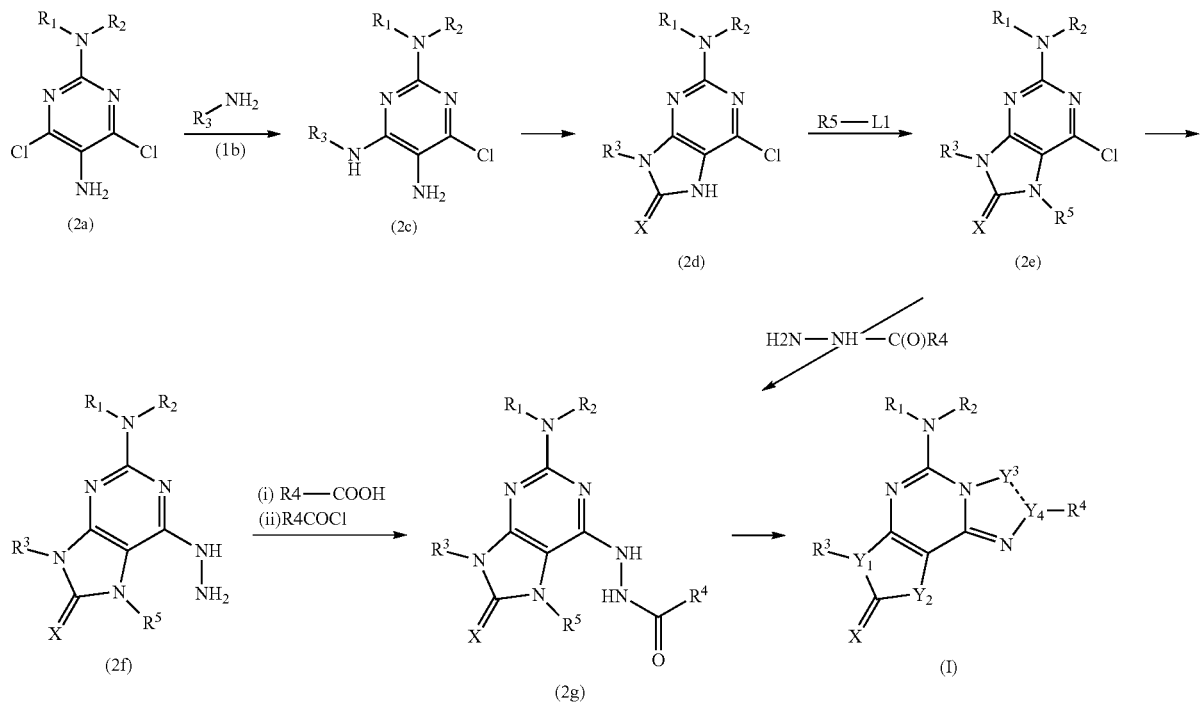

Scheme 2:

The compound of formula (2a) wherein all symbols are defined herein above, is either available commercially or may be prepared by methods well known in the art (WO91/01310A1). The compound of formula (2a) may be reacted with amine of formula (2b) without or with solvent such as methanol, ethanol, isopropanol or polar solvent such as THF, acetone, DMF and non polar solvent such as toluene, xylene in the presence of a base such as $K_2CO_3$, $NaHCO_3$, $Et_3N$, pyridine and the like, to obtain compound of formula (2c) wherein all symbols are defined herein above. The reaction temperature may range from 50-100° C. and the reaction time may range from 4 to 24 hours. After completion of reaction the desired product (2c) may be isolated by conventional methods.

ethanol, isopropanol or polar solvent such as THF, acetone, DMF and non polar solvent such as toluene, xylene and the like, in the absence or presence of a base such as DIPEA, $Na_2CO_3$ and the like to obtain compound of formula (2f). The reaction temperature may range from 50-100° C. and the reaction time may range from 4 to 24 hours. After completion of reaction the desired product (2f) may be isolated by conventional method.

The compound of formula (2f) may be reacted with a carboxylic acid $R^4COOH$ wherein $R^4$ is defined earlier, to yield a formula (2g). The reaction may be carried out with a suitable coupling agent such as EDCI, DCC, HBTU without base or in the presence of a base such as $Et_3N$,N-methyl morfoline, N-methylpyrrolidnone and the like and a solvent such as methanol, ethanol, propanol etc or aprotic solvent such as DMF, CH$_2$Cl$_2$. The temperature may range from 20-30° C. and the reaction time may range from 4 to 24 hours. After completion of reaction the product of formula (2g) may be isolated by conventional method. The compound (2g) may also be prepared from reaction of (2f) and with an acid halide R$^4$COCl to yield (2g). The acylation reaction may be carried out in the presence of base such as Et$_3$N, DIPEA, Pyridine and the like in solvent like DCM, DCE and the like. The reaction temperature may range from 0-30° C. and the reaction time may range from 1 to 24 hours. After completion of reaction the product (2g) was isolated by conventional method.

Alternatively, compound of formula (2g) may be obtained directly from (2e) by reaction with an appropriate hydrazide of formula H2N—NH—C(O)—R$^4$, wherein R$^4$ is defined above. The reaction may be carried out using a suitable solvent such as acetonitile, DMF and the like. The reaction temperature may range from 25-100° C. and the reaction time may range from 4 to 24 hours. After completion of reaction the desired product (2g) may be isolated by conventional methods.

Compounds of formula (2g) may be dehydrated using dehydrating reagent such as BSA or mixture of BSA and HMDS. The reaction temperature may range from 50-100° C. and the reaction time may range from 8 to 24 hours. After completion of reaction, the desired compound of formula (I) wherein Y1 is N and Y2 is NR$^5$ and all other symbols are defined herein above may be isolated by conventional methods.

Scheme 3:

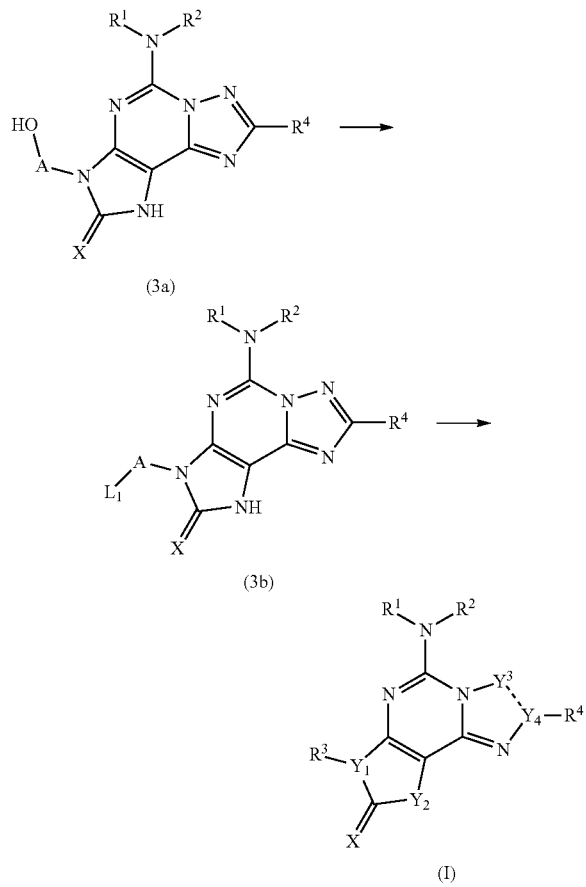

The compound of formula (3a) wherein all symbols are defined herein above may be converted to compound of formula (3b) wherein L1 is leaving group such as tosylate, mesylate, chloride, bromide or iodide and the like and all other symbols are defined herein above, by a suitable method or method known in the literature. The compound of formula (3b) is then reacted with Q-B—ZH, wherein Q, B and Z are defined herein above, in a solvent such as DMF, ACN and the like in presence of a base such as diisopropyl ethyl amine, Et$_3$N, K$_2$CO$_3$, Cs$_2$CO$_3$, NaH and the like or without base. The reaction temperature may range from 50-100° C. and the reaction time may range from 2 to 24 hours. After completion of reaction, the desired product (I) wherein all symbols are defined herein above may be isolated by conventional method.

Scheme 4:

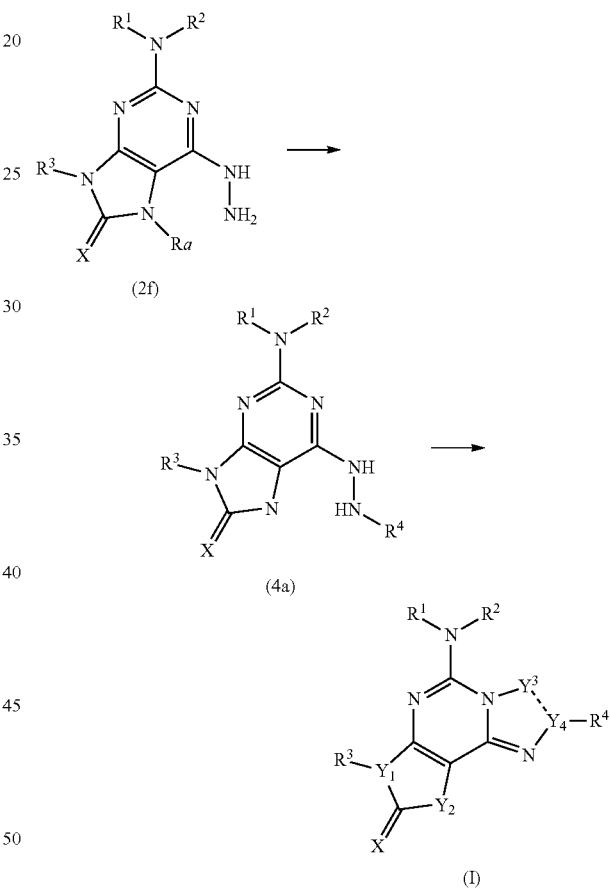

The compound of formula (2f) may be reacted with R$^4$CHO in presence of catalytic amount of acid such as acetic acid or without acid followed by reduction with suitable reducing agent such as sodium cyanoborohydride, sodium triacetoxy borohydride and the like to obtain compound of formula (4a). The organic solvent to be used in the present method may be alcohol such as methanol, ethanol or DCM, dichloroethane. The reaction temperature may range from 0-40° C. and the reaction time may range from 4 to 24 hours. After completion of reaction the desired product (4a) may be isolated by conventional method. Compounds of formula (4a) may be treated with phosgene to provide compounds of formula (I) wherein Y$^3$ is C(=O), Y$^1$ is N and all other symbols are defined herein above.

Scheme 5:

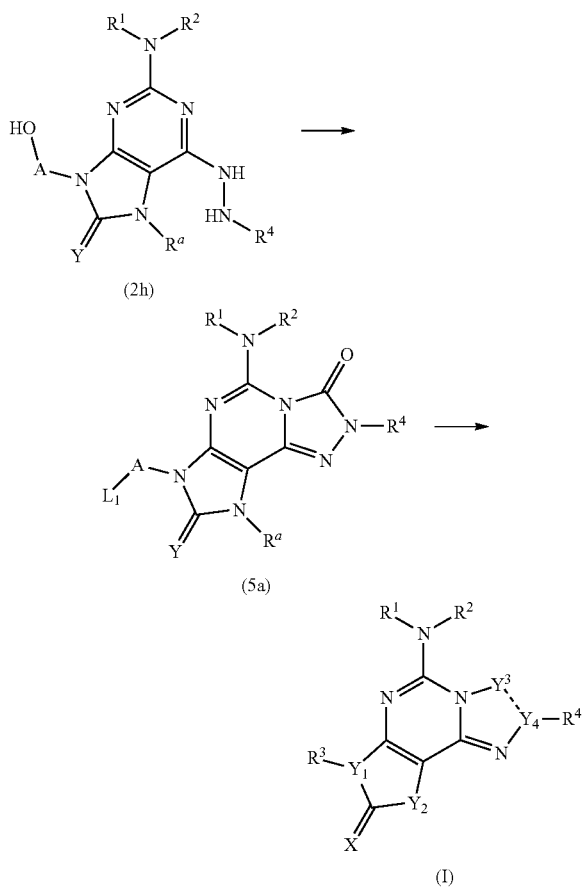

The compound of formula (2h) wherein all symbols are defined herein above may be converted to compounds of formula (5a) wherein L1 is a leaving group such as tosylate, mesylate, chloride, bromide or iodide and the like, or is a suitable hydroxyl protecting group such as a trialkylsilyl group (e.g., t-butyldimethylsilyl group) and all other symbols are defined herein above, by a suitable method or method known in the literature. The compound of formula (5a) may be reacted with Q-B—ZH, wherein Q, B and Z are defined herein above, in a solvent such as DMF, ACN and the like in presence of a base such as diisopropyl ethyl amine, Et$_3$N, K$_2$CO$_3$, Cs$_2$CO$_3$, NaH and the like or without base. The reaction temperature may range from 50-100° C. and the reaction time may range from 2 to 24 hours. After completion of reaction, the desired product (I) wherein all symbols are defined herein above may be isolated by conventional methods.

Wherever desired or necessary, in any of the above mentioned processes, functional groups is transformed to different functional groups such as an ester function being converted to an acid, amide, hydroxymethyl, keto, aldehyde as well as an ester. The said conversions are carried out using reagents and conditions well documented in the literature.

Wherever desired or necessary, in any of the above mentioned processes, any of the compounds of formula (I) is converted into a pharmaceutically acceptable salt or vice versa or converting one salt form into another pharmaceutically acceptable salt form.

According to an embodiment, the compounds of the present disclosure are adenosine A$_{2A}$ receptor antagonists.

Thus, the present disclosure provides a method for the modulation of adenosine A$_{2A}$ receptor activity in mammals which method comprises administering to a mammal in need thereof a therapeutically effective amount of compound of formula (I) or its tautomers, polymorphs, stereoisomers or a pharmaceutically acceptable salts thereof.

As used throughout the specification and in the claims, the term "treatment" embraces all the different forms or modes of treatment as known to those of the pertinent art and in particular includes preventive, curative, delay of progression and palliative treatment.

The term "therapeutically effective amount" as used herein refers to an amount of a drug or a therapeutic agent that will elicit the desired biological or medical response of a tissue, system or an animal (including man) that is being sought by a researcher or clinician.

The term "mammal" or "patient" are used interchangeably herein and include, but are not limited to, humans, dogs, cats, horses, pigs, cows, sheep, monkeys, rabbits, mice and laboratory animals The preferred mammals are humans.

An embodiment of the present disclosure relates to a pharmaceutical composition comprising, as an active ingredient, at least one compound of formula (I) or its tautomers, polymorphs, stereoisomers or a pharmaceutically acceptable salts thereof, together with one or more pharmaceutically acceptable carriers or excipients.

The present disclosure further provides pharmaceutical compositions comprising a therapeutically effective amount of a compound of the present disclosure, alone or in combination with one or more pharmaceutically acceptable carriers.

The pharmaceutical compositions according to the present disclosure are those suitable for enteral, such as oral or rectal, transdermal and parenteral administration to mammals, including man, for the treatment of conditions mediated by the adenosine A$_{2A}$ receptor. Such conditions include, but are not limited to, Parkinsons disease, restless leg syndrome, Alzheimers disease, neurodegenerative disorder, inflammation, wound healing, dermal fibrosis, nocturnal myoclonus, cerebral ischaemia, myocardial ischemia, Huntington's disease, multiple system atrophy, corticobasal degeneration, Wilson's disease or other disorders of basal ganglia which results in dyskinesias, post traumatic stress disorder, hepatic cirrhosis, sepsis, spinal cord injury, retinopathy, hypertension, social memory impairment, depression, neuroprotection, narcolepsy or other sleep related disorders, attention deficit hyperactivity disorder, drug addiction, post traumatic stress disorder and vascular injury.

Generally, the concentration of the compound(s) of the present disclosure in a liquid composition, such as a lotion, will be from about 0.01-about 25 wt %, preferably from about 0.1-about 10 wt %. The concentration in a semi-solid or a solid composition such as a gel or a powder will be about 0.1-about 5 wt %, preferably about 0.5-about 25 wt %.

The amount of a compound of the present disclosure required for use in treatment will vary not only with the particular salt selected but also with the route of administration, the nature of the condition being treated and the age and condition of the patient and will be ultimately at the discretion of the administering physician or clinician. In general, a suitable dose will be in the range of from about 0.001 mg/kg/day to about 20 mg/kg/day For example, a dosage may be from about 0.002 mg/kg to about 10 mg/kg of body weight per day, from about 0.01 mg/kg/day to about 1 mg/kg/day, and from about 0.1 mg/kg/day to about 5 mg/kg/day.

The compound is conveniently administered in unit dosage form, e.g., containing 5 to 1000 µg, about 10 to about 750 µg, about 50 to about 500 µg of active ingredient per unit dosage form.

The desired dose may conveniently be presented in a single dose or as divided doses administered at appropriate intervals, for example, as two, three, four or more sub-doses per day. The sub-dose itself may be further divided, e g, into a number of discrete loosely spaced administrations; such as multiple inhalations from an insufflator or by application of a plurality of drops into the eye Dosages above or below the range cited herein above are within the scope of the present disclosure and may be administered to the individual patient if desired and necessary.

Accordingly, in various embodiments, the present disclosure provides pharmaceutical compositions as described above for the treatment of conditions mediated by adenosine receptor, such as Parkinsons disease, restless leg syndrome, Alzheimers disease, neurodegenerative disorder, inflammation, wound healing, dermal fibrosis, nocturnal myoclonus, cerebral ischaemia, myocardial ischemia, Huntington's disease, multiple system atrophy, corticobasal degeneration, Wilson's disease or other disorders of basal ganglia which results in dyskinesias, post traumatic stress disorder, hepatic cirrhosis, sepsis, spinal cord injury, retinopathy, hypertension, social memory impairment, depression, neuroprotection, narcolepsy or other sleep related disorders, attention deficit hyperactivity disorder, drug addiction, post traumatic stress disorder and vascular injury.

An embodiment of the present disclosure also relates to a pharmaceutical composition comprising a compound of formula (I) or its tautomers, polymorphs, stereoisomers or a pharmaceutically acceptable salts thereof, in combination with one or more therapeutically active agents.

In various embodiments, the present disclosure provides pharmaceutical compositions comprising a therapeutically effective amount of a compound of the disclosure in combination with a therapeutically effective amount of another therapeutic agent, preferably selected from anti-inflammatory agents, anti-diabetic agents, anti-hypertensive agents and anti-dyslipidemic agents.

According to an embodiment, the pharmaceutical compositions may contain a therapeutically effective amount of a compound of the disclosure as defined above, either alone or in a combination with another therapeutic agent, e.g., each at an effective therapeutic dose as reported in the art. Such therapeutic agents include: a) anti-inflammatory agents, such as anticholinergic or antimuscarinic agents; steroids; $LTB_4$ (leukotriene $B_4$) antagonists; dopamine receptor agonists; $PDE_4$ (phosphodiesterase 4) inhibitors; and beta-2 adrenergic receptor agonists; b) anti-diabetic agents, such as insulin, insulin derivatives and mimetics; insulin secretagogues; insulinotropic sulfonylurea receptor ligands; thiazolidone derivatives; GSK3 (glycogen synthase kinase-3) inhibitors; sodium-dependent glucose co-transporter inhibitors; glycogen phosphorylase A inhibitors; biguanides; alpha-glucosidase inhibitors; GLP-1 (glucagon like peptide-1), GLP-1 analogs and GLP-1 mimetics; modulators of PPARs (peroxisome proliferator-activated receptors); DPPIV (dipeptidyl peptidase IV) inhibitors; SCD-1 (stearoyl-CoA desaturase-1) inhibitors; DGAT1 and DGAT2 (diacylglycerol acyltransferase 1 and 2) inhibitors; ACC2 (acetyl CoA carboxylase 2) inhibitors; and breakers of AGE (advanced glycation end products); c) anti-hypertensive agents, such as loop diuretics; angiotensin converting enzyme (ACE) inhibitors; inhibitors of the Na—K-ATPase membrane pump such as digoxin; neutralendopeptidase (NEP) inhibitors; ACE/NEP inhibitors; angiotensin II antagonists; renin inhibitors; β-adrenergic receptor blockers; inotropic agents; calcium channel blockers; aldosterone receptor antagonists; and aldosterone synthase inhibitors; and d) anti-dyslipidemic agents such as 3-hydroxy-3-methyl-glutaryl coenzyme A (HMG-CoA) reductase inhibitors; HDL increasing compounds such as cholesterol ester transfer protein (CETP) inhibitors; squalene synthase inhibitors; FXR (farnesoid X receptor) and LXR (liver X receptor) ligands; cholestyramine; fibrates; nicotinic acid; and aspirin.

According to another embodiment, the present disclosure provides pharmaceutical compositions comprising a therapeutically effective amount of a compound of the disclosure in combination with a therapeutically effective amount of one to three other agents useful in treating Parkinson's disease in a pharmaceutically acceptable carrier.

According to yet another embodiment, the pharmaceutical compositions may contain a therapeutically effective amount of a compound of the disclosure as defined above, either alone or in a combination with a therapeutically effective amount of one to three other agents useful in treating Parkinson's disease. Such agents include L-DOPA, dopaminergic agonists, MAO-B inhibitors, DOPA decarboxylase inhibitors, COMT inhibitors and NMDA receptor.

Pharmaceutical Compositions

The compounds of Formula I are usually administered in the form of pharmaceutical compositions. This disclosure therefore provides pharmaceutical compositions that contain, as the active ingredient, one or more of the compounds of Formula I or its tautomers, polymorphs, stereoisomers or a pharmaceutically acceptable salts thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17.sup.th Ed. (1985) and "Modern Pharmaceutics", Marcel Dekker, Inc. 3.sup.rd Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

The following examples are included to demonstrate preferred embodiments of the present disclosure. It should be appreciated by those of skill in the art that the techniques disclosed in the examples which follow represent techniques discovered by the inventor to function well in the practice of the present disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the present disclosure.

EXAMPLES

The invention is further illustrated by the following examples which in no way should be construed as being further limiting. One skilled in the art will readily appreciate that the specific methods and results described are merely illustrative. Structures of the intermediates as well as the final compounds were confirmed by nuclear magnetic resonance spectra for proton ($^1$H NMR) and LCMS.

Example A1

5-Amino-8-(2-furyl)-3-[2-[4-[4-(2-methoxyethoxy)phenyl]piperazin-1-yl]ethyl]-1-methyl-[1,2,4]triazolo[5,1-f]purin-2-one

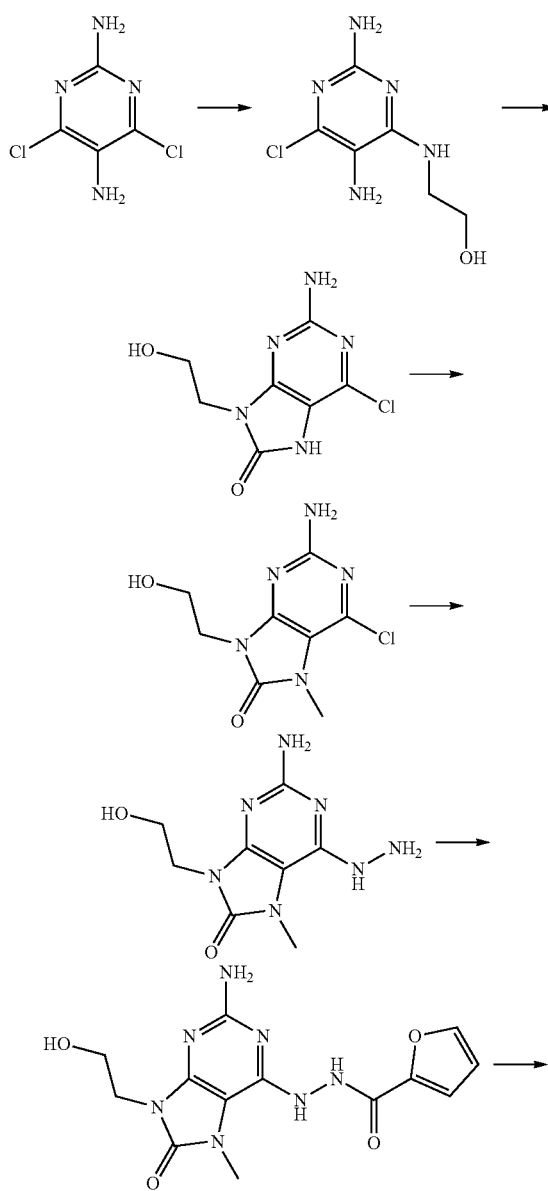

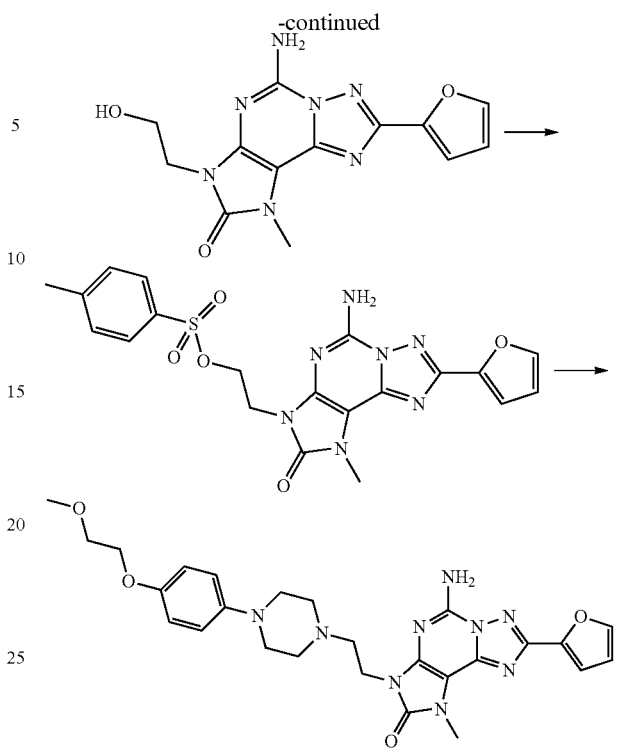

Step-1: 2-[(2,5-Diamino-6-chloro-pyrimidin-4-yl)amino]ethanol

A mixture of 4,6-dichloropyrimidine-2,5-diamine (28 g, 156 mmol), ethanolamine (18 ml, 312 mmol) and ethanol (250 ml) were heated at 100-110° C. for 16 hours. The mixture was cooled and solvent was removed. To the residue methanol (100 ml) was added and stirred for 20 minutes. The solid was filtered off to obtain 2-[(2,5-diamino-6-chloro-pyrimidin-4-yl)amino]ethanol (22.0 g, 70%).

$^1$HNMR (400 MHz, DMSO d6): δ 3.36-3.40 (m, 2H); 3.50-3.54 (m, 2H); 3.88 (bs, 2H); 4.74 (t, J=5.6 Hz, 1H); 5.63 (bs, 2H); 6.51 (t, J=5.6 Hz, 1H)

Step-2: 2-Amino-6-chloro-9-(2-hydroxyethyl)-7H-purin-8-one

A mixture of 2-[(2,5-diamino-6-chloro-pyrimidin-4-yl)amino]ethanol obtained in step 1 (10.0 g, 49.26 mmol) in acetonitrile (400 ml) were cooled to 0° C. To this reaction mixture K$_2$CO$_3$ (20.39 gm, 147.7 mmol) and 4-nitrophenyl chloroformate (19.8 g, 98.52 mmol) was added and stirred at 25-27° C. for 24 hours. This reaction mixture was filtered and washed with acetonitrile (300 ml) and diethyl ether (300 ml) respectively. Solid obtained was dried to obtain crude 2-amino-6-chloro-9-(2-hydroxyethyl)-7H-purin-8-one as a yellow solid. Small amount of crude material was purified by column chromatography to obtain pure product.

$^1$HNMR (400 MHz, DMSO d6): δ 3.61-3.66 (m, 2H); 3.72-3.75 (m, 2H); 4.85 (t, J=6 Hz, 1H); 6.60 (s, 2H); 11.21 (s, 1H)

Step-3: 2-Amino-6-chloro-9-(2-hydroxyethyl)-7-methyl-purin-8-one

A mixture of 2-amino-6-chloro-9-(2-hydroxyethyl)-7H-purin-8-one obtained in step 2 (13 g, 56.7 mmol), $K_2CO_3$ (11.5 g, 84 mmol), methyl iodide (12 g, 85.15 mmol) and DMF (130 ml) were stirred at 25-30° C. for 16 hours. The reaction mixture was concentrated and purified by column chromatography using 60-120 silica gel and 4% methanol in DCM as an eluent to obtain 2-amino-6-chloro-9-(2-hydroxyethyl)-7-methyl-purin-8-one (8 g, 58%) as an off white solid.

$^1$HNMR (400 MHz, DMSO d6): δ 3.42 (s, 3H); 3.65 (t, J=5.6 Hz, 2H); 3.78 (t, J=5.6 Hz, 2H); 4.85 (t, J=5.6 Hz, 1H); 6.69 (bs, 2H).

Step-4: 2-Amino-6-hydrazino-9-(2-hydroxyethyl)-7-methyl-purin-8-one

A mixture of 2-amino-6-chloro-9-(2-hydroxyethyl)-7-methyl-purin-8-one obtained in step 3 (8 g, 32.9 mmol), Hydrazine hydrate (16 ml, 32.9 mmol) and ethanol (300 ml) were heated at 100-110° C. for 16 hours. The reaction mixture was concentrated and solid obtained was filtered off and dried to obtain 2-amino-6-hydrazino-9-(2-hydroxyethyl)-7-methyl-purin-8-one (7 g, 89%) as an off white solid.

$^1$HNMR (400 MHz, DMSO d6): δ 3.37 (s, 3H); 3.58-3.61 (m, 2H); 3.71 (t, J=6 Hz, 2H); 4.29 (bs, 2H); 4.87 (t, J=5.6 Hz, 1H), 6.00 (bs, 2H); 7.63 (s, 1H).

Step-5: N'-[2-Amino-9-(2-hydroxyethyl)-7-methyl-8-oxo-purin-6-yl]furan-2-carbohydrazide 2-amino-6-hydrazino-9-(2-hydroxyethyl)-7-methyl-purin-8-one (4.5 g, 18.18 mmol) obtained in step 4,2-furoic acid (2.53 g, 22.5 mmol), HOBT (2.53 g, 18.8 mmol) and N-methylmorpholine were taken in dimethylformamide (40 ml). 1-Ethyl-3(3'-dimethylaminopropryl)carbodiimide hydrochloride (EDCI.HCl) (5.4 g, 28.2 mmol) was added to the reaction mixture and stirred at 25-27° C. for 14 hours. The reaction mixture was evaporated and residue was purified by column chromatography to obtain N'-[2-amino-9-(2-hydroxyethyl)-7-methyl-8-oxo-purin-6-yl]furan-2-carbohydrazide (5.3 g, 84%) as an off white solid.

$^1$HNMR (400 MHz, DMSO d6): δ 3.43 (s, 3H); 3.59-3.63 (m, 2H); 3.74 (t, J=6 Hz, 2H); 4.88 (t, J=5.6 Hz, 1H); 5.98 (bs, 2H); 6.67 (bs, 1H); 7.25 (d, J=3.2 Hz, 1H); 7.90 (s, 1H); 8.35 (s, 1H); 10.28 (s, 1H).

Step-6: 5-Amino-8-(2-furyl)-3-(2-hydroxyethyl)-1-methyl-[1,2,4]triazolo[5,1-]purin-2-one A mixture of N'-[2-amino-9-(2-hydroxyethyl)-7-methyl-8-oxo-purin-6-yl]furan-2-carbohydrazide obtained in step 5 (5.3 g, 15.9 mmol), N,O-bistrimethylsilylacetamide (27 ml, 111.4 mmol) and hexamethyldisilazane (83 ml, 397 mmol) were heated at 110-120° C. for 16 hours. The reaction mixture was quenched with methanol (100 ml) and water (100 ml) and organic volatiles were evaporated. The solid obtained was filtered off and washed with water (30 ml) followed by diethyl ether (100 ml) to obtain 5-amino-8-(2-furyl)-3-(2-hydroxyethyl)-1-methyl-[1,2,4]triazolo[5,1-f]purin-2-one (3.50 g, 71%) as an off white solid.

$^1$HNMR (400 MHz, DMSO d6): δ 3.56 (s, 3H); 3.67-3.70 (m, 2H); 3.84-3.87 (m, 2H); 4.88 (t, J=5.6 Hz, 1H); 6.73 (bs, 1H); 7.20 (bs, 1H); 7.79 (bs, 2H); 7.94 (bs, 1H).

Step-7: 2-[5-Amino-8-(2-furyl)-1-methyl-2-oxo-[1,2,4]triazolo[5,1-f]purin-3-yl]ethyl 4-methylbenzenesulfonate A mixture of 5-amino-8-(2-furyl)-3-(2-hydroxyethyl)-1-methyl-[1,2,4]triazolo[5,1-f]purin-2-one obtained in step 6 (3.5 g, 11 mmol), p-toluene sulphonylchloride (5.2 g, 27 mmol) were taken in pyridine (30 ml) and stirred at 25-27° C. for 16 hours. To the reaction mixture hexane (100 ml) was added and solid obtained was filtered off and washed with water (100 ml) followed by hexane (100 ml) to obtain 2-[5-amino-8-(2-furyl)-1-methyl-2-oxo-[1,2,4]triazolo[5,1-f]purin-3-yl]ethyl 4-methylbenzenesulfonate (4.1 g, 78%) as a brown solid.

$^1$HNMR (400 MHz, DMSO d6): δ 2.02 (s, 3H); 3.49 (s, 3H); 3.99 (t, J=4.8 Hz, 2H); 4.71 (t, J=4.8 Hz, 2H); 6.73-6.75 (m, 1H); 7.01 (d, J=8 Hz, 2H); 7.23 (d, J=3.2 Hz, 1H); 7.41 (d, J=8.4 Hz, 2H); 7.78 (bs, 2H); 7.96 (d, J=1.2 Hz, 1H).

Step-8: 5-Amino-8-(2-furyl)-3-[2-[4-[4-(2-methoxyethoxy)phenyl]piperazin-1-yl]ethyl]-1-methyl-[1,2,4]triazolo[5,1-f]purin-2-one A mixture of 2-[5-amino-8-(2-furyl)-1-methyl-2-oxo-[1,2,4]triazolo[5,1-f]purin-3-yl]ethyl 4-methylbenzenesulfonate obtained in step 7 (0.25 g, 0.533 mmol), 1-[4-(2-Methoxyethoxy)-phenyl]-piperazine (0.188 g, 0.799 mmol) and DIPEA (0.27 ml, 1.599 mmol) were taken in DMF (5 ml) and stirred at 80° C. for 16 hours. To the reaction mixture water (100 ml) was added and solid obtained was filtered off. The crude product was purified by column chromatography to obtain 5-amino-8-(2-furyl)-3-[2-[4-[4-(2-methoxyethoxy)phenyl]piperazin-1-yl]ethyl]-1-methyl-[1,2,4]triazolo[5,1-f]purin-2-one (0.135 g, 47%) as an off white solid $^1$HNMR (400 MHz, DMSO d6): δ 2.60 (bs, 4H); 2.68 (t, J=6.4 Hz, 2H); 2.96 (bs, 4H); 3.29 (s, 3H); 3.56 (s, 3H); 3.59-3.62 (m, 2H); 3.94-4.00 (m, 4H); 6.71-6.73 (m, 1H); 6.79-6.86 (m, 4H); 7.19 (dd, J=3.2 Hz, 1.2 Hz, 1H); 7.80 (bs, 2H); 7.94 (bs, 1H).

Examples A2A63 were prepared by following similar experimental procedure of Example A1 using the appropriate intermediates.

| Ex. No | Structure/IUPAC name | NMR |
|---|---|---|
| A2 | 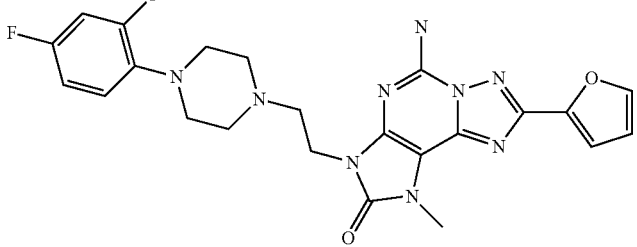<br>5-Amino-3-[2-[4-(2,4-difluorophenyl)piperazin-1-yl]ethyl]-8-(2-furyl)-1-methyl-[1,2,4]triazolo[5,1-f]purin-2-one | $^1$HNMR (400 MHz, DMSO d6): δ 2.62 (bs, 4H); 2.67-2.70 (m, 2H); 2.91 (bs, 4H); 3.57 (s, 3H); 3.95 (bs, 2H); 6.73 (bs, 1H); 6.95-7.04 (m, 2H); 7.15-7.19 (m, 2H); 7.79 (bs, 2H); 7.94 (bs, 1H). |
| A3 | 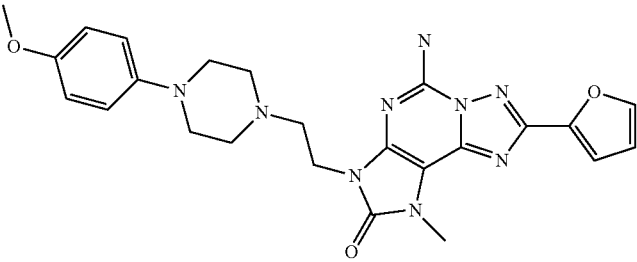 [SMILES: COc1ccc(N2CCN(CCn3c(=O)n(C)c4c3nc(N)n3nc(-c5ccco5)nc43)CC2)cc1]<br>5-Amino-8-(2-furyl)-3-[2-[4-(4-methoxyphenyl)piperazin-1-yl]ethyl]-1-methyl-[1,2,4]triazolo[5,1-f]purin-2-one | $^1$HNMR (400 MHz, DMSO d6): δ 2.61 (bs, 4H); 2.68 (bs, 2H); 2.95 (bs, 4H); 3.57 (s, 3H); 3.67 (s, 3H); 3.96 (bs, 2H); 6.72 (bs, 1H); 6.78-6.87 (m, 4H); 7.19 (bs, 1H); 7.81 (bs, 2H); 7.94 (s, 1H). |
| A4 | 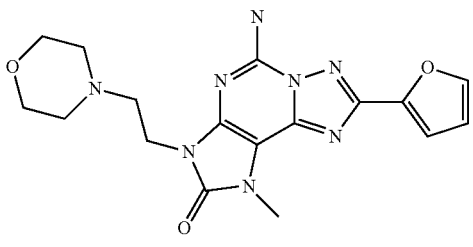<br>5-Amino-8-(2-furyl)-1-methyl-3-(2-morpholinoethyl)-[1,2,4]triazolo[5,1-f]purin-2-one | $^1$HNMR (400 MHz, CDCl3): δ 2.57 (bs, 4H); 2.76 (t, J = 6.4 Hz, 2H); 3.67 (t, J = 4.4 Hz, 4H); 3.76 (s, 3H); 4.06 (t, J = 6.4 Hz, 2H); 5.75 (bs, 2H); 6.60 (bs, 1H); 7.23-7.26 (m, 1H): 7.64 (s, 1H). |
| A5 | 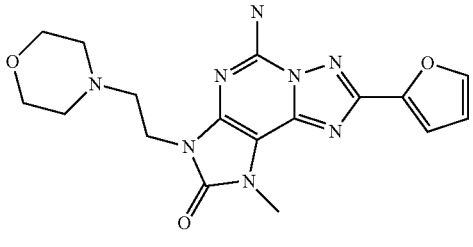<br>5-Amino-3-[2-[4-(2,4-difluorophenyl)-1-piperidyl]ethyl]-8-(2-furyl)-1-methyl-[1,2,4]triazolo[5,1-f]purin-2-one | $^1$H NMR(400 MHz, DMSO d6): δ 1.50-1.58 (m, 3H); 1.71 (d, J = 10.8 Hz, 2H); 2.08 (t, J = 10.4 Hz, 2H); 2.66 (t, J = 6.4 Hz, 2H); 3.05 (d, J = 11.2 Hz, 2H); 3.57 (s, 3H); 3.94 (t, J = 6.8 Hz, 2H); 6.72-6.73 (m, 1H); 7.08 (t, J = 8.8 Hz, 2H); 7.20 (d, J = 3.2 Hz, 1H); 7.23-7.27 (m, 1H); 7.80 (bs, 2H); 7.94 (s, 1H). |

-continued

| Ex. No | Structure/IUPAC name | NMR |
|---|---|---|
| A6 | 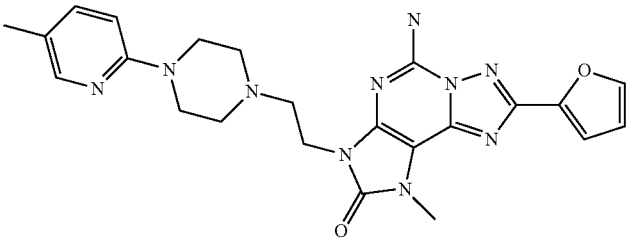 [SMILES: Cc1ccc(N2CCN(CCn3c(=O)n(C)c4c3nc(N)n3nc(-c5ccco5)nc43)CC2)nc1]<br>5-Amino-8-(2-furyl)-1-methyl-3-[2-[4-(5-methyl-2-pyridyl)piperazin-1-yl]ethyl]-[1,2,4]triazolo[5,1-f]purin-2-one | $^1$H NMR(400 MHz, DMSO d6): δ 2.13(s, 3H); 2.55(bs, 4H); 2.67(t, J = 6.4 Hz, 2H); 3.32-3.34 (m, 4H); 3.56 (s, 3H); 3.96 (t, J = 6.4 Hz, 2H); 6.71-6.73 (m, 2H); 7.19 (d, J = 3.2 Hz, 1H); 7.35 (d, J = 8.8 Hz, 1H); 7.81 (bs, 2H); 7.94 (bs, 2H). |
| A7 | 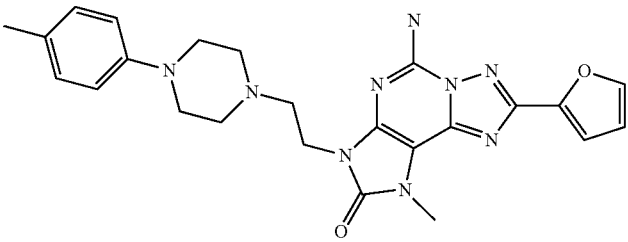 [SMILES: Cc1ccc(N2CCN(CCn3c(=O)n(C)c4c3nc(N)n3nc(-c5ccco5)nc43)CC2)cc1]<br>5-Amino-8-(2-furyl)-1-methyl-3-[2-[4-(p-tolyl)piperazin-1-yl]ethyl]-[1,2,4]triazolo[5,1-f]purin-2-one | $^1$H NMR(400 MHz, DMSO d6): δ 2.18 (s, 3H); 2.60 (bs, 4H); 2.65-2.70(m, 2H); 3.00 (bs, 4H); 3.56 (s, 3H); 3.96 (t, J = 6.8 Hz, 2H); 6.72 (bs, 1H); 6.79 (d, J = 8.4 Hz, 2H); 7.0 (d, J = 8.0 Hz, 2H); 7.19 (d, J = 2.8 Hz, 1H); 7.80 (bs, 2H); 7.94 (s, 1H). |
| A8 | 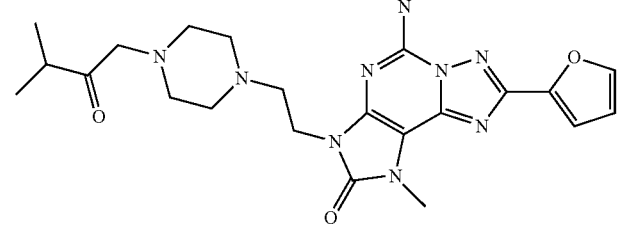 [SMILES: CC(C)C(=O)CN1CCN(CCn2c(=O)n(C)c3c2nc(N)n2nc(-c4ccco4)nc32)CC1]<br>5-Amino-8-(2-furyl)-1-methyl-3-[2-[4-(3-methyl-2-oxo-butyl)piperazin-1-yl]ethyl]-[1,2,4]triazolo[5,1-f]purin-2-one | $^1$H NMR(400 MHz, DMSO): δ 0.97 (d, J = 6.8 Hz, 6H); 2.34 (bs, 4H); 2.40-2.42 (m, 4H); 2.62 (t, J = 6.4 Hz, 2H); 2.67-2.74 (m, 1H); 3.21 (s, 2H); 3.56 (s, 3H); 3.90 (t, J = 6.4 Hz, 2H); 6.72 (dd, J = 2 Hz, 3.6 Hz, 1H); 7.19 (d, J = 3.6 Hz, 1H); 7.79 (bs, 2H); 7.94 (d, J = 1.2 Hz, 1H). |
| A9 | 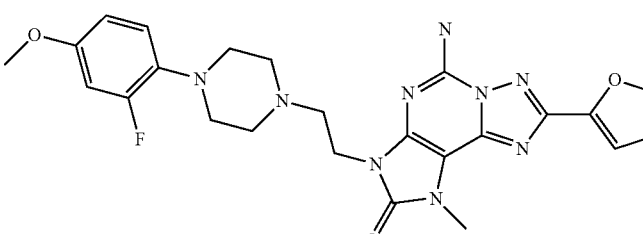<br>5-Amino-3-[2-[4-(2-fluoro-4-methoxy-phenyl)piperazin-1-yl]ethyl]-8-(2-furyl)-1-methyl-[1,2,4]triazolo[5,1-f]purin-2-one | $^1$H NMR(400 MHz, DMSO): δ 2.62 (bs, 4H); 2.68 (t, J = 6.4 Hz, 2H); 2.86 (bs, 4H); 3.57 (s, 3H); 3.70 (s, 3H); 3.95 (t, J = 6.4 Hz, 2H); 6.66 (dd, J = 8.8 Hz, 3.2 Hz, 1H); 6.72 (dd, J = 2 Hz, 3.6 Hz, 1H); 6.67-6.81 (m, 1H); 6.94 (t, J = 9.2 Hz, 1H); 7.19 (d, J = 3.6 Hz, 1H); 7.80 (bs, 2H); 7.94 (d, J = 1.6 Hz, 1H). |

| Ex. No | Structure/IUPAC name | NMR |
|---|---|---|
| A10 | 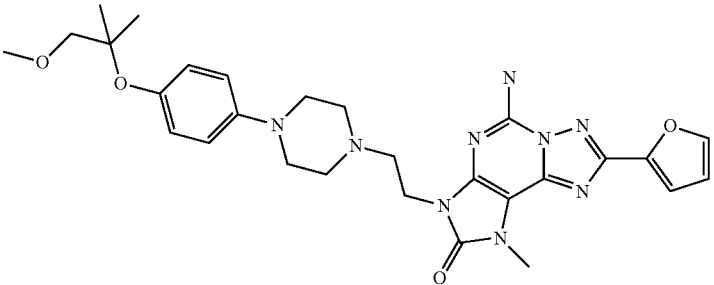 [SMILES: COCC(C)(C)Oc1ccc(N2CCN(CCn3c(=O)n(C)c4c3nc(N)n3nc(-c5ccco5)nc43)CC2)cc1]<br>5-Amino-8-(2-furyl)-3-[2-[4-[4-(2-methoxy-1,1-dimethyl-ethoxy)phenyl]piperazin-1-yl]ethyl]-1-methyl-[1,2,4]triazolo[5,1-f]purin-2-one | $^1$H NMR(400 MHz, DMSO): δ 1.15 (s, 6H); 2.60 (bs, 4H); 2.68 (t, J = 6.8 Hz, 2H); 3.01 (bs, 4H); 3.23 (s, 2H); 3.29 (s, 3H); 3.57 (s, 3H); 3.96 (t, J = 6.4 Hz, 2H); 6.72 (dd, J = 1.6 Hz, 3.6 Hz, 1H); 6.81 (s, 4H); 7.19 (d, J = 3.6 Hz, 1H); 7.81 (bs, 2H); 7.94 (bs, 1H). |
| A11 | 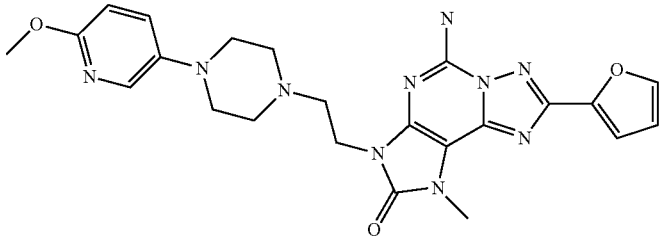 [SMILES: COc1ccc(N2CCN(CCn3c(=O)n(C)c4c3nc(N)n3nc(-c5ccco5)nc43)CC2)cn1]<br>5-Amino-8-(2-furyl)-3-[2-[4-(6-methoxy-3-pyridyl)piperazin-1-yl]ethyl]-1-methyl-[1,2,4]triazolo[5,1-f]purin-2-one | $^1$H NMR(400 MHz, DMSO): δ 2.61 (bs, 4H); 2.67-2.70 (m, 2H); 2.99 (bs, 4H); 3.57 (s, 3H); 3.76 (s, 3H); 3.96 (t, J = 6.4 Hz, 2H); 6.69 (d, J = 9.2 Hz, 1H); 6.72(dd, J = 2 Hz, 3.6 Hz, 1H); 7.19 (d, J = 3.6 Hz, 1H); 7.41 (dd, J = 9.2 Hz, 3.2 Hz, 1H); 7.74 (d, J = 2.8 Hz, 1H); 7.80 (bs, 2H); 7.94 (s, 1H). |
| A12 | 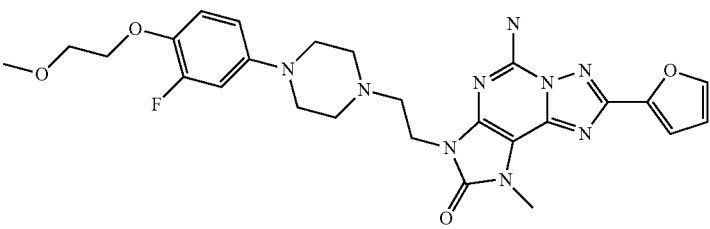 [SMILES: COCCOc1ccc(N2CCN(CCn3c(=O)n(C)c4c3nc(N)n3nc(-c5ccco5)nc43)CC2)cc1F]<br>5-Amino-3-[2-[4-[3-fluoro-4-(2-methoxyethoxy)phenyl]piperazin-1-yl]ethyl]-8-(2-furyl)-1-methyl-[1,2,4]triazolo[5,1-f]purin-2-one | $^1$H NMR(400 MHz, DMSO): δ 2.59 (bs, 4H); 2.67 (t, J = 6.4 Hz, 2H); 2.99(bs, 4H); 3.29 (s, 3H); 3.56 (s, 3H); 3.60-3.62 (m, 2H); 3.95 (t, J = 6 Hz, 2H); 4.03-4.06 (m, 2H); 6.62 (d, J = 8.8 Hz, 1H); 6.72(dd, J = 2 Hz, 3.6 Hz, 1H); 6.80-6.84 (m, 1H); 6.99 (t, J = 9.6 Hz, 1H); 7.19(d, J = 3.2 Hz, 1H); 7.81 (bs, 2H); 7.94(s, 1H). |
| A13 | 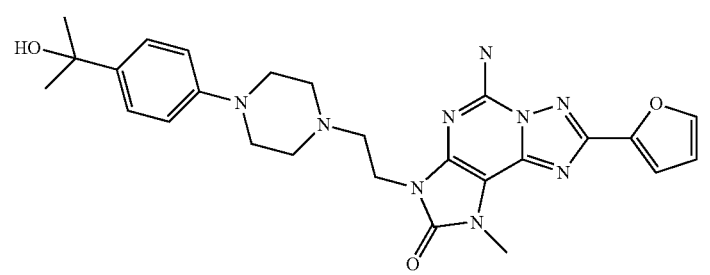 [SMILES: Cn1c(=O)n(CCN2CCN(c3ccc(C(C)(C)O)cc3)CC2)c2nc(N)n3nc(-c4ccco4)nc3c21]<br>5-Amino-8-(2-furyl)-3-[2-[4-[4-(1-hydroxy-1-methyl-ethyl)phenyl]piperazin-1-yl]ethyl]-1-methyl-[1,2,4]triazolo[5,1-f]purin-2-one | 1H NMR (400 MHz, DMSO): δ 1.37 (s, 6H); 2.58-2.62 (m, 4H); 2.66-2.68 (m, 2H); 3.03 (bs, 4H); 3.57 (s, 3H); 3.96 (t, J = 6.8 Hz, 2H); 4.81 (s, 1H); 6.72 (dd, J = 1.6 Hz, 3.2 Hz, 1H); 6.83 (d, J = 9.2 Hz, 2H); 7.19 (d, J = 3.2 Hz, 1H); 7.27 (d, J = 8.8 Hz, 2H); 7.81 (bs, 2H); 7.94 (s, 1H). |

-continued

| Ex. No | Structure/IUPAC name | NMR |
|---|---|---|
| A14 | 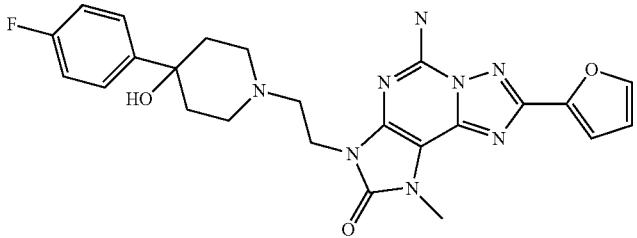 [SMILES: Cn1c(=O)n(CCN2CCC(O)(c3ccc(F)cc3)CC2)c2nc(N)n3nc(-c4ccco4)nc3c21]<br>5-Amino-3-[2-[4-(4-fluorophenyl)-4-hydroxy-1-piperidyl]ethyl]-8-(2-furyl)-1-methyl-[1,2,4]triazolo[5,1-f]purin-2-one | 1H NMR (400 MHz, DMSO): 1.54-1.57 (m, 2H); 1.80-1.85 (m, 2H); 2.42-2.45 (m, 2H); 2.66 (t, J = 6.8 Hz, 2H); 2.74-2.77 (m, 2H); 3.57 (s, 3H); 3.94 (t, J = 6.8 Hz, 2H); 4.85 (s, 1H); 6.72 (dd, J = 1.6 Hz, 3.2 Hz, 1H); 7.07-7.12 (m, 2H); 7.20 (d, J = 3.2 Hz, 1H); 7.44-7.48 (m, 2H); 7.79 (bs, 2H); 7.94 (bs, 1H). |
| A15 | 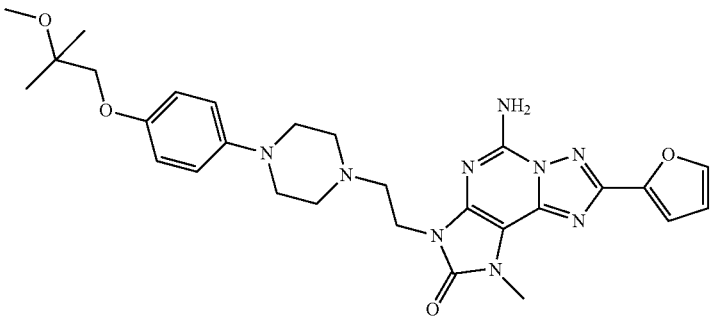 [SMILES: COC(C)(C)COc1ccc(N2CCN(CCn3c(=O)n(C)c4c3nc(N)n3nc(-c5ccco5)nc43)CC2)cc1]<br>5-Amino-8-(2-furyl)-3-[2-[4-[4-(2-methoxy-2-methyl-propoxy)phenyl]piperazin-1-yl]ethyl]-1-methyl-[1,2,4]triazolo[5,1-f]purin-2-one | $^1$HNMR (400 MHz, DMSO d6): δ 1.18 (s, 6H); 2.56(bs, 4H); 2.68 (t, J = 6.8 Hz, 2H); 2.95 (bs, 4H); 3.14 (s, 3H); 3.56 (s, 3H); 3.73 (s, 2H); 3.96 (t, J = 6.8 Hz, 2H); 6.72 (dd, J = 2 Hz, 3.6 Hz, 1H); 6.80-6.86 (m, 4H); 7.19 (d, J = 3.6 Hz, 1H); 7.81 (bs, 2H); 7.94 (d, J = 1.2 Hz, 1H). |
| A16 | 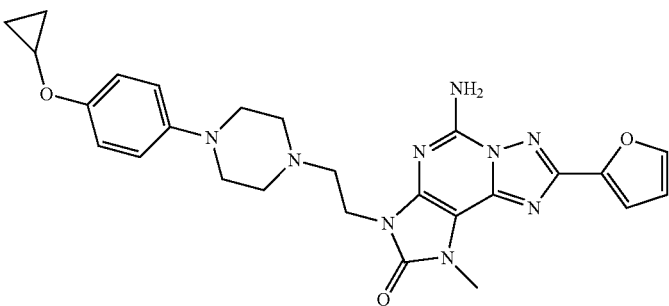 [SMILES: Cn1c(=O)n(CCN2CCN(c3ccc(OC4CC4)cc3)CC2)c2nc(N)n3nc(-c4ccco4)nc3c21]<br>5-Amino-3-[2-[4-[4-(cyclopropoxy)phenyl]piperazin-1-yl]ethyl]-8-(2-furyl)-1-methyl-[1,2,4]triazolo[5,1-f]purin-2-one | $^1$HNMR (400 MHz, DMSO d6): δ 0.57-0.61 (m, 2H); 0.69-0.74 (m, 2H); 2.56-2.62 (m, 4H); 2.68 (t, J = 6.4 Hz, 2H); 2.96 (bs, 4H); 3.56 (s, 3H); 3.70-3.75 (m, 1H); 3.96 (t, J = 6.4 Hz, 2H); 6.72 (dd, J = 1.6 Hz, 3.6 Hz, 1H); 6.84-6.91 (m, 4H); 7.19-7.20 (m, 1H); 7.81 (bs, 2H); 7.94 (bs, 1H). |
| A17 | 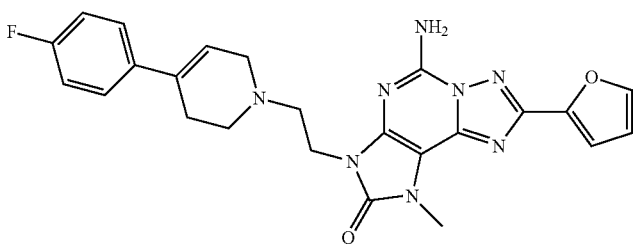 [SMILES: Cn1c(=O)n(CCN2CC=C(c3ccc(F)cc3)CC2)c2nc(N)n3nc(-c4ccco4)nc3c21]<br>5-Amino-3-[2-[4-(4-fluorophenyl)-3,6-dihydro-2H-pyridin-1-yl]ethyl]-8-(2-furyl)-1-methyl-[1,2,4]triazolo[5,1-f]purin-2-one | $^1$HNMR (400 MHz, DMSO d6): δ 2.42 (bs, 2H); 2.71-2.78 (m, 4H); 3.17(bs, 2H); 3.56 (s, 3H); 3.99 (t, J = 6.4 Hz, 2H); 6.11 (bs, 1H); 6.72 (bs, 1H); 7.14(t, J = 8.8 Hz, 2H); 7.19 (d, J = 3.2 Hz, 1H); 7.43-7.46 (m, 2H); 7.82 (bs, 2H); 7.94 (s, 1H). |

| Ex. No | Structure/IUPAC name | NMR |
|---|---|---|
| A18 | 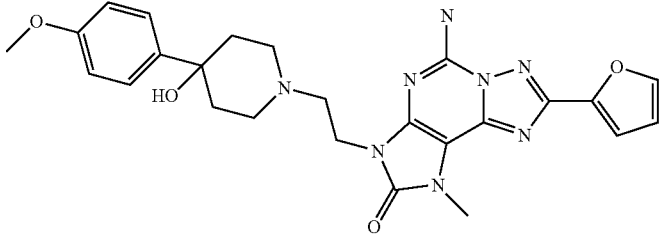 [SMILES: COc1ccc(C2(O)CCN(CCn3c(=O)n(C)c4c3nc(N)n3nc(-c5ccco5)nc43)CC2)cc1]<br>5-Amino-8-(2-furyl)-3-[2-[4-hydroxy-4-(4-methoxyphenyl)-1-piperidyl]ethyl]-1-methyl-[1,2,4]triazolo[5,1-f]purin-2-one | $^1$H NMR(400 MHz, DMSO d6): δ1.51-1.54 (m, 2H); 1.74-1.81 (m, 2H); 2.40-2.47 (m, 2H); 2.64 (t, J = 6.8 Hz, 2H); 2.69-2.72 (m, 2H); 3.55 (s, 3H); 3.69 (s, 3H); 3.92 (t, J = 6.8 Hz, 2H); 4.66 (bs, 1H); 6.71 (dd, J = 2 Hz, 3.6 Hz, 1H); 6.82 (d, J = 8.8 Hz, 2H); 7.18-7.19 (m, 1H); 7.31 (d, J = 9.2 Hz, 2H); 7.77 (bs, 2H); 7.92 (s, 1H). |
| A19 | 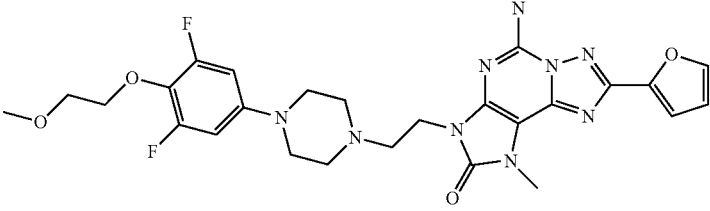 [SMILES: COCCOc1c(F)cc(N2CCN(CCn3c(=O)n(C)c4c3nc(N)n3nc(-c5ccco5)nc43)CC2)cc1F]<br>5-Amino-3-[2-[4-[3,5-difluoro-4-(2-methoxyethoxy)phenyl]piperazin-1-yl]ethyl]-8-(2-furyl)-1-methyl-[1,2,4]triazolo[5,1-f]purin-2-one | $^1$H NMR(400 MHz, DMSO d6): δ 2.57 (bs, 4H); 2.65-2.69 (m, 2H); 3.06(bs, 4H); 3.27 (s, 3H); 3.56 (t, J = 4 Hz, 5H); 3.95 (t, J = 6.4 Hz, 2H); 4.03 (t, J = 4.4 Hz, 2H); 6.64(s, 1H); 6.67 (s, 1H); 6.72(dd, J = 2 Hz, 3.6 Hz, 1H); 7.19 (d, J = 3.6 Hz, 1H); 7.81 (bs, 2H); 7.94 (s, 1H). |
| A20 | 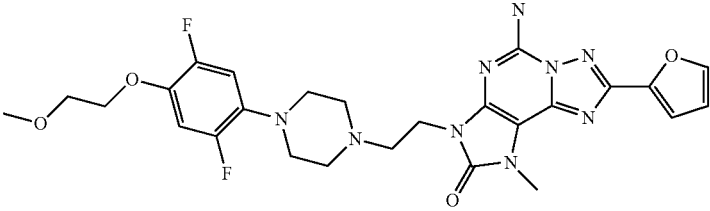 [SMILES: COCCOc1cc(F)c(N2CCN(CCn3c(=O)n(C)c4c3nc(N)n3nc(-c5ccco5)nc43)CC2)cc1F]<br>5-Amino-3-[2-[4-[2,5-difluoro-4-(2-methoxyethoxy)phenyl]piperazin-1-yl]ethyl]-8-(2-furyl)-1-methyl-[1,2,4]triazolo[5,1-f]purin-2-one | $^1$H NMR(400 MHz, DMSO d6): δ 2.61 (bs, 4H); 2.67-2.70 (m, 2H); 2.87( bs, 4H); 3.30(s, 3H); 3.57 (s, 3H); 3.61-3.63 (m, 2H); 3.95(t, J = 6.4 Hz, 2H); 4.10(t, J = 4.4 Hz, 2H); 6.72(dd, J = 1.6 Hz, 3.2 Hz, 1H); 6.90-6.95(m, 1H); 7.08-7.14(m, 1H); 7.20(d, J = 3.2 Hz, 1H); 7.80(bs, 2H); 7.94(bs, 1H). |
| A21 | 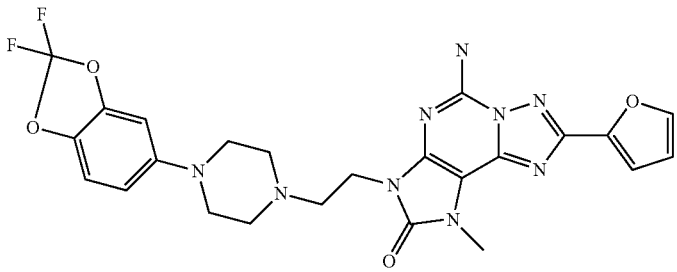 [SMILES: Cn1c(=O)n(CCN2CCN(c3ccc4c(c3)OC(F)(F)O4)CC2)c2nc(N)n3nc(-c4ccco4)nc3c21]<br>5-Amino-3-[2-[4-(2,2-difluoro-1,3-benzodioxol-5-yl)piperazin-1-yl]ethyl]-8-(2-furyl)-1-methyl-[1,2,4]triazolo[5,1-f]purin-2-one | $^1$H NMR(400 MHz, DMSO d6): δ 2.60 (bs, 4H); 2.69 (t, J = 6.4 Hz, 2H); 3.05 (bs, 4H); 3.57 (s, 3H); 3.96 (t, J = 6.8 Hz, 2H); 6.66 (dd, J = 8.8 Hz, 2.0 Hz, 1H); 6.72 (bs, 1H); 7.05 (d, J = 2.0 Hz, 1H); 7.19-7.21 (m, 2H); 7.80 (bs, 2H); 7.94 (s, 1H). |

-continued

| Ex. No | Structure/IUPAC name | NMR |
|---|---|---|
| A22 | 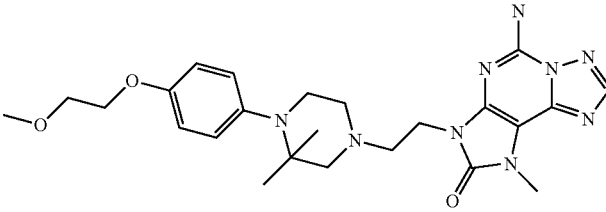<br>5-Amino-8-(2-furyl)-3-[2-[4-[4-(2-methoxyethoxy)phenyl]-3,3-dimethyl-piperazin-1-yl]ethyl]-1-methyl-[1,2,4]triazolo[5,1-f]purin-2-one | $^1$H NMR(400 MHz, DMSO d6): δ 0.98 (s, 6H); 2.63 (s, 2H); 2.76 (t, J = 4.8 Hz, 2H); 2.87 (t, J = 4.8 Hz, 2H); 2.98-3.00 (m, 2H); 3.44 (s, 3H); 3.72 (t, J = 4.8 Hz, 2H); 3.76 (s, 3H); 4.00 (t, J = 6.8 Hz, 2H); 4.06 (t, J = 4.4 Hz, 2H); 5.70 (bs, 2H); 6.60 (dd, J = 2.0 Hz, 3.6 Hz, 1H); 6.79-6.85 (m, 4H); 7.23 (d, J = 3.2 Hz, 1H); 7.64 (bs, 1H). |
| A23 | 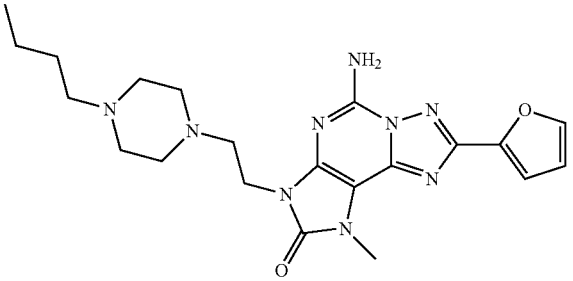 [SMILES: CCCCN1CCN(CCn2c(=O)n(C)c3c2nc(N)n2nc(-c4ccco4)nc32)CC1]<br>5-Amino-3-[2-(4-butylpiperazin-1-yl)ethyl]-8-(2-furyl)-1-methyl-[1,2,4]triazolo[5,1-f]purin-2-one | $^1$HNMR (400 MHz, DMSO d6): δ 0.86 (t, J = 7.2 Hz, 3H); 1.23-1.30 (m, 3H); 1.38 (bs, 2H); 2.21-2.45 (m, 9H); 2.61(t, J = 6.4 Hz, 2H); 3.55 (s, 3H); 3.90 (t, J = 6.8 Hz, 2H); 6.72 (dd, J = 2 Hz, 3.6 Hz, 1H); 7.20 (dd, J = 0.8 Hz, 3.6 Hz, 1H); 7.79 (bs, 2H); 7.93-7.94 (m, 1H). |
| A24 | 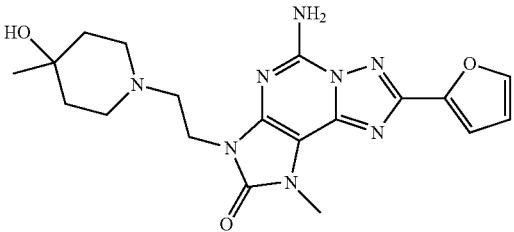 [SMILES: Cn1c(=O)n(CCN2CCC(C)(O)CC2)c2nc(N)n3nc(-c4ccco4)nc3c21]<br>5-Amino-8-(2-furyl)-3-[2-(4-hydroxy-4-methyl-1-piperidyl)ethyl]-1-methyl-[1,2,4]triazolo[5,1-f]purin-2-one | $^1$HNMR (400 MHz, DMSO d6): δ 1.06 (s, 3H); 1.37-1.40 (m, 4H); 2.40-2.46 (m, 4H); 2.60 (t, J = 6.8 Hz, 2H); 3.55 (s, 3H); 3.89 (t, J = 6.8 Hz, 2H); 4.07 (s, 1H); 6.72 (dd, J = 2 Hz, 3.6 Hz, 1H); 7.19 (d, J = 3.6 Hz, 1H); 7.78 (s, 2H); 7.93 (s, 1H) |
| A25 | 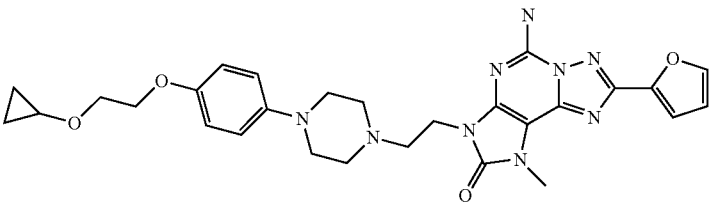 [SMILES: Cn1c(=O)n(CCN2CCN(c3ccc(OCCOC4CC4)cc3)CC2)c2nc(N)n3nc(-c4ccco4)nc3c21]<br>5-Amino-3-[2-[4-[4-[2-(cyclopropoxy)ethoxy]phenyl]piperazin-1-yl]ethyl]-8-(2-furyl)-1-methyl-[1,2,4]triazolo[5,1-f]purin-2-one | $^1$HNMR(400 MHz, DMSO d6): δ 0.41-0.46 (m, 4H), 2.59 (bs, 4H); 2.66 (t, J = 6.4 Hz, 2H); 2.94-2.95(bs, 4H); 3.55 (s, 3H); 3.69 (t, J = 4.8 Hz, 3H); 3.92-3.97 (m, 4H); 6.70 (dd, J = 2 Hz, 3.6 Hz, 1H); 6.77-6.84 (m, 4H); 7.18 (d, J = 2.8 Hz, 1H); 7.80 (bs, 2H); 7.93-7.94 (m, 1H). |

| Ex. No | Structure/IUPAC name | NMR |
|---|---|---|
| A26 | 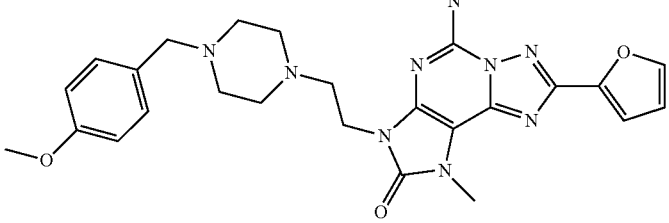<br>5-Amino-8-(2-furyl)-3-[2-[4-[(4-methoxyphenyl)methyl]piperazin-1-yl]ethyl]-1-methyl-[1,2,4]triazolo[5,1-f]purin-2-one | $^1$HNMR(400 MHz, DMSO d6): δ 2.27-2.34(m, 6H); 2.45-2.67 (m, 6H); 3.56(s, 3H); 3.72 (s, 3H); 3.89 (t, J = 6.4 Hz, 2H); 6.72 (dd, J = 1.6 Hz, 3.6 Hz, 1H); 6.86 (d, J = 8.8 Hz, 2H); 7.17 (d, J = 8.8 Hz. 2H); 7.20 (d, J = 3.6 Hz, 1H): 7.78 (bs, 2H); 7.94 (bs, 1H). |
| A27 | 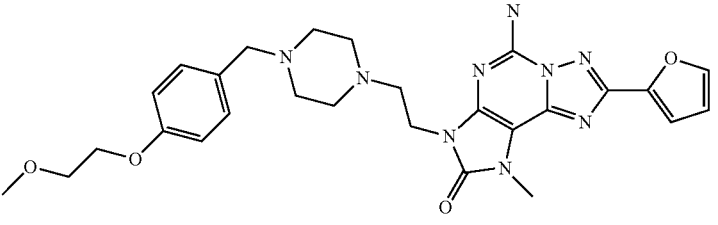 [SMILES: COCCOc1ccc(CN2CCN(CCn3c(=O)n(C)c4c3nc(N)n3nc(-c5ccco5)nc43)CC2)cc1]<br>5-Amino-8-(2-furyl)-3-[2-[4-[[4-(2-methoxyethoxy)phenyl]methyl]piperazin-1-yl]ethyl]-1-methyl-[1,2,4]triazolo[5,1-f]purin-2-one | $^1$HNMR(400 MHz, DMSO d6): δ 2.26-2.30(m, 4H); 2.57-2.65 (m, 4H); 3.27 (s, 3H); 3.28-3.36 (m, 4H); 3.54 (s, 3H); 3.62 (t, J = 4.8 Hz, 2H); 3.68 (t, J = 6.4 Hz, 2H); 4.03 (t, J = 4.8 Hz, 2H); 6.70 (bs, 1H); 6.83(s, 1H); 6.85(s, 1H); 7.13 (bs, 1H); 7.15 (s, 1H); 7.18 (d, J = 3.6 Hz, 1H); 7.76 (bs, 2H); 7.92 (s, 1H). |
| A28 | 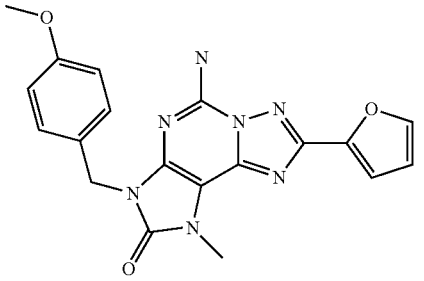 [SMILES: COc1ccc(Cn2c(=O)n(C)c3c2nc(N)n2nc(-c4ccco4)nc32)cc1]<br>5-Amino-8-(2-furyl)-3-[(4-methoxyphenyl)methyl]-1-methyl-[1,2,4]triazolo[5,1-f]purin-2-one | $^1$HNMR(400 MHz, DMSO d6): δ 3.75 (s, 3H); 3.76 (s, 3H), 5.14 (s, 2H), 5.73(bs, 2H); 6.59 (dd, J = 2 Hz, 3.6 Hz, 1H); 6.83-6.86 (m, 2H); 7.23 (d, J = 3.2 Hz, 1H); 7.43 (d, J = 8.8 Hz, 2H); 7.63(bs, 1H). |
| A29 | 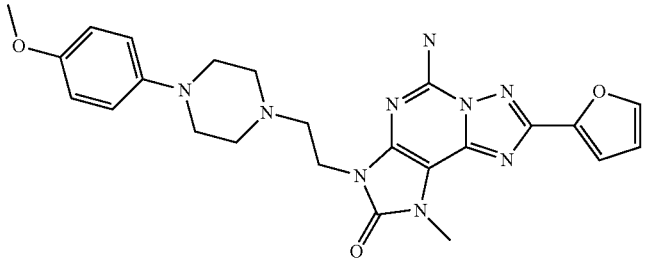 [SMILES: COc1ccc(N2CCN(CCn3c(=O)n(C)c4c3nc(N)n3nc(-c5ccco5)nc43)CC2)cc1]<br>5-Amino-8-(2-furyl)-3-[2-[4-(4-methoxyphenyl)piperazin-1-yl]ethyl]-1-methyl-[1,2,4]triazolo[5,1-f]purin-2-one | HNMR(400 MHz, DMSO d6): δ 2.61 (bs, 4H); 2.68 (bs, 2H); 2.95(bs, 4H); 3.57 (s, 3H); 3.67 (s, 3H); 3.96 (bs, 2H); 6.72 (bs, 1H); 6.78-6.86 (m, 4H); 7.19 (bs, 1H); 7.81 (bs, 2H); 7.94 (s, 1H). |

| Ex. No | Structure/IUPAC name | NMR |
|---|---|---|
| A30 | 5-Amino-8-(2-furyl)-3-[2-[4-[3-(2-methoxyethoxy)phenyl]piperazin-1-yl]ethyl]-1-methyl-[1,2,4]triazolo[5,1-f]purin-2-one | HNMR(400 MHz, DMSO d6): δ 2.59 (bs, 4H); 2.67 (t, J = 6 Hz, 2H); 3.06 (bs, 4H); 3.29(s, 3H); 3.56 (s, 3H); 3.62 (t, J = 4.4 Hz, 2H); 3.96(t, J = 6.4 Hz, 2H); 4.03 (t, J = 4.4 Hz, 2H); 6.34 (d, J = 8 Hz, 1H); 6.42 (s, 1H); 6.49(d, J = 8 Hz, 1H); 6.72 (bs, 1H); 7.07 (t, J = 8.4 Hz, 1H); 7.20(d, J = 2.8 Hz, 1H); 7.81 (bs, 2H); 7.94 (s, 1H). |
| A31 | 5-Amino-3-[2-[4-[2-fluoro-4-(2-methoxyethoxy)phenyl]piperazin-1-yl]ethyl]-8-(2-furyl)-1-methyl-[1,2,4]triazolo[5,1-f]purin-2-one | $^1$HNMR (400 MHz, DMSO d6): δ 2.62 (bs, 4H); 2.68 (t, J = 6.8 Hz, 2H); 2.85 (bs, 4H); 3.28 (s, 3H); 3.57 (s, 3H); 3.59-3.62 (m, 2H); 3.95 (t, J = 6.8 Hz, 2H); 4.01-4.04 (m, 2H); 6.66-6.68 (m, 1H); 6.72 (dd, J = 2 Hz, 3.6 Hz, 1H); 6.79 (dd, J = 2.8 Hz, 14 Hz, 1H); 6.92 (t, J = 9.6 Hz, 1H); 7.19 (d, J = 3.2 Hz, 1H); 7.93 (bs, 2H); 7.93-7.94 (m, 1H). |
| A32 | 4-[4-[2-[5-Amino-8-(2-furyl)-1-methyl-2-oxo-[1,2,4]triazolo[5,1-f]purin-3-yl]ethyl]piperazin-1-yl]benzonitrile | HNMR(400 MHz, DMSO d6): δ 2.59 (bs, 4H); 2.68(t, J = 6.4 Hz, 2H); 3.27(t, J = 4.8 Hz, 4H); 3.56 (s, 3H); 3.96 (t, J = 6.4 Hz, 2H); 6.72(dd, J = 2 Hz, 3.6 Hz, 1H); 6.99 (d, J = 8.8 Hz, 2H); 7.19 (d, J = 3.6 Hz, 1H); 7.56 (d, J = 8.8 Hz, 2H); 7.80 (bs, 2H); 7.93 (bs, 1H). |
| A33 | 4-[4-[2-[5-Amino-8-(2-furyl)-1-methyl-2-oxo-[1,2,4]triazolo[5,1-f]purin-3-yl]ethyl]piperazin-1-yl]-2-fluoro-benzonitrile. | HNMR(400 MHz, DMSO d6): δ 2.57 (bs, 4H,); 2.66-2.70 (m, 2H); 3.31 (bs, 4H,); 3.56 (s, 3H); 3.96 (t, J = 6.4 Hz, 2H); 6.72 (dd, J = 2 Hz, 3.6 Hz, 1H); 6.83 (dd, J = 2 Hz, 8.8 Hz, 1H); 6.92(d, J = 14 Hz, 1H); 7.19 (d, J = 3.2 Hz, 1H); 7.58(t, J = 8 Hz, 1H); 7.80 (bs, 2H); 7.94(s, 1H). |

| Ex. No | Structure/IUPAC name | NMR |
|---|---|---|
| A34 | 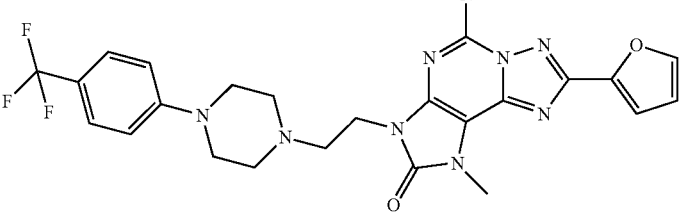<br>5-Amino-8-(2-furyl)-1-methyl-3-[2-[4-[4-(trifluoromethyl)phenyl]piperazin-1-yl]ethyl]-[1,2,4]triazolo[5,1-f]purin-2-one. | HNMR(400 MHz, DMSO d6): δ 2.61 (bs, 4H); 2.67-2.69 (m, 2H); 3.22(bs, 4H); 3.57(s, 3H); 3.97 (bs, 2H); 6.72 (bs, 1H); 7.03(d, J = 8.4 Hz, 2H); 7.19 (bs, 1H); 7.48(d, J = 8.4 Hz, 2H); 7.82 (bs, 2H); 7.94 (s, 1H). |
| A35 | 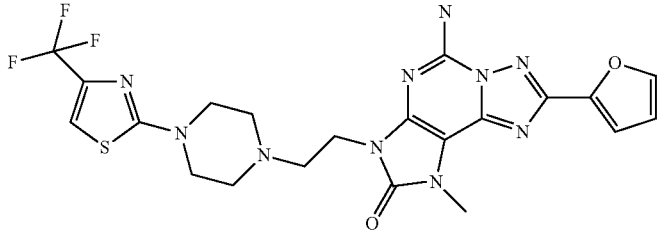 [SMILES: Cn1c(=O)n(CCN2CCN(c3nc(C(F)(F)F)cs3)CC2)c2nc(N)n3nc(-c4ccco4)nc3c21]<br>5-Amino-8-(2-furyl)-1-methyl-3-[2-[4-[4-(trifluoromethyl)thiazol-2-yl]piperazin-1-yl]ethyl]-[1,2,4]triazolo[5,1-f]purin-2-one. | HNMR(400 MHz, DMSO d6): δ 2.60 (t, J = 4.8 Hz, 4H); 2.67-2.71 (m, 2H); 3.31-3.37 (m, 4H); 3.57(s, 3H); 3.95(t, J = 6.4 Hz, 2H); 6.72 (dd, J = 2 Hz, 3.6 Hz, 1H); 7.19(d, J = 3.2 Hz, 1H); 7.54 (d, J = 0.8 Hz, 1H); 7.81 (bs, 2H); 7.93 (d, J = 0.8 Hz, 1H). |
| A36 | 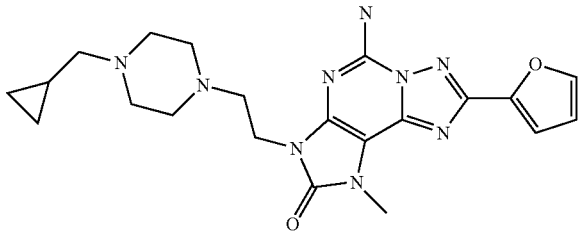 [SMILES: Cn1c(=O)n(CCN2CCN(CC3CC3)CC2)c2nc(N)n3nc(-c4ccco4)nc3c21]<br>5-Amino-3-[2-[4-(cyclopropylmethyl)piperazin-1-yl]ethyl]-8-(2-furyl)-1-methyl-[1,2,4]triazolo[5,1-f]purin-2-one | $^1$HNMR(400 MHz, CDCl$_3$): δ 0.09 (d, J = 4.4 Hz, 2H); 0.50 (d, J = 6.8 Hz, 2H); 0.82-0.89 (m, 1H); 2.24 (d, J = 6.0 Hz, 2H); 2.52-2.72 (m, 8H); 2.80 (t, J = 6.4 Hz, 2H); 3.76 (s, 3H); 4.07 (t, J = 6.8 Hz, 2H); 5.89 (bs, 2H); 6.61 (bs, 1H); 7.22 (d, J = 2.4 Hz, 1H); 7.64 (s, 1H). |
| A37 | 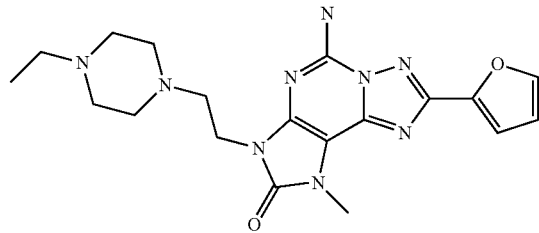 [SMILES: CCN1CCN(CCn2c(=O)n(C)c3c2nc(N)n2nc(-c4ccco4)nc32)CC1]<br>5-Amino-3-[2-(4-ethylpiperazin-1-yl)ethyl]-8-(2-furyl)-1-methyl-[1,2,4]triazolo[5,1-f]purin-2-one | $^1$HNMR(400 MHz, CDCl$_3$): δ 1.08 (t, J = 7.6 Hz, 3H); 2.39-2.41 (m, 4H); 2.45-2.52 (m, 2H); 2.62-2.66 (m, 4H); 2.78 (t, J = 6.8 Hz, 2H); 3.76 (s, 3H); 4.07 (t, J = 6.4 Hz, 2H); 5.82 (bs, 2H); 6.60 (s, 1H); 7.22 (d, J = 3.2 Hz, 1H); 7.64 (s, 1H). |

| Ex. No | Structure/IUPAC name | NMR |
|---|---|---|
| A38 | 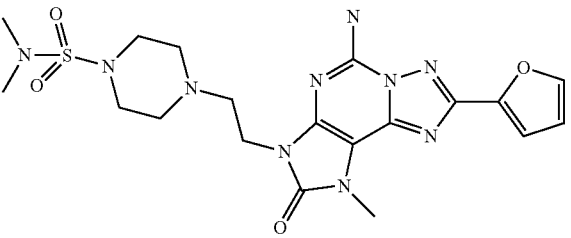 [SMILES: CN(C)S(=O)(=O)N1CCN(CCn2c(=O)n(C)c3c2nc(N)n2nc(-c4ccco4)nc32)CC1]<br>4-[2-[5-Amino-8-(2-furyl)-1-methyl-2-oxo-[1,2,4]triazolo[5,1-f]purin-3-yl]ethyl]-N,N-dimethyl-piperazine-1-sulfonamide | $^1$HNMR(400 MHz, CDCl$_3$): δ 2.62 (t, J = 4.4 Hz, 4H); 2.79 (t, J = 6.4 Hz, 2H); 2.81 (s, 6H); 3.22 (t, J = 4.4 Hz, 4H): 3.77 (s, 3H); 4.06 (t, J = 6.8 Hz, 2H); 5.74 (bs, 2H); 6.60 (dd, J = 2.0 Hz, 3.2 Hz, 1H); 7.24 (d, J = 3.6 Hz, 1H); 7.65 (s, 1H). |
| A39 | 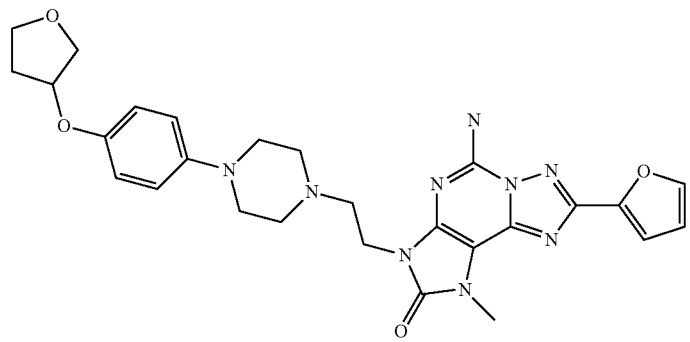 [SMILES: Cn1c(=O)n(CCN2CCN(c3ccc(OC4CCOC4)cc3)CC2)c2nc(N)n3nc(-c4ccco4)nc3c21]<br>5-Amino-8-(2-furyl)-1-methyl-3-[2-[4-(4-tetrahydrofuran-3-yloxyphenyl)piperazin-1-yl]ethyl]-[1,2,4]triazolo[5,1-f]purin-2-one | $^1$HNMR(400 MHz, DMSO d6): δ 1.89-1.94 (m, 1H); 2.09-2.18 (m, 1H); 2.60 (bs, 4H); 2.67 (t, J = 6.4 Hz, 2H); 2.96 (bs, 4H); 3.56 (s, 3H); 3.69-3.85 (m, 4H); 3.95 (t, J = 6.4 Hz, 2H); 4.89 (bs, 1H); 6.72 (dd, J = 2.0, 3.2 Hz, 1H); 6.78 (d, J = 9.2 Hz, 2H); 6.85 (d, J = 9.2 Hz, 2H); 7.20 (d, J = 3.2 Hz, 1H); 7.80 (bs, 2H); 7.93 (s, 1H). |
| A40 | 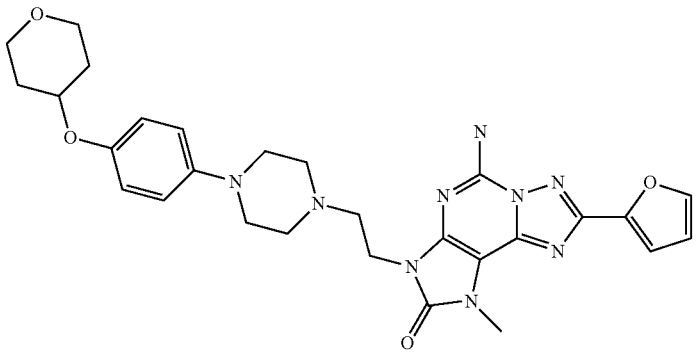 [SMILES: Cn1c(=O)n(CCN2CCN(c3ccc(OC4CCOCC4)cc3)CC2)c2nc(N)n3nc(-c4ccco4)nc3c21]<br>5-Amino-8-(2-furyl)-1-methyl-3-[2-[4-(4-tetrahydropyran-4-yloxyphenyl)piperazin-1-yl]ethyl]-[1,2,4]triazolo[5,1-f]purin-2-one | $^1$HNMR (400 MHz, DMSO d6): δ 1.47-1.56 (m, 2H); 1.88-1.92 (m, 2H); 2.60 (bs, 4H); 2.67 (t, J = 6.4 Hz, 2H); 2.95 (bs, 4H); 3.57 (s, 3H); 3.57-3.61 (m, 2H); 3.79-3.84 (m, 2H); 3.95 (t, J = 6.4 Hz, 2H); 4.38 (sep, J = 4.0 Hz, 1H); 6.72 (dd, J = 2.0, 3.6 Hz, 1H); 6.83 (s, 4H); 7.20 (d, J = 3.2 Hz, 1H): 7.79 (bs, 2H); 7.94 (s, 1H). |
| A41 | 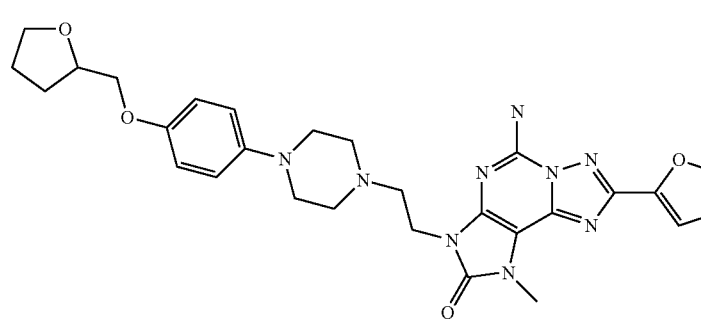<br>5-Amino-8-(2-furyl)-1-methyl-3-[2-[4-[4-(tetrahydrofuran-2-ylmethoxy)phenyl]piperazin-1-yl]ethyl]-[1,2,4]triazolo[5,1-f]purin-2-one | $^1$HNMR(400 MHz, DMSO d6): δ 1.59-1.67 (m, 1H); 1.79-1.88 (m 2H); 1.93-2.01 (m, 1H); 2.60 (bs, 4H); 2.67 (t, J = 6.4 Hz, 2H); 2.95 (bs, 4H); 3.56 (s, 3H); 3.65 (dd, J = 7.6 Hz,14.0 Hz, 1H); 3.76 (dd, J = 6.8 Hz, 14.4 Hz, 1H); 3.80-3.86 (m, 2H); 3.95 (t, J = 6.8 Hz, 2H); 4.06-4.12 (m, 1H); 6.72 (dd, J = 2.0, 3.2 Hz, 1H); 6.78-6.85 (m, 4H); 7.29 (d, J = 3.2 Hz, 1H): 7.80 (bs, 2H); 7.94 (s, 1H). |

| Ex. No | Structure/IUPAC name | NMR |
|---|---|---|
| A42 | 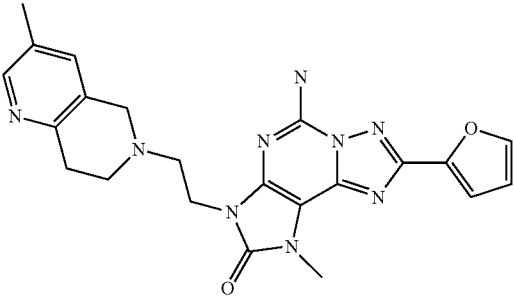 [SMILES: Cc1cnc2c(c1)CN(CCn1c(=O)n(C)c3c1nc(N)n1nc(-c4ccco4)nc31)CC2]<br>5-Amino-8-(2-furyl)-1-methyl-3-[2-(3-methyl-7,8-dihydro-5H-1,6-naphthyridin-6-yl)ethyl]-[1,2,4]triazolo[5,1-f]purin-2-one | $^1$HNMR(400 MHz, CDCl$_3$): δ 2.26 (s, 3H); 2.94-2.97 (m, 6H); 3.72 (s, 2H); 3.75 (s, 3H); 4.17 (t, J = 6.4 Hz, 2H); 5.74 (bs, 2H); 6.59 (dd, J = 1.6 Hz, 3.6 Hz, 1H); 7.13 (s, J = 3.6 Hz, 1H); 7.21-7.24 (m, 1H); 7.63 (s, 1H); 8.20 (bs, 1H), |
| A43 | 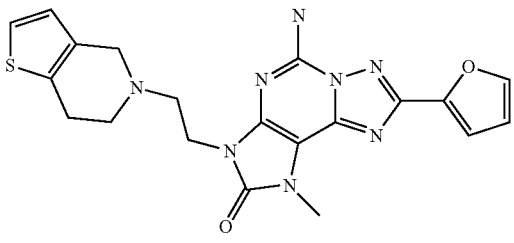 [SMILES: Cn1c(=O)n(CCN2CCc3sccc3C2)c2nc(N)n3nc(-c4ccco4)nc3c21]<br>5-Amino-3-[2-(6,7-dihydro-4H-thieno[3,2-c]pyridin-5-yl)ethyl]-8-(2-furyl)-1-methyl-[1,2,4]triazolo[5,1-f]purin-2-one | $^1$HNMR(400 MHz, DMSO d6): δ 2.74 (bs, 2H); 2.79-2.86 (m, 4H); 3.55 (s, 5H); 4.00 (t, J = 6.0 Hz, 2H); 6.72 (bs, 1H); 6.78 (d, J = 5.2 Hz, 1H); 7.19 (d, J = 3.2 Hz, 1H); 7.24 (d, J = 4.8 Hz, 1H); 7.81 (bs, 2H): 7.93 (s, 1H). |
| A44 | 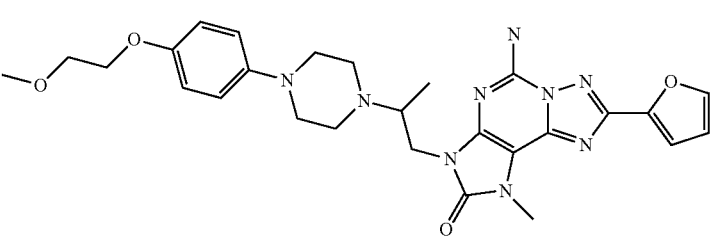 [SMILES: COCCOc1ccc(N2CCN(C(C)Cn3c(=O)n(C)c4c3nc(N)n3nc(-c5ccco5)nc43)CC2)cc1]<br>5-Amino-8-(2-furyl)-3-[2-[4-[4-(2-methoxyethoxy)phenyl]piperazin-1-yl]propyl]-1-methyl-[1,2,4]triazolo[5,1-f]purin-2-one | $^1$HNMR(400 MHz, DMSO d6): δ 0.97 (d, J = 6.4 Hz, 3H); 2.84-2.86(m, 8H); 3.23 (dd, J = 7.2 Hz, 14.0 Hz, 1H); 3.28 (s, 3H); 3.56 (s, 3H); 3.60 (t, J = 4.4 Hz, 2H); 3.69 (dd, J = 6.8 Hz, 14.0 Hz, 1H); 3.93 (dd, J = 8.4 Hz, 13.6 Hz, 1H); 3.97 (t, J = 4.4 Hz, 2H); 6.71-6.72 (m, 1H); 6.79 (q, J = 9.6 Hz, 4H); 7.19 (d, J = 3.6 Hz, 1H); 7.77 (bs, 2H); 7.93 (s, 1H). |
| A45 | 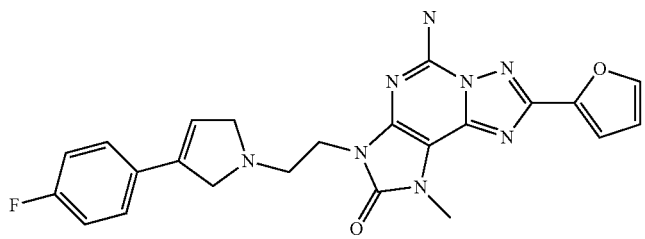 [SMILES: Cn1c(=O)n(CCN2CC=C(c3ccc(F)cc3)C2)c2nc(N)n3nc(-c4ccco4)nc3c21]<br>5-Amino-3-[2-[3-(4-fluorophenyl)-2,5-dihydropyrrol-1-yl]ethyl]-8-(2-furyl)-1-methyl-[1,2,4]triazolo[5,1-f]purin-2-one | $^1$HNMR (400 MHz, DMSO d6): δ 3.01 (t, J = 6.4 Hz, 2H); 3.56 (s, 3H); 3.66 (bs, 2H); 3.85 (bs, 2H); 3.95 (t, J = 6.4 Hz, 2H); 6.26 (s, 1H); 6.72-6.73 (m, 1H); 7.15-7.20 (m, 3H): 7.43-7.47 (m, 2H); 7.84 (bs, 2H); 7.94-7.94 (m, 1H) |

| Ex. No | Structure/IUPAC name | NMR |
|---|---|---|
| A46 | 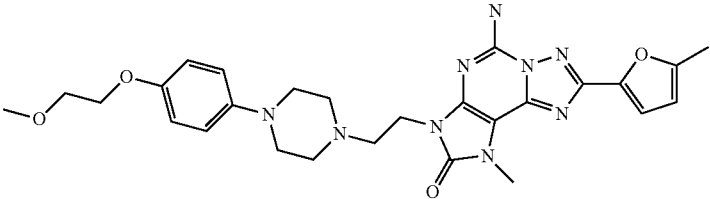<br>5-Amino-3-[2-[4-[4-(2-methoxyethoxy)phenyl]piperazin-1-yl]ethyl]-1-methyl-8-(5-methyl-2-furyl)-[1,2,4]triazolo[5,1-f]purin-2-one | $^1$HNMR(400 MHz, DMSO d6): δ 2.38 (s, 3H); 2.58 (bs, 4H); 2.66 (t, J = 5.6 Hz, 2H); 2.93 (bs, 4H); 3.27 (s, 3H); 3.54 (s, 3H); 3.57-3.59 (m, 2H); 3.91-3.97 (m, 4H); 6.31 (d, J = 2.4 Hz, 1H); 6.76-6.83 (m, 4H); 7.06 (d, J = 2.8 Hz, 1H); 7.75 (bs, 2H). |
| A47 | 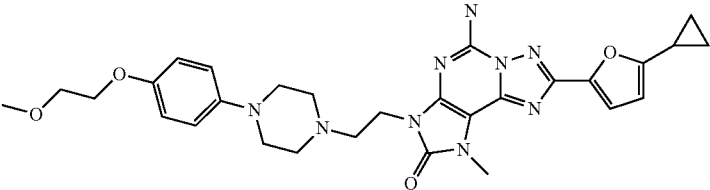 [SMILES: COCCOc1ccc(N2CCN(CCn3c(=O)n(C)c4c3nc(N)n3nc(-c5ccc(C6CC6)o5)nc43)CC2)cc1]<br>5-Amino-8-(5-cyclopropyl-2-furyl)-3-[2-[4-[4-(2-methoxyethoxy)phenyl]piperazin-1-yl]ethyl]-1-methyl-[1,2,4]triazolo[5,1-f]purin-2-one | $^1$HNMR(400 MHz, DMSO d6): δ 0.75-0.79 (m, 2H); 0.92-0.97 (m, 2H); 2.03-2.05 (m, 1H); 2.58 (bs, 4H); 2.65 (bs, 2H); 2.93 (bs, 4H); 3.27 (s, 3H); 3.53 (s, 3H); 3.59 (t, J = 4.4 Hz, 2H); 3.93-3.98 (m, 4H); 6.27 (d, J = 3.6 Hz, 1H); 6.77-6.84 (m, 4H); 7.05 (d, J = 3.6 Hz, 1H); 7.74 (bs, 2H). |
| A48 | 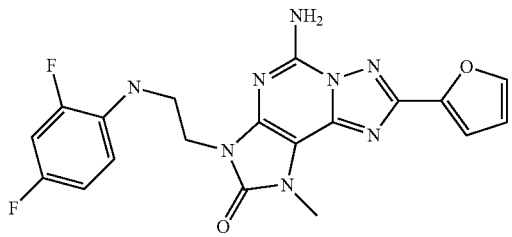 [SMILES: Cn1c(=O)n(CCNc2ccc(F)cc2F)c2nc(N)n3nc(-c4ccco4)nc3c21]<br>5-Amino-3-[2-(2,4-difluoroanilino)ethyl]-8-(2-furyl)-1-methyl-[1,2,4]triazolo[5,1-f]purin-2-one | $^1$HNMR (400 MHz, DMSO d6): δ 3.36-3.41 (m, 2H); 3.53 (s, 3H); 3.95 (t, J = 6.8 Hz, 2H); 5.6 (bs, 1H); 6.72 (dd, J = 2 Hz, 3.6 Hz, 1H); 6.82-6.92 (m, 2H); 7.00-7.07 (m, 1H); 7.18 (d, J = 3.6 Hz, 1H); 7.80 (bs, 2H); 7.92 (bs, 1H) |
| A49 | 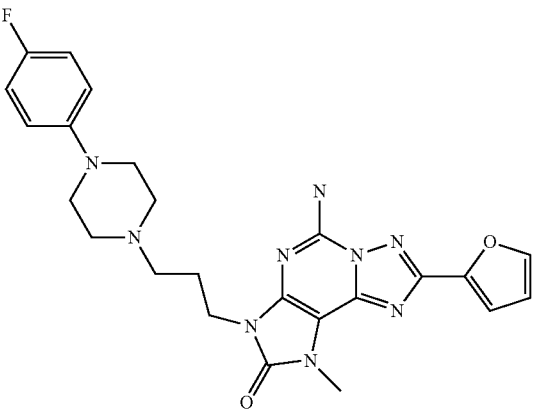 [SMILES: Cn1c(=O)n(CCCN2CCN(c3ccc(F)cc3)CC2)c2nc(N)n3nc(-c4ccco4)nc3c21]<br>5-Amino-3-[3-[4-(4-fluorophenyl)piperazin-1-yl]propyl]-8-(2-furyl)-1-methyl-[1,2,4]triazolo[5,1-f]purin-2-one | HNMR(400 MHz, CD3OD): δ 2.05 (t, J = 7.6 Hz, 2H), 2.51 (t, J = 7.2 Hz, 2H), 2.56 (t, J = 5.2 Hz, 4H); 2.98 (t, J = 5.2 Hz, 4H); 3.70(s, 3H); 4.03 (t, J = 6.4 Hz, 2H); 6.65 (dd, J = 2 Hz, 3.6 Hz, 1H); 6.89-6.92 (m, 4H); 7.25 (dd, J = 3.2 Hz, 0.8 Hz, 1H); 7.75 (d, J = 0.8 Hz, 1H). |

| Ex. No | Structure/IUPAC name | NMR |
|---|---|---|
| A50 | 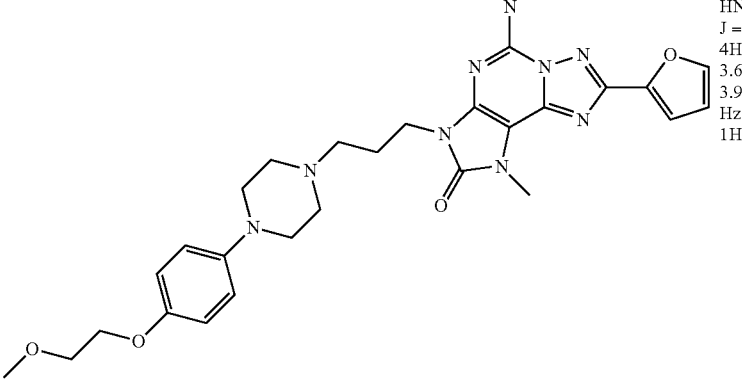<br>5-Amino-8-(2-furyl)-3-[3-[4-[4-(2-methoxyethoxy)phenyl]piperazin-1-yl]propyl]-1-methyl-[1,2,4]triazolo[5,1-f]purin-2-one | HNMR(400 MHz, DMSO d6): δ 1.89(t, J = 7.2 Hz, 2H), 2.38 (t, J = 6.4 Hz, 2H), 2.44 (bs, 4H); 2.90 (bs, 4H); 3.29 (s, 3H); 3.56 (s, 3H); 3.61 (t, J = 4.8 Hz, 2H); 3.87 (t, J = 7.2 Hz, 2H); 3.98(t, J = 4.8 Hz, 2H); 6.72 (dd, J = 2 Hz, 3.6 Hz, 1H); 6.76-6.82 (m, 4H); 7.2(d, J = 3.2 Hz, 1H); 7.80 (bs, 2H); 7.94(s, 1H). |
| A51 | 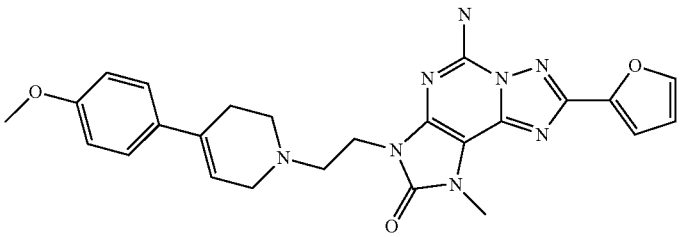 [SMILES: COc1ccc(C2=CCN(CCn3c(=O)n(C)c4c3nc(N)n3nc(-c5ccco5)nc43)CC2)cc1]<br>5-Amino-8-(2-furyl)-3-[2-[4-(4-methoxyphenyl)-3,6-dihydro-2H-pyridin-1-yl]ethyl]-1-methyl-[1,2,4]triazolo[5,1-f]purin-2-one | $^1$H NMR(400 MHz, DMSO d6): δ 2.37 (bs, 2H); 2.69(t, J = 5.2 Hz, 2H); 2.74 (t, J = 6.4 Hz, 2H); 3.13 (bs, 2H); 3.54 (s, 3H); 3.71 (s, 3H); 3.96 (t, J = 6.4 Hz, 2H); 5.99 (bs, 1H); 6.72(dd, J = 2 Hz, 3.6 Hz, 1H); 6.85 (d, J = 8.8 Hz, 2H); 7.17 (d, J = 3.6 Hz, 1H); 7.31 (d, J = 8.8 Hz, 2H); 7.79 (bs, 2H); 7.91(s, 1H). |
| A52 | 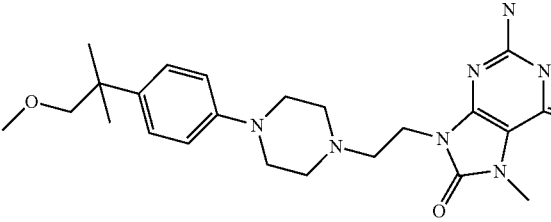<br>5-Amino-8-(2-furyl)-3-[2-[4-[4-(2-methoxy-1,1-dimethyl-ethyl)phenyl]piperazin-1-yl]ethyl]-1-methyl-[1,2,4]triazolo[5,1-f]purin-2-one | $^1$HNMR (400 MHz, DMSO d6): δ 1.20 (bs, 6H); 2.60 (bs, 4H); 2.68 (t, J = 6.8 Hz, 2H); 3.03 (bs, 4H); 3.19 (s, 3H); 3.27 (s, 2H); 3.56 (s, 3H); 3.96 (t, J = 6.4 Hz, 2H); 6.72 (dd, J = 2 Hz, 3.6 Hz, 1H); 6.82 (d, J = 8.4 Hz, 2H); 7.17-7.20 (m, 3H); 7.80 (bs, 2H); 7.94 (s, 1H). |
| A53 | 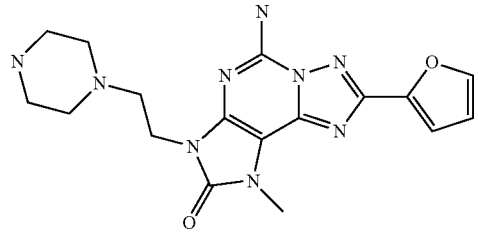 [SMILES: Cn1c(=O)n(CCN2CCNCC2)c2nc(N)n3nc(-c4ccco4)nc3c21]<br>5-Amino-8-(2-furyl)-1-methyl-3-(2-piperazin-1-ylethyl)-[1,2,4]triazolo[5,1-f]purin-2-one | $^1$HNMR (400 MHz, DMSO d6): δ 2.35 (bs, 4H); 2.57 (t, J = 6.8 Hz, 2H); 2.60-2.63 (m, 4H); 3.56 (s, 3H); 3.90 (t, J = 6.8 Hz, 2H); 6.72 (dd, J = 2 Hz, 3.6 Hz, 1H); 7.19 (d, J = 2.8 Hz, 1H); 7.79 (bs, 2H); 7.94 (d, J = 1.2 Hz, 1H). |

| Ex. No | Structure/IUPAC name | NMR |
|---|---|---|
| A54 | 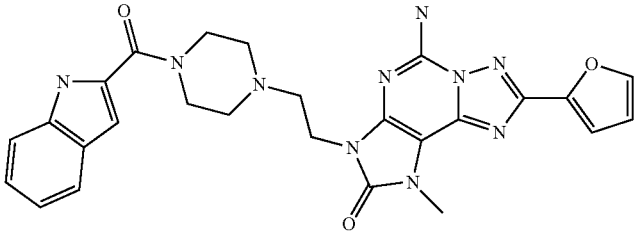 [SMILES: Cn1c(=O)n(CCN2CCN(C(=O)c3cc4ccccc4[nH]3)CC2)c2nc(N)n3nc(-c4ccco4)nc3c21]<br>5-Amino-8-(2-furyl)-3-[2-[4-(1H-indole-2-carbonyl)piperazin-1-yl]ethyl]-1-methyl-[1,2,4]triazolo[5,1-f]purin-2-one | $^1$HNMR (400 MHz, DMSO d6): δ 2.55 (bs, 4H); 2.68 (t, J = 6 Hz, 2H); 2.84 (s, 3H); 3.69 (bs, 4H); 3.96 (t, J = 6 Hz, 2H); 6.72 (dd, J = 2 Hz, 3.6 Hz, 1H); 6.75 (s, 1H); 7.03 (t, J = 8 Hz, 1H); 7.15-7.20 (m, 2H); 7.40 (d, J = 8.4 Hz, 1H); 7.59 (d, J = 8 Hz, 1H); 7.81 (bs, 2H); 7.94 (d, J = 1.6 Hz, 1H), 11.59(bs, 1H). |
| A55 | 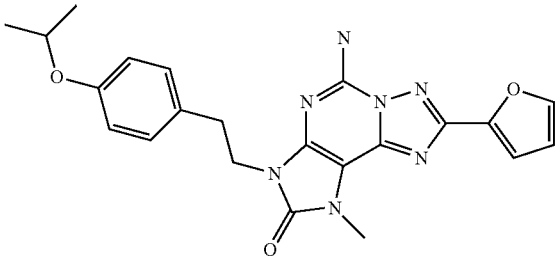 [SMILES: CC(C)Oc1ccc(CCn2c(=O)n(C)c3c2nc(N)n2nc(-c4ccco4)nc32)cc1]<br>5-Amino-8-(2-furyl)-3-[2-(4-isopropoxyphenyl)ethyl]-1-methyl-[1,2,4]triazolo[5,1-f]purin-2-one | HNMR(400 MHz, DMSO d6): δ 1.21 (d, J = 6 Hz, 6H); 2.95 (t, J = 7.6 Hz, 2H); 3.55 (s, 3H); 3.98 (t, J = 7.6 Hz, 2H); 4.50-4.56 (m, 1H), 6.73 (bs, 1H); 6.81 (d, J = 8.4 Hz, 2H); 7.09 (d, J = 8.4 Hz, 2H); 7.20 (d, J = 2.4 Hz, 1H); 7.81 (bs, 2H), 7.94 (s, 1H). |
| A56 | 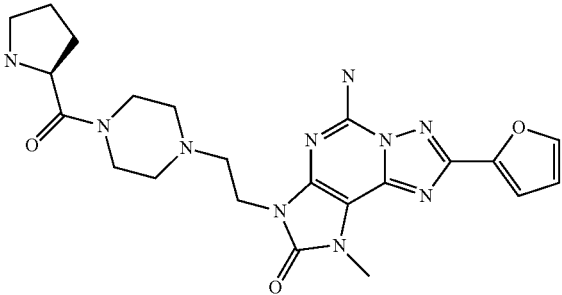 [SMILES: Cn1c(=O)n(CCN2CCN(C(=O)[C@@H]3CCCN3)CC2)c2nc(N)n3nc(-c4ccco4)nc3c21]<br>5-Amino-8-(2-furyl)-1-methyl-3-[2-[4-[(2S)-pyrrolidine-2-carbonyl]piperazin-1-yl]ethyl]-[1,2,4]triazolo[5,1-f]purin-2-one | $^1$HNMR (400 MHz, DMSO d6): δ 1.51-1.59 (m, 2H); 1.66-1.71 (m, 1H); 1.98-2.03 (m, 1H); 2.41-2.49 (m, 4H); 2.63-2.70 (m, 3H); 2.98-3.03 (m, 1H); 3.37-3.42 (m, 4H); 3.56 (s, 3H); 3.88 (t, J = 7.6 Hz, 1H); 3.93 (t, J = 6.4 Hz, 2H); 6.72 (dd, J = 2 Hz, 3.6 Hz, 1H); 7.20 (d, J = 3.2 Hz, 1H); 7.80 (bs, 2H); 7.92-7.94 (m, 1H). |
| A57 | 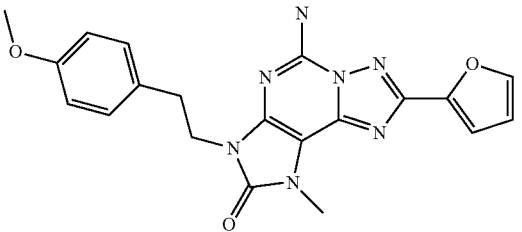 [SMILES: COc1ccc(CCn2c(=O)n(C)c3c2nc(N)n2nc(-c4ccco4)nc32)cc1]<br>5-Amino-8-(2-furyl)-3-[2-(4-methoxyphenyl)ethyl]-1-methyl-[1,2,4]triazolo[5,1-f]purin-2-one | HNMR(400 MHz, DMSO d6): δ 2.95 (t, J = 8 Hz, 2H); 3.52 (s, 3H); 3.69 (s, 3H), 3.97 (t, J = 8 Hz, 2H); 6.71 (dd, J = 2 Hz, 3.6 Hz, 1H); 6.80 (dd, J = 2 Hz, 6.8 Hz, 2H); 7.10 (d, J = 8.8 Hz, 2H); 7.18 (dd, J = 0.8 Hz, 3.2 Hz, 1H); 7.80 (bs, 2H), 7.94 (dd, J = 1 Hz, 2 Hz, 1H). |

-continued

| Ex. No | Structure/IUPAC name | NMR |
|---|---|---|
| A58 | 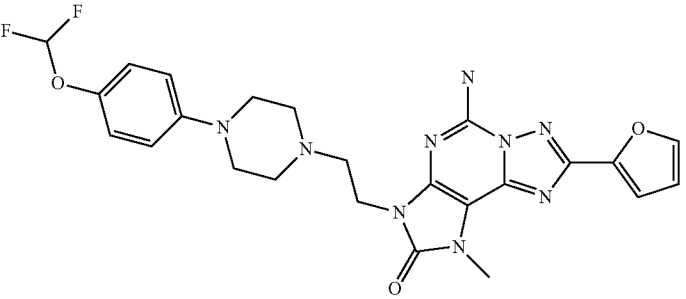 [SMILES: Cn1c(=O)n(CCN2CCN(c3ccc(OC(F)F)cc3)CC2)c2nc(N)n3nc(-c4ccco4)nc3c21]<br>5-amino-3-[2-[4-[4-(difluoromethoxy)phenyl]piperazin-1-yl]ethyl]-8-(2-furyl)-1-methyl-[1,2,4]triazolo[5,1-f]purin-2-one | HNMR(400 MHz, DMSO d6): δ 2.61 (bs, 4H); 2.68 (bs, 2H); 3.05(bs, 4H); 3.57 (s, 3H), 3.96 (bs, 2H); 6.72 (bs, 1H); 6.92 (d, J = 8 Hz, 2H); 7.01 (d, J = 10 Hz, 2H); 7.03(d, J = 148 Hz, 1H); 7.19 (bs, 1H); 7.80 (bs, 2H); 7.94 (s, 1H). |
| A59 | 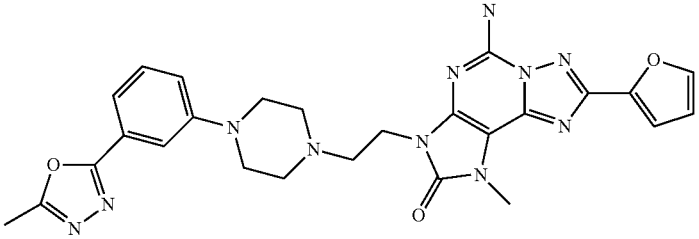 [SMILES: Cc1nnc(-c2cccc(N3CCN(CCn4c(=O)n(C)c5c4nc(N)n4nc(-c6ccco6)nc54)CC3)c2)o1]<br>5-Amino-8-(2-furyl)-1-methyl-3-[2-[4-[3-(5-methyl-1,3,4-oxadiazol-2-yl)phenyl]piperazin-1-yl]ethyl]-[1,2,4]triazolo[5,1-f]purin-2-one | $^1$HNMR (400 MHz, DMSO d6): δ 2.57 (s, 3H); 2.64 (bs, 4H); 2.70 (t, J = 6.8 Hz, 2H); 3.17 (bs, 4H); 3.56 (s, 3H); 3.97 (t, J = 6.8 Hz, 2H); 6.72 (dd, J = 1.6 Hz, 3.6 Hz, 1H); 7.15-7.17 (m, 1H); 7.19 (d, J = 3.2 Hz, 1H); 7.33-7.41 (m, 3H); 7.81 (bs, 2H); 7.94(bs, 1H). |
| A60 | 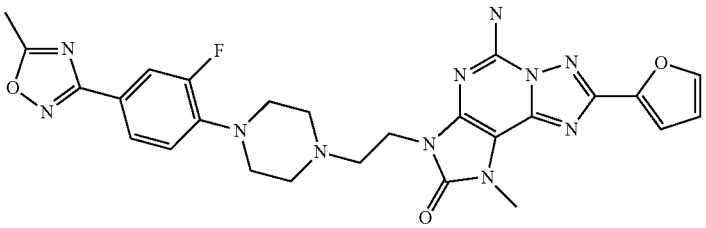 [SMILES: Cc1nc(-c2ccc(N3CCN(CCn4c(=O)n(C)c5c4nc(N)n4nc(-c6ccco6)nc54)CC3)c(F)c2)no1]<br>5-Amino-3-[2-[4-[2-fluoro-4-(5-methyl-1,2,4-oxadiazol-3-yl)phenyl]piperazin-1-yl]ethyl]-8-(2-furyl)-1-methyl-[1,2,4]triazolo[5,1-f]purin-2-one | $^1$HNMR (400 MHz, DMSO d6): δ 2.62 (s, 3H); 2.64 (bs, 4H); 2.69 (t, J = 6.4 Hz, 2H); 3.07 (bs, 4H); 3.56 (s, 3H); 3.95 (t, J = 6.8 Hz, 2H); 6.72 (dd, J = 1.6 Hz, 3.6 Hz, 1H); 7.12 (t, J = 8.8 Hz, 1H); 7.18 (d, J = 2.8 Hz, 1H); 7.59-7.63 (m, 1H); 7.69-7.72 (m, 1H); 7.78 (bs, 2H); 7.92-7.93 (m, 1H). |
| A61 | 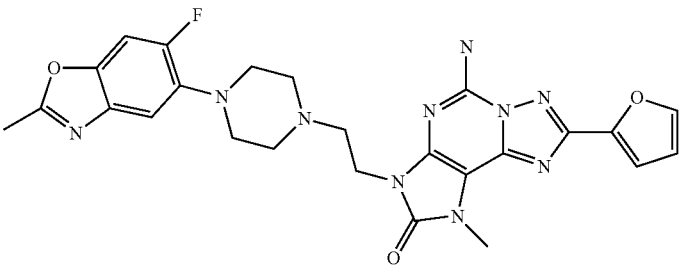 [SMILES: Cc1nc2cc(N3CCN(CCn4c(=O)n(C)c5c4nc(N)n4nc(-c6ccco6)nc54)CC3)c(F)cc2o1]<br>5-Amino-3-[2-[4-(6-fluoro-2-methyl-1,3-benzoxazol-5-yl)piperazin-1-yl]ethyl]-8-(2-furyl)-1-methyl-[1,2,4]triazolo[5,1-f]purin-2-one | $^1$HNMR (400 MHz, DMSO d6): δ 2.56 (s, 3H); 2.67 (bs, 4H); 2.70 (t, J = 6.8 Hz, 2H); 2.94 (bs, 4H); 3.57 (s, 3H); 3.96 (t, J = 6.8 Hz, 2H); 6.72 (dd, J = 1.6 Hz, 3.6 Hz, 1H); 7.20 (dd, J = 1.2 Hz, 3.6 Hz, 1H); 7.26 (d, J = 8 Hz, 1H); 7.61 (d, J = 11.2 Hz, 1H); 7.80 (bs, 2H); 7.93-7.94 (m, 1H) |

| Ex. No | Structure/IUPAC name | NMR |
|---|---|---|
| A62 | 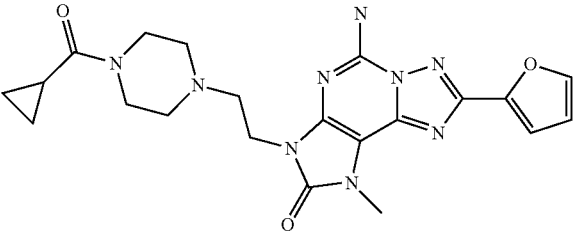 [SMILES: Cn1c(=O)n(CCN2CCN(C(=O)C3CC3)CC2)c2nc(N)n3nc(-c4ccco4)nc3c21]  5-Amino-3-[2-[4-(cyclopropanecarbonyl)piperazin-1-yl]ethyl]-8-(2-furyl)-1-methyl-[1,2,4]triazolo[5,1-f]purin-2-one | $^1$HNMR (400 MHz, DMSO d6): δ 0.66-0.70 (m, 4H); 1.90-1.94 (m, 1H); 2.41 (bs, 4H); 2.65 (t, J = 6 Hz, 2H); 3.38 (bs, 2H); 3.56 (bs, 5H); 3.93 (t, J = 6.4 Hz, 2H); 6.71 (bs, 1H); 7.19 (d, J = 2.4 Hz, 1H); 7.79 (bs, 2H); 7.93 (bs, 1H). |
| A63 | 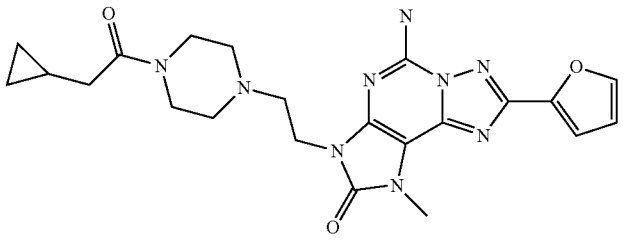 [SMILES: Cn1c(=O)n(CCN2CCN(C(=O)CC3CC3)CC2)c2nc(N)n3nc(-c4ccco4)nc3c21]  5-Amino-3-[2-[4-(2-cyclopropylacetyl)piperazin-1-yl]ethyl]-8-(2-furyl)-1-methyl-[1,2,4]triazolo[5,1-f]purin-2-one | $^1$HNMR (400 MHz, DMSO d6): δ 0.07-0.10 (m, 2H); 0.40-0.44 (m, 2H); 0.88-0.94 (m, 1H); 2.21 (d, J = 6.4 Hz, 2H); 2.41-2.45 (m, 4H); 2.64 (t, J = 6.4 Hz, 2H); 3.38 (bs, 4H); 3.56 (s, 3H); 3.93 (t, J = 6.4 Hz, 2H); 6.72 (dd, J = 2 Hz, 3.6 Hz, 1H); 7.19-7.20 (m, 1H); 7.80 (bs, 2H); 7.93 (d, J = 0.8 Hz, 1H). |

Example B1

5-Amino-8-(2-furyl)-3-[2-[4-[4-(2-hydroxyethoxy)phenyl]piperazin-1-yl]ethyl]-1-methyl-[1,2,4]triazolo[5,1-f]purin-2-one

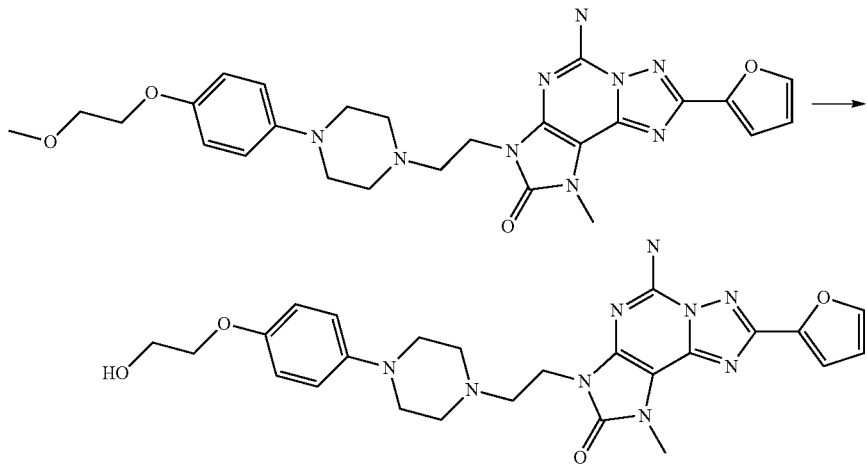

To a solution of compound 5-amino-8-(2-furyl)-3-[2-[4-[4-(2-methoxyethoxy)phenyl]piperazin-1-yl]ethyl]-1-methyl-[1,2,4]triazolo[5,1-f]purin-2-one (Example A1) (0.075 g, 0.140 mmol), in DCM (10 ml) was added BBr$_3$ (0.15 ml, 0.154 mmol) drop wise at 0° C. and stirred at 25° C. for 20 hours. The reaction mixture was quenched with sat. NaHCO$_3$ (25 ml) and extracted with DCM (3×20 ml). The crude product was purified by column chromatography to obtain 5-amino-8-(2-furyl)-3-[2-[4-[4-(2-hydroxyethoxy)phenyl]piperazin-1-yl]ethyl]-1-methyl-[1,2,4]triazolo[5,1-f]purin-2-one (70 mg, 90%) as an off white solid HNMR (400 MHz, DMSO d6): δ 2.60 (bs, 4H); 2.67 (t, J=6 Hz, 2H); 2.95 (bs, 4H); 3.55 (s, 3H); 3.65 (q, J=5.2 Hz, 2H); 3.87 (t, J=5.2 Hz, 2H); 3.95 (t, J=6.4 Hz, 2H); 4.8 (t, J=5.2 Hz, 1H); 6.71-6.72 (m, 1H); 6.78-6.85 (m, 4H); 7.19 (d, J=2.8 Hz, 1H); 7.79 (bs, 2H); 7.93 (bs, 1H).

Examples B2 were prepared by following similar experimental procedure of Example B1 using the appropriate intermediates

| B2 | 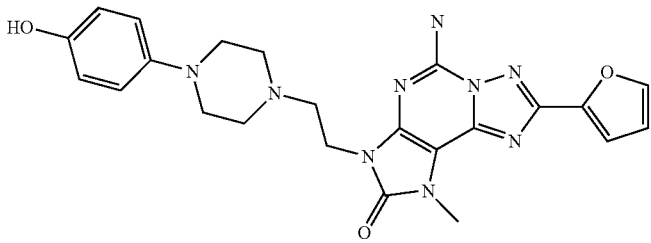 [SMILES: Cn1c(=O)n(CCN2CCN(c3ccc(O)cc3)CC2)c2nc(N)n3nc(-c4ccco4)nc3c21] 5-Amino-8-(2-furyl)-3-[2-[4-(4-hydroxyphenyl)piperazin-1-yl]ethyl]-1-methyl-[1,2,4]triazolo[5,1-f]purin-2-one | $^1$HNMR(400 MHz, DMSO d6): δ 2.59 (bs, 4H); 2.67 (t, J = 6.4 Hz, 2H); 2.90 (bs, 4H); 3.56 (s, 3H); 3.95 (t, J = 6.4 Hz, 2H); 6.62 (d, J = 8.8 Hz, 2H); 6.72-6.74 (m, 1H); 6.74 (d, J = 9.2 Hz, 2H); 7.19 (d, J = 3.2 Hz, 1H); 7.80 (bs, 2H): 7.94 (bs, 1H); 8.80 (s, 1H). |

Example C1

5-Amino-1-(cyclopropylmethyl)-3-[2-[4-(4-ethoxyphenyl)piperazin-1-yl]ethyl]-8-(2-furyl)-[1,2,4]triazolo[5,1-f]purin-2-one

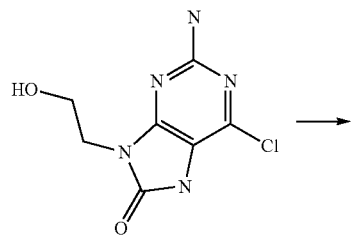

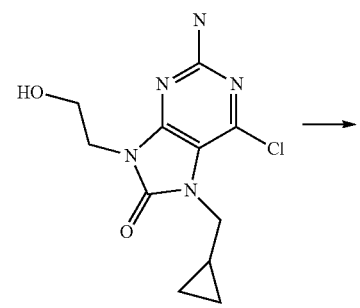

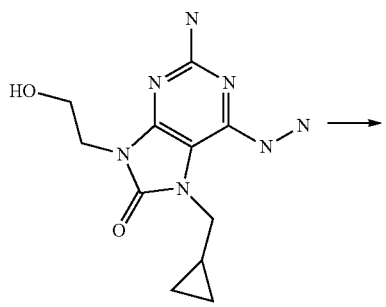

-continued

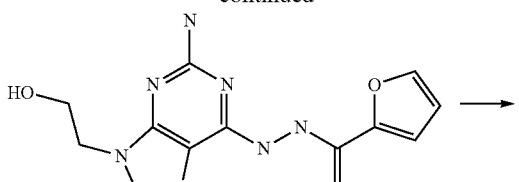

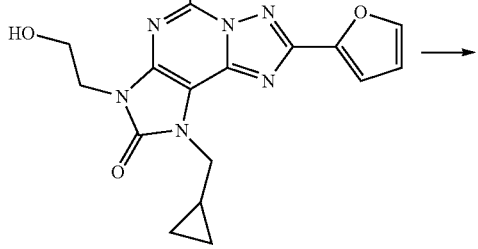

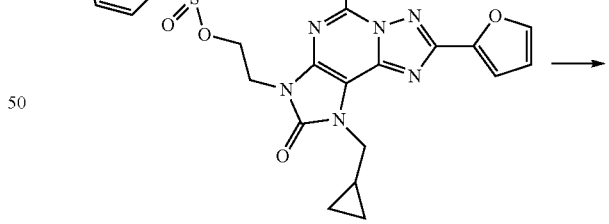

Step-1: 2-Amino-6-chloro-7-(cyclopropylmethyl)-9-(2-hydroxyethyl)purin-8-one (Procedure is Same as Step-3 in Example A1)

¹HNMR (400 MHz, DMSO d6): δ 0.35-0.39 (m, 2H); 0.41-0.49 (m, 2H); 1.16-1.23 (m, 1H); 3.63-3.67 (m, 2H); 3.77-3.81 (m, 4H); 4.87 (t, J=5.2 Hz, 1H); 6.71 (bs, 2H)

Step-2: 2-Amino-7-(cyclopropylmethyl)-6-hydrazino-9-(2-hydroxyethyl)purin-8-one (Procedure is Same as Step-4 in Example A1)

¹HNMR (400 MHz, DMSO d6): δ 0.28-0.30 (m, 2H); 0.35-0.37 (m, 2H); 1.00-1.04 (m, 1H), 3.57-3.66 (m, 2H); 3.72-3.79 (m, 4H); 4.33 (bs, 2H); 4.88 (t, J=5.6 Hz, 1H); 6.00 (bs, 2H); 7.52 (bs, 1H).

Step-3: N'-[2-Amino-7-(cyclopropylmethyl)-9-(2-hydroxyethyl)-8-oxo-purin-6-yl]furan-2-carbohydrazide (Procedure is Same as Step-5 in Example A1)

Crude product was used in next step

Step-4: 5-Amino-1-(cyclopropylmethyl)-8-(2-furyl)-3-(2-hydroxyethyl)-[1,2,4]triazolo[5,1-f]purin-2-one (Procedure is Same as Step-6 in Example A1)

¹HNMR (400 MHz, DMSO d6): δ 0.46 (d, J=6.8 Hz, 4H); 1.34-1.36 (m, 1H), 3.69-3.72 (m, 2H); 3.85-3.90 (m, 4H); 4.90 (t, J=5.6 Hz, 1H); 6.72 (bs, 1H); 7.19 (d, J=3.2 Hz, 1H); 7.81 (bs, 2H); 7.95 (s, 1H).

Step-5: 2-[5-Amino-1-(cyclopropylmethyl)-8-(2-furyl)-2-oxo-[1,2,4]triazolo[5,1-t]purin-3-yl]ethyl 4-methylbenzenesulfonate (Procedure is Same as Step-7 in Example A1)

¹HNMR (400 MHz, DMSO d6): δ 0.51 (d, J=7.6 Hz, 4H); 1.34-1.36 (m, 1H); 1.99 (s, 3H); 3.79 (d, J=7.2 Hz, 2H); 4.02 (t, J=4.8 Hz, 2H); 4.47 (t, J=4.8 Hz, 2H); 6.73-6.75 (m, 1H); 6.99 (d, J=8 Hz, 2H); 7.22-7.23 (m, 1H); 7.42 (d, J=8 Hz, 2H); 7.77 (bs, 2H); 7.97 (bs, 1H).

Step-6: 5-Amino-1-(cyclopropylmethyl)-3-[2-[4-(4-ethoxyphenyl)piperazin-1-yl]ethyl]-8-(2-furyl)-[1,2,4]triazolo[5,1-f]purin-2-one (Procedure is Same as Step-8 in Example A1)

¹HNMR (400 MHz, DMSO d6): δ 0.46 (bs, 4H); 1.27 (t, J=6.4 Hz, 3H); 1.29 (bs, 1H); 2.59 (bs, 4H); 2.69 (s, 2H); 2.93 (bs, 4H); 3.85-3.97 (m, 6H); 6.72 (bs, 1H); 6.76-6.82 (m, 4H); 7.19 (bs, 1H); 7.82 (bs, 2H); 7.94 (s, 1H).

Examples C2-C4 was prepared by following similar experimental procedure of Example C1 using the appropriate intermediates

| Ex. No | Structure/IUPAC name | NMR |
|---|---|---|
| C2 | 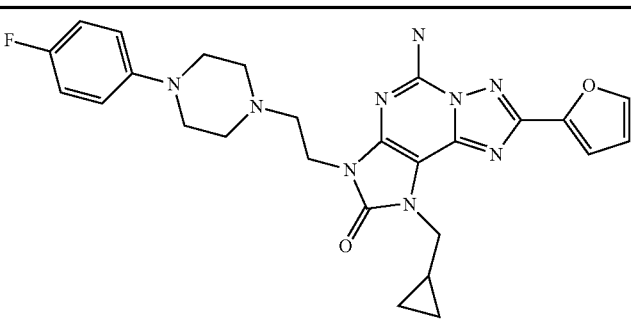<br>5-Amino-1-(cyclopropylmethyl)-3-[2-[4-(4-fluorophenyl)piperazin-1-yl]ethyl]-8-(2-furyl)-[1,2,4]triazolo[5,1-f]purin-2-one | ¹HNMR (400 MHz, DMSO d6): δ 0.44 (d, J = 8 Hz, 4H); 1.32-1.35 (m, 1H); 2.60 (bs, 4H); 2.70 (t, J = 7.6 Hz, 2H); 3.00 (bs, 4H); 3.86 (d, J = 7.2 Hz, 2H); 3.98 (t, J = 6.8 Hz, 2H); 6.72 (bs, 1H); 6.89-6.93 (m, 2H); 7.00-7.05 (m, 2H); 7.19 (d, J = 3.6 Hz, 1H); 7.83 (bs, 2H); 7.94 (s, 1H). |

| Ex. No | Structure/IUPAC name | NMR |
|---|---|---|
| C3 | 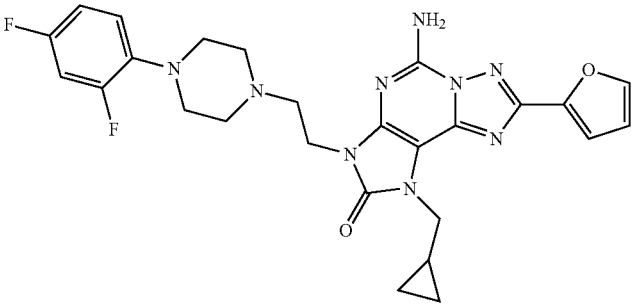 [SMILES: Nc1nc2c(c3nc(-c4ccco4)nn13)n(CC1CC1)c(=O)n2CCN1CCN(c2ccc(F)cc2F)CC1]

5-Amino-1-(cyclopropylmethyl)-3-[2-[4-(2,4-difluorophenyl)piperazin-1-yl]ethyl]-8-(2-furyl)-[1,2,4]triazolo[5,1-f]purin-2-one | $^1$H NMR(400 MHz, DMSO d6): δ 0.44-0.47 (m, 4H); 1.32-1.37 (m, 1H); 2.62 (bs, 4H); 2.71 (t, J = 6.4 Hz, 2H); 2.89 (bs, 4H); 3.87 (d, J = 7.2 Hz, 2H); 3.97 (t, J = 6.4 Hz, 2H); 6.72 (dd, J = 2 Hz, 3.2 Hz, 1H); 6.94-7.04 (m, 2H); 7.17-7.21 (m, 2H); 7.81 (bs, 2H); 7.94 (bs, 1H). |
| C4 | 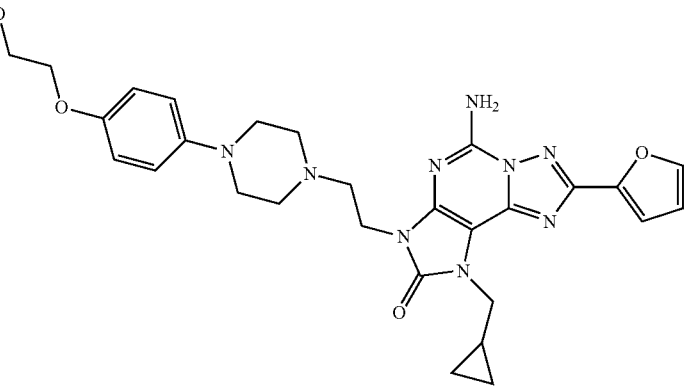

5-Amino-1-(cyclopropylmethyl)-8-(2-furyl)-3-[2-[4-[4-(2-methoxyethoxy)phenyl]piperazin-1-yl]ethyl]-[1,2,4]triazolo[5,1-f]purin-2-one | $^1$H NMR(400 MHz, DMSO d6): δ 0.43-0.46 (m, 4H); 1.32-1.37 (m, 1H); 2.57-2.62 (m, 4H); 2.68-2.72 (m, 2H); 2.92-2.96 (m, 4H); 3.29 (s, 3H); 3.58-3.62 (m, 2H); 3.86 (d, J = 7.2 Hz, 2H); 3.96-3.99 (m, 4H); 6.72 (dd, J = 1.6 Hz, 3.6 Hz, 1H); 6.78-6.85 (m, 4H); 7.18 (d, J = 3.2 Hz, 1H); 7.82 (bs, 2H); 7.94 (bs, 1H). |

Example D1

5-Amino-1-(cyclopropylmethyl)-3-[2-(4-fluorophenoxy)ethyl]-8-(2-furyl)-[1,2,4]triazolo[5,1-f]purin-2-one

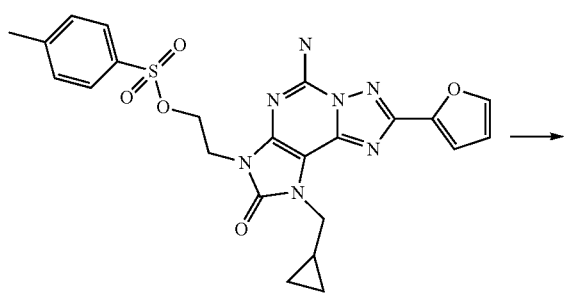 → 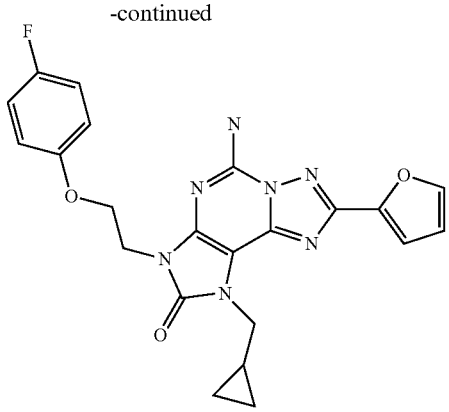

A mixture of 2-[5-amino-1-(cyclopropylmethyl)-8-(2-furyl)-2-oxo-[1,2,4]triazolo[5,1-f]purin-3-yl]ethyl 4-methylbenzenesulfonate obtained in step 7 of C1 (0.045 g, 0.088 mmol), 4-fluorophenol (0.018 g, 0.176 mmol) and K$_2$CO$_3$ (0.036 g, 0.22 mmol) were taken in DMF (2 ml) and stirred at 80° C. for 16 hours. To the reaction mixture water (25 ml) was added and extracted with ethyl acetate (3×20 ml). The crude product was purified by column chromatography to 5-amino-1-(cyclopropylmethyl)-3-[2-(4-fluorophenoxy)ethyl]-8-(2-furyl)-[1,2,4]triazolo[5,1-f]purin-2-one (8 mg, 20%) as an off white solid ¹HNMR (400 MHz, DMSO d6): δ 0.46 (d, J=8.4 Hz, 4H); 1.32-1.36 (m, 1H); 3.86 (d, J=7.2 Hz, 2H); 4.18 (t, J=5.6 Hz, 2H); 4.30 (t, J=6 Hz, 2H); 6.72-6.73 (m, 1H); 6.90-6.94 (m, 2H); 7.06-7.11 (m, 2H); 7.19 (d, J=3.2 Hz, 1H); 7.87 (bs. 2H); 7.95 (d, J=0.8 Hz, 1H).

Examples D2-D3 was prepared by following similar experimental procedure of Example D1 using the appropriate intermediates

| D2 | 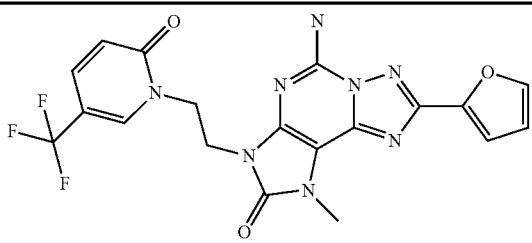 | ¹H NMR(400 MHz, DMSO d6): δ 3.50 (s, 3H); 4.12-4.17 (m, 2H); 4.23-4.28 (m, 2H); 6.49 (d, J = 9.6 Hz, 1H); 6.72 (dd, J = 2 Hz, 3.2 Hz, 1H); 7.20 (d, J = 3.2 Hz, 1H); 7.54 (dd, J = 9.6 Hz, 2.8 Hz, 1H); 7.70 (bs, 2H); 7.93 (s, 1H); 7.94 (s, 1H). |
|---|---|---|
| | 5-Amino-8-(2-furyl)-1-methyl-3-[2-[2-oxo-5-(trifluoromethyl)-1-pyridyl]ethyl]-[1,2,4]triazolo[5,1-f]purin-2-one | |
| D3 | 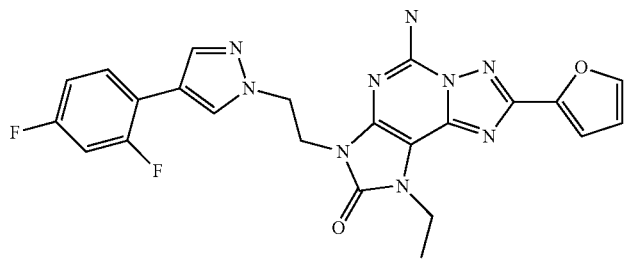 [SMILES: CCn1c(=O)n(CCn2cc(-c3ccc(F)cc3F)cn2)c2nc(N)n3nc(-c4ccco4)nc3c21] | ¹H NMR(400 MHz, DMSO): δ 1.27 (t, J = 6.8 Hz, 3H); 3.97 (q, J = 6.8 Hz, 2H); 4.21 (bs, 2H); 4.55 (bs, 2H); 6.72 (bs, 1H); 7.07 (t, J = 8 Hz, 1H); 7.19-7.28 (m, 2H); 7.66(q, J = 7.6 Hz, 1H); 7.83 (bs, 3H); 7.95 (s, 1H); 8.02 (s, 1H). |
| | 5-Amino-3-[2-[4-(2,4-difluorophenyl)pyrazol-1-yl]ethyl]-1-ethyl-8-(2-furyl)-[1,2,4]triazolo[5,1-f]purin-2-one | |

Example E1

1-[2-[5-Amino-1-(cyclopropylmethyl)-8-(2-furyl)-2-oxo-[1,2,4]triazolo[5,1-f]purin-3-yl]ethyl]pyrazole-4-carboxylic acid

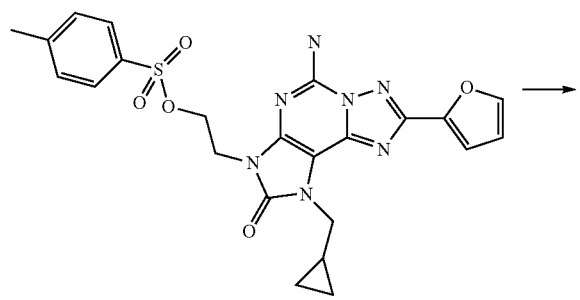

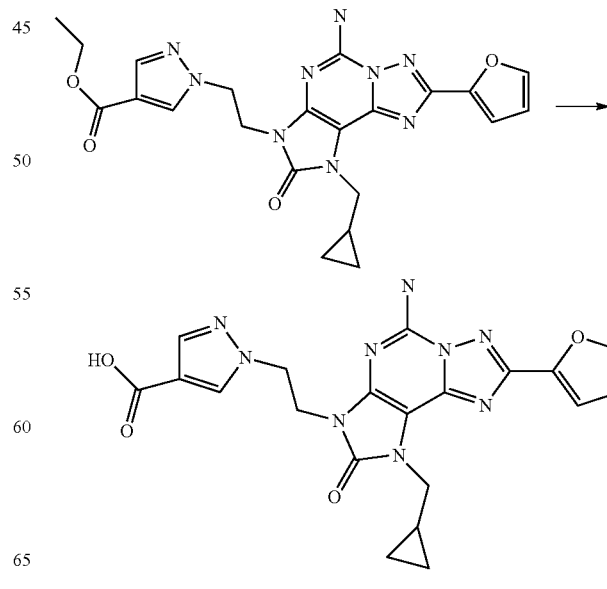

Step-1: Ethyl 1-[2-[5-amino-1-(cyclopropylmethyl)-8-(2-furyl)-2-oxo-[1,2,4]triazolo[5,1-f]purin-3-yl]ethyl]pyrazole-4-carboxylate (Carried Out as Described in Example D1)

¹HNMR (400 MHz, DMSO d6): δ 0.41-0.43 (m, 4H); 1.21 (t, J=6.8 Hz, 3H); 1.32-1.36 (m, 1H); 3.79 (d, J=7.2 Hz, 2H); 4.15 (q, J=7.2 Hz, 2H); 4.21 (t, J=5.2 Hz, 2H); 4.55 t, J=5.2 Hz, 2H); 6.72-6.73 (m, 1H); 7.20 (d, J=2.8 Hz, 1H); 7.75 (s, 1H); 7.83 (bs, 2H); 7.95 (s, 1H); 8.22 (s, 1H).

Step-2: 1-[2-[5-Amino-1-(cyclopropylmethyl)-8-(2-furyl)-2-oxo-[1,2,4]triazolo[5,1-f]purin-3-yl]ethyl]pyrazole-4-carboxylic acid A mixture of ethyl 1-[2-[5-amino-1-(cyclopropylmethyl)-8-(2-furyl)-2-oxo-[1,2,4]triazolo[5,1-f]purin-3-yl]ethyl]pyrazole-4-carboxylate obtained in step 1 (0.055 g, 0.115 mmol) was dissolved in solution of tetrahydrofuran (6 ml) and methanol (4 ml). To this reaction mixture a solution of lithium hydroxide (0.013 g, 0.576 mmol, in 2 ml water) was added and stirred at 25-27° C. for 16 hours. The reaction mixture was concentrated and acidified with saturated solution of citric acid to get $P^H$~2-3 and solid obtained was filtered off and washed with water (10 ml) followed by diethyl ether (15 ml). It was dried to obtain 1-[2-[5-amino-1-(cyclopropylmethyl)-8-(2-furyl)-2-oxo-[1,2,4]triazolo[5,1-f]purin-3-yl]ethyl]pyrazole-4-carboxylic acid (0.025 g, 49%) as an off white solid.

¹HNMR (400 MHz, DMSO d6 HNMR (400 MHz, DMSO d6): δ 0.29-0.31 (m, 4H); 1.12-1.16 (m, 1H); 3.67 (d, J=6.8 Hz, 2H); 4.08 (bs, 2H); 4.42 (bs, 2H); 6.60 (bs, 1H); 7.07 (bs, 1H); 7.57 (s, 1H); 7.71 (bs, 2H); 7.83 (s, 1H); 8.03 (s, 1H); 12.05 (bs, 1H).

Examples E2 was prepared by following similar experimental procedure of Example E1 using the appropriate intermediates Example F1

1-[2-[5-amino-1-(cyclopropylmethyl)-8-(2-furyl)-2-oxo-[1,2,4]triazolo[5,1-f]purin-3-yl]ethyl]-N-cyclopropyl-pyrazole-4-carboxamide

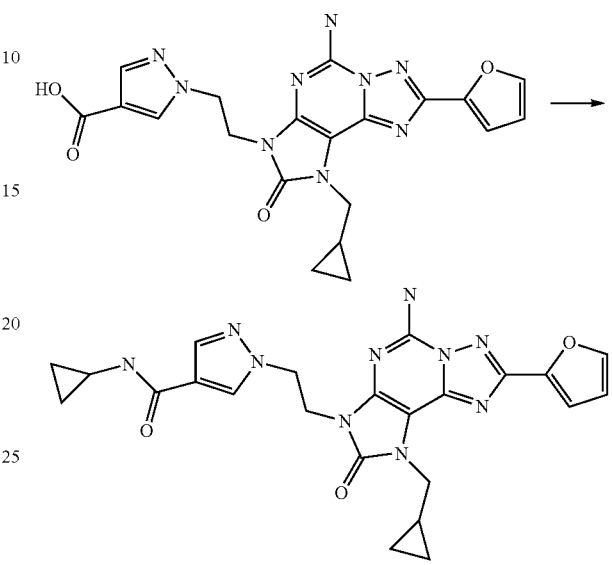

Step-1 1-[2-[5-Amino-1-(cyclopropylmethyl)-8-(2-furyl)-2-oxo-[1,2,4]triazolo[5,1-f]purin-3-yl]ethyl]-N-cyclopropyl-pyrazole-4-carboxamide A mixture of 1-[2-[5-amino-1-(cyclopropylmethyl)-8-(2-furyl)-2-oxo-[1,2,4]triazolo[5,1-f]purin-3-yl]ethyl]pyrazole-4-carboxylic acid (0.050 g, 0.111 mmol) was taken in thionyl chloride (0.04 ml, 0.557 mmol) and stirred at 75° C. for 2 hours. The reaction mixture was concentrated and residue was dissolved in DCM (2 ml). To the above solution cyclopropyl amine (0.015 ml, 0.222 mmol) was added at 0° C. and stirred at same temperature for 2 hours and filtered to obtain 1-[2-[5-amino-1-(cyclopropylmethyl)-8-(2-furyl)-2-oxo-[1,2,4]triazolo[5,1-f]purin-3-yl]ethyl]-N-cyclopropyl-pyrazole-4-carboxamide (5.0 mg, 9%) as an off white solid.

¹H NMR (400 MHz, DMSO d6): δ 0.4-0.42 (m, 4H); 0.58-0.62 (m, 2H); 0.72-0.76 (m, 2H); 1.21 (bs, 2H); 2.64-2.66 (m, 1H); 3.77 (d, J=7.2 Hz, 2H); 4.16 (bs, 2H); 4.50 (bs, 2H); 6.70-6.71 (m, 1H); 7.18 (d, J=3.2 Hz, 1H); 7.71 (s, 1H); 7.82 (bs, 2H); 7.93 (bs, 1H); 7.99 (s, 1H).

| E2 | | |
|---|---|---|
| 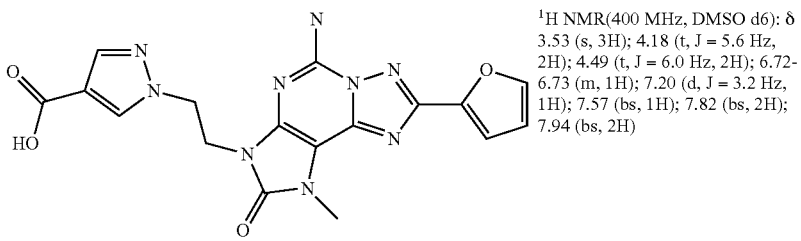 1-[2-[5-Amino-8-(2-furyl)-1-methyl-2-oxo-[1,2,4]triazolo[5,1-f]purin-3-yl]ethyl]pyrazole-4-carboxylic acid | | ¹H NMR(400 MHz, DMSO d6): δ 3.53 (s, 3H); 4.18 (t, J = 5.6 Hz, 2H); 4.49 (t, J = 6.0 Hz, 2H); 6.72-6.73 (m, 1H); 7.20 (d, J = 3.2 Hz, 1H); 7.57 (bs, 1H); 7.82 (bs, 2H); 7.94 (bs, 2H) |

Examples F2-F12 was prepared by following similar experimental procedure of Example F1 using the appropriate intermediates F2 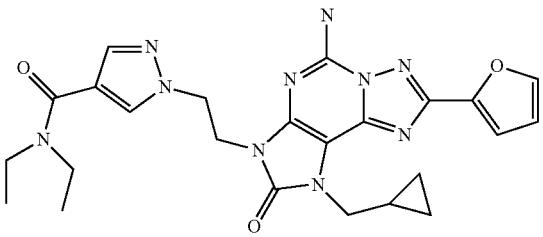 [SMILES: CCN(CC)C(=O)c1cnn(CCn2c(=O)n(CC3CC3)c3c2nc(N)n2nc(-c4ccco4)nc32)c1]

1-[2-[5-amino-1-(cyclopropylmethyl)-8-(2-furyl)-2-oxo-[1,2,4]triazolo[5,1-f]purin-3-yl]ethyl]-N,N-diethyl-pyrazole-4-carboxamide ¹H NMR(400 MHz, DMSO d6): δ 0.41-0.43 (m, 4H); 1.01 (t, J = 7.2 Hz, 6H); 1.23-1.27 (m, 1H); 3.24-3.30 (m, 4H); 3.80 (d, J = 6.8 Hz, 2H); 4.20 (t, J = 6.4 Hz, 2H); 4.54 (t, J = 6.4 Hz, 2H); 6.72 (bs, 1H); 7.19 (d, J = 3.2 Hz, 1H); 7.55 (s, 1H); 7.81(bs, 1H); 7.86(bs, 2H); 7.94 (s, 1H).

F3 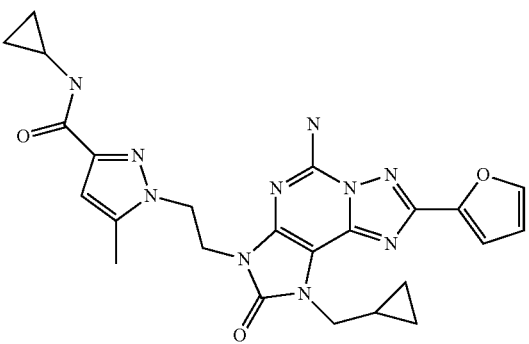 [SMILES: Cc1cc(C(=O)NC2CC2)nn1CCn1c(=O)n(CC2CC2)c2c1nc(N)n1nc(-c3ccco3)nc21]

1-[2-[5-Amino-1-(cyclopropylmethyl)-8-(2-furyl)-2-oxo-[1,2,4]triazolo[5,1-f]purin-3-yl]ethyl]-N-cyclopropyl-5-methyl-pyrazole-3-carboxamide ¹H NMR(400 MHz, DMSO d6): δ 0.43-0.48 (m, 6H); 0.55-0.58 (m, 2H); 1.28-1.32 (m, 1H); 2.22(s, 3H); 2.64-2.70(m, 1H); 3.81 (d, J = 6.8 Hz, 2H); 4.15(t, J = 6.4 Hz, 2H); 4.42 (t, J = 6.4 Hz, 2H); 6.33 (s, 1H); 6.72 (dd, J = 1.6 Hz, 3.6 Hz, 1H); 7.18 (d, J = 3.2 Hz, 1H); 7.68 (d, J = 4 Hz, 1H); 7.81 (bs, 2H); 7.94 (s, 1H).

F4 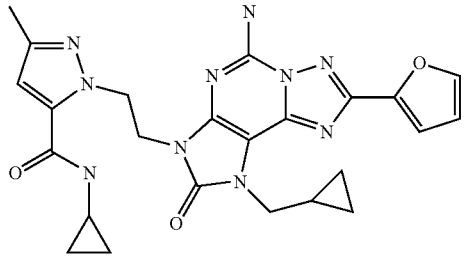 [SMILES: Cc1cc(C(=O)NC2CC2)n(CCn2c(=O)n(CC3CC3)c3c2nc(N)n2nc(-c4ccco4)nc32)n1]

2-[2-[5-Amino-1-(cyclopropylmethyl)-8-(2-furyl)-2-oxo-[1,2,4]triazolo[5,1-f]purin-3-yl]ethyl]-N-cyclopropyl-5-methyl-pyrazole-3-carboxamide ¹H NMR(400 MHz, DMSO d6): δ 0.43-0.48 (m, 6H); 0.58-0.62 (m, 2H); 1.26-1.30 (m, 1H); 1.97 (s, 3H); 2.64-2.69 (m, 1H); 3.79 (d, J = 6.8 Hz, 2H); 4.15 (t, J = 4.8 Hz, 2H); 4.76 (t, J = 4.8 Hz, 2H); 6.49 (s, 1H); 6.72 (dd, J = 1.6 Hz, 3.6 Hz, 1H); 7.18 (d, J = 3.2 Hz, 1H); 7.74 (bs, 2H); 7.95 (s, 1H); 8.21 (d, J = 3.6 Hz, 1H).

F5 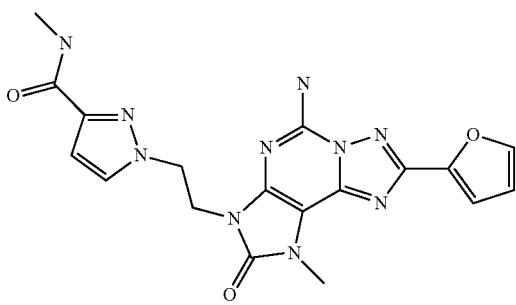 [SMILES: CNC(=O)c1ccn(CCn2c(=O)n(C)c3c2nc(N)n2nc(-c4ccco4)nc32)n1]

1-[2-[5-Amino-8-(2-furyl)-1-methyl-2-oxo-[1,2,4]triazolo[5,1-f]purin-3-yl]ethyl]-N-methyl-pyrazole-3-carboxamide ¹H NMR(400 MHz, DMSO d6): δ 2.66 (d, J = 5.2 Hz, 3H); 3.51 (s, 3H); 4.20 (t, J = 6 Hz, 2H); 4.52 (t, J = 6.4 Hz, 2H); 6.52 (d, J = 2.4 Hz, 1H); 6.71 (bs, 1H); 7.18 (d, J = 2.8 Hz, 1H); 7.70 (d, J = 2.4 Hz, 1H); 7.78 (bs, 2H); 7.81-7.86(m, 1H); 7.92(bs, 1H).

| F6 | 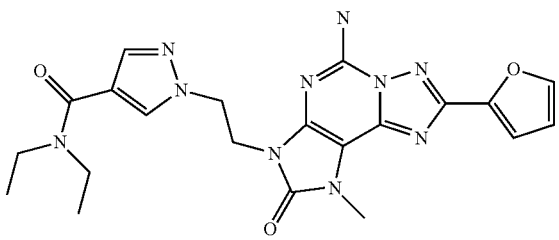 [SMILES: CCN(CC)C(=O)c1cnn(CCn2c(=O)n(C)c3c2nc(N)n2nc(-c4ccco4)nc32)c1] 1-[2-[5-Amino-8-(2-furyl)-1-methyl-2-oxo-[1,2,4]triazolo[5,1-f]purin-3-yl]ethyl]-N,N-diethyl-pyrazole-4-carboxamide | ¹H NMR(400 MHz, DMSO d6): δ 1.02 (t, J = 6.8 Hz, 6H); 3.25-3.34 (m, 4H); 3.52 (s, 3H); 4.19 (t, J = 5.6 Hz, 2H); 4.52 (t, J = 5.6 Hz, 2H); 6.72 (bs, 1H); 7.20 (d, J = 3.2 Hz, 1H); 7.58 (s, 1H); 7.79 (bs, 2H); 7.89 (s, 1H); 7.94 (s, 1H) |
|---|---|---|
| F7 | 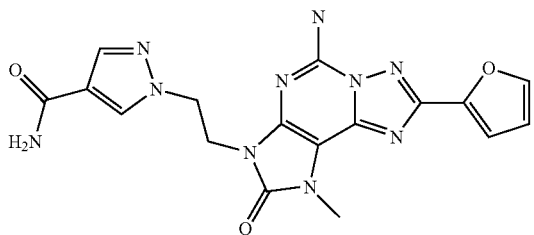 1-[2-[5-amino-8-(2-furyl)-1-methyl-2-oxo-[1,2,4]triazolo[5,1-f]purin-3-yl]ethyl]pyrazole-4-carboxamide | ¹H NMR(400 MHz, DMSO d6): δ 3.52 (s, 3H); 4.18 (t, J = 6 Hz, 2H); 4.51 (t, J = 6 Hz, 2H); 6.71-6.72 (bs, 1H); 6.96 (bs, 1H); 7.20 (d, J = 2.8 Hz, 1H); 7.46 (bs, 1H); 7.58 (s, 1H); 7.82 (bs, 2H); 7.94 (s, 1H); 8.03 (s, 1H). |
| F8 | 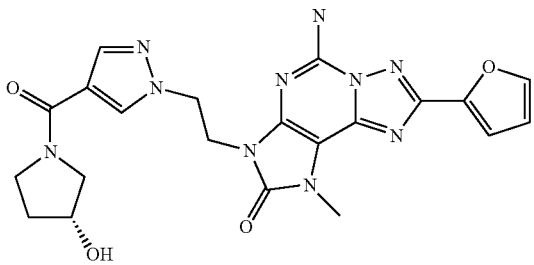 [SMILES: Cn1c(=O)n(CCn2cc(C(=O)N3CC[C@@H](O)C3)cn2)c2nc(N)n3nc(-c4ccco4)nc3c21] 5-Amino-8-(2-furyl)-3-[2-[4-[(3R)-3-hydroxypyrrolidine-1-carbonyl]pyrazol-1-yl]ethyl]-1-methyl-[1,2,4]triazolo[5,1-f]purin-2-one | ¹H NMR(400 MHz, DMSO d6): δ 1.77-1.87 (m, 2H); 3.42-3.48 (m, 2H); 3.53 (s, 3H); 3.59-3.66 (m, 2H); 4.20 (m, 2H); 4.30(bs, 1H); 4.53 (t, J = 5.6 Hz, 2H); 4.97 (d, J = 24.4 Hz, 1H); 6.73 (bs, 1H); 7.20 (d, J = 3.2 Hz, 1H); 7.70 (d, J = 6.4 Hz, 1H); 7.81 (bs, 2H); 7.95 (s, 1H); 8.10 (d, J = 4.4 Hz, 1H). |
| F9 | 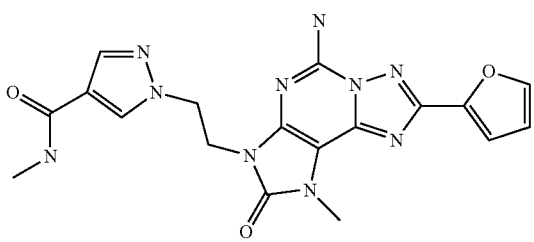 [SMILES: CNC(=O)c1cnn(CCn2c(=O)n(C)c3c2nc(N)n2nc(-c4ccco4)nc32)c1] 1-[2-[5-Amino-8-(2-furyl)-1-methyl-2-oxo-[1,2,4]triazolo[5,1-f]purin-3-yl]ethyl]-N-methyl-pyrazole-4-carboxamide | ¹H NMR(400 MHz, DMSO d6): δ 2.64 (d, J = 4.4 Hz, 3H); 3.50 (s, 3H); 4.15 (t, J = 5.6 Hz, 2H); 4.50 (t, J = 5.6 Hz, 2H); 6.70 (dd, J = 2 Hz, 3.6 Hz, 1H); 7.18 (dd, J = 0.4 Hz, 3.6 Hz, 1H); 7.72 (s, 1H); 7.80 (bs, 2H); 7.92-7.93 (m, 2H); 8.02 (s, 1H). |

| | | |
|---|---|---|
| F10 | 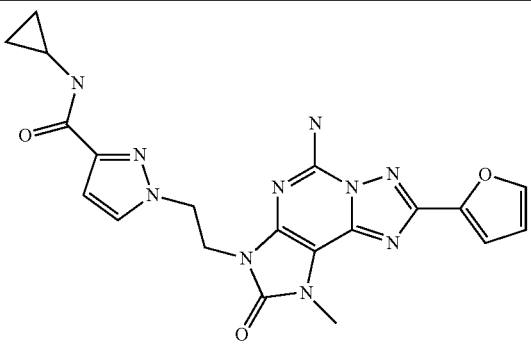<br>1-[2-[5-Amino-8-(2-furyl)-1-methyl-2-oxo-[1,2,4]triazolo[5,1-f]purin-3-yl]ethyl]-N-cyclopropyl-pyrazole-3-carboxamide | $^1$H NMR(400 MHz, DMSO d6): δ 0.46-0.50 (m, 2H); 0.55-0.60 (m, 2H); 2.67-2.71 (m, 1H); 3.51 (s, 3H); 4.18 (t, J = 6.4 Hz, 2H); 4.51 (t, J = 6 Hz, 2H); 6.52-6.54 (m, 1H); 6.72 (dd, J = 2 Hz, 3.6 Hz, 1H); 7.18 (d, J = 3.2 Hz, 1H); 7.71 (d, J = 2.4 Hz, 1H); 7.78 (bs, 2H); 7.84 (d, J = 4.4 Hz, 1H); 7.92-7.93 (d, J = 1.6 Hz, 1H). |
| F11 | 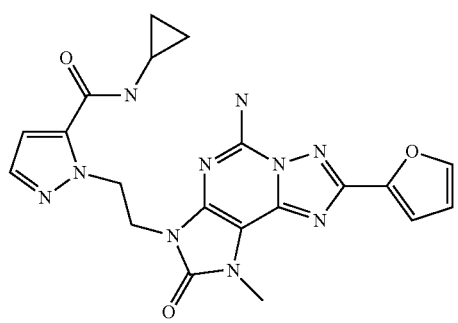 [SMILES: Cn1c(=O)n(CCn2nccc2C(=O)NC2CC2)c2nc(N)n3nc(-c4ccco4)nc3c21]<br>1-[2-[5-Amino-8-(2-furyl)-1-methyl-2-oxo-[1,2,4]triazolo[5,1-f]purin-3-yl]ethyl]-N-cyclopropyl-pyrazole-4-carboxamide | $^1$H NMR(400 MHz, DMSO d6): δ 0.41-0.45 (m, 2H); 0.56-0.60 (m, 2H); 3.06-3.09 (m, 1H); 3.47 (s, 3H); 4.14 (t, J = 5.2 Hz, 2H); 4.84 (t, J = 4.8 Hz, 2H); 6.68-6.71 (m, 1H); 7.17 (d, J = 3.2 Hz, 1H); 7.29 (d, J = 2 Hz, 1H); 7.69 (bs, 2H); 7.92 (s, 1H); 8.14 (s, 1H); 8.28 (d, J = 4 Hz, 1H). |
| F12 | 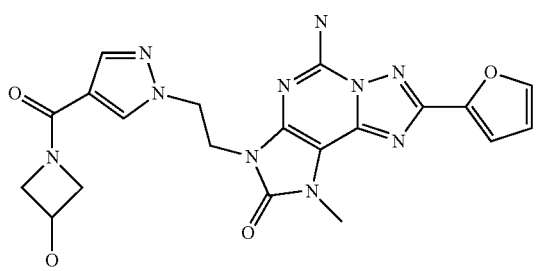 [SMILES: Cn1c(=O)n(CCn2cc(C(=O)N3CC(O)C3)cn2)c2nc(N)n3nc(-c4ccco4)nc3c21]<br>5-Amino-8-(2-furyl)-3-[2-[4-(3-hydroxyazetidine-1-carbonyl)pyrazol-1-yl]ethyl]-1-methyl-[1,2,4]triazolo[5,1-f]purin-2-one | $^1$H NMR(400 MHz, DMSO d6): δ 3.50 (s, 3H); 3.61-3.65 (m, 1H); 3.93-3.96 (m, 1H); 4.05-4.12 (m, 1H); 4.17 (t, J = 5.6 Hz, 2H); 4.35-4.46 (m, 2H); 4.50 (t, J = 6.0 Hz, 2H); 5.72 (d, J = 6.4 Hz, 1H); 6.70 (dd, J = 1.6 Hz, 3.6 Hz, 1H); 7.18 (d, J = 3.6 Hz, 1H); 7.64 (s, 1H); 7.79 (bs, 2H); 7.92 (s, 1H); 8.05 (s, 1H). |

Example G1

5-Amino-1-ethyl-8-(2-furyl)-3-[2-[4-[4-(2-methoxy-ethoxy)phenyl]piperazin-1-yl]ethyl]-[1,2,4]triazolo[5,1-f]purin-2-one

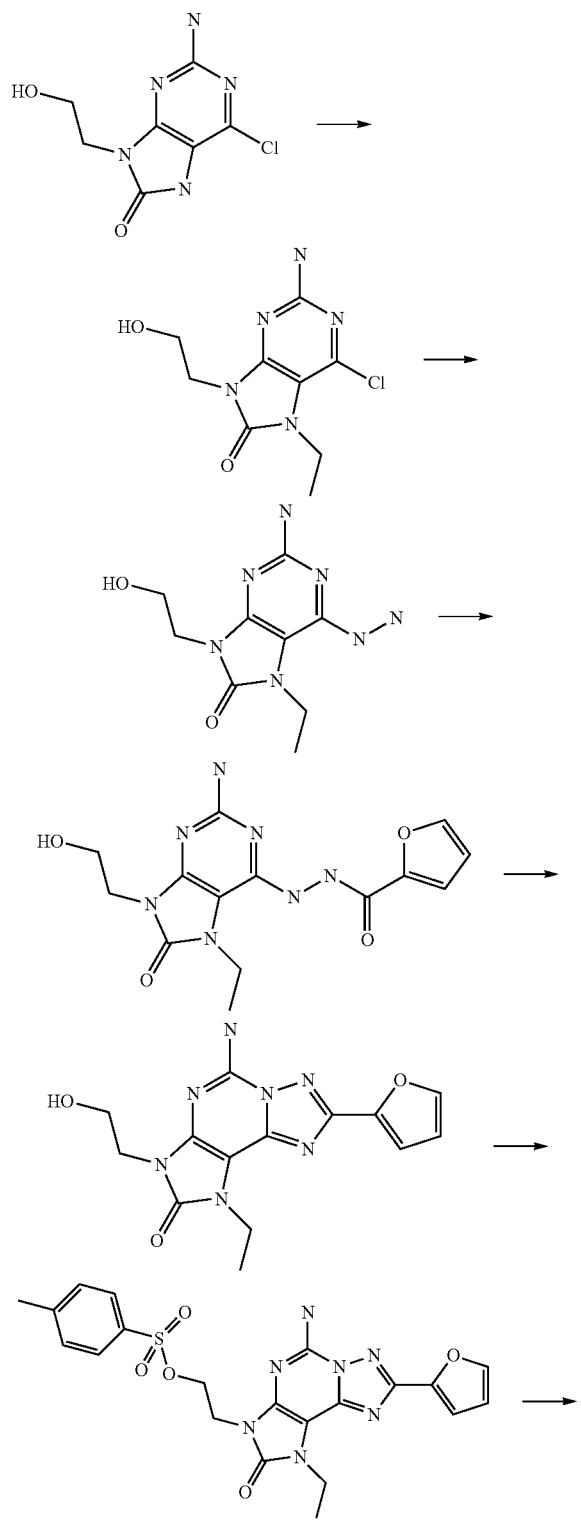

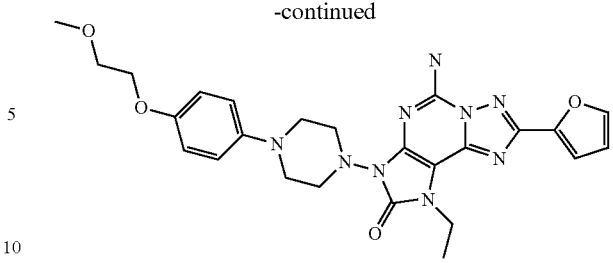

Step-1: 2-Amino-6-chloro-7-ethyl-9-(2-hydroxy-ethyl)purin-8-one (Procedure is Same as Step-3 in Example A1)

¹HNMR (400 MHz, DMSO d6): δ 1.21 (t, J=7.2 Hz, 3H); 3.64 (s, 2H); 3.78 (t, J=6 Hz, 2H); 3.92 (q, J=7.2 Hz, 2H); 4.92 (bs, 1H); 6.7 (bs, 2H).

Step-2: 2-Amino-7-ethyl-6-hydrazino-9-(2-hydroxy-ethyl)purin-8-one (Procedure is Same as Step-4 in Example A1)

¹HNMR (400 MHz, DMSO d6): δ 1.07 (t, J=6.8 Hz, 3H); 3.59 (q, J=6 Hz, 2H); 3.72 (t, J=6 Hz, 2H); 3.91 (q, J=6.8 Hz, 2H); 4.32 (bs, 2H); 4.86 (t, J=5.6 Hz, 1H); 5.99 (bs, 2H), 7.55 (bs, 1H).

Step-3: N'-[2-Amino-7-ethyl-9-(2-hydroxyethyl)-8-oxo-purin-6-yl]furan-2-carbohydrazide (Procedure is Same as Step-5 in Example A1)

Crude product was used in next step

Step-4: 5-Amino-1-ethyl-8-(2-furyl)-3-(2-hydroxy-ethyl)-[1,2,4]triazolo[5,1-f]purin-2-one (Procedure is Same as Step-6 in Example A1)

¹HNMR (400 MHz, DMSO d6): δ 1.34 (t, J=7.2 Hz, 3H); 3.67 (q, J=5.6 Hz, 2H); 3.84 (t, J=5.6 Hz, 2H); 4.01 (q, J=7.2 Hz, 2H); 4.87 (t, J=6 Hz, 1H); 6.70 (bs, 1H); 7.17 (d, J=2.8 Hz, 1H); 7.18 (bs, 2H); 7.92 (bs, 1H).

Step-5: 2-[5-Amino-1-ethyl-8-(2-furyl)-2-oxo-[1,2,4]triazolo[5,1-f]purin-3-yl]ethyl 4-methylbenzenesulfonate (Procedure is Same as Step-7 in Example A1)

¹HNMR (400 MHz, DMSO d6): δ 1.35 (t, J=7.2 Hz, 3H); 2.00 (s, 3H); 3.95-4.00 (m, 4H); 4.47 (bs, 2H); 6.74 (s, 1H); 7.00 (d, J=7.6 Hz, 2H); 7.22 (s, 1H); 7.42 (d, J=7.6 Hz, 2H); 7.78 (bs, 2H); 7.97 (bs, 1H).

Step-6: 5-Amino-1-ethyl-8-(2-furyl)-3-[2-[4-[4-(2-methoxyethoxy)phenyl]piperazin-1-yl]ethyl]-[1,2,4]triazolo[5,1-f]purin-2-one (Procedure is Same as Step-8 in Example A1)

HNMR (400 MHz, DMSO d6): δ 1.35 (t, J=7.2 Hz, 3H); 2.60 (bs, 4H); 2.68 (t, J=6.8 Hz, 2H); 2.95 (bs, 4H); 3.28 (s, 3H); 3.61 (t, J=4.4 Hz, 2H); 3.94-4.04 (m, 6H); 6.72 (dd, J=2 Hz, 3.6 Hz, 1H); 6.78-6.85 (m, 4H); 7.19 (d, J=3.2 Hz, 1H); 7.81 (bs, 2H); 7.94 (s, 1H).

Examples G2-G4 was prepared by following similar experimental procedure of Example G1 using the appropriate intermediates

| Ex. No | Structure/IUPAC name | NMR |
|---|---|---|
| G2 | 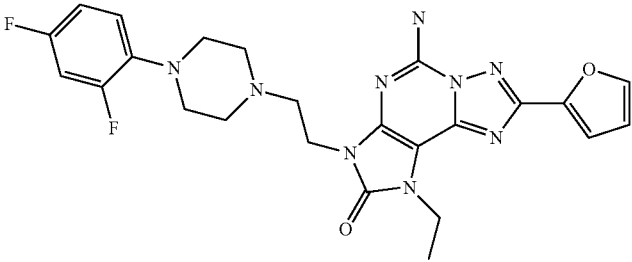 [SMILES: CCn1c(=O)n(CCN2CCN(c3ccc(F)cc3F)CC2)c2nc(N)n3nc(-c4ccco4)nc3c21]<br>5-Amino-3-[2-[4-(2,4-difluorophenyl)piperazin-1-yl]ethyl]-1-ethyl-8-(2-furyl)-[1,2,4]triazolo[5,1-f]purin-2-one | HNMR(400 MHz, DMSO d6): δ 1.35 (t, J = 7.2 Hz, 3H); 2.62(bs, 4H); 2.69 (t, J = 6.4 Hz, 2H); 2.89 (bs, 4H); 3.95 (t, J = 6.4 Hz, 2H); 4.00-4.04 (m, 2H); 6.72 (bs, 1H); 6.94-7.05 (m, 3H); 7.17-7.19 (m, 1H); 7.80 (bs, 2H); 7.94 (s, 1H). |
| G3 | 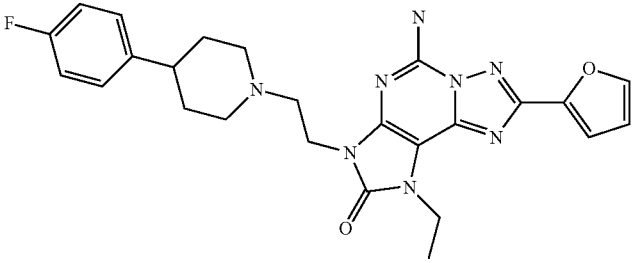 [SMILES: CCn1c(=O)n(CCN2CCC(c3ccc(F)cc3)CC2)c2nc(N)n3nc(-c4ccco4)nc3c21]<br>5-Amino-1-ethyl-3-{2-[4-(4-fluoro-phenyl)-piperidin-1-yl]-ethyl}-8-furan-2-yl-1,3-dihydro-[1,2,4]triazolo[5,1-f]purin-2-one | HNMR(400 MHz, DMSO): δ 1.36 (t, J = 6.8 Hz, 3H); 1.48-1.56(m, 3H); 1.69 (d, J = 12 Hz, 2H); 2.08 (t, J = 10.8 Hz, 2H); 2.66 (t, J = 6 Hz, 2H); 3.04 (d, J = 10.8 Hz, 2H); 3.94 (t, J = 6 Hz, 2H); 4.04 (q, J = 7.2 Hz, 2H); 6.72 (bs, 1H); 7.08 (t, J = 8.8 Hz, 2H); 7.19-7.25 (m, 3H); 7.80 (bs, 2H); 7.95 (s, 1H). |
| G4 | 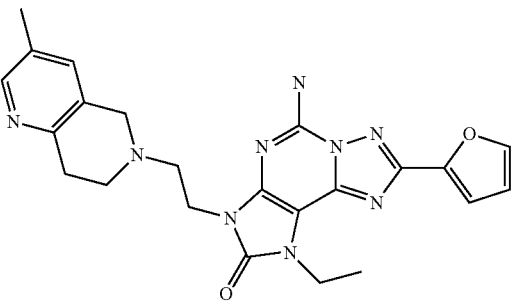 [SMILES: CCn1c(=O)n(CCN2CCc3ncc(C)cc3C2)c2nc(N)n3nc(-c4ccco4)nc3c21]<br>5-Amino-1-ethyl-8-(2-furyl)-3-[2-(3-methyl-7,8-dihydro-5H-1,6-naphthyridin-6-yl)ethyl]-[1,2,4]triazolo[5,1-f]purin-2-one | $^1$HNMR(400 MHz, DMSO d6): δ 1.30 (t, J = 7.2 Hz, 3H); 2.19 (s, 3H); 2.74-2.76 (m, 2H); 2.82 (t, J = 6.8 Hz, 4H); 3.62 (s, 2H); 3.97-4.02 (m, 4H); 6.69 (dd, J = 1.6 Hz, 3.2 Hz, 1H); 7.16 (dd, J = 0.8 Hz, 3.2 Hz, 1H); 7.24 (bs, 1H); 7.79 (bs, 2H); 7.91 (dd, J = 0.4 Hz, 1.6 Hz, 1H); 8.11 (bs, 1H). |

Example H1

5-Amino-8-(2-furyl)-3-[2-[4-[4-(2-methoxyethoxy)phenyl]piperazin-1-yl]ethyl]-1-(2,2,2-trifluoroethyl)-[1,2,4]triazolo[5,1-f]purin-2-one

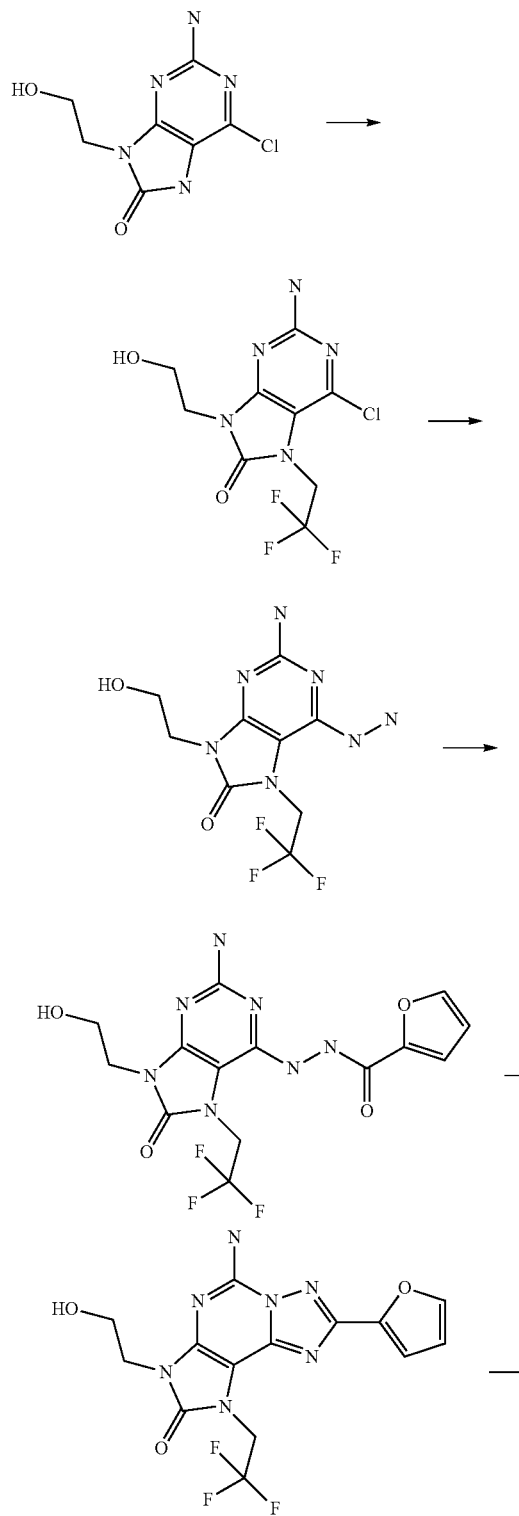

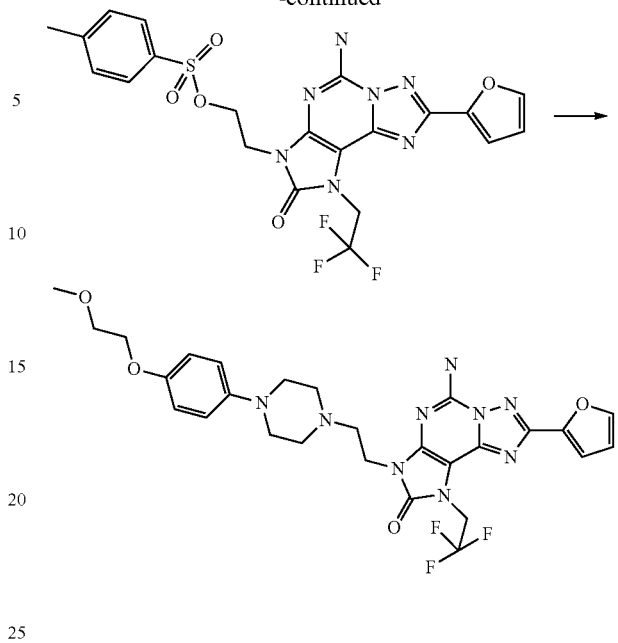

Step-1: 2-Amino-6-chloro-9-(2-hydroxyethyl)-7-(2,2,2-trifluoroethyl)purin-8-one (Procedure is Same as Step-3 in Example A1)

Crude product was used in next step

Step-2: 2-Amino-6-hydrazino-9-(2-hydroxyethyl)-7-(2,2,2-trifluoroethyl)purin-8-one (Procedure is Same as Step-4 in Example A1)

$^1$HNMR (400 MHz, DMSO d6): 6, 3.59 (t, J=6.4 Hz, 2H); 3.73 (t, J=6.4 Hz, 2H); 4.37 (bs, 2H); 4.88 (q, J=9.2 Hz, 3H); 6.06 (bs, 2H); 7.66 (s, 1H).

Step-3: N'-[2-Amino-9-(2-hydroxyethyl)-8-oxo-7-(2,2,2-trifluoroethyl)purin-6-yl]furan-2-carbohydrazide (Procedure is Same as Step-5 in Example A1)

$^1$HNMR (400 MHz, DMSO d6): δ 3.60-3.64 (m, 2H); 3.78 (t, J=6.4 Hz, 2H); 4.91 (q, J=8.8 Hz, 3H); 6.15 (bs, 2H); 6.66 (dd, J=2 Hz, 3.6 Hz, 1H); 7.27 (d, J=3.2 Hz, 1H); 7.90 (s, 1H); 8.44 (s, 1H); 10.28 (s, 1H).

Step-4: 5-Amino-8-(2-furyl)-3-(2-hydroxyethyl)-1-(2,2,2-trifluoroethyl) [1,2,4]triazolo[5,1-f]purin-2-one (Procedure is Same as Step-6 in Example A1)

$^1$HNMR (400 MHz, DMSO d6): δ 3.72 (q, J=6.4 Hz, 2H); 3.89 (t, J=6.4 Hz, 2H); 4.80 (q, J=8.8 Hz, 2H); 4.92 (t, J=6 Hz, 1H); 6.72 (dd, J=2 Hz, 3.6 Hz, 1H); 7.19 (d, J=3.2 Hz, 1H); 7.95 (bs, 3H).

Step-5: 2-[5-Amino-8-(2-furyl)-2-oxo-1-(2,2,2-trifluoroethyl)-[1,2,4]triazolo[5,1-f]purin-3-yl]ethyl 4-methylbenzenesulfonate (Procedure is Same as Step-7 in Example A1)

$^1$HNMR (400 MHz, DMSO d6): δ 1.96 (s, 3H); 4.02 (t, J=4 Hz, 2H); 4.45 (t, J=4 Hz, 2H); 4.74 (q, J=8.8 Hz, 2H); 6.72 (bs, 1H); 6.98 (d, J=8 Hz, 1H); 7.20 (d, J=3.2 Hz, 1H); 7.40 (d, J=8 Hz, 3H); 7.89 (bs, 2H); 7.95 (s, 1H).

Step-6: 5-Amino-8-(2-furyl)-3-[2-[4-[4-(2-methoxy-ethoxy)phenyl]piperazin-1-yl]ethyl]-1-(2,2,2-trifluoroethyl)-[1,2,4]triazolo[5,1-f]purin-2-one (Procedure is Same as Step-8 in Example A1)

HNMR (400 MHz, DMSO d6): δ 2.59 (bs, 4H); 2.70 (t, J=6.8 Hz, 2H); 2.93 (bs, 4H); 3.28 (s, 3H); 3.61 (t, J=4.8 Hz, 2H); 3.97-4.00 (m, 4H); 4.79 (q, J=8.8 Hz, 2H); 6.72 (dd, J=2 Hz, 3.6 Hz, 1H); 6.78-6.84 (m, 4H); 7.19 (d, J=3.2 Hz, 1H); 7.95 (s, 1H); 7.96 (bs, 2H).

Examples H2 was prepared by following similar experimental procedure of Example H1 using the appropriate intermediates

| Ex. No | Structure/IUPAC name | NMR |
|---|---|---|
| H2 | 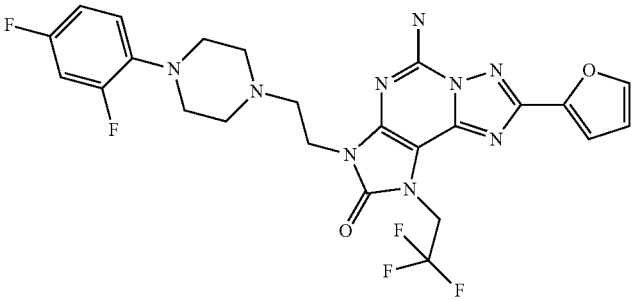 [SMILES: Nc1nc2c(c3nc(-c4ccco4)nn13)n(CC(F)(F)F)c(=O)n2CCN1CCN(c2ccc(F)cc2F)CC1]<br>5-Amino-3-{2-[4-(2,4-difluoro-phenyl)-piperazin-1-yl]-ethyl}-8-furan-2-yl-1-(2,2,2-trifluoro-ethyl)-1,3-dihydro-[1,2,4]triazolo[5,1-f]purin-2-one | HNMR(400 MHz, DMSO d6): δ 2.63 (bs, 4H); 2.72 (t, J = 6 Hz, 2H); 2.89 (bs, 4H); 4.00 (t, J = 6.0 Hz, 2H); 4.82 (q, J = 9.2 Hz, 2H); 6.74 (bs, 1H); 6.97-7.02 (m, 2H); 7.19-7.21 (m, 2H); 7.97 (bs, 3H). |

Example I1

5-Amino-8-(2-furyl)-3-[2-[4-[4-(2-methoxyethoxy)phenyl]piperazin-1-yl]ethyl]-1-(2-methoxyethyl)-[1,2,4]triazolo[5,1-f]purin-2-one)

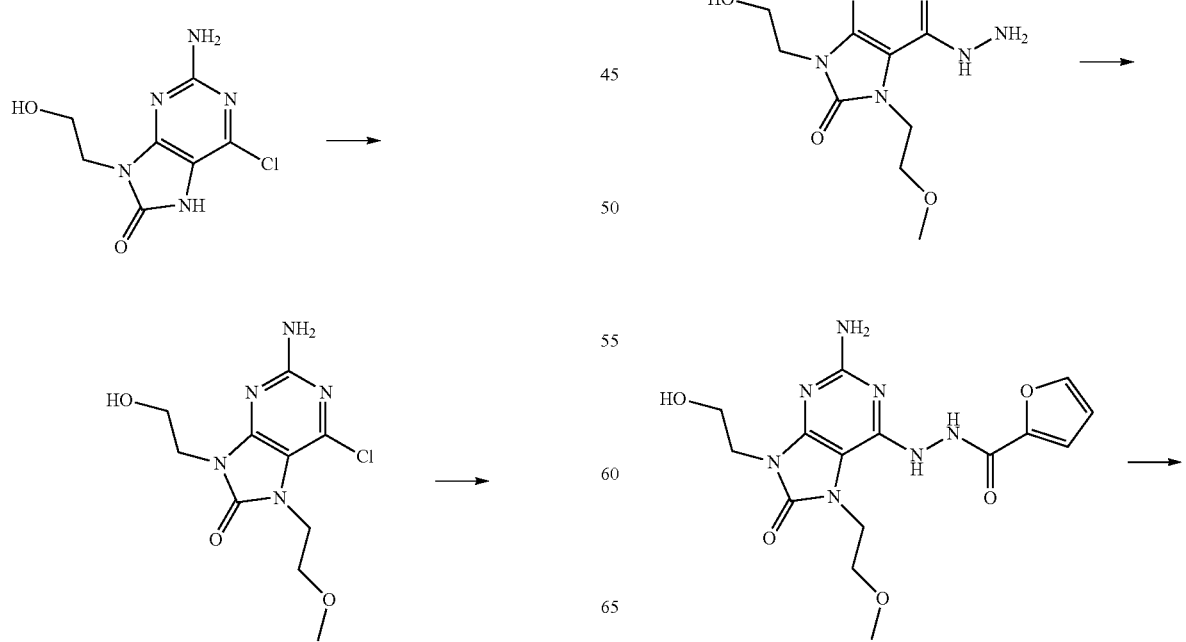

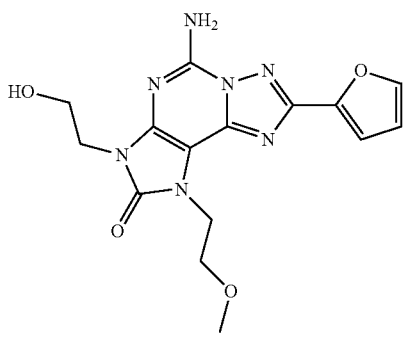

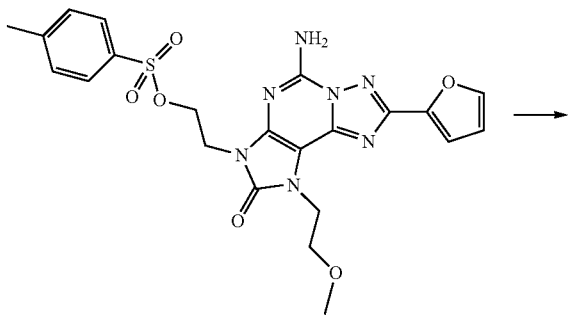

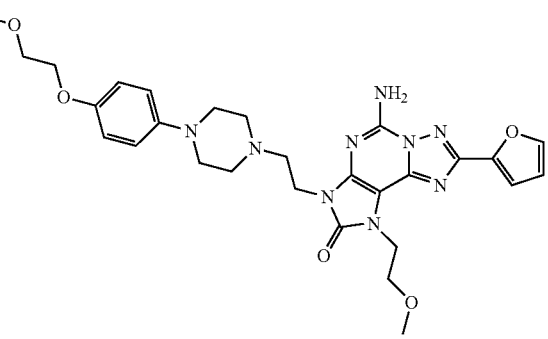

Step-1: 2-Amino-6-chloro-9-(2-hydroxyethyl)-7-(2-methoxyethyl)purin-8-one (Procedure is Same as Step-3 in Example A1)

¹HNMR (400 MHz, DMSO d6): δ 3.24 (s, 3H); 3.56 (t, J=6 Hz, 2H); 3.62 (q, J=5.2 Hz, 2H); 3.78 (t, J=6 Hz, 2H); 4.05 (t, J=6 Hz, 2H); 4.86 (t, J=6 Hz, 1H); 6.71 (bs, 2H).

Step-2: 2-Amino-6-hydrazino-9-(2-hydroxyethyl)-7-(2-methoxyethyl)purin-8-one (Procedure is Same as Step-4 in Example A1)

¹HNMR (400 MHz, DMSO d6): δ 3.24 (s, 3H); 3.49 (t, J=5.2 Hz, 2H); 3.58-3.60 (m, 2H); 3.72 (t, J=6 Hz, 2H); 3.99 (t, J=4.8 Hz, 2H); 4.28 (bs, 2H); 4.87 (t, J=5 Hz, 1H); 6.02 (bs, 2H); 7.46 (bs, 1H).

Step-3: N'-[2-Amino-9-(2-hydroxyethyl)-7-(2-methoxyethyl)-8-oxo-purin-6-yl]furan-2-carbohydrazide (Procedure is Same as Step-5 in Example A1)

¹HNMR (400 MHz, DMSO d6): δ 3.28 (s, 3H); 3.57-3.63 (m, 4H); 3.75 (t, J=6 Hz, 2H); 4.05 (t, J=4.8 Hz, 2H); 4.90 (bs, 1H); 6.02 (bs, 2H); 6.66 (dd, J=2 Hz, 3.6 Hz, 1H); 7.26 (d, J=3.2 Hz, 1H); 7.90 (s, 1H); 8.45 (bs, 1H); 10.33 (s, 1H).

Step-4: 5-Amino-8-(2-furyl)-3-(2-hydroxyethyl)-1-(2-methoxyethyl)-[1,2,4]triazolo[5,1-f]purin-2-one (Procedure is Same as Step-6 in Example A1)

¹HNMR (400 MHz, DMSO d6): δ 3.25 (s, 3H); 3.69 (q, J=6 Hz, 2H); 3.78 (t, J=6 Hz, 2H); 3.87 (t, J=6 Hz, 2H); 4.15 (t, J=6 Hz, 2H); 4.89 (t, J=5.2 Hz, 1H); 6.72 (bs, 1H); 7.19 (d, J=3.6 Hz, 1H); 7.81 (bs, 2H); 7.94 (s, 1H).

Step-5: 2-[5-Amino-8-(2-furyl)-1-(2-methoxyethyl)-2-oxo-[1,2,4]triazolo[5,1-f]purin-3-yl]ethyl 4-methylbenzenesulfonate (Procedure is Same as Step-7 in Example A1)

¹HNMR (400 MHz, DMSO d6): δ 1.98 (s, 3H); 3.27 (s, 3H); 3.77 (t, J=5.6 Hz, 2H); 3.99 (t, J=5.2 Hz, 2H); 4.09 (t, J=5.2 Hz, 2H); 4.43 (t, J=4.8 Hz, 2H); 6.72 (dd, J=2 Hz, 3.6 Hz, 1H); 6.95 (d, J=8 Hz, 2H); 7.19 (dd, J=0.8 Hz, 3.6 Hz, 1H); 7.40 (d, J=8.4 Hz, 2H); 7.73 (bs, 2H); 7.95 (d, J=1.2 Hz, 1H).

Step-6: 5-Amino-8-(2-furyl)-3-[2-[4-[4-(2-methoxyethoxy)phenyl]piperazin-1-yl]ethyl]-1-(2-methoxyethyl)-[1,2,4]triazolo[5,1-f]purin-2-one (Procedure is Same as Step-8 in Example A1)

¹HNMR (400 MHz, DMSO d6): δ 2.60 (bs, 4H); 2.69 (t, J=6 Hz, 2H); 2.94 (bs, 4H); 3.22 (s, 3H); 3.28 (s, 3H); 3.59-3.62 (m, 2H); 3.77 (t, J=5.6 Hz, 2H); 3.94-3.99 (m, 4H); 4.15 (t, J=5.2 Hz, 2H); 6.71 (dd, J=2 Hz, 3.6 Hz, 1H); 6.79-6.85 (m, 4H); 7.17 (d, J=3.2 Hz, 1H); 7.81 (bs, 2H); 7.94 (s, 1H).

Examples I2 was prepared by following similar experimental procedure of Example I121 using the appropriate intermediates

| Ex. No | Structure/IUPAC name | NMR |
|---|---|---|
| I2 | 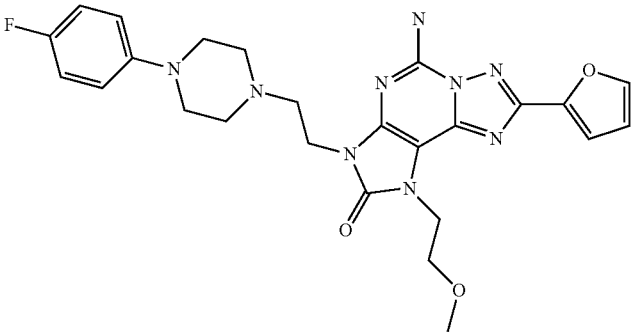 [SMILES: COCCn1c(=O)n(CCN2CCN(c3ccc(F)cc3)CC2)c2nc(N)n3nc(-c4ccco4)nc3c21]

5-amino-3-[2-[4-(4-fluorophenyl)piperazin-1-yl]ethyl]-8-(2-furyl)-1-(2-methoxyethyl)-[1,2,4]triazolo[5,1-f]purin-2-one | HNMR(400 MHz, DMSO d6): δ 2.60 (t, J = 4.4 Hz, 4H); 2.69 (t, J = 6.4 Hz, 2H); 3.00 (bs, 4H); 3.22 (s, 3H); 3.77 (t, J = 6 Hz, 2H); 3.97 (t, J = 6.4 Hz, 2H); 4.16 (t, J = 5.6 Hz, 2H); 6.71(dd, J = 2 Hz, 3.6 Hz, 1H); 6.89-6.93 (m, 2H); 7.00 (t, J = 8.8 Hz, 2H); 7.17 (d, J = 2.4 Hz, 1H); 7.82 (bs, 2H); 7.94 (bs, 1H). |

Example J1

5-Amino-3-[2-[4-(4-fluorophenyl)piperazin-1-yl]ethyl]-8-(2-furyl)-1-(2-hydroxyethyl)-[1,2,4]triazolo[5,1-f]purin-2-one one

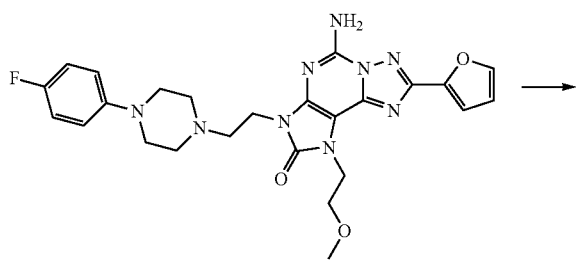

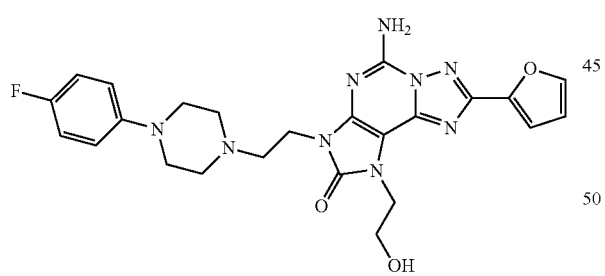

To a solution of compound 5-amino-3-[2-[4-(4-fluorophenyl)piperazin-1-yl]ethyl]-8-(2-furyl)-1-(2-methoxyethyl)-[1,2,4]triazolo[5,1-f]purin-2-one (Example I2) (0.050 g, 0.095 mmol), in DCM (3 ml) was added $BBr_3$ (0.1 ml, 0.105 mmol) drop wise at 0° C. and stirred at 25° C. for 20 hours. The reaction mixture was quenched with sat. $NaHCO_3$ (25 ml) and extracted with DCM (3×20 ml). The crude product was purified by LCMS to obtain 5-Amino-3-[2-[4-(4-fluorophenyl)piperazin-1-yl]ethyl]-8-(2-furyl)-1-(2-hydroxyethyl)-[1,2,4]triazolo[5,1-f]purin-2-one (5 mg, 10%) as an off white solid HNMR (400 MHz, DMSO d6): δ 2.60 (bs, 4H); 2.67 (t, J=6.8 Hz, 2H); 3.0 (t, J=4.8 Hz, 4H); 3.80 (q, J=6 Hz, 2H); 3.95 (t, J=6.4 Hz, 2H); 4.03 (t, J=6.4Hz, 2H); 4.84 (t, J=5.2 Hz, 1H); 6.71 (dd, J=2 Hz, 3.6 Hz, 1H); 6.89-6.92 (m, 2H); 7.01 (t, J=9.2 Hz, 2H), 7.17 (dd, J=0.8 Hz, 3.2 Hz, 1H); 7.79 (bs, 2H); 7.92 (dd, J=0.8 Hz, 1.6 Hz, 1H).

Example K1

5-Amino-1-cyclopropyl-8-(2-furyl)-3-[2-[4-[4-(2-methoxyethoxy)phenyl]piperazin-1-yl]ethyl]-[1,2,4]triazolo[5,1-f]purin-2-one

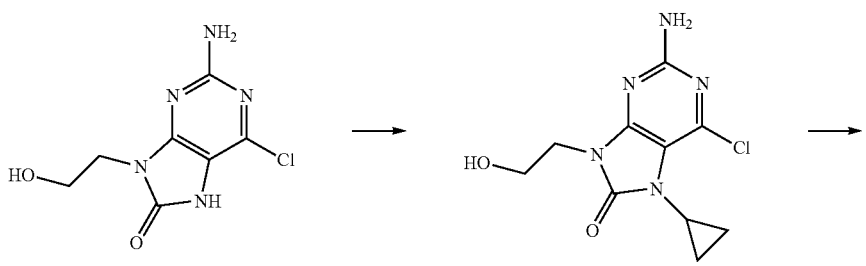

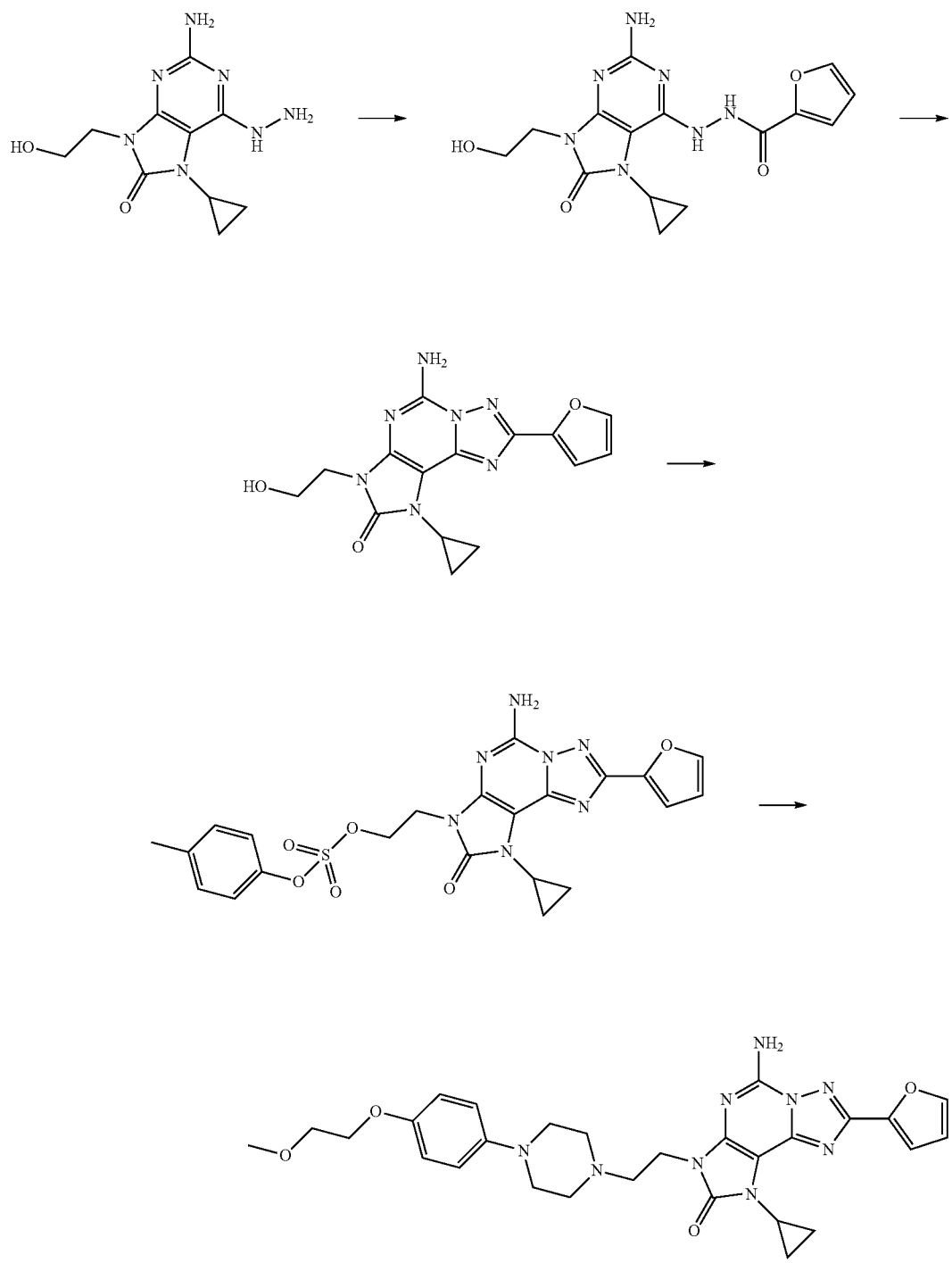

Step-1: 2-Amino-6-chloro-7-cyclopropyl-9-(2-hydroxyethyl)purin-8-one

A mixture of cyclopropylboronic acid (0.369 g, 44 mmol), 2-amino-6-chloro-9-(2-hydroxyethyl)-7H-purin-8-one (5 g, 22 mmol) and Na₂CO₃ (0.462 g, 44 mmol) were taken in dichloroethane (20 ml) and dimethylformamide (10 ml). A suspension of Cu(OAc)₂ (0.399 g, 22 mmol) and bipyridine (0.343 g, 22 mmol) in hot dichloroethane (30 ml) was added to the above mixture. The mixture was stirred at 70° C. for 18 hours under air. The resulting mixture was cooled to room temperature, and a saturated aqueous NH₄Cl solution was added, followed by water. The organic layer was separated and the aqueous layer was extracted three times with DCM. The combined organic layers were washed with brine, dried over Na₂SO₄, and concentrated under reduced pressure to get crude 2-amino-6-chloro-7-cyclopropyl-9-(2-hydroxyethyl)purin-8-one (1.6 g, 27%) as an off white solid. ¹HNMR (400 MHz, DMSO d6): δ 0.97-1.02 (m, 4H); 2.89-2.92 (m, 1H); 3.61-3.67 (m, 2H); 3.71-3.74 (m, 2H); 4.83 (t, J=12.8 Hz, 1H); 6.67 (bs, 2H)

Step-2: 2-Amino-7-cyclopropyl-6-hydrazino-9-(2-hydroxyethyl)purin-8-one (Procedure is Same as Step-4 in Example A1)

¹HNMR (400 MHz, DMSO d6): δ 0.84-0.87 (m, 2H); 0.96-1.01 (m, 2H); 3.03-3.06 (m, 1H); 3.54-3.60 (m, 2H); 3.66 (t, J=6 Hz, 2H); 4.32 (bs, 2H); 4.85 (t, J=5.6 Hz, 1H); 5.99 (bs, 2H); 7.23 (bs, 1H)

Step-3: N'-[2-Amino-7-cyclopropyl-9-(2-hydroxyethyl)-8-oxo-purin-6-yl]furan-2-carbohydrazide (Procedure is Same as Step-5 in Example A1)

Crude material was taken for next reaction.

Step-4: 5-Amino-1-cyclopropyl-8-(2-furyl)-3-(2-hydroxyethyl)-[1,2,4]triazolo[5,1-f]purin-2-one (Procedure is Same as Step-6 in Example A1)

¹HNMR (400 MHz, DMSO d6): δ 1.00-1.12 (m, 4H); 3.13-3.18 (m, 1H); 3.65-3.69 (m, 2H); 3.83 (t, J=6.4 Hz, 2H); 4.88 (t, J=5.6 Hz, 1H); 6.72 (dd, J=2 Hz, 3.6 Hz, 1H); 7.19 (d, J=3.2 Hz, 1H); 7.79 (bs, 2H); 7.94-7.95 (m, 1H)

Step-5: 2-[5-Amino-1-cyclopropyl-8-(2-furyl)-2-oxo-[1,2,4]triazolo[5,1-f]purin-3-yl]ethyl p-tolyl sulfate (Procedure is Same as Step-7 in Example A1)

¹HNMR (400 MHz, DMSO d6): δ 1.01-1.08 (m, 4H); 1.98 (s, 3H); 3.06-3.11 (m, 1H); 3.95 (t, J=4.41-1z, 2H); 4.44 (t, J=4.8 Hz, 2H); 6.71-6.73 (m, 1H); 6.99 (d, J=8.4 Hz, 2H); 7.19 (d, J=3.6 Hz, 1H); 7.41 (d, J=8.4 Hz, 2H); 7.74 (bs, 2H); 7.94 (s, 1H)

Step-6: 5-Amino-1-cyclopropyl-8-(2-furyl)-3-[2-[4-[4-(2-methoxyethoxy)phenyl]piperazin-1-yl]ethyl]-[1,2,4]triazolo[5,1-f]purin-2-one (Procedure is Same as Step-8 in Example A1)

1H NMR (400 MHz, DMSO): δ 1.05-1.08 (m, 4H); 2.56 (bs, 4H); 2.66 (t, J=6.4 Hz, 2H); 2.95 (bs, 4H); 3.15-3.19 (m, 1H); 3.29 (s, 3H); 3.60-3.62 (m, 2H); 3.92 (t, J=6.4 Hz, 2H); 3.98-4.00 (m, 2H); 6.72 (dd, J=2 Hz, 3.6 Hz, 1H); 6.79-6.86 (m, 41-1); 7.18 (d, J=3.2 Hz, 1H); 7.79 (bs, 2H); 7.94 (bs, 1H).

Example L1

5-Amino-8-(2-furyl)-3-[2-[4-[4-(2-methoxyethoxy)phenyl]piperazin-1-yl]ethyl]-1-(2,2,2-trifluoroethyl)-[1,2,4]triazolo[5,1-f]purin-2-one

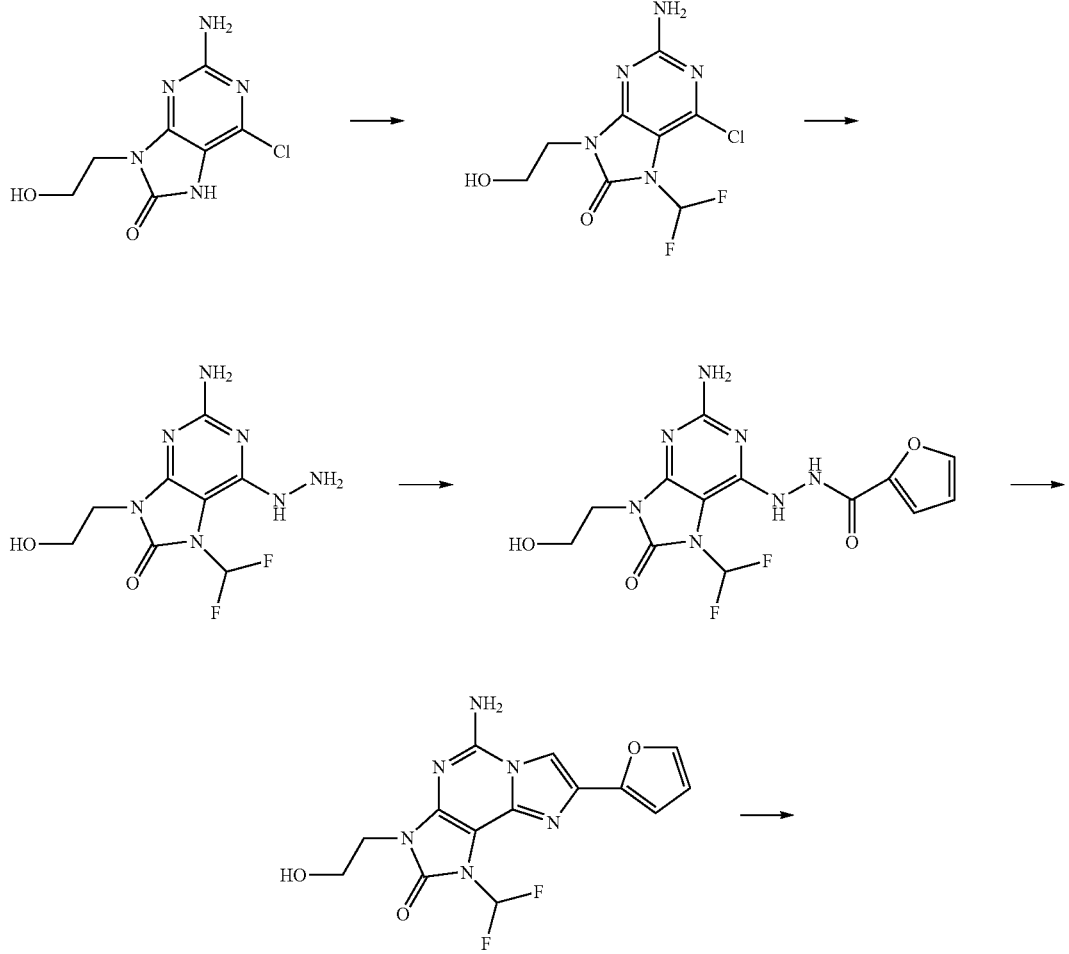

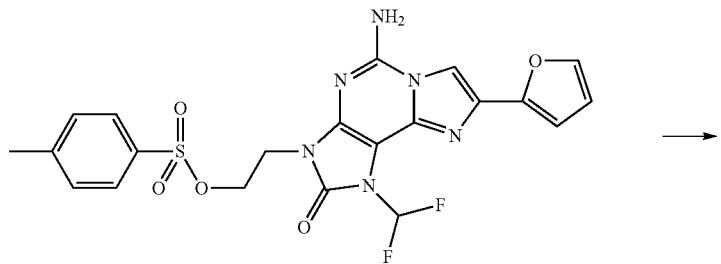

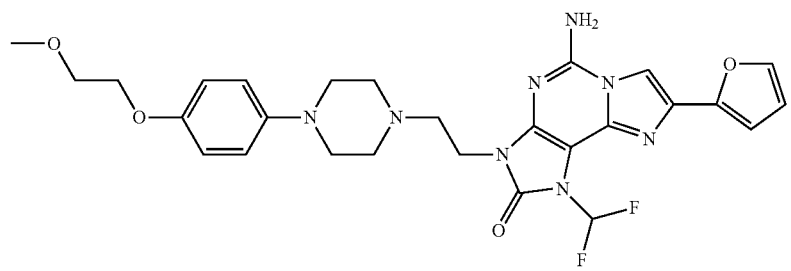

Step-1: 2-Amino-6-chloro-7-(difluoromethyl)-9-(2-hydroxyethyl)purin-8-one (Procedure is Same as Step-3 in Example A1)

¹HNMR (400 MHz, DMSO d6): δ 3.66-3.69 (m, 2H); 3.79 (t, J=6 Hz, 2H); 4.91 (t, J=6 Hz, 1H); 7.04 (bs, 2H); 7.66 (t, J=58 Hz, 1H).

Step-2: 2-Amino-7-(difluoromethyl)-6-hydrazino-9-(2-hydroxyethyl)purin-8-one (Procedure is Same as Step-4 in Example A1)

¹HNMR (400 MHz, DMSO d6): δ 3.63 (bs, 2H); 3.74 (t, J=6 Hz, 2H); 4.54 (bs, 2H); 4.91 (bs, 1H); 6.36 (bs, 2H); 7.70 (t, J=58 Hz, 1H).

Step-3 N'-[2-Amino-7-(difluoromethyl)-9-(2-hydroxyethyl)-8-oxo-purin-6-yl]furan-2-carbohydrazide (Procedure is Same as Step-5 in Example A1)

Crude product was used in next step

Step-4: 5-Amino-1-(difluoromethyl)-8-(2-furyl)-3-(2-hydroxyethyl)-[1,2,4]triazolo[5,1-f]purin-2-one (Procedure is Same as Step-6 in Example A1)

¹HNMR (400 MHz, DMSO d6): δ 3.72 (q, J=6 Hz, 2H); 3.87 (t, J=5.6 Hz, 2H); 4.94 (t, J=6 Hz, 1H); 6.72 (dd, J=2 Hz, 3.6 Hz, 1H); 7.19 (d, J=3.2 Hz, 1H); 7.72 (t, J=58 Hz, 1H); 7.95 (s, 1H); 8.12 (bs, 2H).

Step-5: 2-[5-Amino-1-(difluoromethyl)-8-(2-furyl)-2-oxo-[1,2,4]triazolo[5,1-f]purin-3-yl]ethyl 4-methylbenzenesulfonate (Procedure is Same as Step-7 in Example A1)

¹HNMR (400 MHz, DMSO d6): δ 1.98 (s, 3H); 4.02 (t, J=4.8 Hz, 2H); 4.47 (t, J=5.2 Hz, 2H); 6.74 (dd, J=2 Hz, 3.6 Hz, 1H); 7.01 (d, J=8 Hz, 2H); 7.22 (d, J=2.8 Hz, 1H); 7.45 (d, J=8 Hz, 2H); 7.69 (t, J=58 Hz, 1H); 7.97 (s, 1H); 8.11 (bs, 2H).

Step-6: 5-Amino-1-(difluoromethyl)-8-(2-furyl)-3-[2-[4-[4-(2-methoxyethoxy)phenyl]piperazin-1-yl]ethyl]-[1,2,4]triazolo[5,1-f]purin-2-one (Procedure is Same as Step-8 in Example A1)

HNMR (400 MHz, DMSO d6): δ 2.60 (bs, 4H); 2.70 (t, J=6.8 Hz, 2H); 2.93 (bs, 4H); 3.28 (s, 3H); 3.59-3.61 (m, 2H);

3.95-3.99 (m, 4H); 6.72 (dd, J=1.6 Hz, 3.6 Hz, 1H); 6.78-6.85 (m, 4H); 7.18 (d, J=2.8 Hz, 1H); 7.73 (t, J=58 Hz, 1H); 7.94 (d, J=0.8 Hz, 1H); 8.13 (bs, 2H).

Example M1

5-Amino-3-[2-[4-[4-(2-methoxyethoxy)phenyl]piperazin-1-yl]ethyl]-1-methyl-8-thiazol-2-yl-[1,2,4]triazolo[5,1-f]purin-2-one

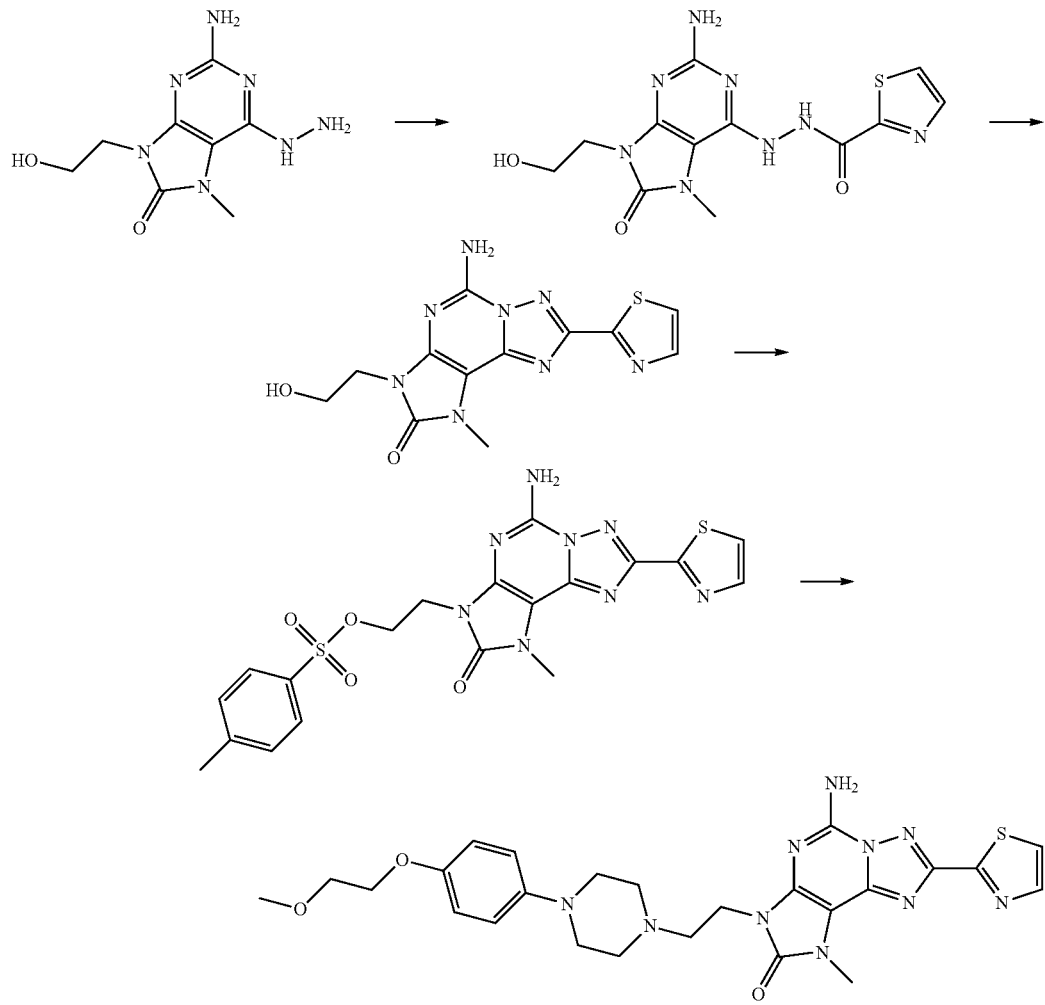

Step-1: N'-[2-Amino-9-(2-hydroxyethyl)-7-methyl-8-oxo-purin-6-yl]thiazole-2-carbohydrazide (Procedure is Same as Step-5 in Example A1)

$^1$HNMR (400 MHz, DMSO d6): δ 3.43 (s, 3H); 3.58-3.63 (m, 2H); 3.74 (t, J=5.6 Hz, 2H); 4.88 (t, J=6.0 Hz, 1H); 5.98 (s, 2H); 8.09-8.12 (m, 2H); 8.53 (s, 1H); 10.65 (s, 1H).

Step-2: 5-Amino-3-(2-hydroxyethyl)-1-methyl-8-thiazol-2-yl-[1,2,4]triazolo[5,1-f]purin-2-one (Procedure is Same as Step-6 in Example A1)

$^1$HNMR (400 MHz, DMSO d6): δ 3.58 (s, 3H); 3.70 (q, J=5.6 Hz, 2H); 3.87 (t, J=6.4 Hz, 2H); 4.89 (t, J=6.0 Hz, 1H): 7.90 (bs, 2H); 8.02 (d, J=3.2 Hz, 1H); 8.09 (d, J=3.2 Hz, 1H).

Step-3: 2-(5-Amino-1-methyl-2-oxo-8-thiazol-2-yl-[1,2,4]triazolo[5,1-f]purin-3-yl)ethyl 4 methylbenzenesulfonate (Procedure is Same as Step-7 in Example A1)

$^1$HNMR (400 MHz, DMSO d6): δ 2.03 (s, 3H); 3.51 (s, 3H); 4.01 (t, J=4.4 Hz, 2H); 4.49 (t, J=4.4 Hz, 2H); 7.03 (d, J=8.0 Hz, 2H): 7.41 (d, J=8.0 Hz, 2H); 7.89 (bs, 2H); 8.04 (d, J=3.2 Hz, 1H); 8.12 (d, J=3.2 Hz, 1H).

Step-4: 5-Amino-3-[2-[4-[4-(2-methoxyethoxy)phenyl]piperazin-1-yl]ethyl]-1-methyl-8-thiazol-2-yl-[1,2,4]triazolo[5,1-f]purin-2-one (Procedure is Same as Step-8 in Example A1)

$^1$HNMR (400 MHz, DMSO d6): δ 2.59 (bs, 4H); 2.67 (t, J=6.8 Hz, 2H); 2.94 (b§, 4H); 3.27 (s, 3H); 3.56 (s, 3H); 3.59 (t, J=4.4 Hz, 2H); 3.93-3.98 (m, 4H); 6.76-6.83 (m, 4H); 7.90 (bs, 2H); 8.00 (d, J=3.2 Hz, 1H); 7.41 (d, J=2.8 Hz, 1H).

Examples M2-M9 was prepared by following similar experimental procedure of Example M1 using the appropriate intermediates

| Ex. No | Structure/IUPAC name | NMR |
|---|---|---|
| M2 | 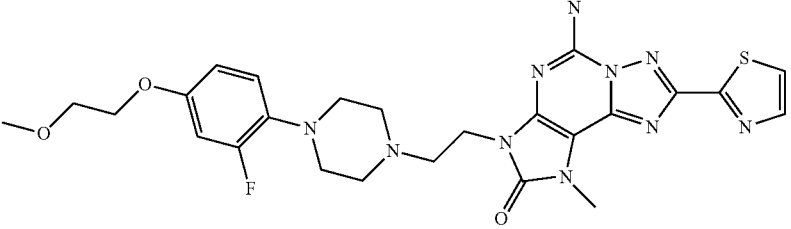 [SMILES: COCCOc1ccc(N2CCN(CCn3c(=O)n(C)c4c3nc(N)n3nc(-c5nccs5)nc43)CC2)c(F)c1]

5-Amino-3-[2-[4-[3-fluoro-4-(2-methoxyethoxy)phenyl]piperazin-1-yl]ethyl]-1-methyl-8-thiazol-2-yl-[1,2,4]triazolo[5,1-f]purin-2-one | $^1$HNMR(400 MHz, DMSO d6): δ 2.60(bs, 4H); 2.67(t, J = 7.2 Hz, 2H); 2.84 (bs, 4H); 3.26 (s, 3H); 3.57 (s, 3H); 3.59 (t, J = 4.4 Hz, 2H); 3.94 (t, J = 6.4 Hz, 2H); 4.00 (t, J = 4.4 Hz, 2H); 6.65 (dd, J = 2.4, 8.8 Hz, 1H); 6.77 (dd, J = 2.4, 14.4 Hz, 1H); 6.91 (t, J = 9.2 Hz, 1H); 7.89 (bs, 2H); 8.00 (d, J = 3.2 Hz, 1H); 8.07 (d, J = 3.2 Hz, 1H). |
| M3 | 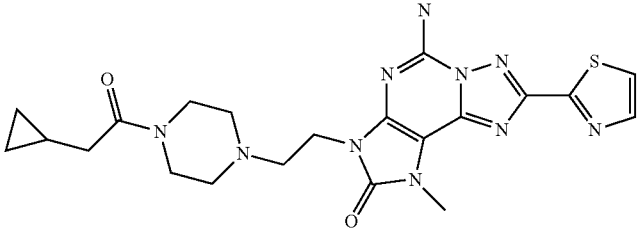 [SMILES: Cn1c(=O)n(CCN2CCN(C(=O)CC3CC3)CC2)c2nc(N)n3nc(-c4nccs4)nc3c21]

5-Amino-3-[2-[4-(2-cyclopropylacetyl)piperazin-1-yl]ethyl]-1-methyl-8-thiazol-2-yl-[1,2,4]triazolo[5,1-f]purin-2-one | $^1$HNMR(400 MHz, CDCl$_3$): δ 0.14-0.18 (m, 2H); 0.53-0.57 (m, 2H); 1.00-1.02 (m, 1H); 2.25 (d, J = 6.8 Hz, 2H); 2.56 (bs, 4H); 2.78 (t, J = 6.4 Hz, 2H); 3.41 (t, J = 5.2 Hz, 2H); 3.59 (bs, 2H); 3.79 (s, 3H); 4.08 (t, J = 6.4 Hz, 2H); 5.85 (bs, 2H ); 7.57 (d, J = 3.2 Hz, 1H); 8.06 (d, J = 3.2 Hz, 1H). |
| M4 | 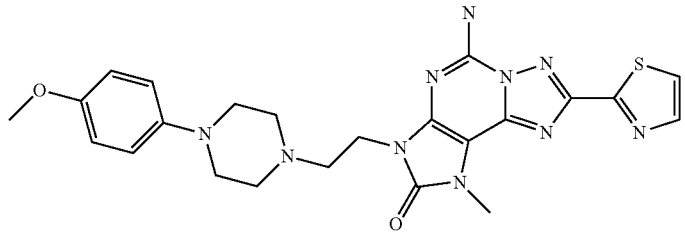 [SMILES: COc1ccc(N2CCN(CCn3c(=O)n(C)c4c3nc(N)n3nc(-c5nccs5)nc43)CC2)cc1]

5-Amino-3-[2-[4-(4-methoxyphenyl)piperazin-1-yl]ethyl]-1-methyl-8-thiazol-2-yl-[1,2,4]triazolo[5,1-f]purin-2-one | $^1$HNMR(400 MHz, DMSO d6): δ 2.61 (bs, 4H); 2.68 (t, J = 5.2 Hz, 2H); 2.95 (bs, 4H); 3.58 (s, 3H); 3.66 (s, 3H); 3.97 (t, J = 6.4 Hz, 2H); 6.79 (d, J = 9.2 Hz, 2H); 6.86 (d, J = 9.2 Hz, 2H); 7.92 (bs, 2H), 8.02 (d, J = 3.2 Hz, 1H); 8.09 (d, J = 3.6 Hz, 1H). |
| M5 | 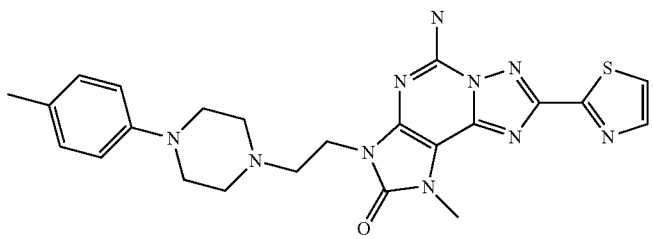 [SMILES: Cc1ccc(N2CCN(CCn3c(=O)n(C)c4c3nc(N)n3nc(-c5nccs5)nc43)CC2)cc1]

5-Amino-1-methyl-3-[2-[4-(p-tolyl)piperazin-1-yl]ethyl]-8-thiazol-2-yl-[1,2,4]triazolo[5,1-f]purin-2-one | $^1$HNMR(400 MHz, DMSO d6): δ 2.18 (s, 3H); 2.61 (bs, 4H); 2.68 (t, J = 6.8 Hz, 2H); 3.01 (bs, 4H); 3.58 (s, 3H); 3.97 (t, J = 6.0 Hz, 2H); 6.80 (d, J = 8.4 Hz, 2H); 7.00 (d, J = 8.4 Hz, 2H); 7.92 (bs, 2H); 8.02 (d, J = 2.8 Hz, 1H); 8.09 (d, J = 3.2 Hz, 1H). |

| Ex. No | Structure/IUPAC name | NMR |
|---|---|---|
| M6 | 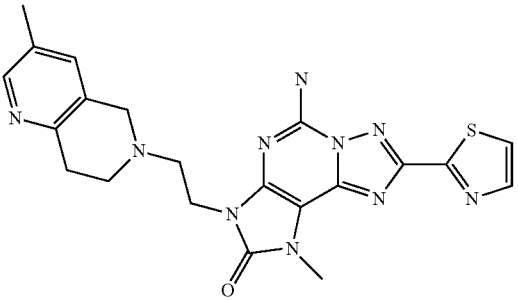 [SMILES: Cc1cnc2c(c1)CN(CCn1c(=O)n(C)c3c1nc(N)n1nc(-c4nccs4)nc31)CC2]<br>5-Amino-1-methyl-3-[2-(3-methyl-7,8-dihydro-5H-1,6-naphthyridin-6-yl)ethyl]-8-thiazol-2-yl-[1,2,4]triazolo[5,1-f]purin-2-one | $^1$HNMR(400 MHz, DMSO d6): δ 2.21 (s, 3H), 2.75-2.79 (m, 2H); 2.83-2.85 (m, 4H); 3.57 (s, 3H); 3.64 (s, 2H); 4.03 (t, J = 6.4 Hz, 2H); 7.28 (bs, 1H); 7.93 (bs, 2H); 8.01 (d, J = 3.6 Hz, 1H); 8.08 (d, J = 2.8 Hz, 1H); 8.14 (bs, 1H). |
| M7 | 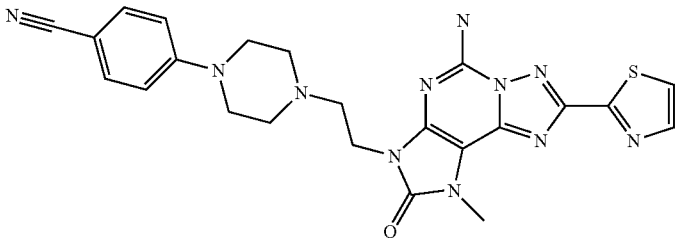 [SMILES: Cn1c(=O)n(CCN2CCN(c3ccc(C#N)cc3)CC2)c2nc(N)n3nc(-c4nccs4)nc3c21]<br>4-[4-[2-(5-Amino-1-methyl-2-oxo-8-thiazol-2-yl-[1,2,4]triazolo[5,1-f]purin-3-yl)ethyl]piperazin-1-yl]benzonitrile | $^1$HNMR(400 MHz, DMSO d6): δ 2.59(bs, 4H); 2.68 (t, J = 6.0 Hz, 2H); 3.27 (bs, 4H); 3.58 (s, 3H); 3.97 (t, J = 6.0 Hz, 2H); 6.99 (d, J = 8.8 Hz, 2H); 7.57 (d, J = 8.4 Hz, 2H); 7.93 (bs, 2H); 8.02 (d, J = 2.8 Hz, 1H); 8.09 (d, J = 3.2 Hz, 1H). |
| M8 | 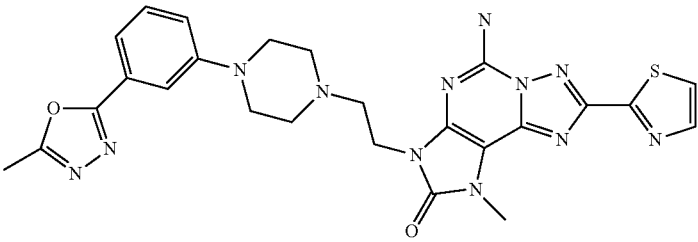 [SMILES: Cc1nnc(-c2cccc(N3CCN(CCn4c(=O)n(C)c5c4nc(N)n4nc(-c6nccs6)nc54)CC3)c2)o1]<br>5-Amino-1-methyl-3-[2-[4-[3-(5-methyl-1,3,4-oxadiazol-2-yl)phenyl]piperazin-1-yl]ethyl]-8-thiazol-2-yl-[1,2,4]triazolo[5,1-f]purin-2-one | $^1$HNMR(400 MHz, DMSO d6): δ 2.58 (s, 3H); 2.65 (bs, 4H); 2.71 (t, J = 6.0 Hz, 2H); 3.18 (bs, 4H); 3.59 (s, 3H); 3.99 (t, J = 6.4 Hz, 2H); 7.18 (d, J = 7.2 Hz, 1H); 7.35 (d, J = 7.2 Hz, 1H); 7.38-7.42 (m, 2H); 7.95 (bs, 2H); 8.03 (d, J = 3.2 Hz, 1H); 8.10 (d, J = 3.2 Hz, 1H). |
| M9 | 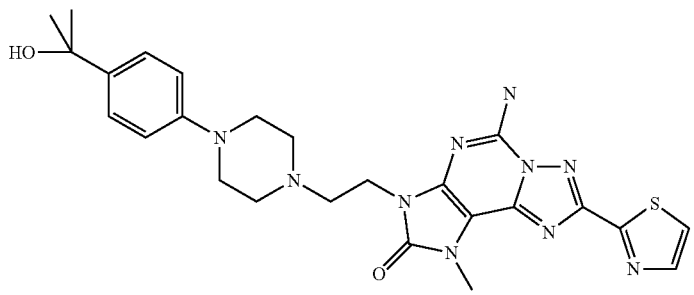 [SMILES: Cn1c(=O)n(CCN2CCN(c3ccc(C(C)(C)O)cc3)CC2)c2nc(N)n3nc(-c4nccs4)nc3c21]<br>5-amino-3-[2-[4-[4-(1-hydroxy-1-methyl-ethyl)phenyl]piperazin-1-yl]ethyl]-1-methyl-8-thiazol-2-yl-[1,2,4]triazolo[5,1-f]purin-2-one | $^1$H NMR(400 MHz, DMSO): δ 1.37 (m, 6H); 2.61 (m, 4H); 2.67-2.71 (m, 2H); 3.04 (bs, 4H); 3.58 (s, 3H); 3.97 (bs, 2H); 4.82 (bs, 1H); 6.83 (d, J = 8.4 Hz, 2H); 7.27 (d, J = 8.0 Hz, 2H); 7.92 (bs, 2H); 8.03 (bs, 1H); 8.09 (bs, 1H). |

Example N1

5-Amino-3-[2-[4-[4-(2-methoxyethoxy)phenyl]piperazin-1-yl]ethyl]-1-methyl-8-(2-pyridyl)-[1,2,4]triazolo[5,1-f]purin-2-one

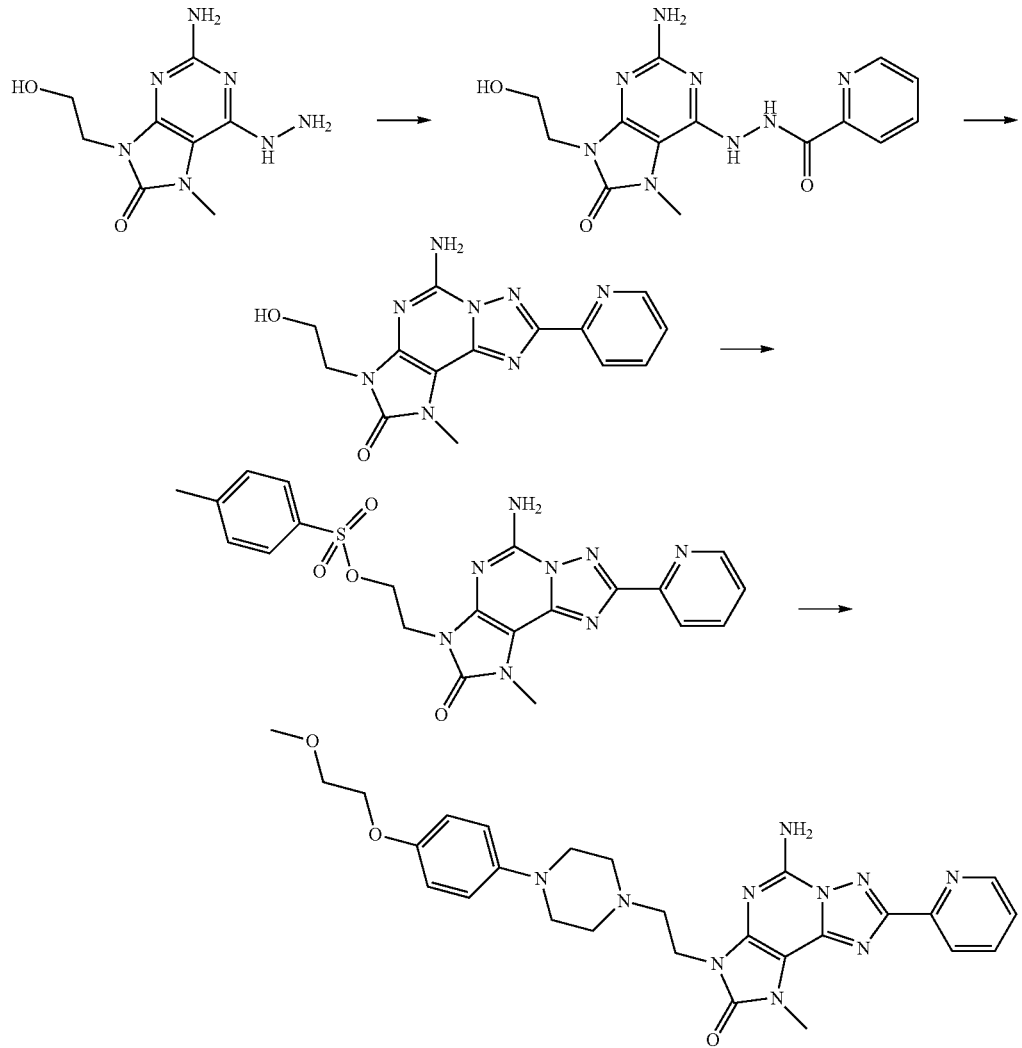

Step-1: N'-[2-Amino-9-(2-hydroxyethyl)-7-methyl-8-oxo-purin-6-yl]pyridine-2 carbohydrazide (Procedure is Same Step-5 as in Example A1)

Crude product was used in next step

Step-2: 5-Amino-3-(2-hydroxyethyl)-1-methyl-8-(2-pyridyl)-[1,2,4]triazolo[5,1-f]purin-2-one (Procedure is Same as Step-6 in Example A1)

¹HNMR (400 MHz, DMSO d6): δ 3.60 (s, 3H); 3.69-3.71 (m, 2H); 3.88 (t, J=6 Hz, 2H); 4.89 (t, J=6 Hz, 1H); 7.55 (t, J=6 Hz, 1H); 7.86 (bs, 2H); 8.01 (t, J=7.6 Hz, 1H); 8.29 (d, J=7.6 Hz, 1H); 8.75 (d, J=4.4 Hz, 1H).

Step-3: 2-[5-Amino-1-methyl-2-oxo-8-(2-pyridyl)-[1,2,4]triazolo[5,1-f]purin-3-yl]ethyl 4-methylbenzenesulfonate (Procedure is Same as Step-7 in Example A1)

¹HNMR (400 MHz, DMSO d6): δ 1.99 (s, 3H); 3.53 (s, 3H); 4.01 (bs, 2H); 4.49 (bs, 2H); 7.01 (d, J=8 Hz, 2H); 7.42 (d, J=8 Hz, 2H); 7.58 (t, J=6 Hz, 1H); 7.85 (bs, 2H); 8.04 (t, J=8 Hz, 1H); 8.31 (d, J=8 Hz, 1H); 8.78 (d, J=4.8 Hz, 1H).

Step-4: 5-Amino-3-[2-[4-[4-(2-methoxyethoxy)phenyl]piperazin-1-yl]ethyl]-1-methyl-8-(2-pyridyl)-[1,2,4]triazolo[5,1-f]purin-2-one (Procedure is Same as Step-8 in Example A1)

HNMR (400 MHz, DMSO d6): δ 2.61 (bs, 4H); 2.69 (t, J=6.4 Hz, 2H); 2.95 (bs, 41-1); 3.28 (s, 3H); 3.60 (t, J=4.8 Hz,

5H); 3.95-3.99 (m, 4H); 6.78-6.86 (m, 4H); 7.53-7.56 (m, 1H); 7.87 (bs, 2H); 7.98-8.03 (m, 1H); 8.29 (d, J=8 Hz, 1H); 8.74-8.75 (m, 1H)

Examples N2-N4 was prepared by following similar experimental procedure of EXAMPLE N1 using the appropriate intermediates

| Ex. No | Structure/IUPAC name | NMR |
|---|---|---|
| N2 | 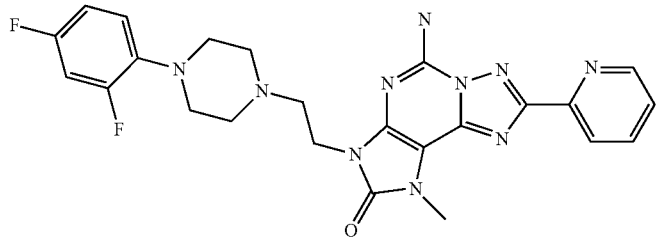 [SMILES: Cn1c(=O)n(CCN2CCN(c3ccc(F)cc3F)CC2)c2nc(N)n3nc(-c4ccccn4)nc3c21]<br>5-Amino-3-[2-[4-(2,4-difluorophenyl)piperazin-1-yl]ethyl]-1-methyl-8-(2-pyridyl)-[1,2,4]triazolo[5,1-f]purin-2-one | HNMR(400 MHz, DMSO d6): δ 2.64 (bs, 4H); 2.69 (bs, 2H); 2.91(bs, 4H); 3.62 (s, 3H); 3.97 (bs, 2H ); 6.95-7.06 (m, 2H ); 7.19 (t, J = 10 Hz, 1H); 7.56 (t, J = 6 Hz, 1H); 7.87 (bs, 2H); 8.02 (t, J = 7.6 Hz, 1H ); 8.29 (d, J = 7.6 Hz, 1H); 8.75-8.76 (m, 1H) |
| N3 | 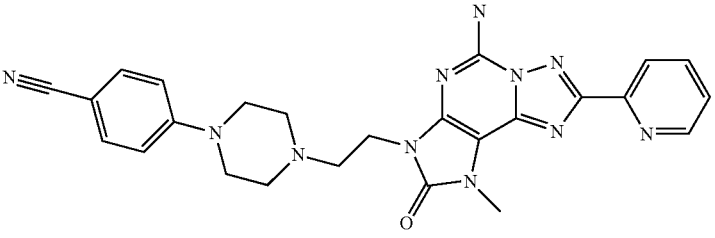 [SMILES: Cn1c(=O)n(CCN2CCN(c3ccc(C#N)cc3)CC2)c2nc(N)n3nc(-c4ccccn4)nc3c21]<br>4-[4-[2-[5-Amino-1-methyl-2-oxo-8-(2-pyridyl)-[1,2,4]triazolo[5,1-f]purin-3-yl]ethyl]piperazin-1-yl]benzonitrile | $^1$H NMR(400 MHz, DMSO d6): δ 2.58 (bs, 4H); 2.64-2.68 (m, 2H); 3.25 (bs, 4H); 3.59 (s, 3H); 3.94-3.98 (m, 2H); 6.98 (d, J = 8.8 Hz, 2H); 7.52-7.56 (m, 3H); 7.85 (bs, 2H); 7.97-8.01 (m, 1H); 8.27 (d, J = 7.6 Hz, 1H); 8.73 (d, J = 4.8 Hz, 1H). |
| N4 | 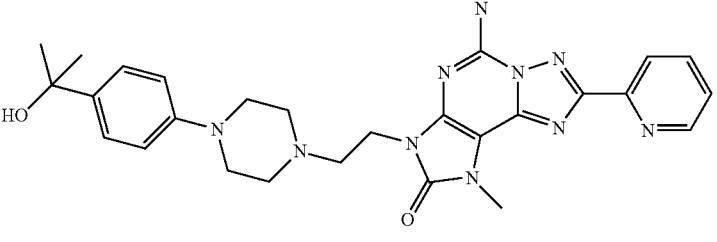 [SMILES: Cn1c(=O)n(CCN2CCN(c3ccc(C(C)(C)O)cc3)CC2)c2nc(N)n3nc(-c4ccccn4)nc3c21]<br>5-Amino-3-[2-[4-[4-(1-hydroxy-1-methyl-ethyl)phenyl]piperazin-1-yl]ethyl]-1-methyl-8-(2-pyridyl)-[1,2,4]triazolo[5,1-f]purin-2-one | $^1$H NMR(400 MHz, DMSO d6): δ 1.37 (s, 6H); 2.62 (bs, 4H); 2.67-2.70 (m, 2H); 3.04 (bs, 4H); 3.61 (s, 3H); 3.98 (bs, 2H); 4.81 (s, 1H); 6.83 (d, J = 8.4 Hz, 2H); 7.27 (d, J = 8 Hz, 2H); 7.54-7.57 (m, 1H); 7.87 (bs, 2H); 8.01 (t, J = 7.2 Hz, 1H); 8.29 (d, J = 7.6 Hz, 1H); 8.75 (d, J = 4 Hz, 1H). |

Example O1

5-Amino-3-[2-[4-[4-(2-methoxyethoxy)phenyl]piperazin-1-yl]ethyl]-1-methyl-8-pyrazin-2-yl-[1,2,4]triazolo[5,1-f]purin-2-one

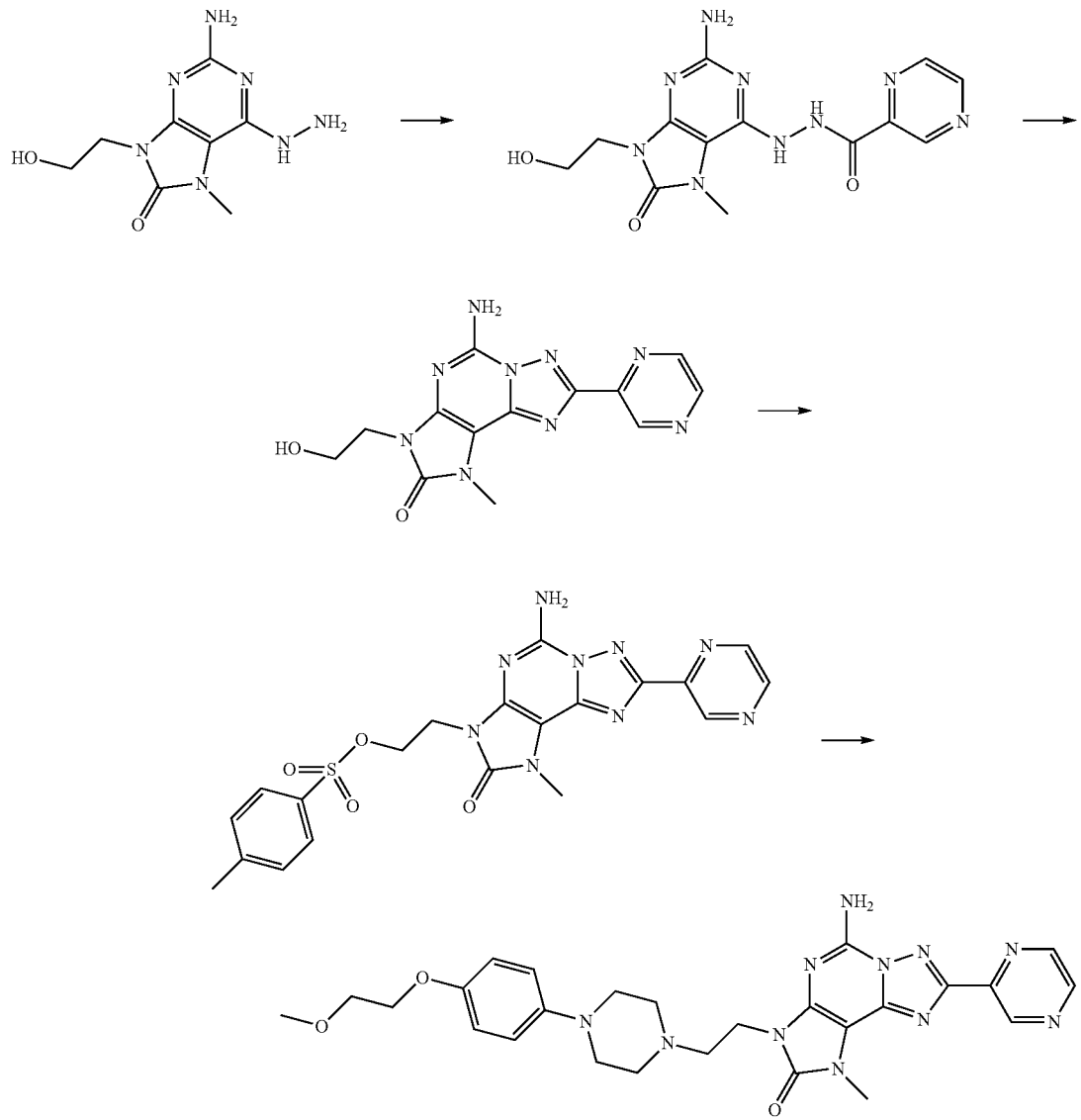

Step 1: N'-[2-Amino-9-(2-hydroxyethyl)-7-methyl-8-oxo-purin-6-yl]pyrazine-2-carbohydrazide (Procedure is Same as Step-5 in Example A1)

$^1$H NMR (400 MHz, DMSO d6): δ 3.45 (s, 3H); 3.58-3.64 (m, 2H); 3.75 (t, J=6.4 Hz, 2H); 5.97 (s, 2H); 8.54 (s, 1H); 8.80 (s, 1H); 8.92 (d, J=2 Hz, 1H); 9.21 (s, 1H); 10.68 (s, 1H).

Step 2: 5-Amino-3-(2-hydroxyethyl)-1-methyl-8-pyrazin-2-yl-[1,2,4]triazolo[5,1-f]purin-2-one (Procedure is Same as Step-6 in Example A1)

$^1$H NMR (400 MHz, DMSO d6): δ 3.58 (s, 3H); 3.65-3.70 (m, 2H); 3.86 (t, J=6 Hz, 2H); 4.88 (t, J=6 Hz, 1H); 7.91 (bs, 2H); 8.79-8.82 (m, 2H); 9.44 (s, 1H).

Step 3: 2-(5-Amino-1-methyl-2-oxo-8-pyrazin-2-yl-[1,2,4]triazolo[5,1-f]purin-3-yl)ethyl 4-methylbenzenesulfonate (Procedure is Same as Step-7 in Example A1)

$^1$H NMR (400 MHz, DMSO d6): δ 2.01 (s, 3H); 3.53 (s, 3H); 4.02 (bs, 2H); 4.48 (bs, 2H); 7.02 (d, J=7.61-1z, 2H); 7.42 (d, J=8 Hz, 2H); 7.92 (bs, 2H); 8.82-8.87 (m, 2H); 9.48 (s, 1H).

Step 4: 5-Amino-3-[2-[4-[4-(2-methoxyethoxy)phenyl]piperazin-1-yl]ethyl]-1-methyl-8-pyrazin-2-yl-[1,2,4]triazolo[5,1-f]purin-2-(Procedure is Same as Step-8 in Example A1)

$^1$H NMR (400 MHz, DMSO d6): δ 2.61 (bs, 4H); 2.69 (t, J=6.4 Hz, 2H); 2.96 (bs, 4H); 3.29 (s, 3H); 3.61 (bs, 5H);

3.97-3.99 (m, 4H); 6.79-6.86 (m, 41-1); 7.95 (bs, 2H); 8.82-8.84 (m, 2H); 9.46 (s, 1H).

Examples O2-O3 was prepared by following similar experimental procedure of EXAMPLE O1 using the appropriate intermediates

| | | |
|---|---|---|
| O2 | 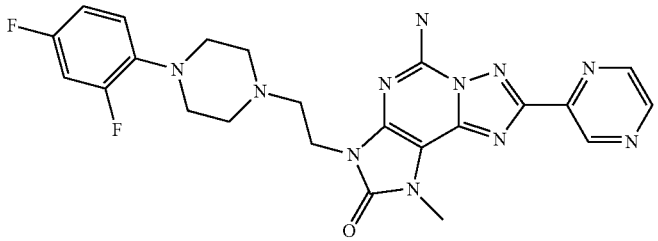 [SMILES: Cn1c(=O)n(CCN2CCN(c3ccc(F)cc3F)CC2)c2nc(N)n3nc(-c4cnccn4)nc3c21]<br>5-Amino-3-[2-[4-(2,4-difluorophenyl)piperazin-1-yl]ethyl]-1-methyl-8-pyrazin-2-yl-[1,2,4]triazolo[5,1-f]purin-2-one | ¹H NMR(400 MHz, DMSO d6):<br>δ 2.64 (bs, 4H); 2.71 (t, J = 6.0 Hz, 2H); 2.91 (bs, 4H); 3.62 (s, 3H); 3.98 (t, J = 6.0 Hz, 2H); 6.94-7.06 (m, 2H); 7.15-7.21 (m, 1H); 7.94 (bs, 2H); 8.82-8.85 (m, 2H); 9.46 (d, J = 1.6 Hz, 1H). |
| O3 | 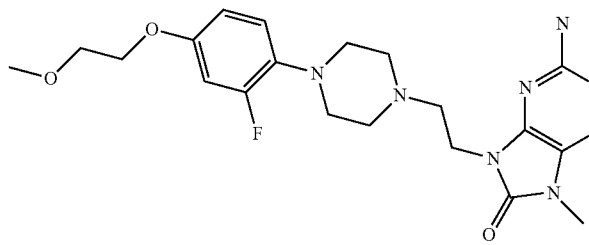<br>5-Amino-3-[2-[4-[2-fluoro-4-(2-methoxyethoxy)phenyl]piperazin-1-yl]ethyl]-1-methyl-8-pyrazin-2-yl-[1,2,4]triazolo[5,1-f]purin-2-one | ¹H NMR(400 MHz, DMSO d6): δ 2.60 (bs, 4H); 2.68 (t, J = 6 Hz, 2H); 2.84 (bs, 4H); 3.26 (s, 3H); 3.59 (bs, 5H); 3.92-3.97 (m, 2H); 3.99-4.01 (m, 2H); 6.65 (dd, J = 8.8 Hz, 2.4 Hz, 1H); 6.78 (dd, J = 14.4 Hz, 2.8 Hz, 1H); 6.91 (t, J = 9.6 Hz, 1H); 7.92 (bs, 2H); 8.79-8.83 (m, 2H); 9.44 (s, 1H). |

Example: P1

5-Amino-8-(2-furyl)-3-[[1-(4-methoxyphenyl)pyrrolidin-3-yl]methyl]-1-methyl-[1,2,4]triazolo[5,1-f]purin-2-one

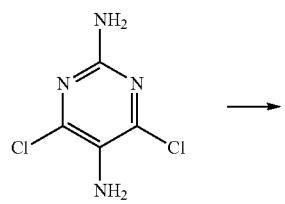

→

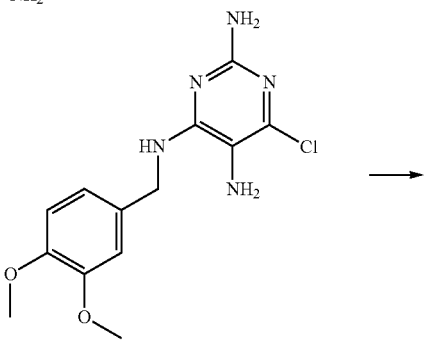

→

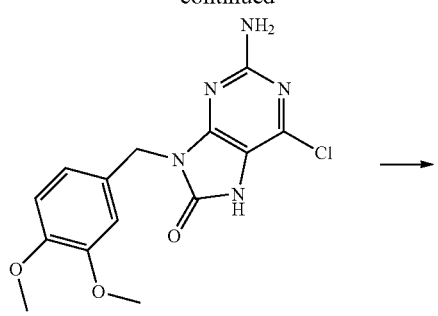

-continued

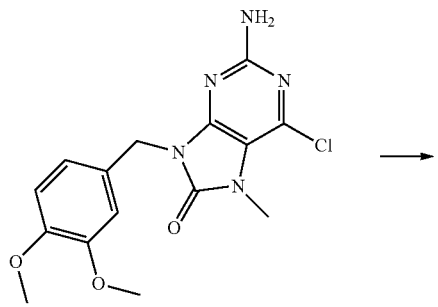

→

121
-continued

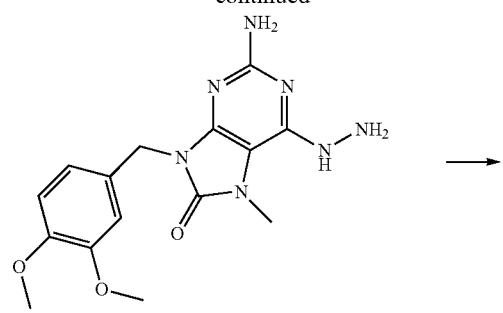

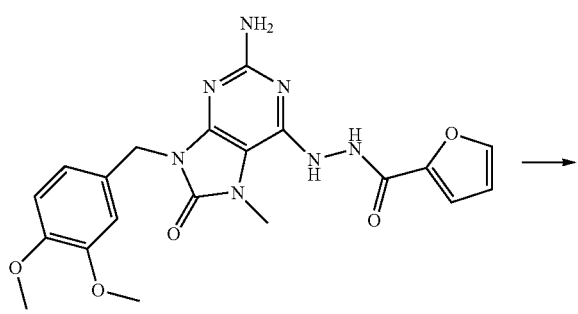

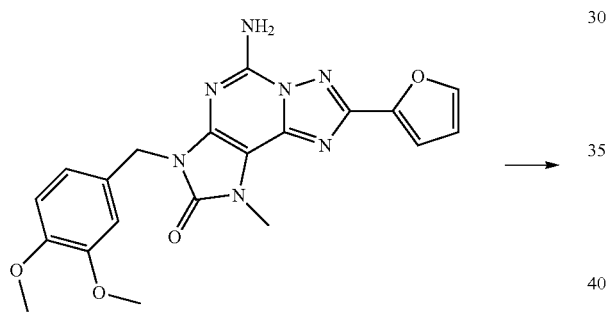

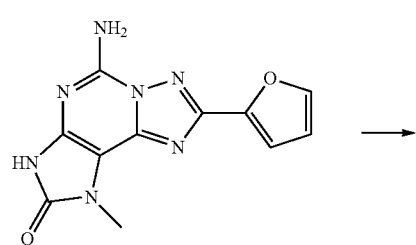

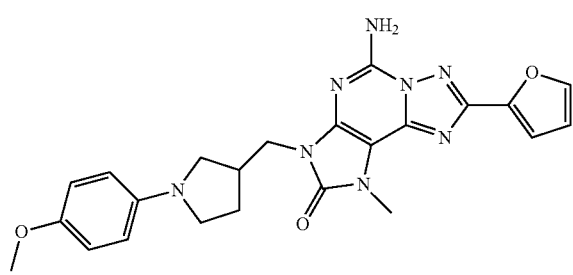

122

Step-1: 6-Chloro-N4-[(2,4-dimethoxyphenyl)methyl]pyrimidine-2,4,5-triamine

A mixture of 4,6-dichloropyrimidine-2,5-diamine (5.5 ml, 30.72 mmol), ethanol (50 ml), 2,6-dichloropyrimidin-4-amine (5.0 g, 27.93 mmol), and potassium carbonate (2.3 g, 16.75 mmol) were heated to 85-90° C. for 16 hours. Reaction mixture was cooled to room temperature, and filtered through celite bed, washed with ethanol and evaporated to dryness to obtain pure 6-Chloro-N4-[(2,4-dimethoxyphenyl)methyl]pyrimidine-2,4,5-triamine (8.4 g, 97%).

$^1$HNMR (400 MHz, DMSO d6): δ 3.73 (s, 3H); 3.79 (s, 3H); 3.98 (bs, 2H); 4.42 (d, J=5.6 Hz, 2H); 5.64 (s, 2H); 6.46 (dd, J=2.4 Hz, 8.4 Hz, 1H); 6.55 (d, J=2.4 Hz, 1H); 6.71 (t, J=6.0 Hz, 1H); 7.10 (d, J=8.4 Hz, 1H).

Step-2: 2-Amino-6-chloro-9-[(3,4-dimethoxyphenyl)methyl]-7H-purin-8-one

A mixture of 6-Chloro-N4-[(2,4-dimethoxyphenyl)methyl]pyrimidine-2,4,5-triamine (8.4 g, 27.11 mmol), acetonitrile (400 ml), potassium carbonate (11.2 g, 81.33 mmol) and p-nitrophenyl chloroformate (11.0 g, 54.22 mmol) were stirred at 25° C. for 48 hours. Reaction mixture was cooled to room temperature and filtered through celite bed, washed with cold acetonitrile and evaporated to dryness to obtain pure 2-Amino-6-chloro-9-[(3,4-dimethoxyphenyl)methyl]-7H-purin-8-one (9.0 g, 98%)

Crude product was taken in next step

Step-3: 2-Amino-6-chloro-9-[(3,4-dimethoxyphenyl)methyl]-7-methyl-purin-8-one

A mixture of 2-amino-6-chloro-9-[(3,4-dimethoxyphenyl)methyl]-7H-purin-8-one (8.8 g, 26.21 mmol), DMF (90 ml), potassium carbonate (5.4 g, 39.31 mmol) and methyl iodide (1.96 ml, 31.45 mmol) stirred at 25° C. for 3 hours. Reaction mixture was cooled to 0° C. Water was added and solid obtained was filtered off to obtain 2-amino-6-chloro-9-[(3,4-dimethoxyphenyl)methyl]-7-methyl-purin-8-one (9.0 g, 98%).

$^1$HNMR (400 MHz, DMSO d6): δ 3.72 (s, 3H); 3.82 (s, 3H); 3.90 (s, 3H); 4.73 (s, 2H); 6.35 (bs, 2H); 6.38-6.41 (m, 1H); 6.56-6.58 (m, 1H); 6.61-6.63 (m, 1H).

Step-4: 2-Amino-9-[(3,4-dimethoxyphenyl)methyl]-6-hydrazino-7-methyl-purin-8-one A mixture of 2-amino-6-chloro-9-[(3,4-dimethoxyphenyl)methyl]-7-methyl-purin-8-one obtained in step 3 (9.0 g, 25.73 mmol), Hydrazine hydrate (16 ml, 257.3 mmol) and ethanol (675 ml) were heated at 90-95° C. for 40 hours. The reaction mixture was concentrated and solid obtained was filtered off and dried to obtain 2-amino-9-[(3,4-dimethoxyphenyl)methyl]-6-hydrazino-7-methyl-purin-8-one (6.5 g, 74%) as an off white solid.

$^1$HNMR (400 MHz, DMSO d6): δ 3.40 (s, 3H); 3.69 (s, 3H); 3.80 (s, 3H); 4.29 (bs, 2H); 4.72 (bs, 2H); 5.97 (bs, 2H); 6.37 (dd, J=2.0 Hz, 8.4 Hz, 1H); 6.49-6.54 (m, 2H); 7.66 (s, 1H).

Step-5: N'-[2-amino-9-[(3,4-dimethoxyphenyl)methyl]-7-methyl-8-oxo-purin-6-yl]furan-2-carbohydrazide 2-amino-9-[(3,4-dimethoxyphenyl)methyl]-6-hydrazino-7-methyl-purin-8-one (4.6 g, 13.38 mmol) obtained in step 4, 2-furoic acid (1.5 g, 13.38 mmol), HOBT (1.8 g, 13.38 mmol) and N-methylmorpholine (2.20 ml, 20.07 mmol) were taken in dimethylformamide (15 ml). EDC.HCl (3.8 g, 20.07 mmol) was added to the reaction mixture and stirred at 25-27° C. for 3 hours. Reaction mixture was cooled to 0° C. Water was added and solid obtained was filtered off, washed with cold water, n-hexane and dried to obtain N'-[2-amino-9-[(3,4-dimethoxyphenyl)methyl]-7-methyl-8-oxo-purin-6-yl]furan-2-carbohydrazide (5.5 g, 95) as an off white solid.

$^1$HNMR (400 MHz, DMSO d6): δ 3.48 (s, 3H); 3.71 (s, 3H); 3.83 (s, 3H); 4.76 (bs, 2H); 5.99 (bs, 2H); 6.41 (dd, J=2.4 Hz, 8.4 Hz, 1H); 6.57-6.59 (m, 2H); 6.67 (dd, J=2.0 Hz, 3.6 Hz, 1H); 7.25 (d, J=3.6 Hz, 1H); 7.90 (d, J=0.8 Hz, 1H); 8.42 (s, 1H); 10.28 (s, 1H).

Step-6: 5-Amino-3-[(3,4-dimethoxyphenyl)methyl]-8-(2-furyl)-1-methyl-[1,2,4]triazolo[5,1-t]purin-2-one A mixture of N'-[2-amino-9-[(3,4-dimethoxyphenyl)methyl]-7-methyl-8-oxo-purin-6-yl]furan-2-carbohydrazide obtained in step 5 (5.5 g, 12.51 mmol), N,O-bistrimethylsilylacetamide (21.4 ml, 87.61 mmol) and hexamethyldisilazane (49.5 ml, 312.91 mmol) were heated at 145-150° C. for 3 hours. The reaction mixture was quenched with methanol (100 ml) and water (100 ml) and solvent was concentrated. The solid obtained was filtered off and washed with water (30 ml) followed by diethyl ether (100 ml) to obtain 5-amino-3-[(3,4-dimethoxyphenyl)methyl]-8-(2-furyl)-1-methyl-[1,2,4]triazolo[5,1-f]purin-2-one (5.1 g, 97%) as an off white solid.

$^1$HNMR (400 MHz, DMSO d6): δ 3.61 (s, 3H); 3.72 (s, 3H); 3.85 (s, 3H); 4.88 (bs, 2H); 6.39 (dd, J=2.4 Hz, 8.4 Hz, 1H); 6.58 (d, J=2.4 Hz, 1H); 6.68 (d, J=8.4 Hz, 1H); 6.73 (dd, J=2.0, 3.6 Hz, 1H); 7.21 (d, J=3.2 Hz, 1H); 7.78 (bs, 2H); 7.94 (s, 1H).

Step-7: 5-Amino-8-(2-furyl)-1-methyl-3H-[1,2,4]triazolo[5,1-f]purin-2-one

A mixture of 5-amino-3-[(3,4-dimethoxyphenyl)methyl]-8-(2-furyl)-1-methyl-[1,2,4]triazolo[5,1-f]purin-2-one (0.1 g, 0.237 mmol), 1,2-dichlorobenzene (5 ml), and aluminium chloride (0.095 g, 0.711 mmol) were stirred at and heated at 160° C. for 45 minutes. Reaction mixture was cooled to room temperature and purified by LCMS to obtain pure 5-amino-8-(2-furyl)-1-methyl-3H-[1,2,4]triazolo[5,1-f]purin-2-one (0.025 g, 39%).

Crude product was taken in next step

Step-8: 5-Amino-8-(2-furyl)-3-[[1-(4-methoxyphenyl)pyrrolidin-3-yl]methyl]-1-methyl-[1,2,4]triazolo[5,1-f]purin-2-one A mixture of 5-amino-8-(2-furyl)-1-methyl-3H-[1,2,4]triazolo[5,1-f]purin-2-one (0.1 g, 0.368 mmol), DMF (3 ml), potassium carbonate (0.76 g, 0.553 mmol) and [1-(4-methoxyphenyl)pyrrolidin-3-yl]methyl methanesulfonate (0.115 g, 0.405 mmol) stirred at 60° C. for 48 hours. Reaction mixture was cooled to 0° C. Water was added and solid obtained was filtered off. The crude product was purified by HPLC/MS to obtain 5-amino-8-(2-furyl)-3-[[1-(4-methoxyphenyl)pyrrolidin-3-yl]methyl]-1-methyl-[1,2,4]triazolo[5,1-f]purin-2-one (0.012 g, 7%).

$^1$HNMR (400 MHz, DMSO d6): δ 1.77-1.84 (m, 1H); 1.98-2.04 (m, 1H); 2.89 (pent, J=6.8 Hz, 1H); 3.08-3.18 (m, 2H); 3.22-3.29 (m, 2H); 3.52 (s, 3H); 3.64 (s, 3H); 3.84-3.88 (m, 2H); 6.48 (d, J=9.2 Hz, 2H); 6.72 (dd, J=2.0 Hz, 3.6 Hz, 1H); 6.78 (d, J=8.8 Hz, 2H); 7.21 (d, J=2.8 Hz, 1H); 7.82 (bs, 2H); 7.94 (d, J=0.8 Hz, 1H).

Examples P2 was prepared by following similar experimental procedure of EXAMPLE P1 using the appropriate intermediates

| Ex. No | Structure/IUPAC name | NMR |
|---|---|---|
| P2 | 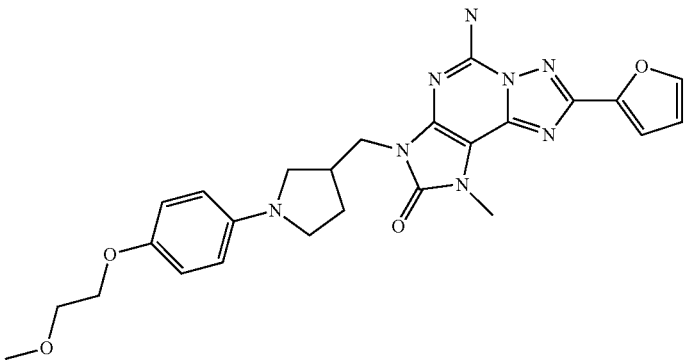 [SMILES: COCCOc1ccc(N2CCC(Cn3c(=O)n(C)c4c3nc(N)n3nc(-c5ccco5)nc43)C2)cc1]<br>5-Amino-8-(2-furyl)-3-[[1-[4-(2-methoxyethoxy)phenyl]pyrrolidin-3-yl]methyl]-1-methyl-[1,2,4]triazolo[5,1-f]purin-2-one<br>hyl}-1-methyl-1,3-dihydro-[1,2,4]triazolo[5,1-i]purin-2-one | $^1$HNMR(400 MHz, DMSO d6): δ 1.75-1.83 (m, 1H); 1.98-2.04 (m, 1H); 2.89 (pent, J = 6.8 Hz, 1H); 3.08-3.18 (m, 3H); 3.22-3.27 (m, 1H); 3.28 (s, 3H); 3.31-3.33 (m, 2H); 3.58 (s, 3H); 3.86-3.3.88 (m, 2H); 3.92-3.96 (m, 2H); 6.46 (d, J = 8.8 Hz, 2H); 6.72 (dd, J = 2.0, 3.6 Hz, 1H); 6.79 (d, J = 9.2 Hz, 2H); 7.20 (d, J = 3.2 Hz, 1H); 7.82 (bs, 2H); 7.94 (bs, 1H). |

Example Q1

5-amino-8-(2-furyl)-3-[2-[4-[4-(2-methoxyethoxy)phenyl]piperazin-1-yl]ethyl]-1-methyl-[1,2,4]triazolo[5,1-f]purine-2-thione

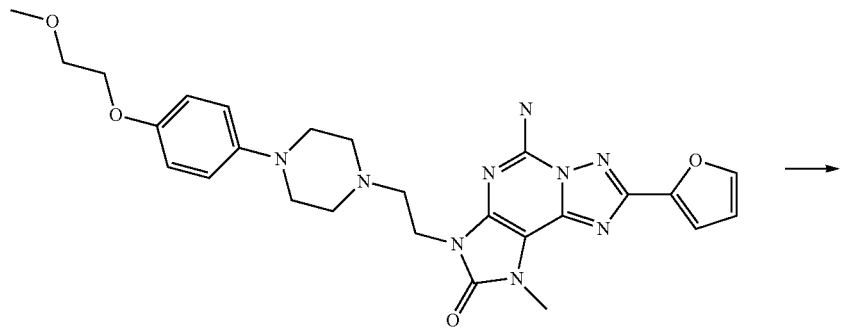

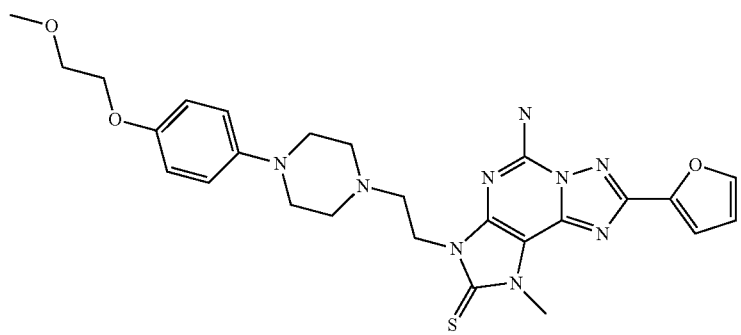

A mixture of 5-amino-8-(2-furyl)-3-[2-[4-[4-(2-methoxyethoxy)phenyl]piperazin-1-yl]ethyl]-1-methyl-[1,2,4]triazolo[5,1-f]purin-2-one (1.1 g, 2 mmol), Lawessoms reagent (0.83 g, 2 mmol) and toluene (20 ml) were heated in sealed tube at 140-150° C. for 16 hours. The mixture was cooled and to the residue water (100 ml) was added and extracted with dichloromethane (2×100 ml). The crude product was purified by column chromatography to obtain 5-amino-8-(2-furyl)-3-[2-[4-[4-(2-methoxyethoxy)phenyl]piperazin-1-yl]ethyl]-1-methyl-[1,2,4]triazolo[5,1-f]purine-2-thione. (11 mg,) as an off white solid.

HNMR (400 MHz, DMSO d6): δ 2.64 (bs, 4H); 2.75 (t, J=6 Hz, 2H); 2.96 (bs, 4H); 3.28 (s, 3H); 3.60 (t, J=5 Hz, 2H); 3.91 (s, 3H); 3.98 (t, J=5 Hz, 2H); 4.34 (t, J=6 Hz, 2H); 6.74-6.75 (m, 1H); 6.79-6.85 (m, 4H); 7.23 (d, J=3 Hz, 1H); 7.96 (s, 1H); 8.07 (bs, 2H).

Example R1

8-(2-furyl)-3-[2-[4-[4-(2-methoxyethoxy)phenyl]piperazin-1-yl]ethyl]-1-methyl-5-(methylamino)-[1,2,4]triazolo[5,1-f]purin-2-one

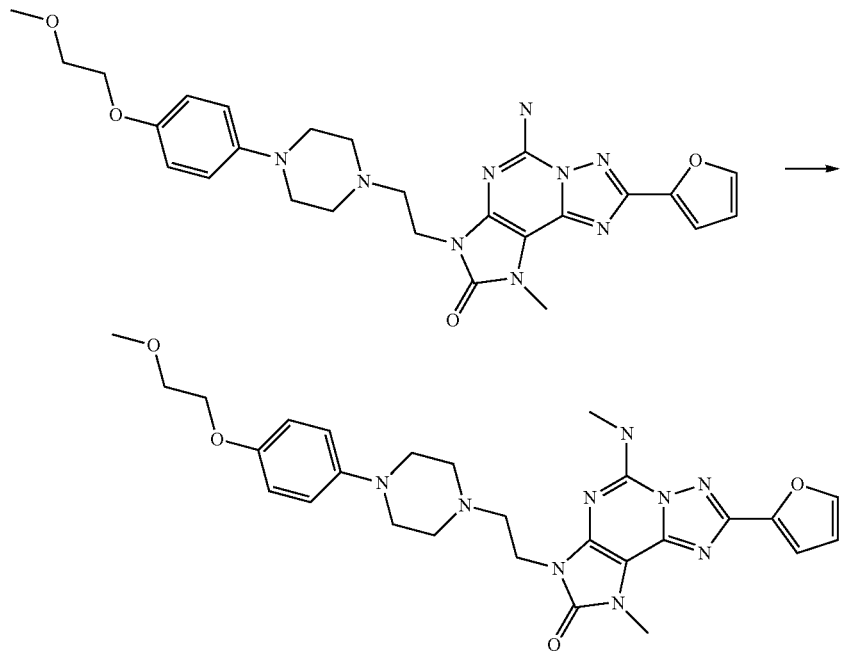

A mixture of 5-amino-8-(2-furyl)-3-[2-[4-[4-(2-methoxyethoxy)phenyl]piperazin-1-yl]ethyl]-1-methyl-[1,2,4]triazolo[5,1-f]purin-2-one (0.1 g, 0.18 mmol) obtained in example 1, NaH (0.043 g, 0.18 mmol) and methyl iodode (0.1 ml, 0.18 mmol)in DMF (2 ml) were stirred at 21° C. for 3 hours. To the reaction mixture water (10 ml) was added and solid obtained was filtered. The crude product was purified by column chromatography to obtain 8-(2-furyl)-3-[2-[4-[4-(2-methoxyethoxy)phenyl]piperazin-1-yl]ethyl]-1-methyl-5-(methylamino)-[1,2,4]triazolo[5,1-f]purin-2-one. (5 mg, 5%) as an off white solid.

HNMR (400 MHz, DMSO d6): δ 2.56 (bs, 4H); 2.71 (t, J=6 Hz, 2H); 2.73 (bs, 4H); 3.02 (d, J=5 Hz, 3H); 3.03 (s, 3H); 3.57 (s, 3H); 3.59-3.61 (m, 2H); 3.96-4.01 (m, 4H); 6.72-6.73 (m, 1H); 6.77-6.84 (m, 4H); 7.19 (d, J=3 Hz, 1H); 7.93-7.94 (m, 1H); 8.05 (d, J=5 Hz, 1H).

The list of examples below, but not limited to these, are synthesized following general synthesis described above:

5-Amino-3-{2-[4-(4-fluoro-phenyl)-piperazin-1-yl]-ethyl}-8-isothiazol-5-yl-1-methyl-1,3-dihydro-[1,2,4]triazolo[5,1-i]purin-2-one,
5-Amino-8-isothiazol-5-yl-3-(2-{4-[4-(2-methoxy-ethoxy)-phenyl]-piperazin-1-yl}-ethyl)-1-methyl-1,3-dihydro-[1,2,4]triazolo[5,1-i]purin-2-one,
5-Amino-3-[2-[4-[2-fluoro-4-(2-methoxyethoxy)phenyl]piperazin-1-yl]ethyl]-8-isothiazol-5-yl-1-methyl-[1,2,4]triazolo[5,1-f]purin-2-one,
5-Amino-8-isoxazol-5-yl-3-[2-[4-[4-(2-methoxyethoxy)phenyl]piperazin-1-yl]ethyl]-1-methyl-[1,2,4]triazolo[5,1-f]purin-2-one,
5-Amino-3-[2-[4-[4-(2-methoxyethoxy)phenyl]piperazin-1-yl]ethyl]-1-methyl-8-oxazol-2-yl-[1,2,4]triazolo[5,1-f]purin-2-one,
5-Amino-3-{2-[4-(4-methoxy-phenyl)-piperazin-1-yl]-ethyl}-1-methyl-8-prop-1-ynyl-1,3-dihydro-[1,2,4]triazolo[5,1-i]purin-2-one,
5-Amino-3-(2-{4-[4-(2-methoxy-ethoxy)-phenyl]-piperazin-1-yl}-ethyl)-1-methyl-8-prop-1-ynyl-1,3-dihydro-[1,2,4]triazolo[5,1-i]purin-2-one,
5-Amino-3-{2-[4-(4-fluoro-benzoyl)-piperazin-1-yl]-ethyl}-8-furan-2-yl-1-methyl-1,3-dihydro-[1,2,4]triazolo[5,1-i]purin-2-one,
5-Amino-3-(2-dimethylamino-ethyl)-8-furan-2-yl-1-methyl-1,3-dihydro-[1,2,4]triazolo[5,1-i]purin-2-one,
5-Amino-8-furan-2-yl-3-[3-(4-methoxy-phenyl)-propyl]-1-methyl-1,3-dihydro-[1,2,4]triazolo[5,1-i]purin-2-one,
5-Amino-8-furan-2-yl-1-methyl-3-(2-pyrazol-1-yl-ethyl)-1,3-dihydro-[1,2,4]triazolo[5,1-i]purin-2-one,
5-Amino-8-furan-2-yl-3-(2-{4-[4-(2-methoxy-ethoxy)-phenyl]-pyrazol-1-yl}-ethyl)-1-methyl-1,3-dihydro-[1,2,4]triazolo[5,1-i]purin-2-one,
5-Amino-8-furan-2-yl-3-{2-[3-(4-methoxy-phenyl)-pyrrol-1-yl]-ethyl}-1-methyl-1,3-dihydro-[1,2,4]triazolo[5,1-i]purin-2-one,
5-Amino-8-furan-2-yl-3-{2-[4-(4-methoxy-phenyl)-imidazol-1-yl]-ethyl}-1-methyl-1,3-dihydro-[1,2,4]triazolo[5,1-i]purin-2-one,
5-Amino-8-furan-2-yl-3-{2-[4-(4-methoxy-phenyl)-[1,2,3]triazol-1-yl]-ethyl}-1-methyl-1,3-dihydro-[1,2,4]triazolo[5,1-i]purin-2-one,
5-Amino-3-[2-(1,3-dihydro-isoindol-2-yl)-ethyl]-8-furan-2-yl-1-methyl-1,3-dihydro-[1,2,4]triazolo[5,1-i]purin-2-one,
5-Amino-8-furan-2-yl-1-methyl-3-(2-piperidin-1-yl-ethyl)-1,3-dihydro-[1,2,4]triazolo[5,1-i]purin-2-one,
5-Amino-8-furan-2-yl-1-methyl-3-(2-pyrrolidin-1-yl-ethyl)-1,3-dihydro-[1,2,4]triazolo[5,1-i]purin-2-one, 5-Amino-8-furan-2-yl-1-methyl-3-[2-(3-methyl-7,8-dihydro-5H-[1,6]naphthyridin-6-yl)-ethyl]-1,3-dihydro-[1,2,4]triazolo[5,1-i]purin-2-one, 5-Amino-8-furan-2-yl-3-{2-[4-(2-methoxy-ethoxy)-phenoxy]-ethyl}-1-methyl-1,3-dihydro-[1,2,4]triazolo[5,1-i]purin-2-one, 5-Amino-8-furan-2-yl-3-{2-[4-(2-methoxy-ethoxy)-phenylamino]-ethyl}-1-methyl-1,3-dihydro-[1,2,4]triazolo[5,1-i]purin-2-one, 5-Amino-8-furan-2-yl-1-methyl-3-[2-(pyridin-2-yloxy)-ethyl]-1,3-dihydro-[1,2,4]triazolo[5,1-i]purin-2-one, 5-Amino-1-ethyl-3-{2-[4-(4-fluoro-phenyl)-piperazin-1-yl]-ethyl}-8-isothiazol-5-yl-1,3-dihydro-[1,2,4]triazolo[5,1-i]purin-2-one, 5-Amino-1-ethyl-8-isothiazol-5-yl-3-(2-{4-[4-(2-methoxy-ethoxy)-phenyl]-piperazin-1-yl}-ethyl)-1,3-dihydro-[1,2,4]triazolo[5,1-i]purin-2-one, 5-Amino-1-ethyl-8-furan-2-yl-3-(2-piperidin-1-yl-ethyl)-1,3-dihydro-[1,2,4]triazolo[5,1-i]purin-2-one, 5-Amino-1-ethyl-8-furan-2-yl-3-[2-(3-methyl-7,8-dihydro-5H-[1,6]naphthyridin-6-yl)-ethyl]-1,3-dihydro-[1,2,4]triazolo[5,1-i]purin-2-one, 5-Amino-3-[2-(2,4-difluoro-phenoxy)-ethyl]-1-ethyl-8-furan-2-yl-1,3-dihydro-[1,2,4]triazolo[5,1-i]purin-2-one, 5-Amino-3-[2-(2,4-difluoro-phenylamino)-ethyl]-1-ethyl-8-furan-2-yl-1,3-dihydro-[1,2,4]triazolo[5,1-i]purin-2-one, 5-Amino-1-cyclopropylmethyl-3-[2-(2,4-difluoro-phenylamino)-ethyl]-8-furan-2-yl-1,3-dihydro-[1,2,4]triazolo[5,1-i]purin-2-one, 5-Amino-1-cyclopropylmethyl-3-[2-(2,4-difluoro-phenoxy)-ethyl]-8-furan-2-yl-1,3-dihydro-[1,2,4]triazolo[5,1-i]purin-2-one, 5-Amino-1-cyclopropylmethyl-3-{2-[4-(4-fluoro-phenyl)-piperidin-1-yl]-ethyl}-8-furan-2-yl-1,3-dihydro-[1,2,4]triazolo[5,1-i]purin-2-one, 5-Amino-3-{2-[4-(4-fluoro-phenyl)-piperidin-1-yl]-ethyl}-8-furan-2-yl-1-(2,2,2-trifluoro-ethyl)-1,3-dihydro-[1,2,4]triazolo[5,1-i]purin-2-one, 5-Amino-8-furan-2-yl-3-{2-[4-(4-methoxy-phenyl)-piperazin-1-yl]-ethyl}-1-(2,2,2-trifluoro-ethyl)-1,3-dihydro-[1,2,4]triazolo[5,1-i]purin-2-one, 5-Amino-3-[2-(4-cyclopropylmethyl-piperazin-1-yl)-ethyl]-8-isothiazol-5-yl-1-(2,2,2-trifluoro-ethyl)-1,3-dihydro-[1,2,4]triazolo[5,1-i]purin-2-one, (5-Amino-8-isothiazol-5-yl-3-{2-[4-(4-methoxy-phenyl)-piperazin-1-yl]-ethyl}-2-oxo-2,3-dihydro-[1,2,4]triazolo[5,1-i]purin-1-yl)-acetonitrile,

[5-Amino-3-{2-[4-(2,4-difluoro-phenyl)-piperazin-1-yl]-ethyl}-8-(3-fluoro-phenyl)-2-oxo-2,3-dihydro-[1,2,4]triazolo[5,1-i]purin-1-yl]-acetonitrile,

[5-Amino-8-furan-2-yl-3-(2-{4-[4-(2-methoxy-ethoxy)-phenyl]-piperazin-1-yl}-ethyl)-2-oxo-2,3-dihydro-[1,2,4]triazolo[5,1-i]purin-1-yl]-acetonitrile, 5-Amino-3-(2-{4-[4-(2-methoxy-ethoxy)-phenyl]-piperazin-1-yl}-ethyl)-1-methyl-8-phenyl-1,3-dihydro-[1,2,4]triazolo[5,1-i]purin-2-one, 3-[5-Amino-3-(2-{4-[4-(2-methoxy-ethoxy)-phenyl]-piperazin-1-yl}-ethyl)-1-methyl-2-oxo-2,3-dihydro-1H-[1,2,4]triazolo[5,1-i]purin-8-yl]-benzonitrile, 3-[5-Amino-3-(2-{4-[4-(2-methoxy-ethoxy)-phenyl]-piperazin-1-yl}-ethyl)-1-methyl-2-oxo-2,3-dihydro-1H-[1,2,4]triazolo[5,1-i]purin-8-yl]-benzonitrile, 5-Amino-8-furan-2-yl-1-methyl-3-vinyl-1,3-dihydro-[1,2,4]triazolo[5,1-f]purin-2-one 5-Amino-3-[3-(4-fluoro-phenyl)-prop-2-ynyl]-8-furan-2-yl-1-methyl-1,3-dihydro-[1,2,4]triazolo[5,1-i]purin-2-one, 5-Amino-8-furan-2-yl-1-methyl-3-[4-(4-methyl-piperazin-1-yl)-but-2-ynyl]-1,3-dihydro-[1,2,4]triazolo[5,1-i]purin-2-one, 5-Amino-8-furan-2-yl-1-isopropyl-3-(2-{4-[4-(2-methoxy-ethoxy)-phenyl]-piperazin-1-yl}-ethyl)-1,3-dihydro-[1,2,4]triazolo[5,1-i]purin-2-one, 5-Amino-2-benzyl-7-(2-{4-[4-(2-methoxy-ethoxy)-phenyl]-piperazin-1-yl}-ethyl)-9-methyl-7,9-dihydro-2H-[1,2,4]triazolo[3,4-i]purine-3,8-dione, 5-Amino-2-benzyl-9-methyl-7-(2-morpholin-4-yl-ethyl)-7,9-dihydro-2H-[1,2,4]triazolo[3,4-i]purine-3,8-dione, 5-Amino-2-(3-chloro-benzyl)-7-[2-(4-isopropyl-piperazin-1-yl)-ethyl]-9-methyl-7,9-dihydro-2H-[1,2,4]triazolo[3,4-i]purine-3,8-dione, 5-Amino-2-cyclopropylmethyl-9-methyl-7-(2-morpholin-4-yl-ethyl)-7,9-dihydro-2H-[1,2,4]triazolo[3,4-i]purine-3,8-dione, 5-Amino-2-cyclopropylmethyl-7-(2,4-difluoro-benzyl)-9-methyl-7,9-dihydro-2H-[1,2,4]triazolo[3,4-i]purine-3,8-dione, 4-Amino-2-furan-2-yl-6-(2-{4-[4-(2-methoxy-ethoxy)-phenyl]-piperazin-1-yl}-ethyl)-6H-8-oxa-1,3,3a,5,6-pentaaza-as-indacen-7-one or 4-Amino-2-furan-2-yl-6-(2-{4-[4-(2-methoxy-ethoxy)-phenyl]-piperazin-1-yl}-ethyl)-8,8-dimethyl-6,8-dihydro-1,3,3a,5,6-pentaaza-as-indacen-7-one.

Biological Activity

Radioligand Binding for $A_{2A}$ Adenosine Receptor

Human $A_{2A}$ adenosine receptor cDNA was stably transfected into HEK-293 cells. HEK-$A_{2A}$ cells were harvested by trypsinization with 0.25% Trypsin-EDTA (Sigma), and washed in 1×PBS at 1500 rpm for 5 minutes at room temperature. The cells were washed twice in wash buffer containing 150 mM NaCl, 1 mM EDTA, 50 mM Tris (pH-7.4) at 1500 rpm for 10 minutes at room temperature and incubated for 10 min at 4° C. in sonication buffer containing 1 mM EDTA, 5 mM (Tris pH 7.4). The cells were sonicated on ice for 6 min with six intermittent pulses of 9 second each and centrifuged at 1000×g for 10 minutes at 4° C. The pellet was discarded and the supernatant was centrifuged at 49,000×g for 45 minutes at 4° C. The protein pellet was resuspended in buffer containing 1 mM EDTA, 5 mM Tris (pH-7.4) supplemented with 1 Unit/ml adenosine deaminase (ADA) and incubated for 30 minutes at room temperature. The lysate was washed twice with buffer containing 1 mM EDTA, 5 mM Tris (pH-7.4) at 49,000×g for 45 minutes at 4° C. and the protein pellet was resuspended in 50 mM Tris, pH-7.4 supplemented with 1 Unit/ml ADA and 10% sucrose. Frozen aliquots were stored at −80° C.

Competition assays were started by mixing 2 nM [$^3$H]-ZM-241385 with various concentrations of test compounds and 5 μg membrane protein in Reaction buffer (50 mM Tris pH 7.4, 1 mM EDTA) supplemented with 1 Unit/ml ADA. The assay reactions were incubated for 90 minutes at room temperature and stopped by filtration using 96 well-plate harvester (Molecular Devices) and washed four times with ice cold 50 mM Tris (pH 7.4). Non specific binding was determined in presence of 200 μM NECA. Radioligand binding was read at Liquid scintillation counter (Perkin Elmer) and the affinities of compounds (i.e. $K_i$ values) were calculated using GraphPad software.

Representative compounds of the present disclosure were tested and had micromolar to nanomolar activity.

| Example No | A2A Cell based Functional Ki* |
|---|---|
| A1 | +++ |
| A7 | +++ |
| A9 | +++ |
| A13 | +++ |
| A31 | +++ |
| A32 | +++ |
| A36 | ++ |
| A38 | +++ |
| A39 | +++ |
| A42 | +++ |
| A57 | +++ |
| A58 | +++ |
| A62 | +++ |
| A63 | ++ |
| C1 | +++ |
| E1 | +++ |
| D3 | +++ |
| G1 | ++ |
| G2 | ++ |
| H2 | +++ |
| M1 | +++ |
| M2 | +++ |
| M3 | ++ |
| M6 | +++ |

++ = BINDING ACTIVITY IN THE RANGE OF 10 TO 100 nM
+++ = BINDING ACTIVITY IN THE RANGE OF 0.1 TO 10 nM

We claim:
1. A compound represented by Formula I

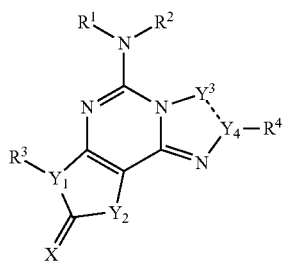

(I)

or its tautomers, polymorphs, stereoisomers, prodrugs, solvate or a pharmaceutically acceptable salts thereof, wherein:
— represents a single bond or a double bond;
X is selected from O, S or $NR^a$;
$Y_1$ is selected from N or CH;
$Y_2$ is selected from $NR^5$, O or $CR^5R^6$;
$Y_3$ is selected from N, CH, $CH_2$, C(=O) or C(=S);
$Y_4$ is selected from N, C or CH;
$R^1$ and $R^2$ are independently selected from hydrogen or alkyl;
$R^3$ is —A—Z—B—Q;
wherein, A is absent or is a group selected from alkylene, alkenylene or alkynylene; wherein one or more methylene groups is optionally replaced by hetero atoms or groups selected from the group consisting of —O—, —S(O)p—, —N($R^a$)—, or —C(O); alkylene, alkenylene and alkynylene is optionally substituted with —$(CR^dR^e)_n OR^7$, $(CR^dR^e)_n COOR^7$, —$(CR^dR^e)_n NR^8R^9$, cyano, halogen, haloalkyl, perhaloalkyl, alkoxyalkoxy, alkyl or cycloalkyl;
Z is absent or is selected from a cycloalkyl or a heterocyclyl;
wherein cycloalkyl and heterocyclyl are unsubstituted or substituted independently with 1, 2, or 3 substituents independently selected from alkyl, alkenyl, alkynyl, acyl, —$(CR^dR^e)_n OR^7$, $(CR^dR^e)_n COOR^7$, —$(CR^dR^e)_n NR^8R^9$, aminocarbonyl, alkoxycarbonylamino, halogen, haloalkyl, perhaloalkyl, azido, cyano, keto, thiocarbonyl, —$SO_3H$, aminocarbonylamino, nitro, —$S(O)_2 NR^a R^a$, —$NR^b S(O)_2 R^b$ or —$S(O)_p R^c$;
B is absent or is a group selected from alkylene, alkenylene or alkynylene; wherein one or more methylene groups is optionally replaced by hetero atoms or groups selected from the group consisting of —O—, —S(O)p—, —N($R^a$)—, or —C(O); alkylene, alkenylene and alkynylene is optionally substituted with hydroxy, amino, aminoalkyl, cyano, halogen, haloalkyl, perhaloalkyl, carboxy, carboxyalkyl, alkoxy, hydroxyalkyl, alkoxyalkyl, alkoxyalkoxy or alkyl;
Q is selected from hydrogen, alkyl, cycloalkyl, cycloalkylalkyl, aryl, arylalkyl, heterocyclyl, heterocyclylalkyl, heteroaryl or heteroarylalkyl;
wherein alkyl, cycloalkyl, cycloalkylalkyl, aryl, arylalkyl, heterocyclyl, heterocyclylalkyl, heteroaryl and heteroarylalkyl are unsubstituted or substituted independently with 1, 2, or 3 substituents independently selected from alkyl, alkenyl, alkynyl, halogen, haloalkyl, perhaloalkyl, azido, cyano, nitro, keto, thiocarbonyl, cyanoalkyl, cyanoalkylcarbonyl, —$(CR^dR^e)_n OR^7$, —$(CR^dR^e)_n C(O)R^7$, —$(CR^dR^e)_n SR^7$, —$(CR^dR^e)_n COOR^7$, —$(CR^dR^e)_n NR^8R^9$, —$(CR^dR^e)_n C(O)NR^8R^9$, —$(CR^dR^e)_n NR^8 C(O)OR^7$, —$(CR^dR^e)_n NR^8 C(O)NR^8R^9$, —$NR^b S(O)_2 R^b$, —$S(O)_p R^c$, —$SO_3 H$, —$S(O)_2 NR^a R^a$, cycloalkyl, cycloalkenyl, cycloalkylalkyl aryl, arylalkyl, heterocyclyl, heterocyclylalkyl, heteroaryl or heteroarylalkyl;
wherein each substituent is unsubstituted or substituted with 1, 2, or 3 substituents independently selected from alkyl, carboxy, carboxyalkyl, aminocarbonyl, hydroxy, alkoxy, halogen, haloalkyl, perhaloalkyl, haloalkoxy, perhaloalkoxy, amino, substituted amino, cyano or —$S(O)_p R^c$;
$R^4$ is selected from the group consisting of hydrogen, alkyl, alkenyl, alkynyl, haloalkyl, hydroxyalkyl, carboxyalkyl, cycloalkyl, cycloalkylalkyl, aryl, arylalkyl, heterocyclyl, heterocyclylalkyl, heteroaryl and heteroarylalkyl;
wherein alkyl, alkenyl, alkynyl, cycloalkyl, cycloalkylalkyl, arylalkyl, aryl, heteroaryl, heteroarylalkyl, heterocyclyl, and heterocyclylalkyl are unsubstituted or substituted independently with up to four substituents independently selected from alkyl, alkenyl, alkynyl, acyl, —$(CR^dR^e)_n OR^7$, $(CR^dR^e)COOR^7$, —$(CR^dR^e)_n NR^8R^9$, aminocarbonyl, alkoxycarbonylamino, aminocarbonylamino, azido, cyano, halogen, haloalkyl, perhaloalkyl, keto, nitro, —$S(O)_2 NR^bR^b$, —$NR^b S(O)_2 R^b$ or —$S(O)_p R^c$, thiocarbonyl, —$SO_3H$, cycloalkyl, cycloalkenyl, aryl, heteroaryl or heterocyclyl;
$R^5$ and $R^6$ are independently selected from the group consisting of hydrogen, hydroxy, —$(CR^dR^e)_n OR^7$, $(CR^dR^e)_n COOR^7$, —$(CR^dR^e)_n NR^8R^9$, cyanoalkyl, haloalkyl, alkoxyalkoxyalkyl, alkyl, alkenyl, alkynyl, cycloalkyl, cycloalkylalkyl, aryl, arylalkyl, heterocyclyl, heterocyclylalkyl, heteroaryl and heteroarylalkyl;
$R^7$ is selected from hydrogen, alkyl, halogen, haloalkyl, carbonylamino, cycloalkyl, cycloalkylalkyl, aryl, arylalkyl, heteroaryl, heteroarylalkyl, heterocyclyl or heterocyclylalkyl;

$R^8$ and $R^9$ are independently selected from the group consisting of hydrogen, alkyl, haloalkyl, —$(CR^dR^e)_nOR^7$, —$(CR^dR^e)_nC(O)R^7$, aryl, arylalkyl, heteroaryl, heteroarylalkyl, cycloalkyl, cycloalkylalkyl, heterocyclyl and heterocyclylalkyl, Or $R^8$ and $R^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, alkenyl, alkynyl, nitro, cyano, —$(CR^dR^e)_nOR^7$, —$(CR^dR^e)_nSR^7$, —$(CR^dR^e)_nNR^8R^9$, oxo, alkylsulfonyl, —$(CR^dR^e)_nCOOR7$, —$(CR^dR^e)_nC(O)NR^8R^9$, cycloalkyl, cycloalkylalkyl, aryl, arylalkyl, heterocyclyl, heterocyclylalkyl, heteroaryl, or heteroarylalkyl;

$R^a$ is selected from hydrogen or alkyl;

$R^b$ at each occurrence is independently selected from the group consisting of hydrogen, alkyl, acyl, carboxyalkyl, carbonylamino, cycloalkyl, cycloalkylalkyl, aryl, arylalkyl, heteroaryl, heteroarylalkyl, heterocyclyl and heterocyclylalkyl;

$R^c$ is selected from alkyl, cycloalkyl, aryl, heterocyclyl or heteroaryl;

$R^d$ and $R^e$ are independently selected from the group consisting of hydrogen, —$OR^7$, halogen, haloalkyl, perhaloalkyl and alkyl;

n is 0, 1, 2, 3 or 4 and p is 0, 1 or 2.

2. The compound of formula (I) as claimed in claim 1 or its tautomers, polymorphs, stereoisomers, prodrugs, solvate or a pharmaceutically acceptable salts thereof, wherein — represents a double bond;

X is selected from O, S or $NR^a$;

$Y_1$ is selected from N or CH;

$Y_2$ is selected from $NR^5$ or $CR^5R^6$;

$Y_3$ is selected from N, CH or $CH_2$;

$Y_4$ is selected from N or C;

$R^1$ and $R^2$ are independently selected from hydrogen or alkyl;

$R^3$ is —A—Z—B—Q;

wherein, A is absent or is alkylene wherein one or more methylene groups is optionally replaced by hetero atoms or groups selected from the group consisting of —O—, —S(O)p-, —$N(R^a)$-, or —C(O); alkylene is optionally substituted with —$(CR^dR^e)_nOR^7$, cyano, halogen, haloalkyl, perhaloalkyl, alkyl or cycloalkyl;

Z is absent or is selected from a cycloalkyl or a heterocyclyl;

wherein cycloalkyl and heterocyclyl are unsubstituted or substituted independently with 1, 2, or 3 substituents independently selected from alkyl, acyl, —$(CR^dR^e)_nOR^7$, $(CR^dR^e)_nCOOR^7$, —$(CR^dR^e)_nNR^8R^9$, aminocarbonyl, alkoxycarbonylamino, halogen, haloalkyl, perhaloalkyl, azido, cyano, halogen, keto, thiocarbonyl, —$SO_3H$, aminocarbonylamino, nitro, —$S(O)_2NR^aR^a$, —$NR^bS(O)_2R^b$ or —$S(O)_pR^c$;

B is absent or is alkylene wherein one or more methylene groups is optionally replaced by hetero atoms or groups selected from the group consisting of —O—, —S(O)p-, —$N(R^a)$-, or —C(O); alkylene is optionally substituted with hydroxy, amino, aminoalkyl, cyano, halogen, haloalkyl, perhaloalkyl, carboxy, carboxyalkyl, alkoxy, hydroxyalkyl, alkoxyalkyl, alkoxyalkoxy or alkyl;

Q is selected from hydrogen, alkyl, cycloalkyl, cycloalkylalkyl, aryl, arylalkyl, heterocyclyl, heterocyclylalkyl, heteroaryl or heteroarylalkyl;

wherein alkyl, cycloalkyl, cycloalkylalkyl, aryl, arylalkyl, heterocyclyl, heterocyclylalkyl, heteroaryl and heteroarylalkyl are unsubstituted or substituted independently with 1, 2, or 3 substituents independently selected from alkyl, alkenyl, alkynyl, alkoxy, alkoxyalkyl, haloalkyl, perhaloalkyl, azido, cyano, nitro, halogen, keto, thiocarbonyl, cyanoalkyl, cyanoalkylcarbonyl, —$(CR^dR^e)_nOR^7$, —$(CR^dR^e)_nC(O)R^7$, —$(CR^dR^e)_nSR^7$, —$(CR^dR^e)_nCOOR^7$, —$(CR^dR^e)_nNR^8R^9$, —$(CR^dR^e)_nC(O)NR^8R^9$, —$(CR^dR^e)_nNR^8C(O)OR^7$, —$(CR^dR^e)_nNR^8C(O)NR^8R^9$, —$NR^bS(O)_2R^b$, —$S(O)_pR^c$, —$SO_3H$, —$S(O)_2NR^aR^a$, cycloalkyl, cycloalkenyl, cycloalkylalkyl aryl, arylalkyl, heterocyclyl, heterocyclylalkyl, heteroaryl or heteroarylalkyl;

wherein each substituent is unsubstituted or substituted with 1, 2, or 3 substituents independently selected from alkyl, carboxy, carboxyalkyl, aminocarbonyl, hydroxy, alkoxy, halogen, haloalkyl, perhaloalkyl, haloalkoxy, perhaloalkoxy, amino, substituted amino, cyano or —$S(O)_pR^c$;

$R^4$ is selected from the group consisting of hydrogen, alkyl, haloalkyl, hydroxyalkyl, carboxyalkyl, cycloalkyl, cycloalkylalkyl, aryl, arylalkyl, heterocyclyl, heterocyclylalkyl, heteroaryl and heteroarylalkyl;

wherein alkyl, cycloalkyl, cycloalkylalkyl, arylalkyl, aryl, heteroaryl, heteroarylalkyl, heterocyclyl, and heterocyclylalkyl are unsubstituted or independently substituted with up to four substituents independently selected from alkyl, acyl, —$(CR^dR^e)_nOR^7$, $(CR^dR^e)_nCOOR^7$, —$(CR^dR^e)_nNR^8R^9$, aminocarbonyl, alkoxycarbonylamino, aminocarbonylamino, azido, cyano, halogen, haloalkyl, perhaloalkyl, keto, nitro, —$S(O)_2NR^bR^b$, —$NR^bS(O)_2R^b$ or —$S(O)_pR^c$, thiocarbonyl, —$SO_3H$, cycloalkyl, cycloalkenyl, aryl, heteroaryl or heterocyclyl;

$R^5$ and $R^6$ are independently selected from the group consisting of hydrogen, hydroxy, —$(CR^dR^e)_nOR^7$, $(CR^dR^e)_nCOOR^7$, —$(CR^dR^e)_nNR^8R^9$, cyanoalkyl, haloalkyl, alkoxyalkoxyalkyl, alkyl, alkenyl, alkynyl, cycloalkyl, cycloalkylalkyl, aryl, arylalkyl, heterocyclyl, heterocyclylalkyl, heteroaryl or heteroarylalkyl;

$R^7$ is selected from hydrogen, alkyl, halogen, haloalkyl, carbonylamino, cycloalkyl, cycloalkylalkyl, aryl, arylalkyl, heteroaryl, heteroarylalkyl, heterocyclyl or heterocyclylalkyl;

$R^8$ and $R^9$ are independently selected from the group consisting of hydrogen, alkyl, haloalkyl, —$(CR^dR^e)_nOR^7$, —$(CR^dR^e)_nC(O)R^7$, aryl, arylalkyl, heteroaryl, heteroarylalkyl, cycloalkyl, cycloalkylalkyl, heterocyclyl and heterocyclylalkyl, or $R^8$ and $R^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, alkenyl, alkynyl, nitro, cyano, —$(CR^dR^e)_nOR^7$, —$(CR^dR^e)_nSR^7$, —$(CR^dR^e)_nNR^8R^9$, oxo, alkylsulfonyl, —$(CR^dR^e)_nCOOR^7$, —$(CR^dR^e)_nC(O)NR^8R^9$, cycloalkyl, cycloalkylalkyl, aryl, arylalkyl, heterocyclyl, heterocyclylalkyl, heteroaryl, or heteroarylalkyl;

$R^a$ is selected from hydrogen or alkyl;

$R^b$ each is independently selected from the group consisting of hydrogen, alkyl, acyl, carboxyalkyl, carbonylamino, cycloalkyl, cycloalkylalkyl, aryl, arylalkyl, heteroaryl, heteroarylalkyl, heterocyclyl and heterocyclylalkyl;

$R^c$ is selected from alkyl, cycloalkyl, aryl, heterocyclyl or heteroaryl;

$R^d$ and $R^e$ are independently selected from the group consisting of hydrogen, —$OR^7$, halogen, haloalkyl, perhaloalkyl and alkyl;

n is 0, 1, 2, 3 or 4 and p is 0, 1 or 2.

3. The compound of formula (I) as claimed in claim 1 or its tautomers, polymorphs, stereoisomers, prodrugs, solvate or a pharmaceutically acceptable salts thereof, wherein — represents a double bond;

X is selected from O or S;

$Y_1$ represents N;

$Y_2$ represents $NR^5$;

$Y_3$ represents N;

$Y_4$ represents C;

$R^1$ and $R^2$ are independently selected from hydrogen or alkyl;

$R^3$ is -A-Z—B-Q;

wherein, A is absent or is alkylene wherein one or more methylene groups is optionally replaced by hetero atoms or groups selected from the group consisting of —O—, —S(O)p-, —N($R^a$)-, or —C(O);

Z is absent or is a heterocyclyl;

wherein the heterocyclyl is unsubstituted or substituted independently with 1, 2, or 3 substituents independently selected from alkyl, acyl, —$(CR^dR^e)_nOR^7$, $(CR^dR^e)_nCOOR^7$, —$(CR^dR^e)_nNR^8R^9$, haloalkyl, perhaloalkyl, cyano, halogen, keto, thiocarbonyl, —$SO_3H$, nitro, —$S(O)_2NR^aR^a$, —$NR^bS(O)_2R^b$ or —$S(O)_pR^c$;

B is absent or is alkylene wherein one or more methylene groups is optionally replaced by hetero atoms or groups selected from the group consisting of —O—, —S(O)p-, —N($R^a$)-, or —C(O);

Q is selected from hydrogen, alkyl, cycloalkyl, aryl, heterocyclyl, or heteroaryl;

wherein alkyl, cycloalkyl, aryl, heterocyclyl and heteroaryl are unsubstituted or independently substituted with 1, 2, or 3 substituents independently selected from alkyl, alkoxy, alkoxyalkyl, haloalkyl, perhaloalkyl, azido, cyano, nitro, halogen, keto, thiocarbonyl, cyanoalkyl, cyanoalkylcarbonyl, —$(CR^dR^e)_nOR^7$, —$(CR^dR^e)_nC(O)R^7$, —$(CR^dR^e)_nSR^7$, —$(CR^dR^e)_nCOOR^7$, —$(CR^dR^e)_nNR^8R^9$, —$(CR^dR^e)_nC(O)NR^8R^9$, —$(CR^dR^e)_nNR^8C(O)OR^7$, —$(CR^dR^e)_nNR^8C(O)NR^8R^9$, —$NR^bS(O)_2R^b$, —$S(O)_pR^c$, —$SO_3H$, —$S(O)_2NR^aR^a$, cycloalkyl, cycloalkenyl, cycloalkylalkyl aryl, arylalkyl, heterocyclyl, heterocyclylalkyl, heteroaryl or heteroarylalkyl;

wherein each substituent is unsubstituted or substituted with 1, 2, or 3 substituents independently selected from alkyl, carboxy, carboxyalkyl, aminocarbonyl, hydroxy, alkoxy, halogen, haloalkyl, perhaloalkyl, haloalkoxy, perhaloalkoxy, amino, substituted amino, cyano or —$S(O)_pR^c$;

$R^4$ is selected from the group consisting of hydrogen, alkyl, haloalkyl, hydroxyalkyl, carboxyalkyl, cycloalkyl, cycloalkylalkyl, aryl, arylalkyl, heterocyclyl, heterocyclylalkyl, heteroaryl and heteroarylalkyl;

wherein alkyl, cycloalkyl, cycloalkylalkyl, arylalkyl, aryl, heteroaryl, heteroarylalkyl, heterocyclyl, and heterocyclylalkyl are unsubstituted or independently substituted with up to four substituents independently selected from alkyl, acyl, —$(CR^dR^e)_nOR^7$, $(CR^dR^e)_nCOOR^7$, —$(CR^dR^e)_nNR^8R^9$, aminocarbonyl, alkoxycarbonylamino, aminocarbonylamino, azido, cyano, halogen, haloalkyl, perhaloalkyl, keto, nitro, —$S(O)_2NR^bR^b$, —$NR^bS(O)_2R^b$ or —$S(O)_pR^c$, thiocarbonyl, —$SO_3H$, cycloalkyl, cycloalkenyl, aryl, heteroaryl or heterocyclyl;

$R^5$ and $R^6$ are independently selected from the group consisting of hydrogen, hydroxy, —$(CR^dR^e)_nOR^7$, $(CR^dR^e)_nCOOR^7$, —$(CR^dR^e)_nNR^8R^9$, cyanoalkyl, haloalkyl, alkoxyalkoxyalkyl, alkyl, alkenyl, alkynyl, cycloalkyl, cycloalkylalkyl, aryl, arylalkyl, heterocyclyl, heterocyclylalkyl, heteroaryl and heteroarylalkyl;

$R^7$ is selected from hydrogen, alkyl, halogen, haloalkyl, carbonylamino, cycloalkyl, cycloalkylalkyl, aryl, arylalkyl, heteroaryl, heteroarylalkyl, heterocyclyl or heterocyclylalkyl;

$R^8$ and $R^9$ are independently selected from the group consisting of hydrogen, alkyl, haloalkyl, —$(CR^dR^e)_nOR^7$, —$(CR^dR^e)_nC(O)R^7$, aryl, arylalkyl, heteroaryl, heteroarylalkyl, cycloalkyl, cycloalkylalkyl, heterocyclyl and heterocyclylalkyl, or $R^8$ and $R^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, alkenyl, alkynyl, nitro, cyano, —$(CR^dR^e)_nOR^7$, —$(CR^dR^e)_nSR^7$, —$(CR^dR^e)_nNR^8R^9$, oxo, alkylsulfonyl, —$(CR^dR^e)_nCOOR^7$, —$(CR^dR^e)_nC(O)NR^8R^9$, cycloalkyl, cycloalkylalkyl, aryl, arylalkyl, heterocyclyl, heterocyclylalkyl, heteroaryl, or heteroarylalkyl;

$R^a$ is selected from hydrogen or alkyl;

$R^b$ each is independently selected from the group consisting of hydrogen, alkyl, acyl, carboxyalkyl, carbonylamino, cycloalkyl, cycloalkylalkyl, aryl, arylalkyl, heteroaryl, heteroarylalkyl, heterocyclyl and heterocyclylalkyl;

$R^c$ is selected from alkyl, cycloalkyl, aryl, heterocyclyl or heteroaryl;

$R^d$ and $R^e$ are independently selected from the group consisting of hydrogen, —$OR^7$, halogen, haloalkyl, perhaloalkyl or alkyl;

n is 0, 1, 2, 3 or 4 and p is 0, 1 or 2.

4. The compound of formula (I) as claimed in claim 1 or its tautomers, polymorphs, stereoisomers, prodrugs, solvate or a pharmaceutically acceptable salts thereof, wherein — represents a double bond;

X selected from O or S;

$Y_1$ represents N;

$Y_2$ represents $NR^5$;

$Y_3$ represents N;

$Y_4$ represents C;

$R^1$ and $R^2$ are independently selected from hydrogen or alkyl;

$R^3$ is -A-Z—B-Q;

wherein, A is absent or is alkylene wherein one or more methylene groups is optionally replaced by hetero atoms or groups selected from the group consisting of —O— or —N($R^a$)-;

Z is absent or is a heterocyclyl;

wherein the heterocyclyl is unsubstituted or substituted independently with 1, 2, or 3 substituents independently selected from alkyl, —(CR$^d$R$^e$)$_n$OR$^7$, (CR$^d$R$^e$)$_n$COOR$^7$, haloalkyl, perhaloalkyl, cyano, halogen, keto or thiocarbonyl;

B is absent or is alkylene wherein one or more methylene groups is optionally replaced by hetero atoms or groups selected from the group consisting of —O—, —N(R$^a$)—, or —C(O);

Q is selected from hydrogen, alkyl, cycloalkyl, aryl, heterocyclyl, or heteroaryl;

wherein alkyl, cycloalkyl, aryl, heterocyclyl and heteroaryl are unsubstituted or independently substituted with 1, 2, or 3 substituents independently selected from alkyl, alkoxy, alkoxyalkyl, haloalkyl, perhaloalkyl, cyano, halogen, keto, thiocarbonyl, cyanoalkyl, —(CR$^d$R$^e$)$_n$OR$^7$, —(CR$^d$R$^e$)$_n$C(O)R$^7$, —(CR$^d$R$^e$)$_n$COOR$^7$, —(CR$^d$R$^e$)$_n$NR$^8$R$^9$, —(CR$^d$R$^e$)$_n$C(O)NR$^8$R$^9$, —(CR$^d$R$^e$)$_n$NR$^8$C(O)OR$^7$, —S(O)$_p$R$^c$, —SO$_3$H, —S(O)$_2$NR$^a$R$^a$, cycloalkyl, cycloalkenyl, aryl, heterocyclyl or heteroaryl;

wherein each substituent is unsubstituted or substituted with 1, 2, or 3 substituents independently selected from alkyl, carboxy, carboxyalkyl, aminocarbonyl, hydroxy, alkoxy, halogen, haloalkyl, perhaloalkyl, haloalkoxy, perhaloalkoxy, amino, substituted amino, cyano or —S(O)$_p$R$^c$;

R$^4$ is selected from the group consisting of hydrogen, alkyl, haloalkyl, hydroxyalkyl, cycloalkyl, aryl, heterocyclyl and heteroaryl;

wherein alkyl, cycloalkyl, aryl, heteroaryl and heterocyclyl are unsubstituted or independently substituted with up to four substituents independently selected from alkyl, —(CR$^d$R$^e$)$_n$OR$^7$, (CR$^d$R$^e$)$_n$COOR$^7$, —(CR$^d$R$^e$)$_n$NR$^8$R$^9$, cyano, halogen, haloalkyl, perhaloalkyl, nitro, —S(O)$_2$NR$^b$R$^b$, —NR$^b$S(O)$_2$R$^b$, —S(O)$_p$R$^c$, thiocarbonyl, —SO$_3$H, cycloalkyl, aryl, heteroaryl or heterocyclyl;

R$^5$ is selected from the group consisting of hydrogen, hydroxy, haloalkyl, —(CR$^d$R$^e$)$_n$OR$^7$, —(CR$^d$R$^e$)$_n$COOR$^7$, alkoxyalkoxyalkyl, alkyl, alkenyl, alkynyl, cycloalkyl, cycloalkylalkyl, aryl, arylalkyl, heterocyclyl, heterocyclylalkyl, heteroaryl or heteroarylalkyl;

R$^7$ is selected from hydrogen, alkyl, halogen, haloalkyl, cycloalkyl, aryl, heteroaryl or heterocyclyl;

R$^8$ and R$^9$ are independently selected from the group consisting of hydrogen, alkyl, haloalkyl, —(CR$^d$R$^e$)$_n$OR$^7$, —(CR$^d$R$^e$)$_n$C(O)R$^7$, aryl, arylalkyl, heteroaryl, heteroarylalkyl, cycloalkyl, cycloalkylalkyl, heterocyclyl and heterocyclylalkyl, or R$^8$ and R$^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, nitro, cyano, —(CR$^d$R$^e$)$_n$OR$^7$, —(CR$^d$R$^e$)$_n$NR$^8$R$^9$, oxo, alkylsulfonyl, —(CR$^d$R$^e$)$_n$COOR$^7$ or —(CR$^d$R$^e$)$_n$C(O)NR$^8$R$^9$;

R$^a$ is selected from hydrogen or alkyl;

R$^b$ each is independently selected from the group consisting of hydrogen, alkyl, acyl, carboxyalkyl, carbonylamino, cycloalkyl, cycloalkylalkyl, aryl, arylalkyl, heteroaryl, heteroarylalkyl, heterocyclyl or heterocyclylalkyl;

R$^c$ is selected from alkyl, cycloalkyl, aryl, heterocyclyl or heteroaryl;

R$^d$ and R$^e$ are independently selected from the group consisting of hydrogen, —OR$^7$, halogen, haloalkyl, perhaloalkyl and alkyl;

n is 0, 1, 2, 3 or 4 and p is 0, 1 or 2.

5. The compound of formula (I) as claimed in claim 1 or its tautomers, polymorphs, stereoisomers, prodrugs, solvate or a pharmaceutically acceptable salts thereof, wherein — represents a double bond;

X is selected from O or S;

Y$_1$ represents N;

Y$_2$ represents NR$^5$;

Y$_3$ represents N;

$_4$ represents C;

R$^1$ and R$^2$ are independently selected from hydrogen or alkyl;

R$^3$ is -A-Z—B-Q;

wherein, A is absent or is alkylene wherein one or more methylene groups is optionally replaced by hetero atoms or groups selected from the group consisting of —O—or —N(R$^a$)—;

Z is absent or is a heterocyclyl selected from dihydrofuranyl, tetrahydrofuranyl, morpholinyl, pyrrolidinyl, dihydropyrrole, dihydropyranyl, tetrahydropyranyl, pyrazolidinyl, imidazolidinyl, dihydropyridinyl, tetrahydropyridinyl, piperidinyl, dihydropyrazinyl, tetrahydropyrazinyl, piperazinyl or dihydropyridinyl;

wherein the heterocyclyl is unsubstituted or substituted independently with 1, 2, or 3 substituents independently selected from alkyl, —(CR$^d$R$^e$)$_n$OR$^7$, (CR$^d$R$^e$)$_n$COOR$^7$, haloalkyl, perhaloalkyl, cyano or halogen;

B is absent or is alkylene wherein one or more methylene groups is optionally replaced by hetero atoms or groups selected from the group consisting of —O—, —N(R$^a$)—, or —C(O);

Q is selected from hydrogen, alkyl, cyclopropyl, cyclopentyl, cyclohexyl, phenyl, tetrahydrofuranyl, pyrrolidinyl, tetrahydropyridinyl, tetrahydropyranyl, piperazinyl, benzodiaxolyl, tetrahydroquinolinyl, morpholinyl, tetrahydronaphthyridinyl, tetrahydrothienopyridinyl, furanyl, pyridinyl, pyrimidinyl, oxazolyl, thiazolyl, oxadiazolyl, thiadiazolyl, indolyl, quinolinyl, isoquinolinyl or benzooxazolyl;

wherein Q is unsubstituted or substituted with 1, 2, or 3 substituents independently selected from alkyl, alkoxy, alkoxyalkyl, haloalkyl, perhaloalkyl, cyano, halogen, keto, thiocarbonyl, cyanoalkyl, —(CR$^d$R$^e$)$_n$OR$^7$, —(CR$^d$R$^e$)$_n$C(O)R$^7$, —(CR$^d$R$^e$)$_n$COOR$^7$, —(CR$^d$R$^e$)$_n$NR$^8$R$^9$, —(CR$^d$R$^e$)$_n$C(O)NR$^8$R$^9$, —(CR$^d$R$^e$)$_n$NR$^8$C(O)OR$^7$, —S(O)$_p$R$^c$, —SO$_3$H, —S(O)$_2$NR$^a$R$^a$, cycloalkyl, cycloalkenyl, aryl, heterocyclyl or heteroaryl;

wherein each substituent is unsubstituted or substituted with 1, 2, or 3 substituents independently selected from alkyl, carboxy, carboxyalkyl, aminocarbonyl, hydroxy, alkoxy, halogen, haloalkyl, perhaloalkyl, haloalkoxy, perhaloalkoxy, amino, substituted amino, cyano or —S(O)$_p$R$^c$;

R$^4$ is selected from the group consisting of hydrogen, alkyl, phenyl, naphthyl, furanyl, thiazolyl, oxazolyl, thiadiazolyl, oxadiazolyl, pyrazinyl, pyridinyl and pyrimidinyl;

wherein R$^4$ is unsubstituted or substituted with up to four substituents independently selected from alkyl, —(CR$^d$R$^e$)$_n$OR$^7$, (CR$^d$R$^e$)$_n$COOR$^7$, —(CR$^d$R$^e$)$_n$NR$^8$R$^9$, cyano, halogen, haloalkyl, perhaloalkyl or cycloalkyl;

R$^5$ is selected from the group consisting of hydrogen, hydroxy, haloalkyl, —(CR$^d$R$^e$)$_n$OR$^7$, —(CR$^d$R$^e$)$_n$COOR$^7$, alkoxyalkoxyalkyl, alkyl, alkenyl, alkynyl, cycloalkyl, cycloalkylalkyl, aryl, arylalkyl, heterocyclyl, heterocyclylalkyl, heteroaryl and heteroarylalkyl;

$R^7$ is selected from hydrogen, alkyl, halogen, haloalkyl, cycloalkyl, aryl, heteroaryl or heterocyclyl;

$R^8$ and $R^9$ are independently selected from the group consisting of hydrogen, alkyl, haloalkyl, $-(CR^dR^e)_nOR^7$, $-(CR^dR^e)_nC(O)R^7$, aryl, arylalkyl, heteroaryl, heteroarylalkyl, cycloalkyl, cycloalkylalkyl, heterocyclyl and heterocyclylalkyl, or $R^8$ and $R^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, nitro, cyano, $-(CR^dR^e)_nOR^7$, $-(CR^dR^e)_nNR^8R^9$, oxo, alkylsulfonyl, $-(CR^dR^e)_nCOOR^7$ or $-(CR^dR^e)_nC(O)NR^8R^9$;

$R^a$ is selected from hydrogen or alkyl;

$R^b$ at each occurrence is independently selected from the group consisting of hydrogen, alkyl, acyl, carboxyalkyl, carbonylamino, cycloalkyl, cycloalkylalkyl, aryl, arylalkyl, heteroaryl, heteroarylalkyl, heterocyclyl or heterocyclylalkyl;

$R^c$ is selected from alkyl, cycloalkyl, aryl, heterocyclyl or heteroaryl;

$R^d$ and $R^e$ are independently selected from the group consisting of hydrogen, $-OR^7$, halogen, haloalkyl, perhaloalkyl and alkyl;

n is 0, 1, 2, 3 or 4 and p is 0, 1 or 2.

6. The compound of formula (I) as claimed in claim 1 or its tautomers, polymorphs, stereoisomers, prodrugs, solvate or a pharmaceutically acceptable salt thereof, which is 5-Amino-8-(2-furyl)-3-[2-[4-[4-(2-methoxyethoxy)phenyl]piperazin-1-yl]ethyl]-1 -methyl- [1,2,4]triazolo [5, 1 -f]purin-2-one, 5-Amino-8-(2-furyl)-3-(2-hydroxyethyl)-1-methyl-[1,2,4]triazolo[5,1-f]purin-2-one, 5-Amino-3-[2-[4-(2,4-difluorophenyl)piperazin-1-yl]ethyl]-8-(2-furyl)-1-methyl -[1,2,4]triazolo[5,1-f]purin-2-one, 5-Amino-8-(2-furyl)-3-[2-[4-(4-methoxyphenyl)piperazin-1-yl]ethyl]-1-methyl -[1,2,4]triazolo[5,1-f]purin-2-one, 5-Amino-8-(2-furyl)-1-methyl-3-(2-morpholinoethyl)-[1,2,4]triazolo[5,1-f]purin-2-one, 5-Amino-3-[2-[4-(2,4-difluorophenyl)-1-piperidyl]ethyl]-8-(2-furyl)-1-methyl -[1,2,4]triazolo[5,1-f]purin-2-one, 5-Amino-8-(2-furyl)-1-methyl-3-[2-[4-(5-methyl-2-pyridyl)piperazin-1-yl]ethyl]-[1,2,4]triazolo[5,1-f]purin-2-one, 5-Amino-8-(2-furyl)-1-methyl-3-[2-[4-(p-tolyl)piperazin-1-yl]ethyl]-[1,2,4]triazolo[5,1-f]purin-2-one, 5-Amino-8-(2-furyl)-1-methyl-3-[2-[4-(3-methyl-2-oxobutyl)piperazin-1-yl]ethyl]-[1,2,4]triazolo[5,1-f]purin-2-one, 5-Amino-3 -[2-[4-(2-fluoro-4-methoxy-phenyl)piperazin-1-yl]ethyl]-8-(2-furyl)-1-methyl-[1,2,4]triazolo[5,1-f]purin-2-one, 5-Amino-8-(2-furyl)-3-[2-[4-[4-(2-methoxy-1,1-dimethyl-ethoxy)phenyl]piperazin -1-yl]ethyl]-1-methyl-[1,2,4]triazolo[5,1-f]purin-2-one, 5-Amino-8-(2-furyl)-3-[2-[4-(6-methoxy-3-pyridyl)piperazin-1-yl]ethyl]-1-methyl -[1,2,4]triazolo[5,1-f]purin-2-one, 5-Amino-3-[2-[4-[3-fluoro-4-(2-methoxyethoxy)phenyl]piperazin-1-yl]ethyl]-8-(2-furyl)-1-methyl-[1,2,4]triazolo[5,1-f]purin-2-one, 5-Amino-8-(2-furyl)-3-[2-[4-[4-(1-hydroxy-1-methylethyl)phenyl]piperazin-1-yl]ethyl]-1-methyl-[1,2,4]triazolo[5,1-f]purin-2-one, 5-Amino-3-[2-[4-(4-fluorophenyl)-4-hydroxy-1-piperidyl]ethyl]-8-(2-furyl)-1-methyl -[1,2,4]triazolo[5,1-f]purin-2-one, 5-Amino-8-(2-furyl)-3-[2-[4-[4-(2-methoxy-2-methylpropoxy)phenyl]piperazin-1-yl]ethyl]-1-methyl-[1,2,4]triazolo[5,1-f]purin-2-one, 5-Amino-3 -[2-[4-[4-(cyclopropoxy)phenyl]piperazin-1-yl]ethyl]-8-(2-furyl)-1-methyl-[1,2,4]triazolo[5,1-f]purin-2-one, 5-Amino-3-[2-[4-(4-fluorophenyl)-3,6-dihydro-2H-pyridin-1-yl]ethyl]-8-(2-furyl)-1-methyl-[1,2,4]triazolo[5,1-f]purin-2-one, 5-Amino-8-(2-furyl)-3-[2-[4-hydroxy-4-(4-methoxyphenyl)-1-piperidyl]ethyl]-1-methyl-[1,2,4]triazolo[5,1-f]purin-2-one, 5-Amino-3-[2-[4-[3,5-difluoro-4-(2-methoxyethoxy)phenyl]piperazin-1-yl]ethyl]-8-(2-furyl)-1-methyl-[1,2,4]triazolo[5,1-f]purin-2-one, 5-Amino-3-[2-[4-[2,5-difluoro-4-(2-methoxyethoxy)phenyl]piperazin-1-yl]ethyl]-8-(2-furyl)-1-methyl-[1,2,4]triazolo[5,1-f]purin-2-one, 5-Amino-3-[2-[4-(2,2-difluoro-1,3-benzodioxol-5-yl)piperazin-1-yl]ethyl]-8-(2-furyl) -1-methyl-[1,2,4]triazolo[5,1-f]purin-2-one, 5-Amino-8-(2-furyl)-3-[2-[4-[4-(2-methoxyethoxy)phenyl]-3,3-dimethyl-piperazin -1-yl]ethyl]-1-methyl-[1,2,4]triazolo[5,1-f]purin-2-one, 5-Amino-3-[2-(4-butylpiperazin-1-yl)ethyl]-8-(2-furyl)-1-methyl-[1,2,4]triazolo[5,1-f]purin-2-one, 5-Amino-8-(2-furyl)-3-[2-(4-hydroxy-4-methyl-1-piperidyl)ethyl]-1-methyl [1,2,4]triazolo[5,1-f]purin-2-one, 5-Amino-3-[2-[4-[4-[2-(cyclopropoxy)ethoxy]phenyl]piperazin-1-yl]ethyl]-8-(2-furyl)-1-methyl-[1,2,4]triazolo[5,1-f]purin-2-one, 5-Amino-8-(2-furyl)-3-[2[4-[(4-methoxyphenyl)methyl]piperazin-1-yl]ethyl]-1-methyl-[1,2,4]triazolo[5,1-f]purin-2-one, 5-Amino-8-(2-furyl)-3-[2[4-[[4-(2-methoxyethoxy)phenyl]methyl]piperazin-1-yl]ethyl]-1-methyl-[1,2,4]triazolo[5,1-f]purin-2-one, 5-Amino-8-(2-furyl)-3-[(4-methoxyphenyl)methyl]-1-methyl-[1,2,4]triazolo[5,1-f]purin-2-one, 5-Amino-8-(2-furyl)-3-[2-[4-(4-methoxyphenyl)piperazin-1-yl]ethyl]-1-methyl [1,2,4]triazolo[5,1-f]purin-2-one, 5-Amino-8-(2-furyl)-3-[2-[4-[3-(2-methoxyethoxy)phenyl]piperazin-1-yl]ethyl]-1-methyl-[1,2,4]triazolo[5,1-f]purin-2-one, 5-Amino-3-[2-[4[2-fluoro-4-(2-methoxyethoxy)phenyl]piperazin-1-yl]ethyl]-8-(2-furyl)-1-methyl-[1,2,4]triazolo[5,1-f]purin-2-one, 4-[4-[2-[5-Amino-8-(2-furyl)-1-methyl-2-oxo-[1,2,4]triazolo[5,1-f]purin -3yl]ethyl]piperazin-1-yl]benzonitrile, 4-[4-[2-[5-Amino-8-(2-furyl)-1-methyl-2-oxo-[1,2,4]triazolo[5,1-f]purin-3-yl]ethyl]piperazin-1-yl]-2-fluorobenzonitrile, 5-Amino-8-(2-furyl)-1-methyl-3-[2-[4-[4-(trifluoromethyl)phenyl]piperazin-1-yl]ethyl]-[1,2,4]triazolo[5,1-f]purin-2-one, 5-Amino-8-(2-furyl)-1-methyl-3-[2-[4-[4-(trifluoromethyl)thiazol-2-yl]piperazin-1-yl]ethyl]-[1,2,4]triazolo[5,1-f]purin-2-one, 5-Amino-3-[2-[4-(cyclopropylmethyl)piperazin-1-yl]ethyl]-8-(2-furyl)-1-methyl [1,2,4]triazolo[5,1-f]purin-2-one, 5-Amino-3-[2-(4-ethylpiperazin-1-yl)ethyl]-8-(2-furyl)-1-methyl-[1,2,4]triazolo[5,1-f]purin-2-one, 4-[2-[5-Amino-8-(2-furyl)-1-methyl-2-oxo-[1,2,4]triazolo[5,1-f]purin-3-yl]ethyl]-N, N-dimethyl-piperazine-1-sulfonamide, 5-Amino-8-(2-furyl)-1-methyl-3[2-[4-(4-tetrahydrofuran-3-yloxyphenyl)piperazin -1-yl]ethyl]-[1,2,4]triazolo[5,1-f]purin-2-one, 5-Amino-8-(2-furyl)-1-methyl-3-[2-[4-(4-tetrahydropyran-4-yloxyphenyl)piperazin -1-yl]ethyl]-[1,2,4]triazolo[5,1-f]purin-2-one, 5-Amino-8-(2-furyl)-1-methyl-3-[2-[4-[4-(tetrahydrofuran-2-ylmethoxy) phenyl]piperazin-1-yl]ethyl]-[1,2,4]triazolo[5,1-f]purin-2-one, 5-Amino-8-(2-furyl)-1-methyl-3-[2-(3-methyl-7,8-dihydro-5H-1,6-naphthyridin-6-yl)ethyl]-[1,2,4]triazolo[5,1-f]purin-2-one, 5-Amino-3-[2-(6 ,7-dihydro-4H-thieno[3,2-c]pyridin-5-yl)ethyl]-8-(2-furyl)-1-methyl [1,2,4]triazolo[5,1-f]purin-2-one, 5-Amino-8-(2-furyl)-3-[2-[4-[4-(2-methoxyethoxy)phenyl]piperazin-1-yl]propyl]-1-methyl-[1,2,4]triazolo[5,1-f]purin-2-one, 5-Amino-3-[2-[3-(4-fluorophenyl)-2,5-dihydropyrrol-1-yl]ethyl]-8-(2-furyl)-1-methyl [1,2,4]triazolo[5,1-f]purin-2-one, 5-Amino-3-[2-[4-[4-(2-methoxyethoxy)phenyl]piperazin-1-yl]ethyl]-1-methyl-8-(5-methyl-2-furyl)-[1,2,4]triazolo[5,1-f]purin-2-one, 5-Amino-8-(5-cyclopropyl-2-furyl)-3-[2-[4-[4-(2-methoxyethoxy)phenyl]piperazin -1-yl]ethyl]-1-methyl-[1,2,4]triazolo[5,1-f]purin-2-one, 5-Amino-3-[2-(2,4-difluoroanilino)ethyl]-8-(2-furyl)-1-methyl-[1,2,4]triazolo[5,1-f]purin-2-one, 5-Amino-3-[3-[4-(4-fluorophenyl)piperazin-1-yl]propyl]-8-(2-furyl)-1-methyl [1,2,4]triazolo[5,1-f]purin-2-one, 5-Amino-8-(2-furyl)-3[3-[4-[4-(2-methoxyethoxy)phenyl]piperazin-1-yl]propyl]-1-methyl-[1,2,4]triazolo[5,1-f]purin-2-one, 5-Amino-8-(2-furyl)-3[2-[4-(4-methoxyphenyl)-3,6-dihydro-2H-pyridin-1-yl]ethyl]-1-methyl-[1,2,4]triazolo[5,1-f]purin-2-one, 5-Amino-8-(2-furyl)-3-[2-[4-[4-(2-methoxy-1,1-dimethyl-ethyl)phenyl]piperazin-1-yl]ethyl]-1-methyl-[1,2,4]triazolo[5,1-f]purin-2-one, 5-Amino-8-(2-furyl)-1-methyl-3-(2-piperazin-1-ylethyl)-[1,2,4]triazolo[5,1-f]purin-2-one, 5-Amino-8-(2-furyl)-3-[2-[4-(1H-indole-2-carbonyl)piperazin-1-yl]ethyl]-1-methyl [1,2,4]triazolo[5,1-f]purin-2-one, 5-Amino-8-(2-furyl)-3-[2-(4-isopropoxyphenyl)ethyl]-1-methyl-[1,2,4]triazolo[5,1-f]purin-2-one, 5-Amino-8-(2-furyl)-1-methyl-3-[2-[4-[(2S)-pyrrolidine-2-carbonyl]piperazin-1-yl]ethyl]-[1,2,4]triazolo[5,1-f]purin-2-one, 5-Amino-8-(2-furyl)-3-[2-(4-methoxyphenyl)ethyl]-1-methyl-[1,2,4]triazolo[5,1-f]purin-2-one, 5-Amino-3-[2-[4-[4-(difluoromethoxy)phenyl]piperazin-1-yl]ethyl]-8-(2-furyl)-1-methyl-[1,2,4]triazolo[5,1-f]purin-2-one, 5-Amino-8-(2-furyl)-1-methyl-3-[2-[4-[3-(5-methyl-1,3,4-oxadiazol-2-yl) phenyl]piperazin-1-yl]ethyl]-[1,2,4]triazolo[5,1-f]purin-2-one, 5-Amino-3-[2-[4-[2-fluoro-4-(5-methyl-1,2,4-oxadiazol-3-yl)phenyl]piperazin-1-yl]ethyl]-8-(2-furyl)-1-methyl-[1,2,4]triazolo[5,1-f]purin-2-one, 5-Amino-3-[2-[4-(6-fluoro-2-methyl-1,3-benzoxazol-5-yl)piperazin-1-yl]ethyl]-8-(2-furyl)-1-methyl-[1,2,4]triazolo[5,1-f]purin-2-one, 5-Amino-3-[2-[4-(cyclopropanecarbonyl)piperazin-1-yl]ethyl]-8-(2-furyl)-1-methyl [1,2,4]triazolo[5,1-f]purin-2-one, 5-Amino-3-[2-[4-(2-cyclopropylacetyl)piperazin-1-yl]ethyl]-8-(2-furyl)-1-methyl [1,2,4]triazolo[5,1-f]purin-2-one, 5-Amino-8-(2-furyl)-3-[2-[4-[4-(2-hydroxyethoxy)phenyl]piperazin-1-yl]ethyl]-1-methyl-[1,2,4]triazolo[5,1-f]purin-2-one, 5-Amino-8-(2-furyl)-3-[2-[4-(4-hydroxyphenyl)piperazin-1-yl]ethyl]-1-methyl [1,2,4]triazolo[5,1-f]purin-2-one, 5-Amino-1-(cyclopropylmethyl)-3-[2-[4-(4-ethoxyphenyl)piperazin-1-yl]ethyl]-8-(2-furyl)-[1,2,4]triazolo[5,1-f]purin-2-one, 5-Amino-1-(cyclopropylmethyl)-3-[2-[4-(4-fluorophenyl)piperazin-1-yl]ethyl]-8-(2-furyl)-[1,2,4]triazolo[5,1-f]purin-2-one, 5-Amino-1-(cyclopropylmethyl)-3-[2-[4-(2,4-difluorophenyl)piperazin-1-yl]ethyl]-8-(2-furyl)-[1,2,4]triazolo[5,1-f]purin-2-one, 5-Amino-1-(cyclopropylmethyl)-8-(2-furyl)-3-[2-[4-[4-(2-methoxyethoxy)phenyl]piperazin-1-yl]ethyl]-[1,2,4]triazolo[5,1-f]purin-2-one, 5-Amino-1-(cyclopropylmethyl)-3-[2-(4-fluorophenoxy)ethyl]-8-(2-furyl) [1,2,4]triazolo[5,1-f]purin-2-one, 5-Amino-8-(2-furyl)-1-methyl-3-[2-[2-oxo-5-(trifluoromethyl)-1-pyridyl]ethyl]-[1,2,4]triazolo[5,1-f]purin-2-one, 5-Amino-3-[2-[4-(2,4-difluorophenyl)pyrazol-1-yl]ethyl]-1-ethyl-8-(2-furyl) [1,2,4]triazolo[5,1-f]purin-2-one, 1-[2-[5-Amino-1-(cyclopropylmethyl)-8-(2-furyl)-2-oxo-[1,2,4]triazolo[5,1-f]purin-3-yl]ethyl]pyrazole-4-carboxylic acid, 1-[2-[5-Amino-8-(2-furyl)-1-methyl-2-oxo-[1,2,4]triazolo[5,1-f]purin-3-yl]ethyl]pyrazole-4-carboxylic acid, 1-[2-[5-Amino-1-(cyclopropylmethyl)-8-(2-furyl)-2-oxo-[1,2,4]triazolo[5,1-f]purin-3-yl]ethyl]-N-cyclopropyl-pyrazole-4-carboxamide, 1-[2-[5-Amino-1-(cyclopropylmethyl)-8-(2-furyl)-2-oxo-[1,2,4]triazolo[5,1-f]purin-3-yl]ethyl]-N,N-diethyl-pyrazole-4-carboxamide, 1-[2-[5-Amino-1-(cyclopropylmethyl)-8-(2-furyl)-2-oxo-[1,2,4]triazolo[5,1-f]purin-3-yl]ethyl]-N-cyclopropyl-5-methyl-pyrazole-3-carboxamide, 2-[2-[5-Amino-1-(cyclopropylmethyl)-8-(2-furyl)-2-oxo-[1,2,4]triazolo[5,1-f]purin-3-yl]ethyl]-N-cyclopropyl-5-methyl-pyrazole-3-carboxamide, 1-[2-[5-Amino-8-(2-furyl)-1-methyl-2-oxo-[1,2,4]triazolo[5,1-f]purin-3-yl]ethyl]-N -methyl-pyrazole-3-carboxamide, 1-[2-[5-Amino-8-(2-furyl)-1-methyl-2-oxo-[1,2,4]triazolo[5,1-f]purin-3-yl]ethyl]-N, N-diethyl-pyrazole-4-carboxamide, 1-[2-[5-amino-8-(2-furyl)-1-methyl-2-oxo-[1,2,4]triazolo[5,1-f]purin-3-yl]ethyl]pyrazole-4-carboxamide, 5-Amino-8-(2-furyl)-3-[2-[4-[(3R)-3-hydroxypyrrolidine-1-carbonyl]pyrazol-1-yl]ethyl]-1-methyl-[1,2,4]triazolo[5,1-f]purin-2-one, 1-[2-[5-Amino-8-(2-furyl)-1-methyl-2-oxo-[1,2,4]triazolo[5,1-f]purin-3-yl]ethyl]-N-methyl-pyrazole-4-carboxamide, 1-[2-[5-Amino-8-(2-furyl)-1-methyl-2-oxo-[1,2,4]triazolo[5,1-f]purin-3-yl]ethyl]-N-cyclopropyl-pyrazole-3-carboxamide, 1-[2-[5-Amino-8-(2-furyl)-1-methyl-2-oxo-[1,2,4]triazolo[5,1-f]purin-3-yl]ethyl]-N-cyclopropyl-pyrazole-4-carboxamide, 5-Amino-8-(2-furyl)-3-[2-[4-(3-hydroxyazetidine-1-carbonyl)pyrazol-1-yl]ethyl]-1-methyl-[1,2,4]triazolo[5,1-f]purin-2-one, 5-Amino-1-ethyl-8-(2-furyl)-3-[2-[4-[4-(2-methoxyethoxy)phenyl]piperazin-1-yl]ethyl]-[1,2,4]triazolo[5,1-f]purin-2-one, 5-Amino-3-[2-[4-(2,4-difluorophenyl)piperazin-1-yl]ethyl]-1-ethyl-8-(2-furyl) -[1,2,4]triazolo[5,1-f]purin-2-one, 5-Amino-1-ethyl-3-{2-[4-(4-fluoro-phenyl)-piperidin-1-yl]-ethyl}-8-furan-2-yl-1, 3-dihydro-[1,2,4]triazolo[5,1-f]purin-2-one, 5-Amino-1-ethyl-8-(2-furyl)-3-[2-(3-methyl-7,8-dihydro-5H-1,6-naphthyridin -6-yl)ethyl]-[1,2,4]triazolo[5,1-f]purin-2-one, 5-Amino-8-(2-furyl)-3-[2-[4-[4-(2-methoxyethoxy)phenyl]piperazin-1-yl]ethyl]-1-(2,2,2-trifluoroethyl)-[1,2,4]triazolo[5,1-f]purin-2-one, 5-Amino-3-{2-[4-(2,4-difluoro-phenyl)-piperazin-1-yl]-ethyl}-8-furan-2-yl-1-(2,2, 2-trifluoro-ethyl)-1,3-dihydro-[1,2,4]triazolo[5,1-f]purin-2-one, 5-Amino-8-(2-furyl)-3-[2-[4-[4-(2-methoxyethoxy)phenyl]piperazin-1-yl]ethyl]-1-(2-methoxyethyl)-[1,2,4]triazolo[5,1-f]purin-2-one, 5-amino-3-[2-[4-(4-fluorophenyl)piperazin-1-yl]ethyl]-8-(2-furyl)-1-(2-methoxyethyl)-[1,2,4]triazolo[5,1-f]purin-2-one, 5-Amino-3-[2-[4-(4-fluorophenyl)piperazin-1-yl]ethyl]-8-(2-furyl)-1-(2-hydroxyethyl)[1,2,4]triazolo[5,1-f]purin-2-one one, 5-Amino-1-cyclopropyl-8-(2-furyl)-3-[2-[4-[4-(2-methoxyethoxy)phenyl]piperazin -1-yl]ethyl]-[1,2,4]triazolo[5,1-f]purin-2-one, 5-Amino-8-(2-furyl)-3-[2-[4-[4-(2-methoxyethoxy)phenyl]piperazin-1-yl]ethyl]-1-(2,2,2-trifluoroethyl)-[1,2,4]triazolo[5,1-f]purin-2-one, 5-Amino-3-[2-[4-[4-(2-methoxyethoxy)phenyl]piperazin-1-yl]ethyl]-1-methyl-8-thiazol-2-yl-[1,2,4]triazolo[5,1-f]purin-2-one, 5-Amino-3-[2-[4-[3-fluoro-4-(2-methoxyethoxy)phenyl]piperazin-1-yl]ethyl]-1-methyl-8-thiazol-2-yl-[1,2,4]triazolo[5,1-f]purin-2-one, 5-Amino-3-[2-[4-(2-cyclopropylacetyl)piperazin-1-yl]ethyl]-1-methyl-8-thiazol -2-yl-[1,2,4]triazolo[5,1-f]purin-2-one, 5-Amino-3-[2-[4-(4-methoxyphenyl)piperazin-1-yl]ethyl]-1-methyl-8-thiazol -2-yl-[1,2,4]triazolo[5,1-f]purin-2-one, 5-Amino-1-methyl-3-[2-[4-(p-tolyl)piperazin-1-yl]ethyl]-8-thiazol-2-yl -[1,2,4]triazolo[5,1-f]purin-2-one, 5-Amino-1-methyl-3-[2-(3-methyl-7,8-dihydro-5H-1,6-naphthyridin-6-yl)ethyl]-8-thiazol-2-yl-[1,2,4]triazolo[5,1-f]purin-2-one, 4-[4-[2-(5-Amino-1-methyl-2-oxo-8-thiazol-2-yl-[1,2,4]triazolo[5,1-f]purin-3-yl)ethyl]piperazin-1-yl]benzonitrile, 5-Amino-1-methyl-3-[2-[4-[3-(5-methyl-1,3,4-oxadiazol-2-yl)phenyl]piperazin-1-yl]ethyl]-8-thiazol-2-yl-[1,2,4]triazolo[5,1-f]purin-2-one, 5-amino-3-[2-[4-[4-(1-hydroxy-1-methyl-ethyl)phenyl]piperazin-1-yl]ethyl]-1-methyl-8-thiazol-2-yl-[1,2,4]triazolo[5,1-f]purin-2-one, 5-Amino-3-[2-[4-[4-(2-methoxyethoxy)phenyl]piperazin-1-yl]ethyl]-1-methyl-8-(2-pyridyl)-[1,2,4]triazolo[5,1-f]purin-2-one, 5-Amino-3-[2-[4-(2,4-difluorophenyl)piperazin-1-yl]ethyl]-1-methyl-8-(2-pyridyl) -[1,2,4]triazolo[5,1-f]purin-2-one, 4-[4-[2-[5-Amino-1-methyl-2-oxo-8-(2-pyridyl)-[1,2,4]triazolo[5,1-f]purin-3-yl]ethyl]piperazin-1-yl]benzonitrile, 5-Amino-3-[2-[4-[4-(1-hydroxy-1-methyl-ethyl)phenyl]piperazin-1-yl]ethyl]-1-methyl-8-(2-pyridyl)-[1,2,4]triazolo[5,1-f]purin-2-one, 5-Amino-3-[2-[4-[4-(2-methoxyethoxy)phenyl]piperazin-1-yl]ethyl]-1-methyl-8-pyrazin-2-yl-[1,2,4]triazolo[5,1-f]purin-2-one, 5-Amino-3-[2-[4-(2,4-difluorophenyl)piperazin-1-yl]ethyl]-1-methyl-8-pyrazin-2-yl -[1,2,4]triazolo[5,1-f]purin-2-one, 5-Amino-3-[2-[4-[2-fluoro-4-(2-methoxyethoxy)phenyl]piperazin-1-yl]ethyl]-1-methyl-8-pyrazin-2-yl-[1,2,4]triazolo[5,1-f]purin-2-one, 5-Amino-8-(2-furyl)-3-[[1-(4-methoxyphenyl)pyrrolidin-3-yl]methyl]-1-methyl -[1,2,4]triazolo[5,1-f]purin-2-one, 5-Amino-8-(2-furyl)-3-[[1-[4-(2-methoxyethoxy)phenyl]pyrrolidin-3-yl]methyl]-1-methyl-[1,2,4]triazolo[5,1-f]purin-2-onehyl}-1-methyl-1,3-dihydro-[1,2,4]triazolo[5,1-i]purin-2-one, 5-amino-8-(2-furyl)-3-[2-[4-[4-(2-methoxyethoxy)phenyl]piperazin-1-yl]ethyl]-1-methyl-[1,2,4]triazolo[5,1-f]purine-2-thione, 8-(2-furyl)-3-[2-[4-[4-(2-methoxyethoxy)phenyl]piperazin-1-yl]ethyl]-1-methyl-5-(methylamino)-[1,2,4]triazolo[5,1-f]purin-2-one, 5-Amino-3-{2-[4-(4-fluoro-phenyl)-piperazin-1-yl]-ethyl}-8-isothiazol-5-yl-1-methyl -1,3-dihydro-[1,2,4]triazolo[5,1-i]purin-2-one, 5-Amino-8-isothiazol-5-yl-3-(2-{4-[4-(2-methoxy-ethoxy)-phenyl]-piperazin-1-yl}-ethyl)-1-methyl-1,3-dihydro-[1,2,4]triazolo[5,1-i]purin-2-one, 5-Amino-3-[2-[4-[2-fluoro-4-(2-methoxyethoxy)phenyl]piperazin-1-yl]ethyl]-8-isothiazol-5-yl-1-methyl-[1,2,4]triazolo[5,1-f]purin-2-one, 5-Amino-8-isoxazol-5-yl-3-[2-[4-[4-(2-methoxyethoxy)phenyl]piperazin-1-yl]ethyl]-1-methyl-[1,2,4]triazolo[5,1-f]purin-2-one, 5-Amino-3-[2-[4-[4-(2-methoxyethoxy)phenyl]piperazin-1-yl]ethyl]-1-methyl-8-oxazol-2-yl-[1,2,4]triazolo[5,1-f]purin-2-one, 5-Amino-3-{2-[4-(4-methoxy-phenyl)-piperazin-1-yl]-ethyl}-1-methyl-8-prop-1-ynyl-1,3-dihydro-[1,2,4]triazolo[5,1-i]purin-2-one, 5-Amino-3-(2-{4-[4-(2-methoxy-ethoxy)-phenyl]-piperazin-1-yl}-ethyl)-1-methyl-8-prop-1-ynyl-1,3-dihydro-[1,2,4]triazolo[5,1-i]purin-2-one, 5-Amino-3-{2-[4-(4-fluoro-benzoyl)-piperazin-1-yl]-ethyl}-8-furan-2-yl-1-methyl -1,3-dihydro-[1,2,4]triazolo[5,1-i]purin-2-one, 5-Amino-3-(2-dimethylamino-ethyl)-8-furan-2-yl-1-methyl-1,3-dihydro-[1,2,4]triazolo[5,1-i]purin-2-one,
5-Amino-8-furan-2-yl-3-[3-(4-methoxy-phenyl)-propyl]-1-methyl-1,3-dihydro-[1,2,4]triazolo[5,1-i]purin-2-one,
5-Amino-8-furan-2-yl-1-methyl-3-(2-pyrazol-1-yl-ethyl)-1,3-dihydro-[1,2,4]triazolo[5,1-i]purin-2-one,
5-Amino-8-furan-2-yl-3-(2-{4-[4-(2-methoxy-ethoxy)-phenyl]-pyrazol-1-yl}-ethyl)-1-methyl-1,3-dihydro-[1,2,4]triazolo[5,1-i]purin-2-one,
5-Amino-8-furan-2-yl-3-{2-[3-(4-methoxy-phenyl)-pyrrol-1-yl]-ethyl}-1-methyl-1,3-dihydro-[1,2,4]triazolo[5,1-i]purin-2-one,
5-Amino-8-furan-2-yl-3-{2-[4-(4-methoxy-phenyl)-imidazol-1-yl]-ethyl}-1-methyl-1,3-dihydro-[1,2,4]triazolo[5,1-i]purin-2-one,
5-Amino-8-furan-2-yl-3-{2-[4-(4-methoxy-phenyl)-[1,2,3]triazol-1-yl]-ethyl}-1-methyl-1,3-dihydro-[1,2,4]triazolo[5,1-i]purin-2-one,
5-Amino-3-[2-(1,3-dihydro-isoindol-2-yl)-ethyl]-8-furan-2-yl-1-methyl-1,3-dihydro-[1,2,4]triazolo[5,1-i]purin-2-one,
5-Amino-8-furan-2-yl-1-methyl-3-(2-piperidin-1-yl-ethyl)-1,3-dihydro-[1,2,4]triazolo[5,1-i]purin-2-one,
5-Amino-8-furan-2-yl-1-methyl-3-(2-pyrrolidin-1-yl-ethyl)-1,3-dihydro-[1,2,4]triazolo[5,1-i]purin-2-one,
5-Amino-8-furan-2-yl-1-methyl-3-[2-(3-methyl-7,8-dihydro-5H-[1,6]naphthyridin-6-yl)ethyl]-1,3-dihydro-[1,2,4]triazolo[5,1-i]purin-2-one,
5-Amino-8-furan-2-yl-3-{2-[4-(2-methoxy-ethoxy)-phenoxy]-ethyl}-1-methyl-1,3-dihydro-[1,2,4]triazolo[5,1-i]purin-2-one,
5-Amino-8-furan-2-yl-3-{2-[4-(2-methoxy-ethoxy)-phenylamino]-ethyl}-1-methyl-1,3-dihydro-[1,2,4]triazolo[5,1-i]purin-2-one,
5-Amino-8-furan-2-yl-1-methyl-3-[2-(pyridin-2-yloxy)-ethyl]-1,3-dihydro-[1,2,4]triazolo[5,1-i]purin-2-one,
5-Amino-1-ethyl-3-{2-[4-(4-fluoro-phenyl)-piperazin-1-yl]-ethyl}-8-isothiazol-5-yl-1,3-dihydro-[1,2,4]triazolo[5,1-i]purin-2-one,
5-Amino-1-ethyl-8-isothiazol-5-yl-3-(2-{4-[4-(2-methoxy-ethoxy)-phenyl]-piperazin-1-yl}-ethyl)-1,3-dihydro-[1,2,4]triazolo[5,1-i]purin-2-one,
5-Amino-1-ethyl-8-furan-2-yl-3-(2-piperidin-1-yl-ethyl)-1,3-dihydro-[1,2,4]triazolo[5,1-i]purin-2-one,
5-Amino-1-ethyl-8-furan-2-yl-3-[2-(3-methyl-7,8-dihydro-5H-[1,6]naphthyridin-6-yl)-ethyl]-1,3-dihydro-[1,2,4]triazolo[5,1-i]purin-2-one,
5-Amino-3-[2-(2,4-difluoro-phenoxy)-ethyl]-1-ethyl-8-furan-2-yl-1,3-dihydro-[1,2,4]triazolo[5,1-i]purin-2-one,
5-Amino-3-[2-(2,4-difluoro-phenylamino)-ethyl]-1-ethyl-8-furan-2-yl-1,3-dihydro-[1,2,4]triazolo[5,1-i]purin-2-one,
5-Amino-1-cyclopropylmethyl-3-[2-(2,4-difluoro-phenylamino)-ethyl]-8-furan-2-yl-1,3-dihydro-[1,2,4]triazolo[5,1-i]purin-2-one,
5-Amino-1-cyclopropylmethyl-3-[2-(2,4-difluoro-phenoxy)-ethyl]-8-furan-2-yl-1,3-dihydro-[1,2,4]triazolo[5,1-i]purin-2-one,
5-Amino-1-cyclopropylmethyl-3-{2-[4-(4-fluoro-phenyl)-piperidin-1-yl]-ethyl}-8-furan-2-yl-1,3-dihydro-[1,2,4]triazolo[5,1-i]purin-2-one,
5-Amino-3-{2-[4-(4-fluoro-phenyl)-piperidin-1-yl]-ethyl}-8-furan-2-yl-1-(2,2,2-trifluoro-ethyl)-1,3-dihydro-[1,2,4]triazolo[5,1-i]purin-2-one,
5-Amino-8-furan-2-yl-3-{2-[4-(4-methoxy-phenyl)-piperazin-1-yl]-ethyl}-1-(2,2,2-trifluoro-ethyl)-1,3-dihydro-[1,2,4]triazolo[5,1-i]purin-2-one,
5-Amino-3-[2-(4-cyclopropylmethyl-piperazin-1-yl)-ethyl]-8-isothiazol-5-yl-1-(2,2,2-trifluoro-ethyl)-1,3-dihydro-[1,2,4]triazolo[5,1-i]purin-2-one,
(5-Amino-8-isothiazol-5-yl-3-{2-[4-(4-methoxy-phenyl)-piperazin-1-yl]-ethyl}-2-oxo-2,3-dihydro-[1,2,4]triazolo[5,1-i]purin-1-yl)-acetonitrile,
[5-Amino-3-{2-[4-(2,4-difluoro-phenyl)-piperazin-1-yl]-ethyl}-8-(3-fluoro-phenyl)-2-oxo-2,3-dihydro-[1,2,4]triazolo[5,1-i]purin-1-yl]-acetonitrile,
[5-Amino-8-furan-2-yl-3-(2-{4-[4-(2-methoxy-ethoxy)-phenyl]-piperazin-1-yl}-ethyl)-2-oxo-2,3-dihydro-[1,2,4]triazolo[5,1-i]purin-1-yl]-acetonitrile,
5-Amino-3-(2-{4-[4-(2-methoxy-ethoxy)-phenyl]-piperazin-1-yl}-ethyl)-1-methyl-8-phenyl-1,3-dihydro-[1,2,4]triazolo[5,1-i]purin-2-one,
3-[5-Amino-3-(2-{4-[4-(2-methoxy-ethoxy)-phenyl]-piperazin-1-yl}-ethyl)-1-methyl-2-oxo-2,3-dihydro-1H-[1,2,4]triazolo[5,1-i]purin-8-yl]-benzonitrile,
3-[5-Amino-3-(2-{4-[4-(2-methoxy-ethoxy)-phenyl]-piperazin-1-yl}-ethyl)-1-methyl-2-oxo-2,3-dihydro-1H-[1,2,4]triazolo[5,1-i]purin-8-yl]-benzonitrile,
5-Amino-8-furan-2-yl-1-methyl-3-vinyl-1,3-dihydro-[1,2,4]triazolo[5,1-i]purin-2-one,
5-Amino-3-[3-(4-fluoro-phenyl)-prop-2-ynyl]-8-furan-2-yl-1-methyl-1,3-dihydro-[1,2,4]triazolo[5,1-i]purin-2-one,
5-Amino-8-furan-2-yl-1-methyl-3-[4-(4-methyl-piperazin-1-yl)-but-2-ynyl]-1,3-dihydro-[1,2,4]triazolo[5,1-i]purin-2-one,
5-Amino-8-furan-2-yl-1-isopropyl-3-(2-{4-[4-(2-methoxy-ethoxy)-phenyl]-piperazin-1-yl}-ethyl)-1,3-dihydro-[1,2,4]triazolo[5,1-i]purin-2-one,
5-Amino-2-benzyl-7-(2-{4-[4-(2-methoxy-ethoxy)-phenyl]-piperazin-1-yl}-ethyl)-9-methyl-7,9-dihydro-2H-[1,2,4]triazolo[3,4-i]purine-3,8-dione,
5-Amino-2-benzyl-9-methyl-7-(2-morpholin-4-yl-ethyl)-7,9-dihydro-2H-[1,2,4]triazolo[3,4-i]purine-3,8-dione,
5-Amino-2-(3-chloro-benzyl)-7-[2-(4-isopropyl-piperazin-1-yl)-ethyl]-9-methyl-7,9-dihydro-2H-[1,2,4]triazolo[3,4-i]purine-3,8-dione,
5-Amino-2-cyclopropylmethyl-9-methyl-7-(2-morpholin-4-yl-ethyl)-7,9-dihydro-2H-[1,2,4]triazolo[3,4-i]purine-3,8-dione,
5-Amino-2-cyclopropylmethyl-7-(2,4-difluoro-benzyl)-9-methyl-7,9-dihydro-2H-[1,2,4]triazolo[3,4-i]purine-3,8-dione,
4-Amino-2-furan-2-yl-6-(2-{4-[4-(2-methoxy-ethoxy)-phenyl]-piperazin-1-yl}-ethyl)-6H-8-oxa-1,3,3a,5,6-pentaaza-as-indacen-7-one, or
4-Amino-2-furan-2-yl-6-(2-{4-[4-(2-methoxy-ethoxy)-phenyl]-piperazin-1-yl}-ethyl)-8,8-dimethyl-6,8-dihydro-1,3,3a,5,6-pentaaza-as-indacen-7-one.

7. A pharmaceutical composition comprising, as an active ingredient, at least one compound of formula (I), as claimed in claim 1, or its tautomers, polymorphs, stereoisomers, prodrugs, solvate or a pharmaceutically acceptable salts thereof, together with one or more pharmaceutically acceptable carriers or excipients.

8. The compound of formula (I) as claimed in claim 1, or its tautomers, polymorphs, stereoisomers, prodrugs, solvate or a pharmaceutically acceptable salts thereof, for treating disease or disorder susceptible to improvement by antagonism of A2A receptor.

9. The compound of formula (I), as claimed in claim 1, or its tautomers, polymorphs, stereoisomers, prodrugs, solvate or a pharmaceutically acceptable salts thereof, for treating Parkinsons disease, restless leg syndrome, Alzheimers disease, neurodegenerative disorder, inflammation, wound healing, dermal fibrosis, nocturnal myoclonus, cerebral ischaemia, myocardial ischemia, Huntington's disease, multiple system atrophy, corticobasal degeneration, Wilson's disease, a disorder of basal ganglia which results in dyskinesias, post traumatic stress disorder, hepatic cirrhosis, sepsis, spinal cord injury, retinopathy, hypertension, social memory impairment, depression, neuroprotection, narcolepsy, a sleep related disorder, attention deficit hyperactivity disorder, drug addiction, post traumatic stress disorder and vascular injury.

10. A pharmaceutical composition comprising, a compound of formula (I) as claimed in claim 1, or its tautomers, polymorphs, stereoisomers, prodrugs, solvate or a pharmaceutically acceptable salts thereof, in combination with one or more therapeutically active agents.

11. The pharmaceutical composition as claimed in claim 10 wherein, the therapeutically active agent is selected from anti-inflammatory agent, anti-diabetic agent, anti-hypertensive agent or anti-dyslipidemic agent.

12. The pharmaceutical composition as claimed in claim 10, wherein the pharmaceutically acceptable therapeutically active agent is selected from anticholinergic agent, antimuscarinic agent, steroid, LTB4 (leukotriene B4) antagonist, dopamine receptor agonists, phosphodiesterase 4 inhibitor, beta-2adrenergic receptor agonist, insulin, insulin derivatives and mimetics, insulin secretagogues, insulinotropic sulfonylurea receptor ligands, thiazolidone derivatives, glycogen synthase kinase-3inhibitor, sodium-dependent glucose co-transporter inhibitor, glycogen phosphorylase A inhibitor, biguanide, alpha-glucosidase inhibitor, glucagon like peptide-1(GLP-1), GLP-1analogs and GLP-1mimetics, modulators of peroxisome proliferator-activated receptors, dipeptidyl peptidase IV inhibitor, stearoyl-CoA desaturase-1inhibitor, diacylglycerol acyltransferase 1and 2inhibitor, acetyl CoA carboxylase 2inhibitor, and breakers of advanced glycation end products, loop diuretics, angiotensin converting enzyme inhibitor, inhibitor of the Na-K-ATPase membrane pump, digoxin, neutralendopeptidase (NEP) inhibitor, ACE/NEP inhibitors, angiotensin II antagonists, renin inhibitors, β-adrenergic receptor blockers, inotropic agents, calcium channel blockers, aldosterone receptor antagonists, and aldosterone synthase inhibitors, 3-hydroxy-3-methyl-glutaryl coenzyme A reductase inhibitor, HDL increasing compounds, cholesterol ester transfer protein inhibitor, squalene synthase inhibitor, farnesoid X receptor and liver X receptor ligand, cholestyramine, fibrates, nicotinic acid, or aspirin.

13. A pharmaceutical composition comprising, a compound of formula (I) as claimed in claim 1, or its tautomers, polymorphs, stereoisomers, prodrugs, solvate or a pharmaceutically acceptable salts thereof, in combination with one to three other agents useful in treating Parkinson's disease in a pharmaceutically acceptable carrier.

14. The pharmaceutical composition as claimed in claim 13, wherein the other agent is selected from L-DOPA, dopaminergic agonists, MAO-B inhibitors, DOPA decarboxylase inhibitors, COMT inhibitors and NMDA receptor.

* * * * *